(12) United States Patent
Courcambeck et al.

(10) Patent No.: US 10,179,770 B2
(45) Date of Patent: Jan. 15, 2019

(54) QUINOLINES DERIVATIVES AS NOVEL ANTICANCER AGENTS

(71) Applicant: GENOSCIENCE PHARMA, Marseilles (FR)

(72) Inventors: Jerome Courcambeck, Marseilles (FR); Philippe Halfon, Marseilles (FR); Firas Bassissi, Marseilles (FR); Sonia Brun, Aix en Provence (FR); Gregory Nicolas, Marseilles (FR); Antoine Beret, Marseilles (FR); Serge Petit, Cusy (FR); Claire Camus, Marseilles (FR); Jean Pierre Nallet, Montanay (FR)

(73) Assignee: GENOSCIENCE PHARMA, Marseilles (FR)

(*) Notice: Subject to any disclaimer, the term of this patent is extended or adjusted under 35 U.S.C. 154(b) by 353 days.

(21) Appl. No.: 14/777,917

(22) PCT Filed: Mar. 13, 2014

(86) PCT No.: PCT/IL2014/050273
§ 371 (c)(1),
(2) Date: Sep. 17, 2015

(87) PCT Pub. No.: WO2014/147611
PCT Pub. Date: Sep. 25, 2014

(65) Prior Publication Data
US 2016/0280653 A1    Sep. 29, 2016

Related U.S. Application Data

(60) Provisional application No. 61/802,891, filed on Mar. 18, 2013.

(51) Int. Cl.
*A61K 31/47*    (2006.01)
*C07D 215/52*    (2006.01)
(Continued)

(52) U.S. Cl.
CPC .......... *C07D 215/52* (2013.01); *A61K 31/47* (2013.01); *A61K 31/4706* (2013.01);
(Continued)

(58) Field of Classification Search
CPC ..................................................... A61K 31/47
See application file for complete search history.

(56) References Cited

U.S. PATENT DOCUMENTS 1,886,481 A    11/1932    Hartmann et al.
4,560,692 A    12/1985    Field et al.

FOREIGN PATENT DOCUMENTS

WO    98/57931 A2    12/1998
WO    0034265 A2    6/2000
(Continued)

OTHER PUBLICATIONS

Soo-Jong Um et al.,"Synthesis of Novel Quinolinecarboxamide Derivatives with Estrogenic Activity", Dept. of Bioscience & Biotechnology/Institute of Bioscience, pp. 677-680, vol. 24, No. 5, (Jan. 2003).
(Continued)

*Primary Examiner* — Benjamin J Packard
(74) *Attorney, Agent, or Firm* — Browdy and Neimark, PLLC

(57) ABSTRACT

The invention provides quinoline derivatives, their manufacture, pharmaceutical compositions containing them, and their use as medicaments. The active compounds of the present invention are useful for the treatment of proliferative neoplastic and non-neoplastic diseases.

29 Claims, 17 Drawing Sheets

(51) Int. Cl.
- C07D 401/04 (2006.01)
- A61K 45/06 (2006.01)
- C07D 215/12 (2006.01)
- C07D 215/18 (2006.01)
- C07D 215/233 (2006.01)
- C07D 401/06 (2006.01)
- C07D 491/113 (2006.01)
- C07D 211/58 (2006.01)
- C07D 211/74 (2006.01)
- A61K 31/4706 (2006.01)
- A61K 31/4709 (2006.01)
- A61K 31/5377 (2006.01)
- C07D 215/42 (2006.01)
- C07D 401/12 (2006.01)

(52) U.S. Cl.
CPC ...... *A61K 31/4709* (2013.01); *A61K 31/5377* (2013.01); *A61K 45/06* (2013.01); *C07D 211/58* (2013.01); *C07D 211/74* (2013.01); *C07D 215/12* (2013.01); *C07D 215/18* (2013.01); *C07D 215/233* (2013.01); *C07D 215/42* (2013.01); *C07D 401/04* (2013.01); *C07D 401/06* (2013.01); *C07D 401/12* (2013.01); *C07D 491/113* (2013.01)

(56) References Cited

FOREIGN PATENT DOCUMENTS

| | | |
|---|---|---|
| WO | 00/76982 A1 | 12/2000 |
| WO | 2005061519 A1 | 7/2005 |
| WO | 2006094237 A2 | 9/2006 |

OTHER PUBLICATIONS

Database Registry, Chemical Abstracts Service (Mar. 17, 2013).
Gilman et al., Some 7-Chloroquinolines as "Open Model" aterbrins, 69:123-14 (1947).
Andersen et al., Oxadiazoles as bioisosteric transformations of carboxylic functionalities. II*, Eur J Med Chem, 31:417-425 (1996).
Strekowski et al., Synthesis and structure-DNA binding relationship analysis of DNA triple-Helix specific intercalators, J Med Chem, 39:3980-3983 (199).
Mikata et al., Effect of side chain location in (2-aminoethyl)-aminomethyl-2-phenylquinolines as antitumor agents, Bioorganic & Medicinal Chemistry Letters, 8:1243-1248 (1998).
Spinks et al., Investigation of Trypanothione reductase as a drug target in Trypanosoma brucei, Chem Med Chem, 4:2060-2069 (2009).
Strekowski et al., Synthesis and activity of substituted 2-Phenylquinolin-4-amines, antagonists of immunostimulatory CpG-Oligodeoxynucleotides, J Med Chem, 46:1242-1249 (2003).
Strekowski et al., Structure-activity relationship analysis of substituted 4-quinolinamines, antagonists of immunostimulatory CpG-oligodeoxynucleotides, Bioorganic & Medicinal Chemistry Letters, 9:1819-1824 (1999).
Chaires et al., Triplex selective 2-(2-Naphthyl)quinoline compounds: Origins of affinity and new design principles, J Am Chem Soc, 125:7272-7283 (2003).
Paliakov et al., Fujita-ban QSAR analysis and CoMFA study of quinoline antagonists of immunostimulatory CpG-oligodeoxynucleotides, Bioorganic & Medicinal Chemistry, 15:324-332 (2007).
Cassal et al., Characterization of series of 4-aminoquinolines that stimulate caspase-7 mediated cleavage of TDP-43 and inhibit its function, Biochimie, 94:1974-1981 (2012).
Manzel et al., Antagonism of immunostimultory CpG-oligodeoxynucleotides by 4-aminoquinolines and other weak bases: mechanistic studies, The Journal of Pharmacology and Experimental Therapeutics, 291(3):1337-1347 (1999).
Say et al., Synthesis of 2-Phenylquinolin-4-amines substituted with diverse amino and aminoalkyl groups, J. Heterocyclic Chem, 43:1613-1620 (2006).
Siim et al., Hypoxia-selective antitumor agents. 15. Modification of rate of nitroreduction and extent of lysosomal uptake by polysubstitution of 4-(Alkylamino)-5-nitroquinoline bioreductive drugs, J. Med. Chem. 40:1381-1390 (1997).
Peck et al., Mono- and difunctional analogs of some quinolineand acridine nitrogen mustards, The Institute for Cancer Research, 26:3409-3414 (1961).
Preston et al., Further investigations of heterocyclic alkylating agents, The Institute for Cancer Research, 7:471-480 (1964).

QUINOLINES DERIVATIVES AS NOVEL ANTICANCER AGENTS

FIELD OF THE INVENTION

The present invention relates to novel quinoline derivatives, their manufacture, pharmaceutical compositions comprising them and their use as medicaments. The active compounds of the present invention are useful for the treatment of proliferative neoplastic and non-neoplastic diseases.

BACKGROUND OF THE INVENTION

All the publications mentioned throughout this application are fully incorporated herein by reference, including all the references cited therein.

The approach to the discovery of new anticancer drugs has recently evolved from cell-based screening to a more mechanistically based approach leading to many target-based drugs, for example with the development of protein kinase inhibitors. However, target-based screening assays may not be predictive of drug effect within the context of the whole cell, the cellular environment consisting of many additional influences on target function. On another hand, unexpected effects in cellular screening may suggest other targets or interactions. Also, the molecular understanding of cancer growth and metastasis is still developing, with the theory of the cancer stem cells (CSCs). In this context the development of new anticancer agents still represents a unique challenge with unpredictable outcome and a place for new and innovative compounds.

The inventors have generated and screened a new 2-arylquinoline compounds library against different human cancer cell lines (LNCaP, SkBr3, HepG2, HT29, B16F10, SK-MEL-28, U87-MG, BxPC-3, Capan-1, Capan-2, MIA PaCa-2, Panc-1, MOLM-14, U937, KG-1, Kasumi-1, HL60, NB4, SKM-1) and discovered novel anticancer agents, which in one case show an additional activity against human cancer stem cells (CSCs) which are widely incriminated in recurrence and relapse of cancer after therapy. An ALDH assay was used as cancer stem cell functional marker to describe the activity against CSCs (Greve, B. et al. Cytometry A 2012 (81) 284-293, Liu, S. et al. PLoS One 2013 (25) e81050, Ran, D. et al. Exp. Hematol. 2009 (37) 1423-1434, Cheung, A. M. et al. Leukemia 2007 (21) 1423-1430, Pearce, D. J. et al. Stem Cells 2005 (23) 752-760).

Therefore, it is an object of the present invention to provide active agents for preventing or inhibiting cell proliferation in a variety of organisms, and to provide methods for their synthesis.

It is another object of the present invention to provide a pharmaceutical composition comprising a therapeutically effective amount of at least one active agent of the invention, alone or in combination with other active agents, and a pharmaceutically acceptable adjuvant, diluent or carrier.

It is another object of the present invention to provide active agents for use in therapy.

It is another object of the present invention to provide a method for the treatment and/or prevention of a proliferative and/or neoplastic disease.

It is another object of the present invention to provide a method for inhibiting the growth or differentiation of a Cancer Stem Cell (CSC), a tumor initiating cell, a mesenchymal-like cell associated with cancer, a mesenchymal cancerous cell, or a mesenchymal cell.

The above and other objects and advantages of the invention will become apparent as the description proceeds.

SUMMARY OF THE INVENTION

The present invention provides a compound of formula (I)

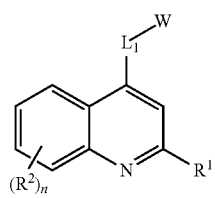

wherein
$R^1$ is selected from optionally substituted aryl, optionally substituted heteroaryl, optionally substituted heteroaromatic 5 to 9-membered ring comprising 1, 2 or 3 heteroatoms independently selected from O, N, and S;
$R^2$ is selected from Cl, F, I, Br, $C_1$-$C_6$ alkyl, $C_1$-$C_6$ alkyl substituted with one or more halogens, $C_1$-$C_6$ alkoxy, hydroxy, nitro or $NR^7R^8$, $NR^7$—(CO)—$R^8$, $NR^7$—(CO)—O—$R^8$, $NR^7$—(CO)—$NR^7R^8$, O—(CO)$R^7$, O—(CO)—O—$R^7$, O—(CO)—$NR^7R^8$, (CO)$R^7$, (CO)—O—$R^7$, (CO)—$NR^7R^8$, $SO_2$—$R^7$, $SO_2NR^7R^8$, $NR^7$—$SO_2$—$R^8$, with $R^7$ and $R^8$ representing independently hydrogen, $C_1$-$C_6$ alkyl, phenyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or benzyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), alkenyl, alkynyl, cycloalkyl, cycloalkenyl, cycloalkynyl aryl and heteroaryl;
$L^1$ is selected from a bond or from optionally substituted $C_1$-$C_{14}$alkyl(-$R^3$), N(—$R^3$), C=O, (CO)—O, (CO)—$NR^7$, and O;
n is 0, 1, 2, 3 or 4;
W is selected from:

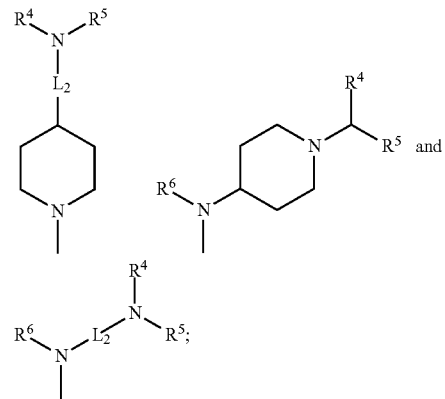

wherein
$L_2$ is selected from a bond or from optionally substituted $C_1$-$C_{14}$alkyl(-$R^3$), N(—$R^3$), C=O, (CO)—O, (CO)—$NR^7$, and O; wherein $R^3$ is selected from H, optionally substituted aryl, optionally substituted heteroaryl, optionally substituted heterocycloalkyl, optionally substituted $C_1$-$C_8$-alkyl, optionally substituted $C_2$-$C_8$-alkenyl, optionally substituted $C_2$-$C_8$-alkynyl, optionally substituted $C_3$-$C_{12}$ cycloalkyl, and optionally substituted $C_3$-$C_{12}$ cycloalkenyl; and wherein $R^7$ is as defined above;

$R^4$ and $R^5$ are independently selected from hydrogen, $C_1$-$C_6$ alkyl or phenyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or benzyl (with the phenyl group optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or $CH_2$—$CH_2$-Phenyl (with the phenyl group optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), (CO)—$R^7$, (CO)—$OR^7$, (CO)—$NR^7R^8$, alkenyl, alkynyl, cycloalkyl, cycloalkenyl, cycloalkynyl, aryl, monocyclic or bicyclic heteroaryl or $R^4$ and $R^5$ are linked to form a heterocyclic group;

$R^6$ is selected from H, $C_1$-$C_6$ alkyl, monocyclic or bicyclic cycloalkyl, alkenyl, alkynyl, aryl and heteroaryl;

wherein the term "optionally substituted" means optionally substituted with one or more substituents independently selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$ with $R^7$ and $R^8$ representing independently hydrogen, $C_1$-$C_6$ alkyl, phenyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or benzyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), alkenyl, alkynyl, cycloalkyl, cycloalkenyl, cycloalkynyl aryl and heteroaryl;

and any pharmaceutically acceptable salt, solvate or prodrug thereof.

In some specific embodiments, the invention provides a compound of formula (I')

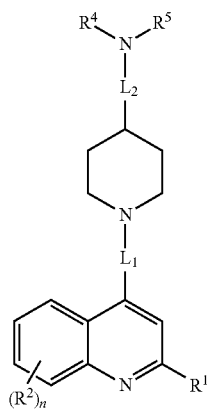

wherein $L_1$, $L_2$, $R^1$, $R^2$, $R^4$, $R^5$ and n are as defined above; and any pharmaceutically acceptable salt, solvate or prodrug thereof.

In some other specific embodiments, the invention provides a compound of formula (I")

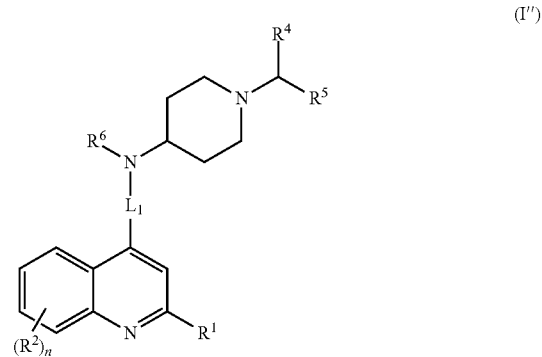

wherein $L_1$, $L_2$, $R^1$, $R^2$, $R^4$, $R^5$, $R^6$, and n are as defined above;

and any pharmaceutically acceptable salt, solvate or prodrug thereof.

In still other specific embodiments, the invention provides a compound of formula (I''')

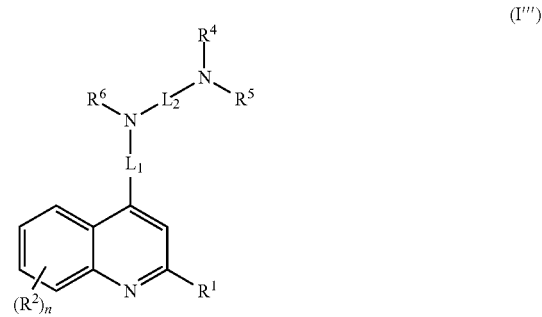

wherein $L_1$, $L_2$, $R^1$, $R^2$, $R^4$, $R^5$, $R^6$ and n are as defined in claim 1;

and any pharmaceutically acceptable salt, solvate or prodrug thereof.

In some specific embodiments, the invention provides a compound selected from:
2-phenyl-4-(4-N,N-diethylamino-piperidin-1-yl)quinoline (I-3);
7-chloro-2-phenyl-4-(4-N,N-diethylamino-piperidin-1-yl)quinoline (II-3);
2-phenyl-4-([1,4']-bipiperidin-1'-yl)quinoline (III-3);
2-phenyl-4-(4-N-tert-butylamino-piperidin-1-yl)quinoline (IV-1);
2-phenyl-4-[(4-morpholin-4-yl)piperidin-1-yl]quinoline (V-1);
2-(2-naphtyl)-4-(4-N,N-diethylamino-piperidin-1-yl)quinoline (VI-5);
2-(4-bromo-phenyl)-7-chloro-4-(4-N,N-diethylamino-piperidin-1-yl)quinoline (VII-4);
2-(4-bromo-phenyl)-4-(4-N,N-diethylamino-piperidin-1-yl)quinoline (VIII-5);
2-(1,1'-biphenyl)-4-yl-4-(4-N,N-diethylamino-piperidin-1-yl)quinoline (IX-1);
2-(4-chloro-phenyl)-4-(4-N,N-diethylamino-piperidin-1-yl)quinoline (X-5);

2-(1,1'-biphenyl)-4-yl-7-chloro-4-(4-N,N-diethylamino-piperidin-1-yl)quinoline (XI-1);
2-(4-chloro-phenyl)-4-(4-N-tert-butylamino-piperidin-1-yl)quinoline (XII-3);
2-(4-methyl-phenyl)-4-(4-N-tert-butylamino-piperidin-1-yl)quinoline (XIII-7);
2-(3,4-dichloro-phenyl)-4-(4-N-tert-butylamino-piperidin-1-yl)quinoline (XIV-7);
2-(4-methoxy-phenyl)-4-(4-N-tert-butylamino-piperidin-1-yl)quinoline (XV-7);
7-Chloro-2-phenyl-4-{1-[4-(N,N-diethylamino)-piperidin-1-yl]-eth-1-yl}quinoline (XVI-3);
7-Chloro-2-phenyl-4-[4-(N,N-diethylamino)-piperidin-1-ylmethyl]quinoline (XVII-5);
4-[4-(N,N-diethylamino)piperidin-1-ylcarbonyl]-2-phenyl-quinoline (XVIII-1);
2-phenyl-4-{1-[4-(N,N-diethylamino)-piperidin-1-yl]-eth-1-yl}quinoline (XIX-2);
2-phenyl-4-[4-(N,N-diethylamino)-piperidin-1-ylmethyl]quinoline (XX-4);
2-phenyl-4-{1-{4-[benzyl(phenethyl)amino]-piperidin-1-yl}-eth-1-yl}quinoline (XXI-3);
2-phenyl-4-{1-[(1,4'-bipiperidin)-1'-yl]-eth-1-yl}quinoline (XXII-3);
2-phenyl-4-{1-[4-(tert-butylamino)-piperidin-1-yl]-eth-1-yl}quinoline (XXIII-1);
2-(2-naphtyl)-4-{1-[4-(N,N-diethylamino)-piperidin-1-yl]-eth-1-yl}quinoline (XXIV-2);
2-phenyl-4-{2-[4-(N,N-diethylamino)-piperidin-1-yl]-propan-2-yl}quinoline trifluoroacetate salt (XXV-6).
7-chloro-2-phenyl-4-[4-(N,N-diethylaminomethyl)-piperidin-1-yl]quinoline (XXVI-3);
2-phenyl-4-[4-(N,N-diethylaminomethyl)-piperidin-1-yl)quinoline (XXVII-1);
7-chloro-2-phenyl-4-[(N-benzylpiperidin-4-yl)-amino]quinoline (XXVIII-1);
7-chloro-2-phenyl-4-[N-methyl-N—(N-benzylpiperidin-4-yl)-amino]quinoline (XXIX-1);
7-chloro-2-phenyl-4-[N-methyl-N—(N-1-phenylethyl-piperidin-4-yl)-amino]quinoline (XXX-2);
2-phenyl-4-[N-methyl-N—(N-1-phenylethyl-piperidin-4-yl)-amino]quinoline (XXXI-1);
N-(1-benzylpiperidin-4-yl)-7-chloro-2-phenylquinoline-4-carboxamide (XXXII-1);
7-chloro-2-phenyl-4-[(N-benzyl-piperidin-4-yl)aminomethyl]quinoline (XXXIII-1);
2-phenyl-4-{1-[(N-benzyl-piperidin-4-yl)amino]-eth-1-yl}quinoline (XXXIV-1);
7-chloro-2-phenyl-4-{1-[(N-benzyl-piperidin-4-yl)amino]-eth-1-yl}quinoline (XXXV-1);
N$^1$,N$^1$-dimethyl-N$^2$-(2-naphthalen-2-yl-quinoline-4-yl)-ethane-1,2-diamine (XXXVI-1);
N$^1$,N$^1$,N$^2$-trimethyl-N$^2$-(2-naphthalen-2-yl-quinoline-4-yl)-ethane-1,2-diamine (XXXVII-1);
N$^1$,N$^1$,N$^2$-trimethyl-N$^2$-(2-phenyl-7-chloro-quinoline-4-ylmethyl)-ethane-1,2-diamine (XXXVIII-1);
N$^1$,N$^1$,N$^3$-trimethyl-N$^3$-[2-(naphthalen-2-yl)-quinoline-4-yl]-propane-1,3-diamine (XXXIX-1);
N1,N$^1$-dimethyl-N$^3$-(2-phenylquinoline-4-yl)propane-1,3-diamine trifluoroacetate salt (XL-2);
N$^1$,N$^1$-dimethyl-N$^3$-(2-phenylquinoline-4-yl)propane-1,3-diamine (XLI-1);
N$^1$,N$^1$-dimethyl-N$^3$-[2-(naphtalen-2-yl)quinoline-4-yl]propane-1,3-diamine (XLII-1);
N-[3-(dimethylamino)propyl]-7-chloro-2-phenylquinoline-4-carboxamide (XLIII-1);
N$^1$,N$^1$-dimethyl-N$^3$-(7-chloro-2-phenylquinoline-4-ylmethyl)-propane-1,3-diamine (XLIV-1);
2-phenyl-4-{1-[4-(morpholino)-piperidinyl]-eth-1-yl}quinoline (XLV-1);

In some other specific embodiments, the invention provides a compound selected from:
2-phenyl-4-(4-N,N-diethylamino-piperidin-1-yl)quinoline hydrochloride salt (I-4);
7-chloro-2-phenyl-4-(4-N,N-diethylamino-piperidin-1-yl)quinoline hydrochloride salt (II-4);
2-phenyl-4-([1,4']-bipiperidin-1'-yl)quinoline hydrochloride salt (III-4);
2-phenyl-4-(4-N-tert-butylamino-piperidin-1-yl)quinoline hydrochloride salt (IV-2);
2-phenyl-4-[(4-morpholin-4-yl)piperidin-1yl]quinoline hydrochloride salt (V-2);
2-(2-naphtyl)-4-(4-N,N-diethylamino-piperidin-1-yl)quinoline hydrochloride salt (VI-6);
2-(4-bromo-phenyl)-7-chloro-4-(4-N,N-diethylamino-piperidin-1-yl)quinoline hydrochloride salt (VII-5);
2-(4-bromo-phenyl)-4-(4-N,N-diethylamino-piperidin-1-yl)quinoline hydrochloride salt (VIII-6);
2-(1,1'-biphenyl)-4-yl-4-(4-N,N-diethylamino-piperidin-1-yl)quinoline hydrochloride salt (IX-2);
2-(4-chloro-phenyl)-4-(4-N,N-diethylamino-piperidin-1-yl)quinoline hydrochloride salt (X-6);
2-(1,1'-biphenyl)-4-yl-7-chloro-4-(4-N,N-diethylamino-piperidin-1-yl)quinoline hydrochloride salt (XI-2);
2-(4-chloro-phenyl)-4-(4-N-tert-butylamino-piperidin-1-yl)quinoline hydrochloride salt (XII-4);
2-(4-methyl-phenyl)-4-(4-N-tert-butylamino-piperidin-1-yl)quinoline hydrochloride salt (XIII-8);
2-(3,4-dichloro-phenyl)-4-(4-N-tert-butylamino-piperidin-1-yl)quinoline hydrochloride salt (XIV-8);
2-(4-methoxy-phenyl)-4-(4-N-tert-butylamino-piperidin-1-yl)quinoline hydrochloride salt (XV-8);
7-Chloro-2-phenyl-4-{1-[4-(N,N-diethylamino)-piperidin-1-yl]-eth-1-yl}quinoline hydrochloride salt (XVI-4);
7-Chloro-2-phenyl-4-[4-(N,N-diethylamino)-piperidin-1-ylmethyl]quinoline hydrochloride salt (XVII-6);
4-[4-(N,N-diethylamino)piperidin-1-ylcarbonyl]-2-phenyl-quinoline hydrochloride salt (XVIII-2);
2-phenyl-4-{1-[4-(N,N-diethylamino)-piperidin-1-yl]-eth-1-yl}quinoline hydrochloride salt (XIX-3);
2-phenyl-4-[4-(N,N-diethylamino)-piperidin-1-ylmethyl]quinoline hydrochloride salt (XX-5);
2-phenyl-4-{1-{4-[benzyl(phenethyl)amino]-piperidin-1-yl}-eth-1-yl}quinoline hydrochloride salt (XXI-4);
2-phenyl-4-{1-[(1,4'-bipiperidin)-1'-yl]-eth-1-yl}quinoline hydrochloride salt (XXII-4);
2-phenyl-4-{1-[4-(tert-butylamino)-piperidin-1-yl]-eth-1-yl}quinoline hydrochloride salt (XXIII-2);
2-(2-naphtyl)-4-{1-[4-(N,N-diethylamino)-piperidin-1-yl]-eth-1-yl}quinoline hydrochloride salt (XXIV-3);
2-phenyl-4-{2-[4-(N,N-diethylamino)-piperidin-1-yl]-propan-2-yl}quinoline trifluoroacetate salt (XXV-6).
7-chloro-2-phenyl-4-[4-(N,N-diethylaminomethyl)-piperidin-1-yl]quinoline hydrochloride salt (XXVI-4);
2-phenyl-4-[4-(N,N-diethylaminomethyl)-piperidin-1-yl)quinoline hydrochloride salt (XXVII-2);
7-chloro-2-phenyl-4-[(N-benzylpiperidin-4-yl)-amino]quinoline hydrochloride salt (XXVIII-2);
7-chloro-2-phenyl-4-[N-methyl-N—(N-benzylpiperidin-4-yl)-amino]quinoline hydrochloride salt (XXIX-2);
7-chloro-2-phenyl-4-[N-methyl-N—(N-1-phenylethyl-piperidin-4-yl)-amino]quinoline hydrochloride salt (XXX-3);
2-phenyl-4-[N-methyl-N—(N-1-phenylethyl-piperidin-4-yl)-amino]quinoline hydrochloride salt (XXXI-2);
N-(1-benzylpiperidin-4-yl)-7-chloro-2-phenylquinoline-4-carboxamide hydrochloride salt (XXXII-2);
7-chloro-2-phenyl-4-[(N-benzyl-piperidin-4-yl)aminomethyl]quinoline hydrochloride salt (XXXIII-2);

2-phenyl-4-{1-[(N-benzyl-piperidin-4-yl)amino]-eth-1-yl}quinoline hydrochloride salt (XXXIV-2);

7-chloro-2-phenyl-4-{1-[(N-benzyl-piperidin-4-yl)amino]-eth-1-yl}quinoline hydrochloride salt (XXXV-2);

$N^1,N^1$-dimethyl-$N^2$-(2-naphthalen-2-yl-quinoline-4-yl)-ethane-1,2-diamine hydrochloride salt (XXXVI-2);

$N^1,N^1,N^2$-trimethyl-$N^2$-(2-naphthalen-2-yl-quinoline-4-yl)-ethane-1,2-diamine hydrochloride salt (XXXVII-2);

$N^1,N^1,N^2$-trimethyl-$N^2$-(2-phenyl-7-chloro-quinoline-4-yl-methyl)-ethane-1,2-diamine hydrochloride salt (XXXVIII-2);

$N^1,N^1,N^3$-trimethyl-$N^3$-[2-(naphthalen-2-yl)-quinoline-4-yl]-propane-1,3-diamine hydrochloride salt (XXXIX-2);

$N^1,N^1$-dimethyl-$N^3$-(2-phenylquinoline-4-yl)propane-1,3-diamine trifluoroacetate salt (XL-2);

$N^1,N^1$-dimethyl-$N^3$-(2-phenylquinoline-4-yl)propane-1,3-diamine hydrochloride salt (XLI-2);

$N^1,N^1$-dimethyl-$N^3$-[2-(naphtalen-2-yl)quinoline-4-yl]propane-1,3-diamine hydrochloride salt (XLII-2);

N-[3-(dimethylamino)propyl]-7-chloro-2-phenylquinoline-4-carboxamide hydrochloride salt (XLIII-2);

$N^1,N^1$-dimethyl-$N^3$-(7-chloro-2-phenylquinoline-4-ylmethyl)-propane-1,3-diamine hydrochloride salt (XLIV-2);

2-phenyl-4-{1-[4-(morpholino)-piperidinyl]-eth-1-yl}quinoline hydrochloride salt (XLV-1);

In a specific embodiment, the invention provides a compound of formula (Ia) (XIX-2):

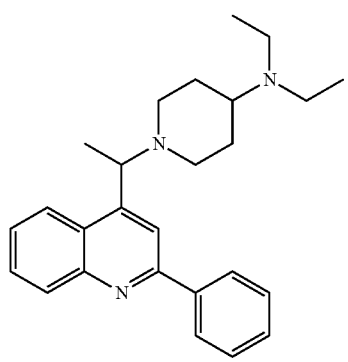

(Ia)

or a pharmaceutically acceptable salt, solvate or prodrug thereof.

In another specific embodiment, the invention provides a compound of formula (Ib) (XLV-1):

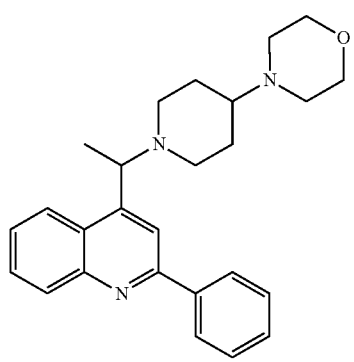

(Ib)

or a pharmaceutically acceptable salt, solvate or prodrug thereof.

In a specific embodiment, the invention provides a compound of formula (Ic) (XII-3):

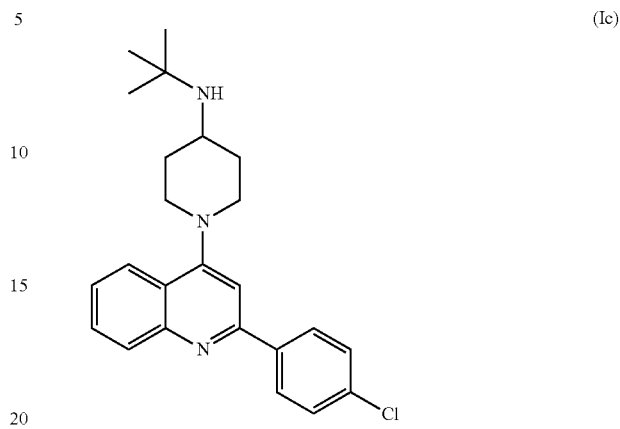

(Ic)

or a pharmaceutically acceptable salt, solvate or prodrug thereof.

In a specific embodiment, the invention provides a compound of formula (Id) (XXIV-2):

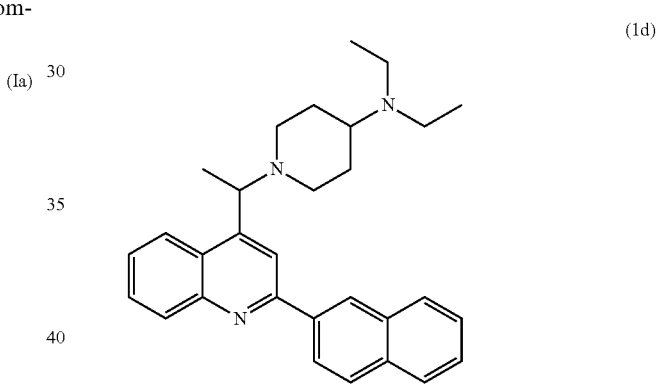

(Id)

or a pharmaceutically acceptable salt, solvate or prodrug thereof.

In another aspect, the invention provides a pharmaceutical composition comprising a therapeutically effective amount of a compound according to the above, or a pharmaceutically acceptable salt, solvate or prodrug thereof, and a pharmaceutically acceptable adjuvant, diluent or carrier.

In some particular embodiments, the pharmaceutical composition of the invention further comprises in combination one or more anti-neoplastic agents.

In some particular embodiments, the pharmaceutical composition according to the above comprises a therapeutically effective amount of the compound of the invention which is formulated or co-formulated in nanoparticles. In some specific embodiments, the nanoparticles comprise a polymeric biodegradable composition. In some particular specific embodiments, the polymer is based on Poly (DL-Lactic-co-glycolic acid) having molecular weight from 7 to 240 kDa; or a copolymer of polylactic acid (PLA and polyglycolic acid (PGA) where the molecular ratio is between 95:5 and 50:50.

In some specific embodiments of the pharmaceutical composition of the invention, the nanoparticles comprise a lisosomal biodegradable composition.

In some specific embodiments of the pharmaceutical composition of the invention, the nanoparticles comprise a biocompatible polymer or copolymer.

In some specific embodiments of the pharmaceutical composition of the invention, the nanoparticles are associated covalently or non-covalently with a polyethylene glycol (PEG).

In some specific embodiments of the pharmaceutical composition of the invention, the nanoparticles have an average size of from about 80 to about 600 nm.

In some specific embodiments of the pharmaceutical composition of the invention, the active compound of the invention is associated with at least one therapeutically active anti-cancer agent.

In some specific embodiments, the pharmaceutical composition of the invention is suitable for oral-, parenteral-, ocular-, transdermal-, nasal-administration, or for inhalation.

In some specific embodiments of the pharmaceutical composition of the invention, the nanoparticles comprise an item selected from PLGA nanoparticles, PLGA-PEG nanoparticles (block type AB, BA, ABA or BAB, where A=PLGA and B=PEG) and targeted nanoparticles.

In some specific embodiments of the pharmaceutical composition of the invention, the nanoparticle is a targeted nanoparticle containing a signaling motif.

In some specific embodiment, the pharmaceutical composition of the invention comprises a combination of a therapeutically effective amount of a compound of the invention and a therapeutically effective amount of one or more anti-neoplastic agents, wherein the components constituting said combination are for simultaneous, separate or sequential use in cancer therapy.

In specific embodiments of the pharmaceutical composition of the invention, the anti-neoplastic agent is selected from the group consisting of everolimus, chloroquine, hydroxychloroquine, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan. IL13-PE38QQR, TNO 1001, IPdR1 KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, the acetate salt of [D-Ser(But)$_6$, Azgly$_{10}$](pyro-Glu-His-Trp-Ser-Tyr-D-Ser(But)-Leu-Arg-Pro-Azgly-NH$_2$ acetate [C$_{59}$H$_{84}$N$_{18}$O$_{14}$—(C$_2$H$_4$O$_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevec, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, 1M862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, nitrogen mustard, methylprednisolone, ibritumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, epoetin alfa and darbepoetin alfa, ipilumumab, vemurafenib, FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, a mTOR inhibitor, an AKT inhibitor, a JAK/STAT inhibitor, a checkpoint-1 or 2 inhibitor, a focal adhesion kinase inhibitor, a Map kinase (mek) inhibitor, a VEGF trap antibody, and mixtures thereof.

In some embodiments, the pharmaceutical composition of the invention is suitable for slow- or sustained-release.

In another aspect, the invention provides a compound for use in therapy, in particular for the treatment and/or prevention of a proliferative and/or neoplastic disease.

In some specific embodiments, the proliferative and/or neoplastic disease is selected from the group consisting of: carcinoma; cancer of the esophagus, head, brain, kidney, liver, lung, nasopharyngeal, neck, ovary, pancreas, prostate, stomach; a leukemia (e.g. acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia); a malignant lymphoma, a malignant melanoma; myeloproliferative diseases; a sarcoma; a tumor of the central nervous system; a germ-line tumor; testicular cancer; thyroid cancer; astrocytoma; colon cancer, melanoma, and a mixed type of neoplasia.

In another aspect, the invention provides a method for the treatment and/or prevention of a proliferative and/or neoplastic disease, comprising the step of administering a therapeutically active amount of a compound of the invention, or a pharmaceutical composition comprising the same, to a human being or animal in need thereof.

In another aspect, the invention provides a method for inhibiting the growth or differentiation of a Cancer Stem Cell (CSC), a tumor initiating cell, a mesenchymal-like cell associated with cancer, a mesenchymal cancerous cell, or a mesenchymal cell comprising the step of administering a therapeutically active amount of a compound of the invention, or a pharmaceutical composition comprising the same, to a human being or an animal in need thereof.

BRIEF DESCRIPTION OF THE DRAWINGS

The above and other characteristics and advantages of the invention will be more readily apparent through the following examples, and with reference to the appended drawings, wherein.

DETAILED DESCRIPTION

Figure 1:
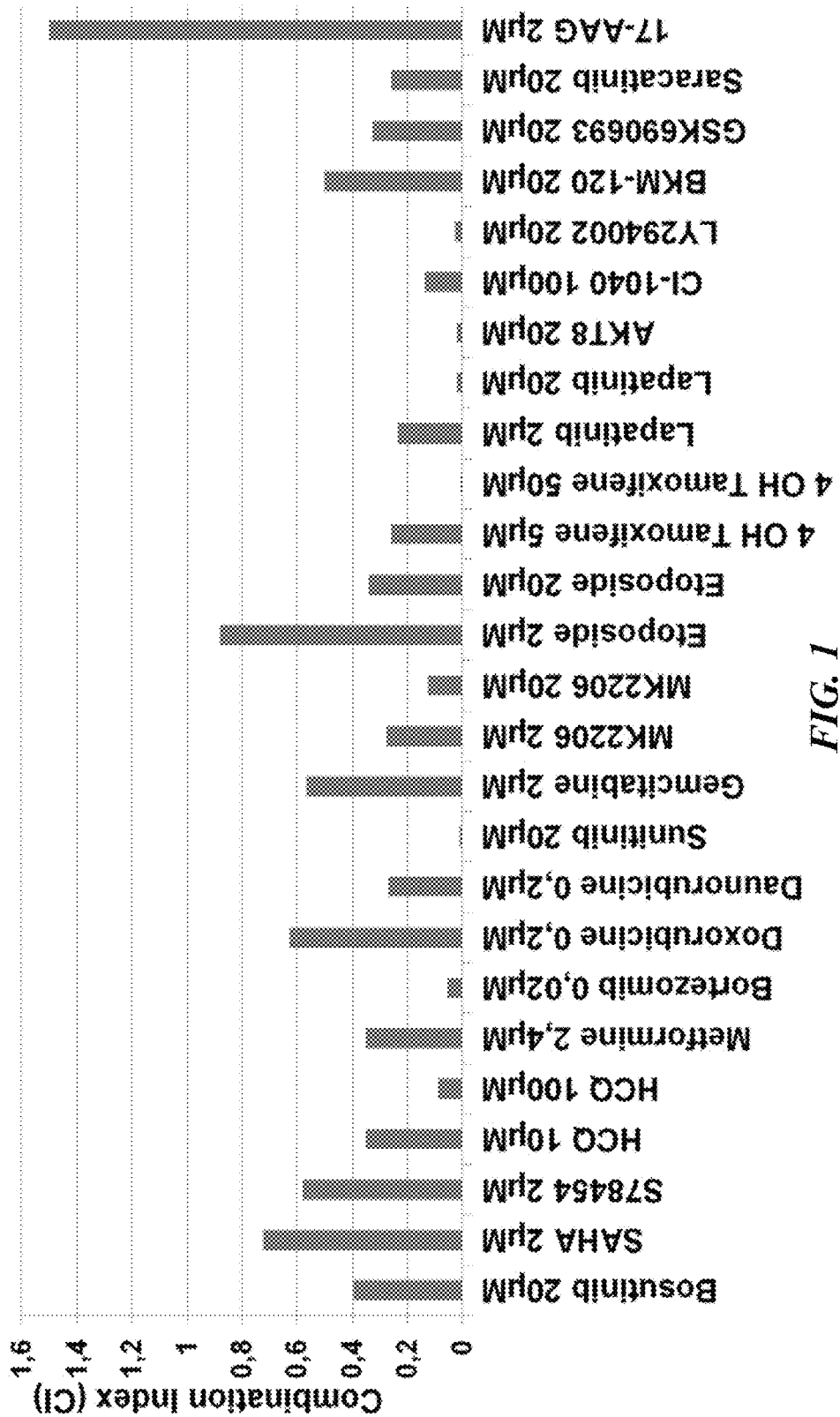
FIG. 1 shows the combination effect [Combination Index (CI) analysis] of compound XIX-3 tested at 18 μM in combination with well described anticancer drugs in HT-29 cell line (Human colon colorectal adenocarcinoma). These preliminary results demonstrated a synergy effect of the combination of compound XIX-3 with standard chemotherapy agents in HT29 cell line (Combination Index: CI<1)

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_6$-alkyl", alone or in combination, signifies a straight-chain or branched-chain alkyl group with 1 to 6 carbon atoms, preferably a straight or branched-chain alkyl group with 1 to 5 carbon atoms and particularly preferred a straight or branched-chain alkyl group with 1 to 3 carbon atoms. Examples of straight-chain and branched $C_1$-$C_6$ alkyl groups are methyl, ethyl, propyl, isopropyl, butyl, isobutyl, tert-butyl, the isomeric pentyls, the isomeric hexyls and the isomeric heptyls, preferably methyl and ethyl and most preferred methyl.

The term "lower alkoxy" or "$C_1$-$C_6$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy and most preferred ethoxy.

The term "lower alkenyl" or "$C_2$-$C_6$-alkenyl" signifies a straight-chain or branched chain hydrocarbon residue comprising an olefinic bond and 2 to 6, preferably 2 to 5, particularly preferred 2 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "cycloalkyl" or "$C_3$-$C_6$-cycloalkyl" denotes a saturated carbocyclic group containing from 3 to 6 carbon atoms, such as cyclopropyl, cyclobutyl, cyclopentyl, cyclohexyl or cycloheptyl. Especially preferred are cyclobutyl and cyclopentyl.

The term "heterocyclic group" signifies a fully saturated or unsaturated, including aromatic or nonaromatic cyclic groups, for example 5 to 6 membered monocyclic groups or 7 to 11 membered bicyclic ring systems which have at least one heteroatom. Each ring of the heterocyclic group may have at least one heteroatom selected from nitrogen atoms, oxygen atoms and/or sulphur atoms. Preferred heterocyclic groups are piperidin and morpholin.

The term "halogen" refers to fluorine, chlorine, bromine and iodine, with fluorine, chlorine and bromine being preferred.

The term "lower halogenalkyl" or "halogen-C1-6-alkyl" refers to lower alkyl groups bearing at least one halogen atom The term "carboxyl" means the group —COOH.

The term "lower carboxylalkyl" or "carboxyl-C1-6-alkyl" refers to lower alkyl groups <<bearing at least one carboxyl group>>.

The term "heteroaryl" in general refers to an aromatic 5- or 11-membered ring which comprises at least one heteroatom and can in addition comprise one or two atoms selected from nitrogen, oxygen and/or sulphur, such as pyridyl, pyrazinyl, pyrimidinyl, pyridazinyl, 2-oxo-1,2-dihydropyridinyl, oxadiazolyl, isoxazolyl, thiadiazolyl, tetrazolyl pyrazolyl, imidazolyl, thiophenyl, furanyl, oxazolyl, isothiazolyl, and thiazolyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolyl, imidazolyl, thiazolyl, thiophenyl, furanyl, oxazolyl, isothiazolyl, pyrazolo[1,5-a]pyridyl, imidazo[1,2-a]pyridyl, quinoxalinyl, benzothiazolyl, benzotriazolyl, indolyl, indazolyl, 3,4-dihydro-1H-isoquinolinyl and 3,4-dihydro-2H-pyrido[3,2-b][1,4]oxazinyl. Preferred heteroaryl groups are pyridyl and pyrazinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, benzenesulfonic acid, N-acetylcysteine and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compounds of formula I can also be present in the form of zwitterions. Particularly preferred pharmaceutically acceptable salts of compounds of formula I are the hydrochloride salts.

The compounds of formula I can also be solvated, e.g. hydrated. The solvation can be effectuated in the course of the manufacturing process or can take place e.g. as a consequence of hygroscopic properties of an initially anhydrous compound of formula I or II (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

As used herein, the terms "subject" or "patient" are used interchangeably. As used herein, the terms "subject" and "subjects" refer to an animal (e.g., birds, reptiles, and mammals), preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the terms "therapies" and "therapy" can refer to any protocol(s), method(s), compositions, formulations, and/or agent(s) that can be used in the prevention, treatment, management, or amelioration of a disease, including viral infections or symptoms associated therewith, cancers, etc. In certain embodiments, the terms "therapies" and "therapy" refer to biological therapy, supportive therapy, and/or other therapies useful in treatment, management, prevention, or amelioration of the different diseases known to one of skill in the art.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, uses thereof in the compositions of the invention are contemplated. Supplementary active compounds can also be incorporated into the compositions.

As used herein, the terms "treat," "treatment," and "treating" refer in the context of administration of a therapy(ies) to a subject to treat a viral infection refer to one, two, three, four, five or more of the following effects resulting from the administration of a therapy or a combination of therapies: (i) the reduction or amelioration of the severity of a disease and/or a symptom associated therewith; (ii) the reduction in the duration of a disease and/or a symptom associated therewith; (iii) the regression of a disease and/or a symptom associated therewith; (iv) the reduction of the titer of a pathogen; (v) the reduction in organ failure associated with a disease; (vi) the reduction in hospitalization of a subject; (vii) the reduction in hospitalization length; (viii) the increase in the survival of a subject; (ix) the elimination of an infection; (x) the inhibition of the progression of an infection and/or a symptom associated therewith; (xi) the prevention of the spread of a virus from a cell, tissue or subject to another cell, tissue or subject; and/or (xii) the enhancement or improvement the therapeutic effect of another therapy.

"Prodrug" means a compound that undergoes conversion to the compound of the invention within a biological system. A prodrug is a chemical derivative inactive or less active than the drug itself. After administration and diffusion in the body, the prodrug derivative undergoes one or more metabolic processes that release the active drug. The conversion of the prodrog to the drug is generally carrier out under the control of enzymatic processes (usually by metabolic means, e.g. hydrolysis, reduction or oxidation) and less frequently by classical chemical reactions during its diffusion in the body. The linkage between the carrier and the drug can be an, but not limited to, ester, amide, carbonate, carbamate, imine, acetal, ether (e.g. glucoro conjugation) oxidizable function and molecular system, reducible function and molecular system, photoactivated function and photoactivated molecular system. For example an ester prodrug of a compound containing a hydroxyl group may be convertible by hydrolysis in vivo to the parent molecule. Suitable esters of the compounds of the invention containing a hydroxyl group, are for example acetates, citrates, lactates, tartrates, malonates, oxalates, salicylates, propionates, succinates, fumarates, maleates, methylene-bis-β-hydroxynaphthoates, g gentisates, isethionates, di-p-toluoyltartrates, methanesulphonates, ethanesulphonates, benzenesulphonates, p-toluenesulphonates, cyclohexylsulphamates and quinates. As another example an ester prodrug of the compound of the invention containing a carboxy group may be convertible by hydrolysis in vivo to the parent molecule (Examples of ester prodrugs are described by F. J. Leinweber, Drug Metab. Res., 18:379, 1987, incorporated herein by reference). Similarly, an acyl prodrug of a compound containing an amino group may be convertible by hydrolysis in vivo to the parent molecule (examples of prodrugs for these and other functional groups, including amines, are described in Prodrugs: Challenges and Rewards (Parts 1 and 2); Ed V. Stella, R. Borchardt et al., Springer, 2007, incorporated herein by reference).

A prodrug carrier system is generally used in order to increase water or lipid solubility, reduce toxicity, increase chemical and biological stability of a sensitive compound, increase the circulating time in the body ($T_{1/2}$) and organ distribution (PK-PD profiling) and site specific targeting.

In a first aspect, the present invention provides a compound of formula (I)

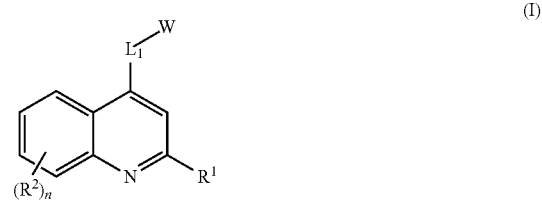

wherein $R^1$ is selected from optionally substituted aryl, optionally substituted heteroaryl, optionally substituted heteroaromatic 5 to 9-membered ring comprising 1, 2 or 3 heteroatoms independently selected from O, N, and S;

$R^2$ is selected from Cl, F, I, Br, $C_1$-$C_6$ alkyl, $C_1$-$C_6$ alkyl substituted with one or more halogens, $C_1$-$C_6$ alkoxy, hydroxy, nitro or $NR^7R^8$, $NR^7$—(CO)—$R^8$, $NR^7$—(CO)—O—$R^8$, $NR^7$—(CO)—$NR^7R^8$, O—(CO)$R^7$, O—(CO)—O—$R^7$, O—(CO)—$NR^7R^8$, (CO)$R^7$, (CO)—O—$R^7$, (CO)—$NR^7R^8$, $SO_2$—$R^7$, $SO_2NR^7R^8$, NR—$SO_2$—$R^8$, with $R^7$ and $R^8$ representing independently hydrogen, $C_1$-$C_6$ alkyl, phenyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or benzyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), alkenyl, alkynyl, cycloalkyl, cycloalkenyl, cycloalkynyl aryl and heteroaryl;

$L^1$ is selected from a bond or from optionally substituted $C_1$-$C_{14}$alkyl(-$R^3$), N(—$R^3$), C=O, (CO)—O, (CO)—$NR^7$, and O;

n is 0, 1, 2, 3 or 4;

W is selected from:

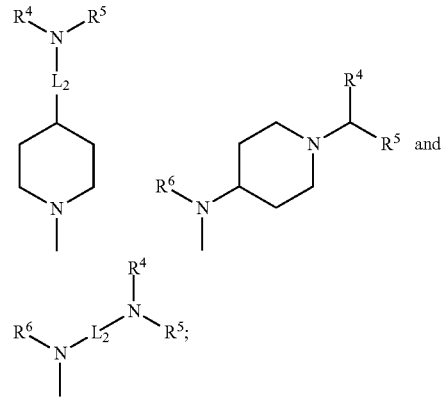

wherein $L_2$ is selected from a bond or from optionally substituted $C_1$-$C_{14}$alkyl(-$R^3$), N(—$R^3$), C=O, (CO)—O, (CO)—$NR^7$, and O; wherein $R^3$ is selected from H, optionally substituted aryl, optionally substituted heteroaryl, optionally substituted heterocycloalkyl, optionally substituted $C_1$-$C_8$-alkyl, optionally substituted $C_2$-$C_8$-alkenyl, optionally substituted $C_2$-$C_8$-alkynyl, optionally substituted $C_3$-$C_{12}$ cycloalkyl, and optionally substituted $C_3$-$C_{12}$ cycloalkenyl; and wherein $R^7$ is as defined above;

$R^4$ and $R^5$ are independently selected from hydrogen, $C_1$-$C_6$ alkyl or phenyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or benzyl (with the phenyl group optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or $CH_2$—$CH_2$-Phenyl (with the phenyl group optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), (CO)—$R^7$, (CO)—$OR^7$, (CO)—$NR^7R^8$, alkenyl, alkynyl, cycloalkyl, cycloalkenyl, cycloalkynyl, aryl, monocyclic or bicyclic heteroaryl or $R^4$ and $R^5$ are linked to form a heterocyclic group;

$R^6$ is selected from H, $C_1$-$C_6$ alkyl, monocyclic or bicyclic cycloalkyl, alkenyl, alkynyl, aryl and heteroaryl;

wherein the term "optionally substituted" means optionally substituted with one or more substituents independently selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$ with $R^7$ and $R^8$ representing independently hydrogen, $C_1$-$C_6$ alkyl, phenyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$) or benzyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), alkenyl, alkynyl, cycloalkyl, cycloalkenyl, cycloalkynyl aryl and heteroaryl;

and any pharmaceutically acceptable salt, solvate or prodrug thereof.

A specific embodiment of the compounds of the invention encompasses compounds having a formula (I')

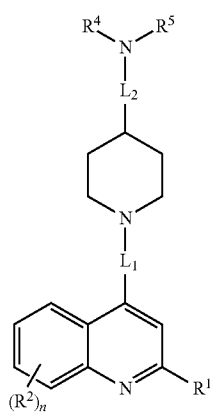

wherein $L_1$, $L_2$, $R^1$, $R^2$, $R^4$ and $R^5$ are as defined above, as well as any pharmaceutically acceptable salt, solvate or prodrug thereof.

A further specific embodiment of the compounds of the invention encompasses compounds having a formula (I")

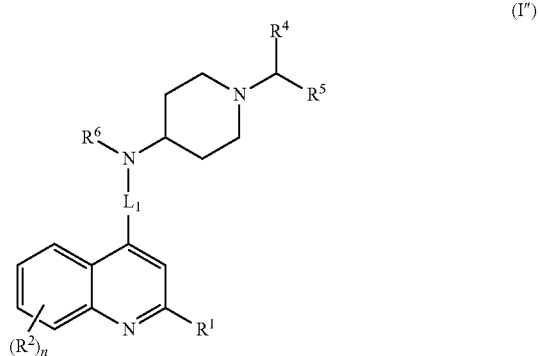

wherein $L_1$, $L_2$, $R^1$, $R^2$, $R^4$, $R^5$, and $R^6$ are as defined above, as well as any pharmaceutically acceptable salt, solvate or prodrug thereof.

A still further specific embodiment of the compounds of the invention encompasses compounds having a formula (I''')

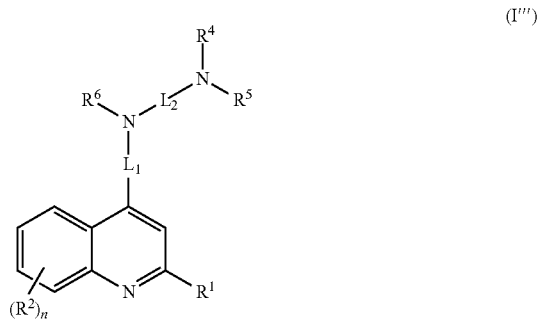

wherein $L_1$, $L_2$, $R^1$, $R^2$, $R^4$, $R^5$ and $R^6$ are as defined above, as well as any pharmaceutically acceptable salt, solvate or prodrug thereof.

Some preferred compounds according to the invention are as follows:

2-phenyl-4-(4-N,N-diethylamino-piperidin-1-yl)quinoline (I-3);
7-chloro-2-phenyl-4-(4-N,N-diethylamino-piperidin-1-yl)quinoline (II-3);
2-phenyl-4-([1,4']-bipiperidin-1'-yl)quinoline (III-3);
2-phenyl-4-(4-N-tert-butylamino-piperidin-1-yl)quinoline (IV-1);
2-phenyl-4-[(4-morpholin-4-yl)piperidin-1yl]quinoline (V-1);
2-(2-naphtyl)-4-(4-N,N-diethylamino-piperidin-1-yl)quinoline (VI-5);
2-(4-bromo-phenyl)-7-chloro-4-(4-N,N-diethylamino-piperidin-1-yl)quinoline (VII-4);
2-(4-bromo-phenyl)-4-(4-N,N-diethylamino-piperidin-1-yl)quinoline (VIII-5);
2-(1,1'-biphenyl)-4-yl-4-(4-N,N-diethylamino-piperidin-1-yl)quinoline (IX-1);
2-(4-chloro-phenyl)-4-(4-N,N-diethylamino-piperidin-1-yl)quinoline (X-5);
2-(1,1'-biphenyl)-4-yl-7-chloro-4-(4-N,N-diethylamino-piperidin-1-yl)quinoline (XI-1);

2-(4-chloro-phenyl)-4-(4-N-tert-butylamino-piperidin-1-yl)quinoline (XII-3);
2-(4-methyl-phenyl)-4-(4-N-tert-butylamino-piperidin-1-yl)quinoline (XIII-7);
2-(3,4-dichloro-phenyl)-4-(4-N-tert-butylamino-piperidin-1-yl)quinoline (XIV-7);
2-(4-methoxy-phenyl)-4-(4-N-tert-butylamino-piperidin-1-yl)quinoline (XV-7);
7-Chloro-2-phenyl-4-{1-[4-(N,N-diethylamino)-piperidin-1-yl]-eth-1-yl}quinoline (XVI-3);
7-Chloro-2-phenyl-4-[4-(N,N-diethylamino)-piperidin-1-ylmethyl]quinoline (XVII-5);
4-[4-(N,N-diethylamino)piperidin-1-ylcarbonyl]-2-phenyl-quinoline (XVIII-1);
2-phenyl-4-{1-[4-(N,N-diethylamino)-piperidin-1-yl]-eth-1-yl}quinoline (XIX-2);
2-phenyl-4-[4-(N,N-diethylamino)-piperidin-1-ylmethyl]quinoline (XX-4);
2-phenyl-4-{1-{4-[benzyl(phenethyl)amino]-piperidin-1-yl}-eth-1-yl}quinoline (XXI-3);
2-phenyl-4-{1-[(1,4'-bipiperidin)-1'-yl]-eth-1-yl}quinoline (XXII-3);
2-phenyl-4-{1-[4-(tert-butylamino)-piperidin-1-yl]-eth-1-yl}quinoline (XXIII-1);
2-(2-naphtyl)-4-{1-[4-(N,N-diethylamino)-piperidin-1-yl]-eth-1-yl}quinoline (XXIV-2);
2-phenyl-4-{2-[4-(N,N-diethylamino)-piperidin-1-yl]-propan-2-yl}quinoline trifluoroacetate salt (XXV-6).
7-chloro-2-phenyl-4-[4-(N,N-diethylaminomethyl)-piperidin-1-yl]quinoline (XXVI-3);
2-phenyl-4-[4-(N,N-diethylaminomethyl)-piperidin-1-yl)quinoline (XXVII-1);
7-chloro-2-phenyl-4-[(N-benzylpiperidin-4-yl)-amino]quinoline (XXVIII-1);
7-chloro-2-phenyl-4-[N-methyl-N—(N-benzylpiperidin-4-yl)-amino]quinoline (XXIX-1);
7-chloro-2-phenyl-4-[N-methyl-N—(N-1-phenylethyl-piperidin-4-yl)-amino]quinoline (XXX-2);
2-phenyl-4-[N-methyl-N—(N-1-phenylethyl-piperidin-4-yl)-amino]quinoline (XXXI-1);
N-(1-benzylpiperidin-4-yl)-7-chloro-2-phenylquinoline-4-carboxamide (XXXII-1);
7-chloro-2-phenyl-4-[(N-benzyl-piperidin-4-yl)aminomethyl]quinoline (XXXIII-1);
2-phenyl-4-{1-[(N-benzyl-piperidin-4-yl)amino]-eth-1-yl}quinoline (XXXIV-1);
7-chloro-2-phenyl-4-{1-[(N-benzyl-piperidin-4-yl)amino]-eth-1-yl}quinoline (XXXV-1);
$N^1,N^1$-dimethyl-$N^2$-(2-naphthalen-2-yl-quinoline-4-yl)-ethane-1,2-diamine (XXXVI-1);
$N^1,N^1,N^2$-trimethyl-$N^2$-(2-naphthalen-2-yl-quinoline-4-yl)-ethane-1,2-diamine (XXXVII-1);
$N^1,N^1,N^2$-trimethyl-$N^2$-(2-phenyl-7-chloro-quinoline-4-ylmethyl)-ethane-1,2-diamine (XXXVIII-1);
$N^1,N^1,N^3$-trimethyl-$N^3$-[2-(naphthalen-2-yl)-quinoline-4-yl]-propane-1,3-diamine (XXXIX-1);
N1,$N^1$-dimethyl-$N^3$-(2-phenylquinoline-4-yl)propane-1,3-diamine trifluoroacetate salt (XL-2);
$N^1,N^1$-dimethyl-$N^3$-(2-phenylquinoline-4-yl)propane-1,3-diamine (XLI-1);
$N^1,N^1$-dimethyl-$N^3$-[2-(naphtalen-2-yl)quinoline-4-yl]propane-1,3-diamine (XLII-1);
N-[3-(dimethylamino)propyl]-7-chloro-2-phenylquinoline-4-carboxamide (XLIII-1);
$N^1,N^1$-dimethyl-$N^3$-(7-chloro-2-phenylquinoline-4-ylmethyl)-propane-1,3-diamine (XLIV-1);
2-phenyl-4-{1-[4-(morpholino)-piperidinyl]-eth-1-yl}quinoline (XLV-1);

Some preferred salts of the compound of the invention are as follows:

2-phenyl-4-(4-N,N-diethylamino-piperidin-1-yl)quinoline hydrochloride salt (I-4);
7-chloro-2-phenyl-4-(4-N,N-diethylamino-piperidin-1-yl)quinoline hydrochloride salt (II-4);
2-phenyl-4-([1,4']-bipiperidin-1'-yl)quinoline hydrochloride salt (III-4);
2-phenyl-4-(4-N-tert-butylamino-piperidin-1-yl)quinoline hydrochloride salt (IV-2);
2-phenyl-4-[(4-morpholin-4-yl)piperidin-1yl]quinoline hydrochloride salt (V-2);
2-(2-naphtyl)-4-(4-N,N-diethylamino-piperidin-1-yl)quinoline hydrochloride salt (VI-6);
2-(4-bromo-phenyl)-7-chloro-4-(4-N,N-diethylamino-piperidin-1-yl)quinoline hydrochloride salt (VII-5);
2-(4-bromo-phenyl)-4-(4-N,N-diethylamino-piperidin-1-yl)quinoline hydrochloride salt (VIII-6);
2-(1,1'-biphenyl)-4-yl-4-(4-N,N-diethylamino-piperidin-1-yl)quinoline hydrochloride salt (IX-2);
2-(4-chloro-phenyl)-4-(4-N,N-diethylamino-piperidin-1-yl)quinoline hydrochloride salt (X-6);
2-(1,1'-biphenyl)-4-yl-7-chloro-4-(4-N,N-diethylamino-piperidin-1-yl)quinoline hydrochloride salt (XI-2);
2-(4-chloro-phenyl)-4-(4-N-tert-butylamino-piperidin-1-yl)quinoline hydrochloride salt (XII-4);
2-(4-methyl-phenyl)-4-(4-N-tert-butylamino-piperidin-1-yl)quinoline hydrochloride salt (XIII-8);
2-(3,4-dichloro-phenyl)-4-(4-N-tert-butylamino-piperidin-1-yl)quinoline hydrochloride salt (XIV-8);
2-(4-methoxy-phenyl)-4-(4-N-tert-butylamino-piperidin-1-yl)quinoline hydrochloride salt (XV-8);
7-Chloro-2-phenyl-4-{1-[4-(N,N-diethylamino)-piperidin-1-yl]-eth-1-yl}quinoline hydrochloride salt (XVI-4);
7-Chloro-2-phenyl-4-[4-(N,N-diethylamino)-piperidin-1-ylmethyl]quinoline hydrochloride salt (XVII-6);
4-[4-(N,N-diethylamino)piperidin-1-ylcarbonyl]-2-phenyl-quinoline hydrochloride salt (XVIII-2);
2-phenyl-4-{1-[4-(N,N-diethylamino)-piperidin-1-yl]-eth-1-yl}quinoline hydrochloride salt (XIX-3);
2-phenyl-4-[4-(N,N-diethylamino)-piperidin-1-ylmethyl]quinoline hydrochloride salt (XX-5);
2-phenyl-4-{1-{4-[benzyl(phenethyl)amino]-piperidin-1-yl}-eth-1-yl}quinoline hydrochloride salt (XXI-4);
2-phenyl-4-{1-[(1,4'-bipiperidin)-1'-yl]-eth-1-yl}quinoline hydrochloride salt (XXII-4);
2-phenyl-4-{1-[4-(tert-butylamino)-piperidin-1-yl]-eth-1-yl}quinoline hydrochloride salt (XXIII-2);
2-(2-naphtyl)-4-{1-[4-(N,N-diethylamino)-piperidin-1-yl]-eth-1-yl}quinoline hydrochloride salt (XXIV-3);
2-phenyl-4-{2-[4-(N,N-diethylamino)-piperidin-1-yl]-propan-2-yl}quinoline trifluoroacetate salt (XXV-6).
7-chloro-2-phenyl-4-[4-(N,N-diethylaminomethyl)-piperidin-1-yl]quinoline hydrochloride salt (XXVI-4);
2-phenyl-4-[4-(N,N-diethylaminomethyl)-piperidin-1-yl)quinoline hydrochloride salt (XXVII-2);
7-chloro-2-phenyl-4-[(N-benzylpiperidin-4-yl)-amino]quinoline hydrochloride salt (XXVIII-2);
7-chloro-2-phenyl-4-[N-methyl-N—(N-benzylpiperidin-4-yl)-amino]quinoline hydrochloride salt (XXIX-2);
7-chloro-2-phenyl-4-[N-methyl-N—(N-1-phenylethyl-piperidin-4-yl)-amino]quinoline hydrochloride salt (XXX-3);
2-phenyl-4-[N-methyl-N—(N-1-phenylethyl-piperidin-4-yl)-amino]quinoline hydrochloride salt (XXXI-2);

N-(1-benzylpiperidin-4-yl)-7-chloro-2-phenylquinoline-4-carboxamide hydrochloride salt (XXXII-2);
7-chloro-2-phenyl-4-[(N-benzyl-piperidin-4-yl)aminomethyl]quinoline hydrochloride salt (XXXIII-2);
2-phenyl-4-{1-[(N-benzyl-piperidin-4-yl)amino]-eth-1-yl}quinoline hydrochloride salt (XXXIV-2);
7-chloro-2-phenyl-4-{1-[(N-benzyl-piperidin-4-yl)amino]-eth-1-yl}quinoline hydrochloride salt (XXXV-2);
$N^1,N^1$-dimethyl-$N^2$-(2-naphthalen-2-yl-quinoline-4-yl)-ethane-1,2-diamine hydrochloride salt (XXXVI-2);
$N^1,N^1,N^2$-trimethyl-$N^2$-(2-naphthalen-2-yl-quinoline-4-yl)-ethane-1,2-diamine hydrochloride salt (XXXVII-2);
$N^1,N^1,N^2$-trimethyl-$N^2$-(2-phenyl-7-chloro-quinoline-4-ylmethyl)-ethane-1,2-diamine hydrochloride salt (XXXVIII-2);
$N^1,N^1,N^3$-trimethyl-$N^3$-[2-(naphthalen-2-yl)-quinoline-4-yl]-propane-1,3-diamine hydrochloride salt (XXXIX-2);
$N^1,N^1$-dimethyl-$N^3$-(2-phenylquinoline-4-yl)propane-1,3-diamine trifluoroacetate salt (XL-2);
$N^1,N^1$-dimethyl-$N^3$-(2-phenylquinoline-4-yl)propane-1,3-diamine hydrochloride salt (XLI-2);
$N^1,N^1$-dimethyl-$N^3$-[2-(naphtalen-2-yl)quinoline-4-yl]propane-1,3-diamine hydrochloride salt (XLII-2);
N-[3-(dimethylamino)propyl]-7-chloro-2-phenylquinoline-4-carboxamide hydrochloride salt (XLIII-2);
$N^1,N^1$-dimethyl-$N^3$-(7-chloro-2-phenylquinoline-4-ylmethyl)-propane-1,3-diamine hydrochloride salt (XLIV-2);
2-phenyl-4-{1-[4-(morpholino)-piperidinyl]-eth-1-yl}quinoline hydrochloride salt (XLV-1);

In a specific embodiment, the compound of the invention is a compound of formula (Ia) (XIX-2):

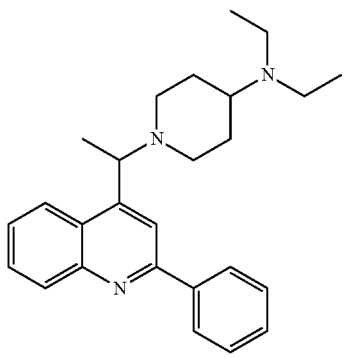

(Ia)

or a pharmaceutically acceptable salt, solvate or prodrug thereof.

In another specific embodiment, the compound of the invention is a compound of formula (Ib) (XLV-1):

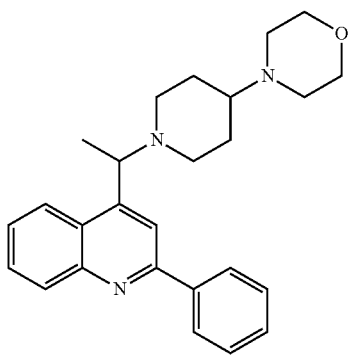

(Ib)

or a pharmaceutically acceptable salt, solvate or prodrug thereof.

In another specific embodiment, the compound of the invention is a compound of formula (Ic) (XII-3):

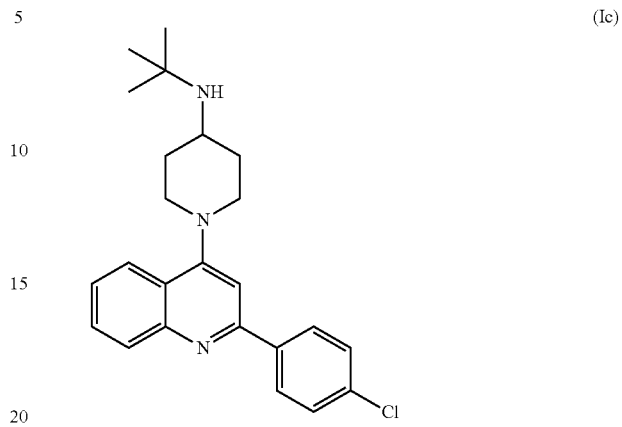

(Ic)

or a pharmaceutically acceptable salt, solvate or prodrug thereof.

In another specific embodiment, the compound of the invention is a compound of formula (Id) (XXIV-2):

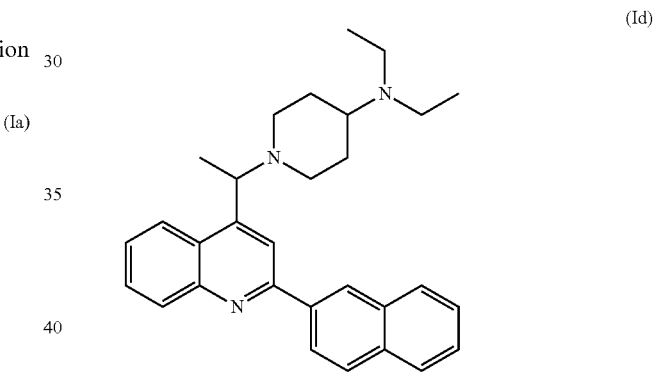

(Id)

or a pharmaceutically acceptable salt, solvate or prodrug thereof.

In a further aspect, the invention provides a pharmaceutical composition comprising a therapeutically effective amount of a compound as described above, or a pharmaceutically acceptable salt, solvate or prodrug thereof, and a pharmaceutically acceptable adjuvant, diluent or carrier. The pharmaceutical composition of the invention may further comprise one or more anti-viral agents or one or more anti-neoplastic agents.

In a particular embodiment of the pharmaceutical composition of the invention, a therapeutically effective amount of the compound as described above is formulated or co-formulated in nanoparticles. Preferred nanoparticles are selected from liposomes and PLGA, PLGA-PEG nanoparticles (block type AB, BA, ABA or BAB, where A=PLGA and B=PEG), targeted nanoparticles (using for example RGD sequence or other signaling or receptor motifs), polymeric nanoparticles and nanoassembling systems, lipid nanoparticles. See for examples: Danhier F. et al. J. Control. Release 2012 (161) 505-522, Dinarvand R. et al. Int. J. Nanomedicine 2011 (6) 877-895, Danhier F. et al. Mol Pharm. 2012 (9) 2961-2973, Mu L. et al. J. Control Release 2003 (86) 33-48, Danhier F. et al. J. Control Release 2010

(148) 135-146. Danhier F. et al. J. Control. Release 2009 (133) 11-17, Sah H. et al. Int. J. Nanomedicine 2013 (8) 747-765, Pan J. et al. Biomaterials 2008 (29) 2663-2672. For example, known products in PLGA formulation: Lupron Depot®, Sandostatin LAR Depot®, Zoladex®, Vivitrol®, Risperdal Consta®, OsteoScaf®, Arestin®, and Atridox®; nanoparticules: Abraxane®; nanoparticule from biocompatible polymer: Livatag®, and liposomes formulation: Myocet®, Daunoxome®, Caelys®/Doxil®.

According to another embodiment the pharmaceutical composition of the invention comprises nanoparticles which are made from polymeric biodegradable composition. Said polymer might be based on Poly (DL-Lactic-co-glycolic acid) having molecular weight from 7 to 240 kDa; or a copolymer of polylactic acid (PLA and polyglycolic acid (PGA) where the molecular ratio is between 95:5 and 50:50.

In a specific embodiment of the invention, the nanoparticles are made from lisosomal biodegradable composition. Optionally, the nanoparticles are associated with the non-active agent polyethylene glycols (PEG). In yet another embodiment, said nanoparticles have an average size of from about 40 to about 600 nm.

In a further embodiment, the pharmaceutical composition of the invention comprises a combination of a therapeutically effective amount of a compound as described above and a therapeutically effective amount of one or more other active agents selected anti-neoplastic agents. The products which constitute said combination may be administered simultaneously, separately or sequentially either in a cancer therapy.

Anti-neoplastic agents included in the compositions of the invention are preferably selected from: everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, TNO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, the acetate salt of [D-Ser(But)6, Azgly10](pyro-Glu-His-Trp-Ser-Tyr-D-Ser(But)-Leu-Arg-Pro-Azgly-NH$_2$ acetate [$C_{59}H_{84}N_{18}O_{14}$—($C_2H_4O_2$)x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, 1M862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, erythropoietin, epoetin alfa and darbepoetin alfa, ipilumumab, vemurafenib, FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trap antibody and mixtures thereof.

The pharmaceutical compositions of the invention are particularly suitable for the treatment and/or prevention and to prevent relapse of cancers and tumors.

Examples of cancers suitable for treatment according to the present invention are: carcinoma, cancer of the esophagus, head, kidney, liver, lung, nasopharyngeal, neck, ovary, pancreas, prostate, and stomach; a leukemia (e.g. acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia), a malignant lymphoma, a malignant melanoma; myeloproliferative diseases; a sarcoma, a tumor of the central nervous system, a germ-line tumor, lung cancer, ovarian cancer, testicular cancer, thyroid cancer, astrocytoma, esophageal cancer, pancreatic cancer, stomach cancer, liver cancer, colon cancer, melanoma, a mixed type of neoplasia.

In a further aspect, the present invention provides a compound as defined above for use as a therapeutically active substance for the treatment and/or prevention and/or relapse prevention of cancer.

In a further aspect, the present invention provides a compound as defined above for use as a therapeutically active substance for inhibiting, arresting or killing cancer stem cells (CSC) like.

In a further aspect, the present invention provides a pharmaceutical composition comprising the compound of the invention which is associated with at least one therapeutically anti-cancer agent.

In a specific embodiment, the pharmaceutical composition of the invention is suitable for oral-, parenteral-, ocular-, transdermal- or nasal-administration, or for inhalation. Optionally, the pharmaceutical composition of the invention is suitable for slow- or sustained-release.

In still a further aspect, the invention provides a method for the treatment and/or prevention of cancers, comprising the step of administering a therapeutically active amount of a compound or a pharmaceutical composition as described above, to a human being or animal in need thereof.

The following examples, which further describe the invention, are offered by way of illustration and are not intended to limit the invention in any manner.

General Procedures for Examples 1 to 44

Reagents and solvents were obtained from commercial suppliers and were used without further purification. Methylene chloride was dried and distilled over $CaCl_2$ and stored over molecular sieves 4 Å under argon. Tetrahydrofuran was dried over sodium/benzophenone ketyl under argon and distilled prior to use. Flash chromatography purifications were performed on Merck silica gel (40-63 μm) as the stationary phase. Analytical High Performance Liquid Chromatography-mass analysis (HPLC-MS):

Conditions A: Column Acquity UPLC BEH C18 (2.1×50 mm) 1.7 μm, mobile phase: A $H_2O$+0.025% TFA, B: MeCN+0.025% TFA. Eluting conditions comprised a linear gradient (minute/% B): 0/10% B, 0.5/10% B, 3/90% B, 5/90% B, 5.1/10% B. Flow rate 0.4 ml/min.

Conditions B: Column macherey-Nagel EC 150/4.6 Nucleosil 100-5 C18 (4.6×150 mm) 5 μm, mobile phase: A $H_2O$+0.1% $HCO_2H$, B: MeOH+0.1% $HCO_2H$. Eluting conditions comprised a linear gradient (minute/% B): 0/20% B, 2/20% B, 10/100% B, 15/100% B, 15.5/20% B. Flow rate 0.8 ml/min.

Conditions C: Column Agilent Zorbax Eclipse Plus C18 (2.1×50 mm) 1.8 μm, mobile phase: A $H_2O$+0.1% $HCO_2H$, B: MeCN+0.1% $HCO_2H$. Eluting conditions comprised a linear gradient (minute/% B): 0/10% B, 0.5/10% B, 3/90% B, 4.5/90% B, 4.51/10% B, 6/10% B. Flow rate 0.4 ml/min.

Conditions D: Column THERMO Hypersil Hyperprep RP C18 (150×4.6 mm) 8 μm, mobile phase: A $H_2O$+0.05% TFA, B: MeCN+0.05% TFA. Eluting conditions comprised a linear gradient (minute/% B): 0/20% B, 8/100% B, 13/100% B. Flow rate 1 ml/min.

Conditions E: Column THERMO Aquasil RP C18 (150× 4.6 mm) 5 μm, mobile phase: A $H_2O$+0.05% TFA, B: MeCN+0.05% TFA. Eluting conditions comprised a linear gradient (minute/% B): 0/0% B, 7/10% B, 19/100% B, 22/100% B. Flow rate 1 ml/min.

Conditions F: Column THERMO BetaBasic RP C4 (150× 4.6 mm) 5 μm, mobile phase: A $H_2O$+0.05% TFA, B: MeCN+0.05% TFA. Eluting conditions comprised a linear gradient (minute/% B): 0/20% B, 8/100% B, 8.10/100% B, 13/100% B. Flow rate 1 ml/min.

Conditions G: Column Waters Acquity BEH RP C18 (50×2.1 mm) 1.7 μm-T=40° C., mobile phase: A $H_2O$+0.1% $HCO_2H$, B: MeCN+0.1% $HCO_2H$. Eluting conditions comprised a linear gradient (minute/% B): 0/5% B, 4/98% B. Flow rate 0.4 ml/min.

EXAMPLE 1

Preparation of 2-phenyl-4-(4-N,N-diethylamino-piperidin-1-yl)quinoline hydrochloride salt (I-4)

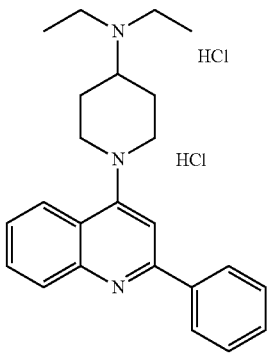 [SMILES: CCN(CC)C1CCN(c2cc(-c3ccccc3)nc3ccccc23)CC1 ; Cl ; Cl]

I-1/ 2-phenyl-4-(4-N-Boc-amino-piperidin-1-yl)quinoline

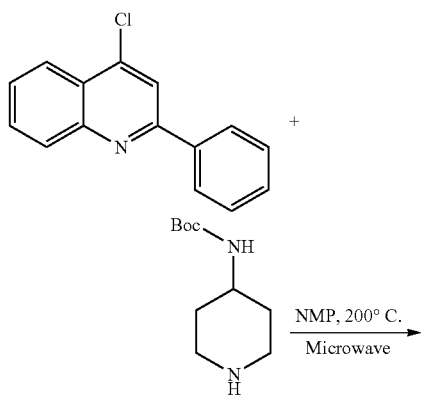

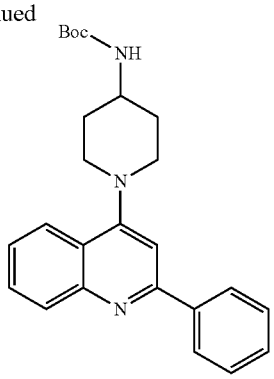

A solution of 0.5 g (2.086 mmol) of 4-chloro-2-phenylquinoline and 2.089 g (10.43 mmol) of 4-(N-Boc-amino)piperidine, in 9 ml of dry N-Methyl-2-pyrrolidone (NMP) was heated for 30 min at 200° C. in a microwave oven. The mixture was then treated with a 1N KOH aqueous solution and extracted with ethyl acetate. The organic layer was washed with water, dried over MgSO$_4$ and concentrated on a rotary evaporator. The residue was purified by silica gel column chromatography (CH$_2$Cl$_2$/Ethyl acetate 95:5) to give 0.286 g (yield 34%) of white powder corresponding to 2-phenyl-4-(4-N-Boc-amino-piperidin-1-yl)quinoline.

HPLC-MS: conditions D: t$_r$=6.56 min, (ES+) C$_{25}$H$_{29}$N$_3$O$_2$ requires 403; found 404 [M+H].

$^1$H NMR (300 MHz, CDCl$_3$).

I-2/ 2-phenyl-4-(4-amino-piperidin-1-yl)quinoline dihydrochloride

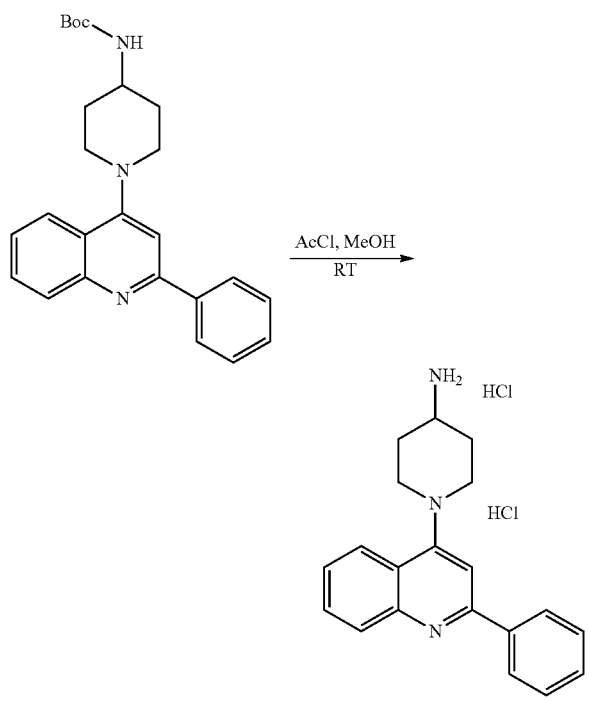

To a solution of 0.28 g (0.693 mmol) of 2-phenyl-4-(4-N-Boc-amino-piperidin-1-yl)quinoline in 5.6 ml of dry methanol was added 240 µl of acetyl chloride (3.47 mmol, 5 eq.) under nitrogen atmosphere. The mixture was stirred for 4 h30 at room temperature and then concentrated on a rotary evaporator to give 290 mg (quantitative yield) of yellow solid corresponding to 2-phenyl-4-(4-amino-piperidin-1-yl)quinoline dihydrochloride.

HPLC: conditions D: t$_r$=3.49 min, (ES+) C$_{20}$H$_{21}$N$_3$ requires 303; found 304 [M+H].

$^1$H NMR (300 MHz, DMSO-d$_6$).

I-3/ 2-phenyl-4-(4-N,N-diethylamino-piperidin-1-yl)quinoline (I-3)

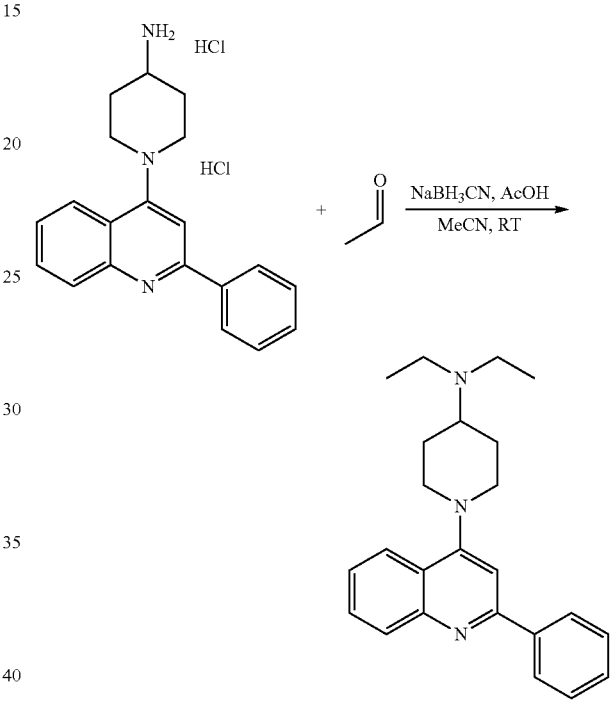

A solution of 0.28 g (0.824 mmol) of 2-phenyl-4-(4-amino-piperidin-1-yl)quinoline dihydrochloride in dichloromethane was stirred with a 1N NaOH aqueous solution. Aqueous layer was then extracted with dichloromethane, dried over MgSO$_4$ filtered and concentrated on a rotary evaporator. The residue was taken up in dry acetonitrile (2 ml) and 465 µl (8.238 mmol) of acetaldehyde and 155 mg (2.471 mmol) of sodium cyanoborohydride were successively added to the solution under nitrogen atmosphere. After stirring for 30 min at room temperature acetic acid was added and the resulting mixture was stirred for 20 h at room temperature. The mixture was concentrated and the residue was added to a 1N NaOH aqueous solution. After extraction with dichloromethane, the organic layer was dried over MgSO$_4$, filtered and evaporated to dryness to give 313 mg of yellow oil. The residue was purified by silica gel column chromatography (dichloromethane/ethyl acetate 8:2 to give 46 mg of a white solid by-product then dichloromethane/methanol 9:1) to yield 85 mg (yield 28%) of a colourless oil corresponding to 2-phenyl-4-(4-N,N-diethylamino-piperidin-1-yl)quinoline.

HPLC: conditions E: t$_r$=12.64 min, (ES+) C$_{24}$H$_{29}$N$_3$ requires 359; found 360 [M+H].

$^1$H NMR (300 MHz, CDCl$_3$).

I-4/ 2-phenyl-4-(4-N,N-diethylamino-piperidin-1-yl)quinoline dihydrochloride (I-4)

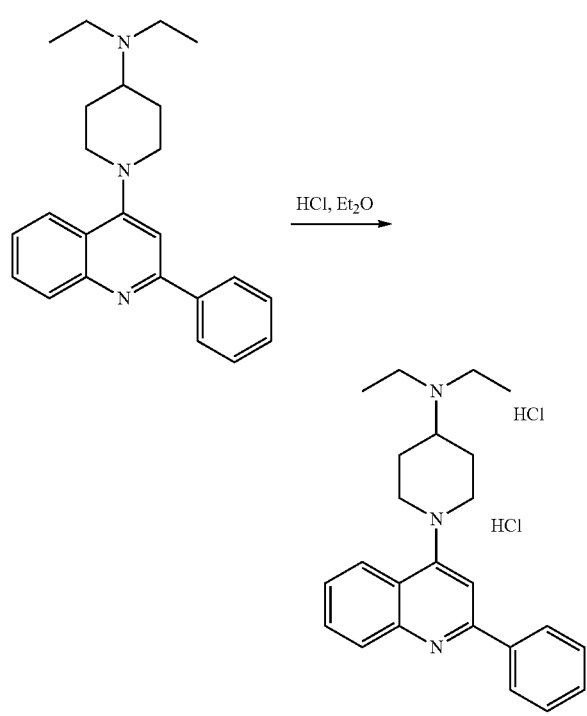

A solution of 65 mg (0.18 mmol) of 2-phenyl-4-(4-N,N-diethylamino-piperidin-1-yl)quinoline in dry dichloromethane was stirred under nitrogen; after adding 362 µl of 1N HCl in ether, the mixture was stirred for 1 h at room temperature and concentrated to give 65 mg (yield 83%) of a yellow solid corresponding to 2-phenyl-4-(4-N,N-diethylamino-piperidin-1-yl)quinoline dihydrochloride.

HPLC: conditions E: $t_r$=12.77 min, (ES+) $C_{24}H_{29}N_3$ requires 359; found 360 [M+H].
$^1$H NMR (300 MHz, DMSO-$d_6$).
$^1$H NMR (300 MHz, DMSO-$d_6$+$D_2O$).

EXAMPLE 2

Preparation of 7-chloro-2-phenyl-4-(4-N,N-diethylamino-piperidin-1-yl)quinoline hydrochloride salt (II-4)

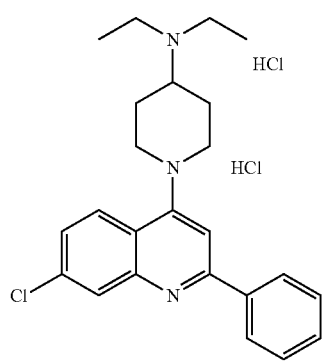 [SMILES: CCN(CC)C1CCN(c2cc(-c3ccccc3)nc3cc(Cl)ccc23)CC1 ; Cl ; Cl]

II-1/ 7-chloro-4-hydroxy-2-phenylquinoline

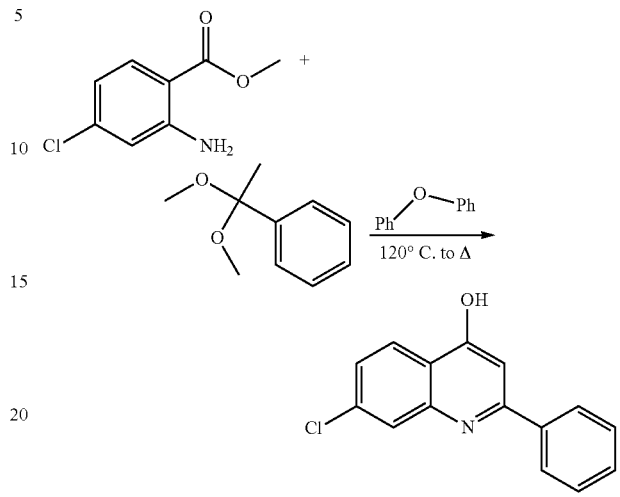

In a round bottom flask equipped with a Dean Stark apparatus was successively added 2.3 g (12.4 mmol) of methyl 2-amino-4-chlorobenzoate and 8 ml of diphenyl ether. Under argon, 2.2 ml (13.6 mmol) of (1,1-dimethoxy-ethyl) benzene were added. The mixture was heated for 1 h45 at 120° C. with a slight water pump vacuum, then 96 h under reflux. The cooled mixture was taken up with 30 ml of petroleum ether then with ether to give 1.26 g (yield 48%) of a beige solid compound corresponding to 7-chloro-4-hydroxy-2-phenylquinoline.

HPLC: conditions D: $t_r$=6.30 min, (ES+) $C_{15}H_{10}ClNO$ requires 255/257; found 256/258 [M+H].
$^1$H NMR (300 MHz, DMSO-$d_6$).

II-2/ 4,7-dichloro-2-phenylquinoline

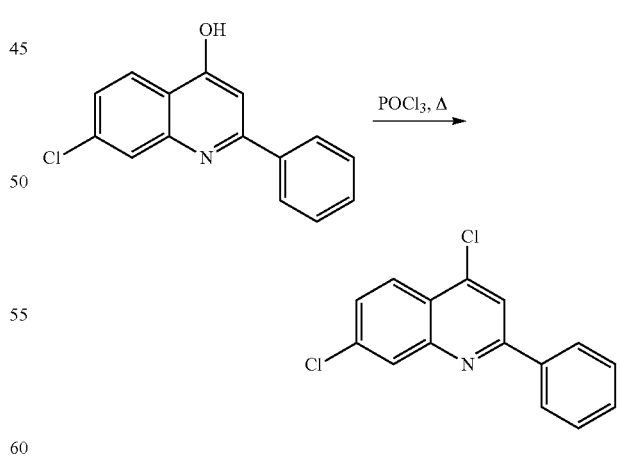

A mixture of 1.65 g (6.61 mmol) of 7-chloro-4-hydroxy-2-phenylquinoline and 3.7 ml of phosphoryl chloride was heated for 3 h under reflux and then concentrated to dryness. The residue was taken up with a saturated aqueous solution of sodium bicarbonate and the aqueous layer was extracted with ethyl acetate. The organic layer was dried over MgSO$_4$, filtered and concentrated on a rotary evaporator. The residue was triturated with petroleum ether to give 1.53 g of a yellow solid. It was purified by silica gel column chromatography (petroleum ether/ethyl acetate 98:2) to yield 874 mg (yield 61%) of a yellow solid corresponding to 4,7-dichloro-2-phenylquinoline.

HPLC: conditions D: $t_r$=11.71 min, (ES+) $C_{15}H_9Cl_2N$ requires 273/275; found 274/276 [M+H].

$^1$H NMR (300 MHz, DMSO-$d_6$)

II-3/ 7-chloro-2-phenyl-4-(4-N,N-diethylamino-piperidin-1-yl)quinoline (II-3)

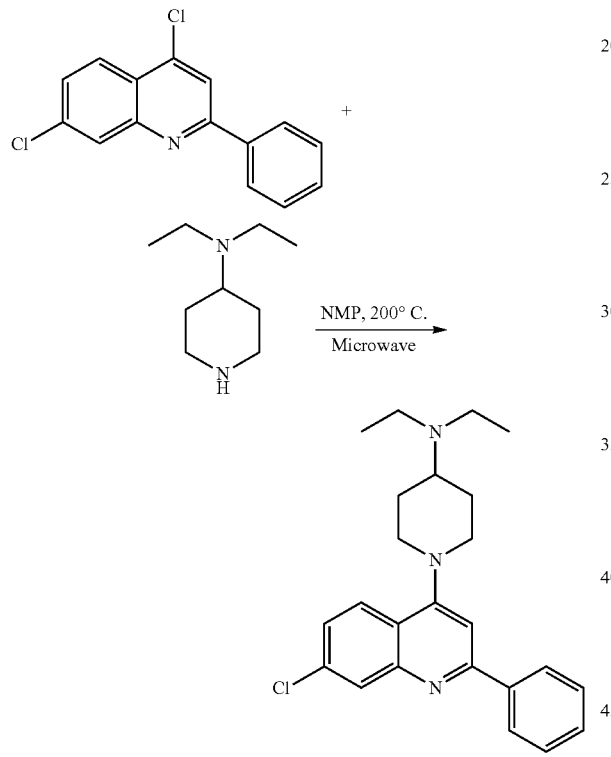

In a microwave vial was successively added, 175 mg (0.64 mmol) of 4,7-dichloro-2-phenylquinoline, 300 mg (1.92 mmol) of 4-diethylamino-piperidine and 1.5 ml of NMP. The solution was heated for 30 min at 200° C. in a microwave oven and treated with a 1N NaOH aqueous solution. The mixture was extracted with ethyl acetate and the organic layer dried over MgSO$_4$, filtered and concentrated. The oily residue was purified by silica gel column chromatography (petroleum ether/ethyl acetate 9:1, then dichloromethane and then dichloromethane/methanol 98:2) to give 110 mg (yield 44%) of yellow oil corresponding to 7-chloro-2-phenyl-4-(4-N,N-diethylamino-piperidin-1-yl)-quinoline.

HPLC: conditions D: $t_r$=4.59 min, (ES+) $C_{24}H_{28}ClN_3$ requires 393/395; found 394/396 [M+H].

$^1$H NMR (300 MHz, CDCl$_3$).

II-4/ 7-chloro-2-phenyl-4-(4-N,N-diethylamino-piperidin-1-yl)quinoline dihydrochloride (II-4)

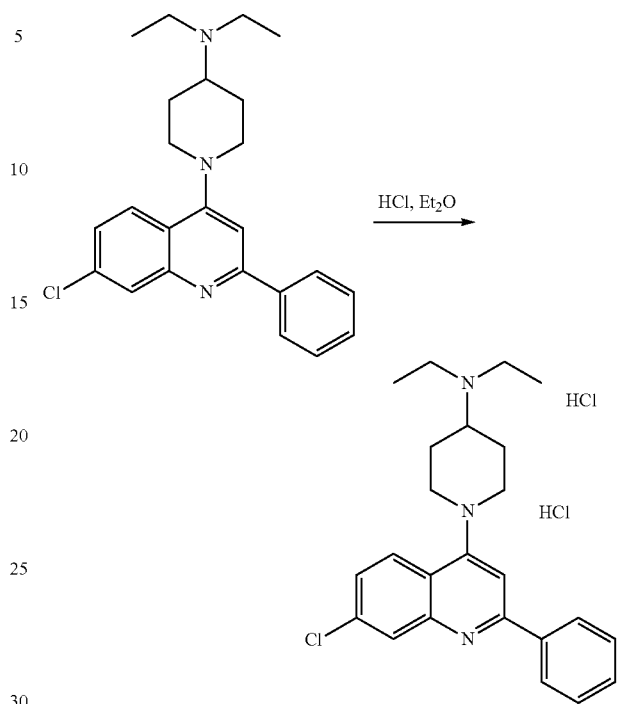

To a solution of 110 mg (0.28 mmol) of 7-chloro-2-phenyl-4-(4-N,N-diethylamino-piperidin-1-yl)quinoline in 500 µl of dry dichloromethane was added 560 µl of a solution of 1N HCl in ether. The white solid precipitate was filtered and triturated with ether, solubilized in 1 ml of pure water and freeze-dried to give 80 mg (yield 61%) of slightly yellow powder corresponding to 7-chloro-2-phenyl-4-(4-N,N-diethylamino-piperidin-1-yl)quinoline dihydrochloride.

HPLC: conditions D: $t_r$=4.59 min, (ES+) $C_{24}H_{28}ClN_3$ requires 393/395; found 394/396 [M+H].

$^1$H NMR (300 MHz, DMSO-$d_6$).
$^1$H NMR (300 MHz, DMSO-$d_6$+$D_2O$).

EXAMPLE 3

Preparation of 2-phenyl-4-([1,4']-bipiperidin-1'-yl)quinolinehydrochloride salt (III-4)

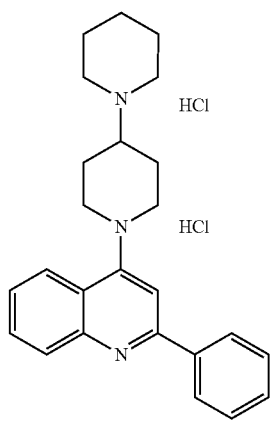 [SMILES: c1ccc(-c2cc(N3CCC(N4CCCCC4)CC3)c3ccccc3n2)cc1 ; Cl ; Cl]

III-1/ 2-phenyl-4-(1,4-dioxa-8-aza-spiro[4,5]dec-8-yl)quinoline

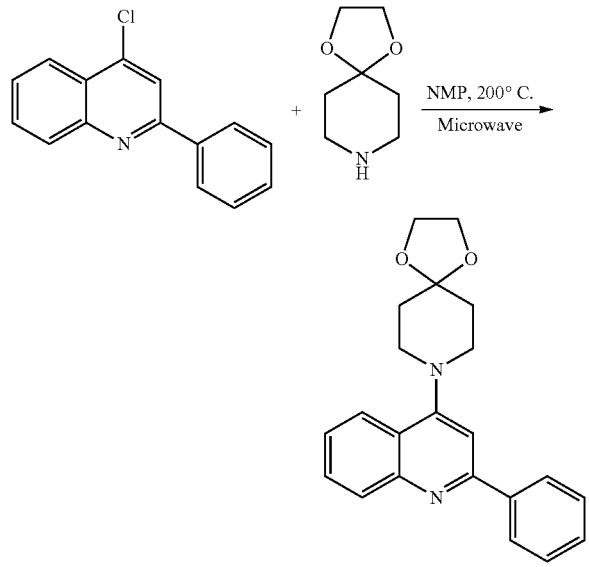

A mixture of 1.7 g (7.09 mmol) of 4-chloro-2-phenylquinoline, 9.09 ml (70.91 mmol) of 1,4-dioxa-8-azaspiro[4,8]decane and a few drops of NMP was heated for 30 min at 200° C. in a microwave oven. The mixture was then diluted with a 1N NaOH aqueous solution and extracted with ethyl acetate. The organic layer was washed with water, dried over MgSO$_4$ and concentrated on a rotary evaporator. The resulting residue was purified by silica gel column chromatography (CH$_2$Cl$_2$/Ethyl acetate 9:1 then 98:2 and then 96:4) to give 2.4 g (yield 97%) of a colourless oil corresponding to 2-phenyl-4-(1,4-dioxa-8-aza-spiro[4,5]dec-8-yl)quinoline.

HPLC: conditions D: t$_r$=6.00 min, (ES+) C$_{22}$H$_{22}$N$_2$O$_2$ requires 346; found 347 [M+H].

$^1$H NMR (300 MHz, CDCl$_3$).

III-2/ 1-(2-phenyl-quinoline-4-yl)-piperidin-4-one

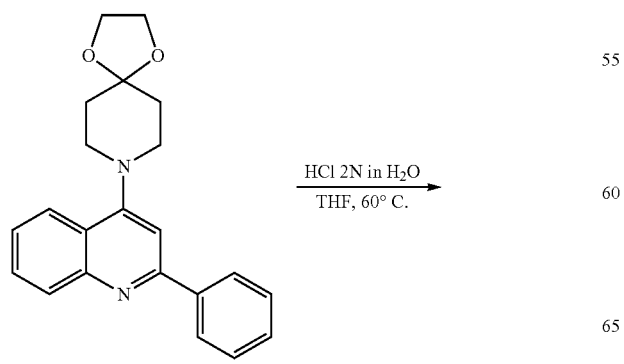

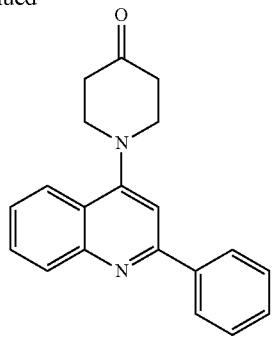

To a solution of 2.39 g (6.898 mmol) of 2-phenyl-4-(1,4-dioxa-8-aza-spiro[4,5]dec-8-yl)quinoline in 14 ml of dry tetrahydrofuran was added 14 ml of 2N HCl aqueous solution. The mixture was stirred for 4 h30 at 60° C. then treated with a 1N NaOH aqueous solution. The basic mixture was extracted with ethyl acetate and the organic layer dried over MgSO$_4$, filtered and concentrated to give yellow oil. The crude product was purified by silica gel column chromatography (dichloromethane/ethyl acetate 99:1, then 98:2) to give 1.09 g (yield 52%) of a colourless oil corresponding to 1-(2-phenyl-quinoline-4-yl)-piperidin-4-one.

HPLC: conditions D: t$_r$=5.05 min, (ES+) C$_{20}$H$_{18}$N$_2$O requires 302; found 303 [M+H].

$^1$H NMR (300 MHz, CDCl$_3$).

III-3/ 2-phenyl-4-([1,4']-bipiperidyl-1'-yl)-quinoline (III-3)

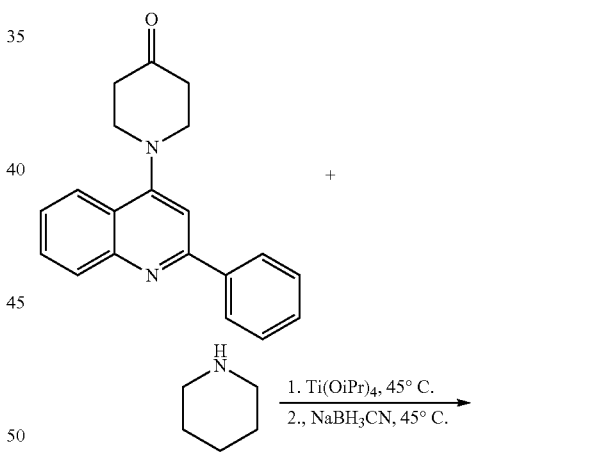

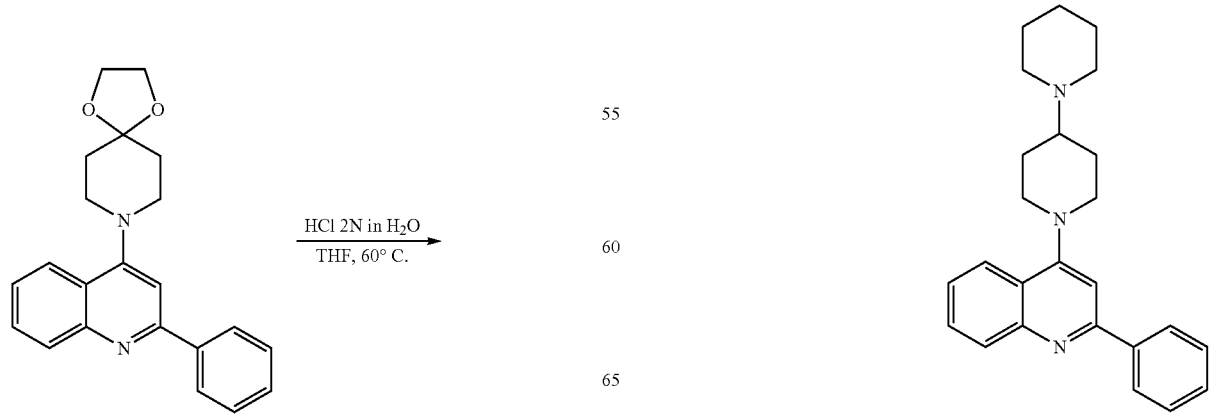

To 300 mg (0.99 mmol) of 1-(2-phenyl-quinoline-4-yl)-piperidin-4-one were added under argon, 147 µl (1.48 mmol) of piperidine and 414 µl (1.39 mmol) of titanium (IV) isopropoxide. The mixture was stirred for 5 h at 45° C., then cooled and diluted with 2 ml of dry ethanol. 137 mg (2.18 mmol) of sodium cyanoborohydride were added and the mixture stirred for 4 h30 at 45° C., then 20 h at room temperature. The mixture was poured onto 33 ml of water, stirred for 1 h at room temperature, filtered through a Celite® pad and the filtrate was extracted with dichloromethane. The organic layer was washed with brine, dried over MgSO$_4$, filtered and concentrated to give 450 mg of a crude white compound. The crude product was purified by silica gel column chromatography (dichloromethane/methanol 99:1 (with a few drops of NH$_4$OH), then 98:2 (with a few drops of NH$_4$OH) to give 208 mg (yield 56%) of a white solid corresponding to 2-phenyl-4-([1,4']-bipiperidin-1'-yl)quinoline.

HPLC: conditions D: t$_r$=2.00 min, (ES+) C$_{25}$H$_{29}$N$_3$ requires 371; found 372 [M+H].
$^1$H NMR (300 MHz, CDCl$_3$).

III-4/ 2-phenyl-4-([1,4']-bipiperidin-1'-yl)quinoline dihydrochloride (III-4)

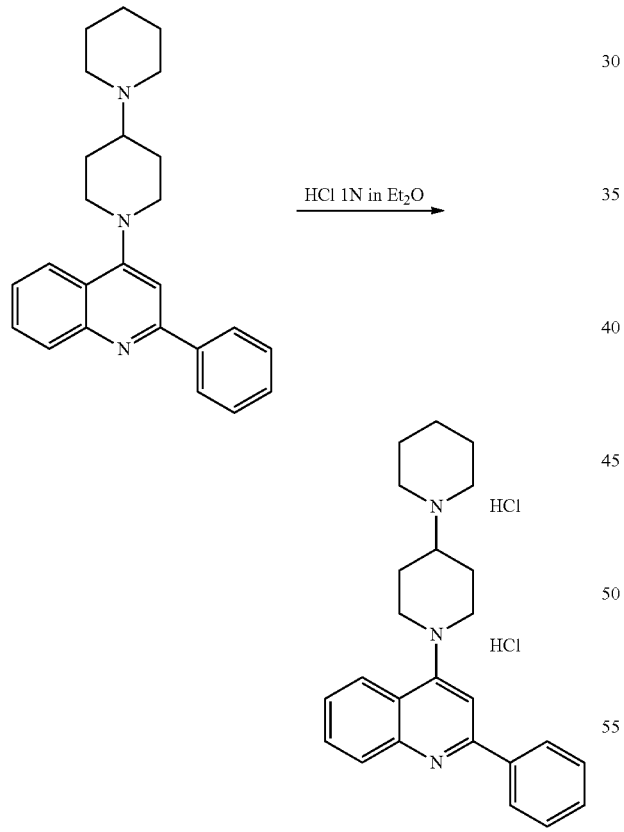

To a solution of 85 mg (0.228 mmol) of 2-phenyl-4-([1,4']-bipiperidin-1'-yl)quinoline in 400 µl of dry dichloromethane was added under argon, 458 µl (0.457 mmol) of a solution of 1N HCl in ether. After stirring for 1 h at room temperature, the mixture was concentrated and solubilized in ethanol, and then petroleum ether was added to precipitate a solid product. It was dissolved in pure water and the solution was filtered on Nalgene 0.2 µm PTFE seringue filter and then freeze-dried to give 81 mg (yield 90%) of a yellow solid compound corresponding to 22-phenyl-4-([1,4']-bipiperidin-1'-yl)quinoline dihydrochloride.

HPLC: conditions D: t$_r$=4.16 min, (ES+) C$_{25}$H$_{29}$N$_3$ requires 371; found 372 [M+H].
$^1$H NMR (DMSO and DMSO-d$_6$).
$^1$H NMR (DMSO and DMSO-d$_6$+D$_2$O).

EXAMPLE 4

Preparation of 2-phenyl-4-(4-N-tert-butylamino-piperidin-1-yl)quinoline hydrochloride salt (IV-2)

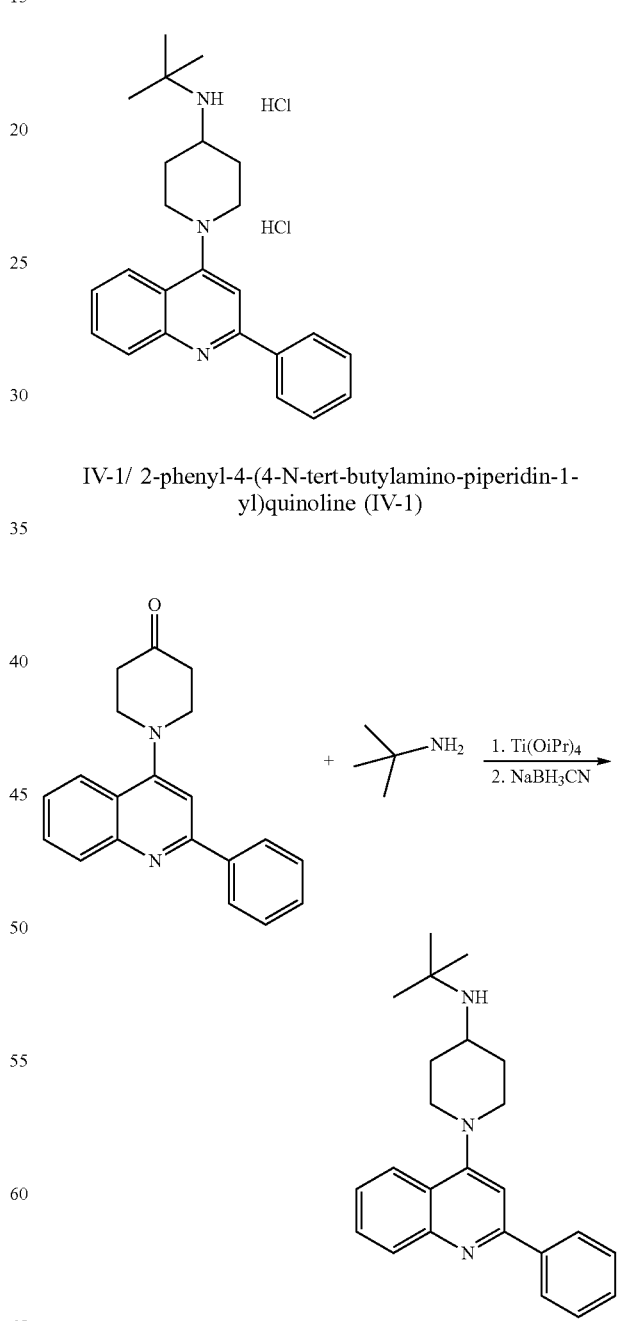

IV-1/ 2-phenyl-4-(4-N-tert-butylamino-piperidin-1-yl)quinoline (IV-1)

To 380 mg (1.256 mmol) of 1-(2-phenyl-quinoline-4-yl)-piperidin-4-one (prepared as described in protocol III-2)

were added (under argon), 198 µl (1.88 mmol) of tert-butylamine and 524 µl (1.758 mmol) of titanium (IV) isopropoxide. The mixture was stirred for 5 h30 at 45° C., then cooled and diluted with 3 ml of dry ethanol. 174 mg (2.763 mmol) of sodium cyanoborohydride were added and the mixture stirred for 5 h at 45° C., and then 20 h at room temperature. The mixture was poured onto 42 ml of water, stirred for 1 h at room temperature, filtered through a Celite® pad and the filtrate was extracted with dichloromethane. The organic layer was washed with brine in water, dried over MgSO$_4$, filtered and concentrated to give 440 mg of a residue. The crude product was purified by silica gel column chromatography (dichloromethane/methanol 99:1 then 98:2 and then 97:3) to give 242 mg (yield 53%) of a white solid compound corresponding to 2-phenyl-4-(4-N-tert-butylamino-piperidin-1-yl)quinoline.

HPLC: conditions D: t$_r$=4.13 min, (ES+) C$_{24}$H$_{29}$N$_3$ requires 359; found 360 [M+H].

$^1$H NMR (300 MHz, CDCl$_3$).

IV-2/ 2-phenyl-4-(4-N-tert-butylamino-piperidin-1-yl)quinoline dihydrochloride (IV-2)

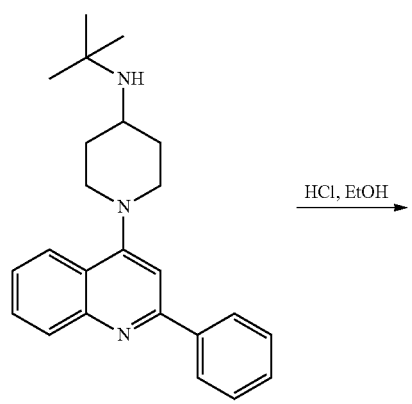

To a solution of 105 mg (0.29 mmol) of 2-phenyl-4-(4-N-tert-butylamino-piperidin-1-yl)quinoline in 500 µl of dry dichloromethane was added under argon, 584 µl (0.584 mmol) of a solution of 1N HCl in ethanol. The solution was stirred for 1 h at room temperature, concentrated and the residue solubilized in ethanol. Petroleum ether was added slowly to precipitate a crude solid. The solid was filtrated, dissolved in pure water and resulting solution was filtered on Nalgene 0.2 µm PTFE seringue filter and then freeze-dried to give 112 mg (yield 88%) of a yellow solid compound corresponding to 2-phenyl-4-(4-N-tert-butylamino-piperidin-1-yl)quinoline dihydrochloride.

HPLC: conditions D: t$_r$=4.18 min, (ES+) C$_{24}$H$_{29}$N$_3$ requires 359; found 360 [M+H].

$^1$H NMR (300 MHz, DMSO-d$_6$).
$^1$H NMR (300 MHz, DMSO-d$_6$+D$_2$O).

EXAMPLE 5

Preparation of 2-phenyl-4-[(4-morpholin-4-yl)piperidin-1yl]quinoline hydrochloride salt (V-2)

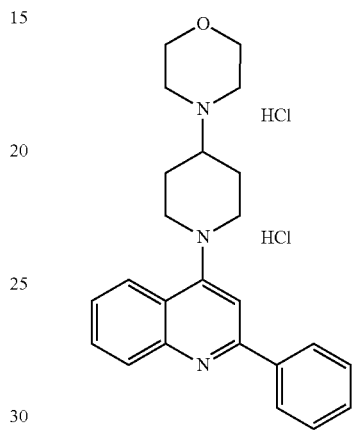

V-1/ 2-phenyl-4-[(4-morpholin-4-yl)piperidin-1yl]quinoline (V-1)

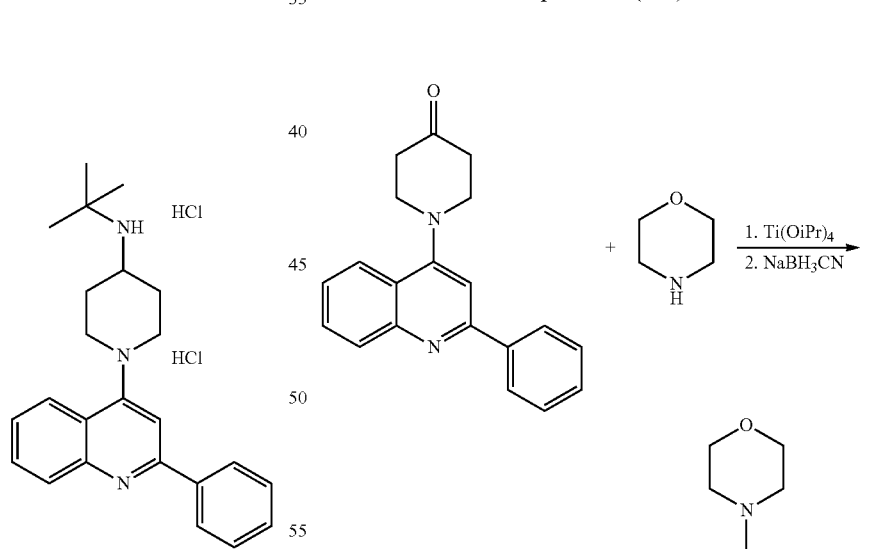

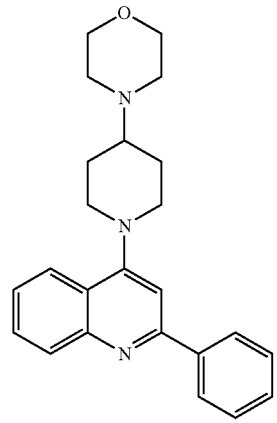 [SMILES: c1ccc(-c2cc(N3CCC(N4CCOCC4)CC3)c3ccccc3n2)cc1 ; Cl ; Cl]

To 380 mg (1.256 mmol) of 1-(2-phenyl-quinoline-4-yl)-piperidin-4-one (prepared as described in protocol III-2) were added under argon, 164 µl (1.88 mmol) of morpholine and 524 µl (1.758 mmol) of titanium (IV) isopropoxide. The mixture was stirred for 4 h at 45° C., then cooled and diluted with 2.5 ml of dry ethanol. 174 mg (2.763 mmol) of sodium cyanoborohydride were added and the mixture stirred for 4 h30 at 45° C. and 20 h at room temperature. The mixture was then poured onto 42 ml of water stirred for 1 h at room temperature, filtered through a Celite® pad and the filtrate was extracted with dichloromethane. The organic layer was washed with brine, dried over MgSO$_4$, filtered and concentrated to give 519 mg of a residue. The crude product was purified by silica gel column chromatography (dichloromethane/methanol 99:1 then 98:2) to give 215 mg of a white solid containing a by-product; this mixture was purified by a new silica gel column chromatography (dichloromethane/ethyl acetate 7:3 then dichloromethane/methanol 9:1) to give 151 mg (yield 32%) of a white solid compound corresponding to 2-phenyl-4-[(4-morpholin-4-yl)piperidin-1 yl]quinoline.

HPLC: conditions E: t$_r$=12.22 min, (ES+) C$_{24}$H$_{27}$N$_3$O requires 373; found 374 [M+H].
$^1$H NMR (300 MHz, CDCl$_3$).

V-2/ 2-phenyl-4-[(4-morpholin-4-yl)piperidin-1yl] quinoline dihydrochloride (V-2)

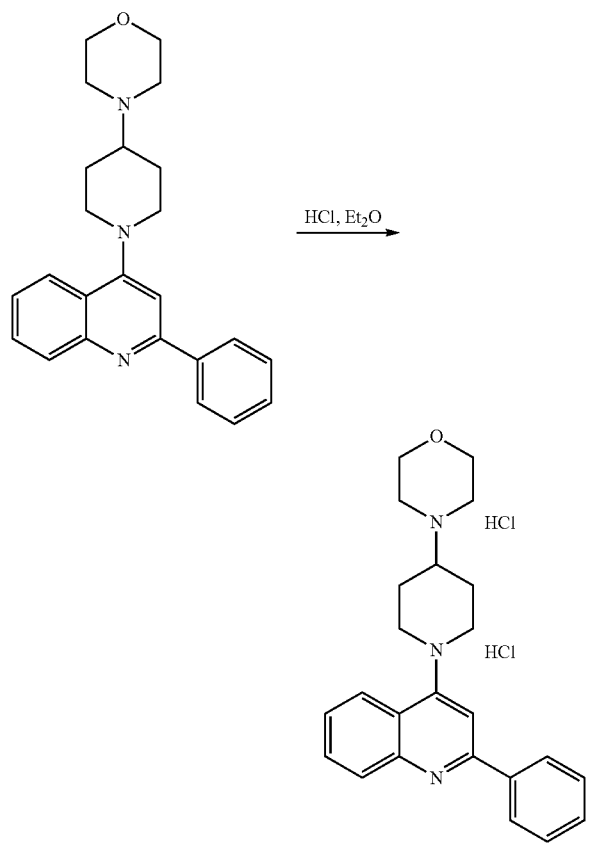

To a solution of 80 mg (0.214 mmol) of 2-phenyl-4-[(4-morpholin-4-yl)piperidin-1yl]quinoline in 400 µl of dry dichloromethane was added under argon, 428 µl (0.428 mmol) of a solution of 1N HCl in ether. The solution was stirred for 1 h at room temperature, concentrated and the residue solubilized in ethanol. Petroleum ether was added slowly to precipitate a crude solid; this product was dissolved in pure water, and the solution filtered on Nalgene 0.2 µm PTFE seringue filter then freeze-dried to give 81 mg (yield 85%) of a yellow solid corresponding to 2-phenyl-4-[(4-morpholin-4-yl)piperidin-1 yl]quinoline dihydrochloride.

HPLC: conditions E: t$_r$=12.37 min, (ES+) C$_{24}$H$_{27}$N$_3$O requires 373; found 374 [M+H].
$^1$H NMR (300 MHz, DMSO-d$_6$).
$^1$H NMR (300 MHz, DMSO-d$_6$+D$_2$O).

EXAMPLE 6

Preparation of 2-(2-naphtyl)-4-(4-N,N-diethyl-amino-piperidin-1-yl)quinoline hydrochloride salt (VI-6)

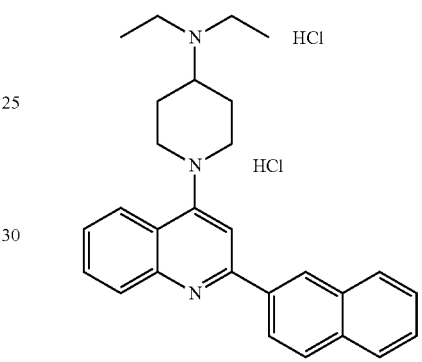

VI-1/ Benzenamine, 2-trifluoromethyl-N-[1-(2-naphthalenyl)ethylidene]-:

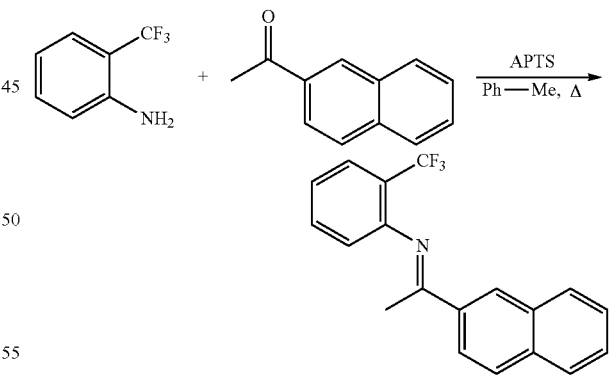

In a round bottom flask equipped with a Dean Stark apparatus was successively added under argon, 4 g (24.82 mmol) of 2-(trifluoromethyl)-aniline, 5.49 g (32.26 mmol) of 2-acetonaphtone, 120 mg of p-toluenesulfonic acid monohydrate and 120 ml of dry toluene. The mixture was heated for 15 h under reflux and concentrated. The residue was purified by a silica gel column chromatography (petroleum ether/ethyl acetate 99:1 then 98:2) to give 2.65 g of a yellow crystallising compound. The solid was triturated with petroleum ether, filtered and dried to give 1.44 g (yield 18%) of a white solid corresponding to benzenamine, 2-trifluoromethyl-N-[1-(2-naphthalenyl)ethylidene]-.

$^1$H NMR (300 MHz, CDCl$_3$).

VI-2/ 2-(2-naphtyl)-4-tert-butoxy-quinoline

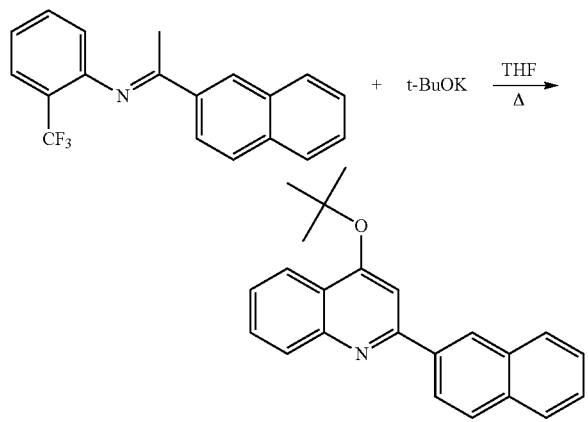

To a solution of 1.4 g (4.47 mmol) of benzenamine, 2-trifluoromethyl-N-[1-(2-naphthalenyl)ethylidene] in 70 ml of dried THF, 2.37 g of potassium tert-butylate were added and the mixture was stirred for 50 min under reflux. The mixture was quenched with water, both layers were separated and the aqueous layer was extracted with dichloromethane. The organic layer was dried over MgSO$_4$, filtered and concentrated to give 1.99 g of a brown oil. The crude compound was purified by a silica gel column chromatography (dichloromethane 100%) to give 1.63 g of yellow oil. This oil was purified again by a silica gel column chromatography (cyclohexane/ethyl acetate 99:1 then 98:2) to give 0.81 g (yield 55%) of yellow oil corresponding to 2-(2-naphtyl)-4-tert-butoxy-quinoline.

HPLC: conditions D: t$_r$=7.44 min, (ES+) C$_{23}$H$_{21}$NO requires 327; found 328 [M+H].

$^1$H NMR (300 MHz, CDCl$_3$).

VI-3/ 2-(2-naphtyl)-4-hydroxy-quinoline

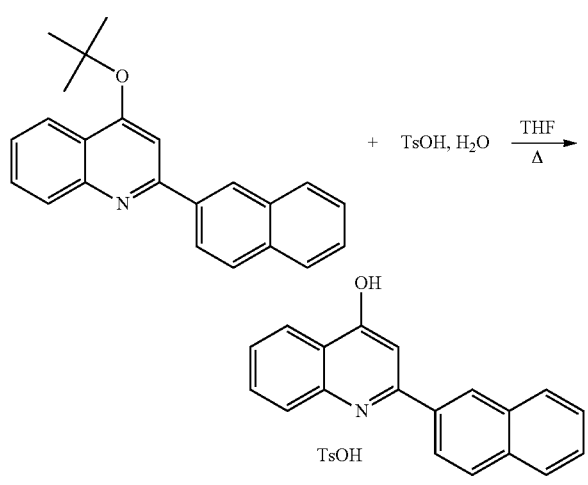

To a solution of 0.81 g (2.473 mmol) of 2-(2-naphtyl)-4-tert-butoxy-quinoline in 20 ml of THF, 0.706 g of p-toluenesulfonic acid monohydrate was added and the mixture was heated for 5 h45 under reflux. After cooling the mixture, a white solid compound was filtered, washed with THF and dried to recover 0.798 g (yield 72%) of white solid corresponding to the p-toluenesulfonate salt of 2-(2-naphtyl)-4-hydroxy-quinoline.

HPLC-MS: conditions D: t$_r$=6.34 min, (ES+) C$_{19}$H$_{13}$NO requires 271; found 272 [M+H].

$^1$H NMR (300 MHz, DMSO-d$_6$).

VI-4/ 2-(2-naphtyl)-4-chloro-quinoline

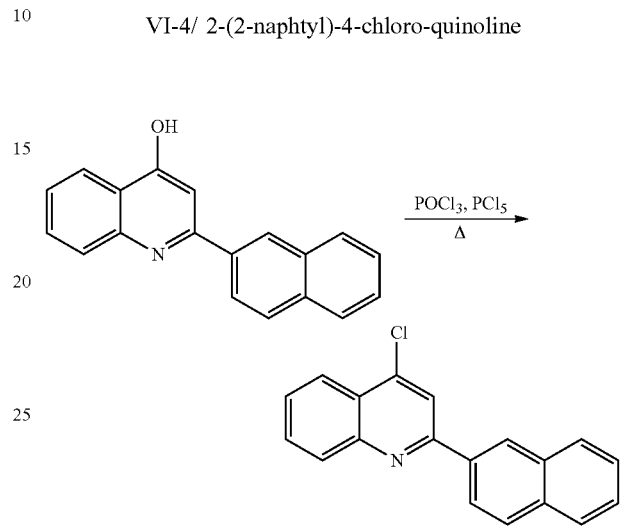

To a mixture of 0.79 g (1.781 mmol) of 2-(2-naphtyl)-4-hydroxy-quinoline in 7.9 ml of phosphoryl chloride were added 232 mg (1.781 mmol) of phosphorus pentachloride. The reaction mixture was refluxed for 1 h15 under argon and then poured slowly into water after cooling (effervescence) and sodium bicarbonate was carefully added. The solid compound obtained was filtered and washed with water, then solubilized in hot ethyl acetate. The solution was dried over MgSO$_4$, filtered and concentrated on a rotary evaporator to give 461 mg (yield 89%) of yellow solid corresponding to 2-(2-naphtyl)-4-chloro-quinoline.

HPLC-MS: conditions D: t$_r$=11.59 min, (ES+) C$_{19}$H$_{12}$ClN requires 289; found 290 [M+H].

$^1$H NMR (300 MHz, CDCl$_3$).

VI-5/ 2-(2-naphtyl)-4-(4-N,N-diethylamino-piperidin-1-yl)quinoline (VI-5)

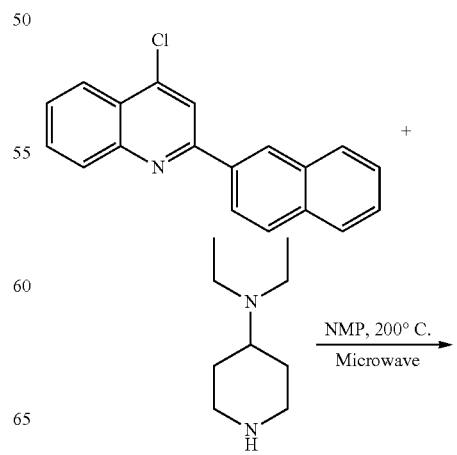

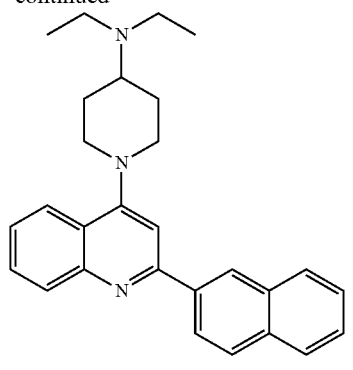

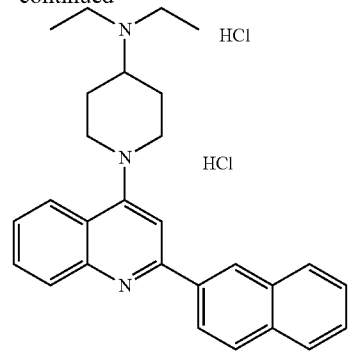

In a microwave vial was successively added, 200 mg (0.69 mmol) of 2-(2-naphtyl)-4-chloro-quinoline, 323 mg (2.07 mmol) of 4-diethylamino-piperidine and 4 ml of NMP. The solution was heated for 30 min at 200° C. in a microwave oven and then treated with a 1N NaOH aqueous solution. The mixture was extracted with ethyl acetate and the organic layer was dried over MgSO$_4$, filtered and concentrated to give 258 mg of an oily residue. This crude product was purified by silica gel column chromatography (dichloromethane/methanol 98:2 then 97:3) to give 200 mg of impure orange oil. This oil was solubilized in a small volume of dichloromethane and petroleum ether was added to precipitate a solid, and the filtrate was concentrated to give 170 mg of impure yellow oil. This oil was purified again by silica gel column chromatography (dichloromethane/methanol 97:3) to give 79 mg of orange oil. An additional purification by a silica gel column chromatography (dichloromethane/methanol 95:5) gave 56 mg (yield 19%) of yellow oil corresponding to 2-(2-naphtyl)-4-(4-N,N-diethylamino-piperidin-1-yl)quinoline.

HPLC-MS: conditions D: $t_r$=4.91 min, (ES+) C$_{28}$H$_{31}$N$_3$ requires 409; found 410 [M+H].

$^1$H NMR (300 MHz, CDCl$_3$).

VI-6/ 2-(2-naphtyl)-4-(4-N,N-diethylamino-piperidin-1-yl)quinoline dihydrochloride (VI-6)

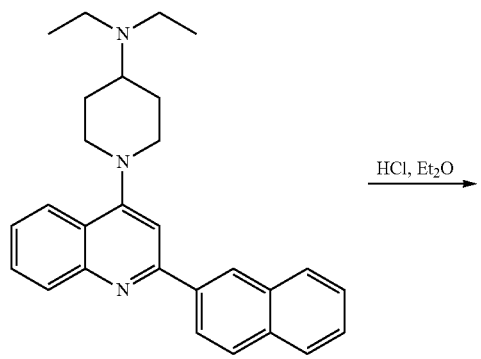

HCl, Et$_2$O

To a solution of 50 mg (0.122 mmol) of 2-(2-naphtyl)-4-(4-N,N-diethylamino-piperidin-1-yl)-quinoline in 200 μl of dry dichloromethane was added under argon, 244 μl (0.244 mmol) of a solution of 1N HCl in ether. The solution was stirred for 1 h at room temperature, concentrated and the residue was solubilized in ethanol. Petroleum ether was added slowly to precipitate a crude solid; this product was dissolved in pure water, and the solution was filtered on Nalgene 0.2 μm PTFE seringue filter then freeze-dried to give 39 mg (yield 67%) of a yellow solid compound corresponding to 2-(2-naphtyl)-4-(4-N,N-diethylamino-piperidin-1-yl)quinoline dihydrochloride.

HPLC-MS: conditions D: $t_r$=4.95 min, (ES+) C$_{28}$H$_{31}$N$_3$ requires 409; found 410 [M+H].

$^1$H NMR (300 MHz, DMSO-d$_6$).

$^1$H NMR (300 MHz, DMSO-d$_6$+D$_2$O).

EXAMPLE 7

Preparation of 2-(4-bromo-phenyl)-7-chloro-4-(4-N,N-diethylamino-piperidin-1-yl)quinoline (VII-4)

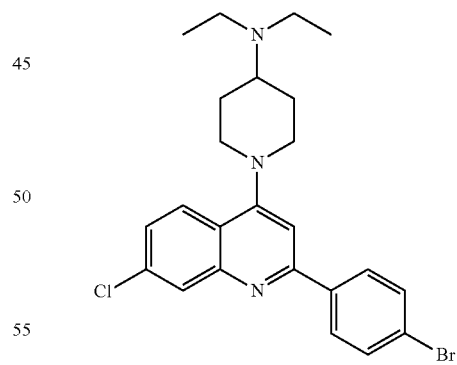

VII-1/ Ethyl 3-(4-bromo-phenyl)-3-oxopropanoate

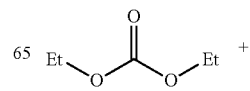

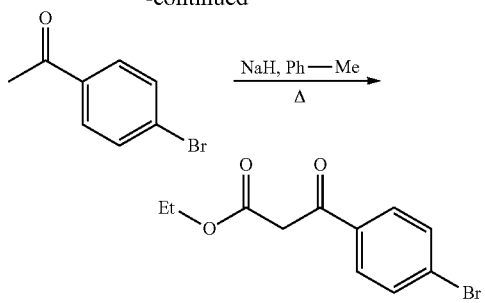

In around bottom flask, 8.04 g (200.96 mmol) of NaH were washed three times with cyclohexane; under argon, 100 ml of dry toluene and 30.4 ml (251.2 mmol) of diethyl carbonate were successively added. Slowly, 10 g (50.24 mmol) of 4'-bromoacetophenone were added and the resulting mixture was stirred one night under reflux. After cooling, 25 ml of acetic acid were added to the reaction mixture, then a solution of 15 ml of concentrated HCl in 100 ml of cooled water. The mixture was extracted with ethyl acetate and the organic layer was treated with a solution of sodium bicarbonate then dried over MgSO$_4$, filtered and concentrated to give 17.4 g of orange oil. This oil was distilled under vacuum to give 8.07 g (yield 59%) of Ethyl 3-(4-bromo-phenyl)-3-oxopropanoate.

HPLC-MS: conditions D: $t_r$=8.03 min, (ES+) $C_{11}H_{11}BrO_3$ requires 270/272; found 271/273 [M+H].

$^1$H NMR (300 MHz, CDCl$_3$).

VII-2/ 2-(4-bromo-phenyl)-7-chloro-4-hydroxy-quinoline

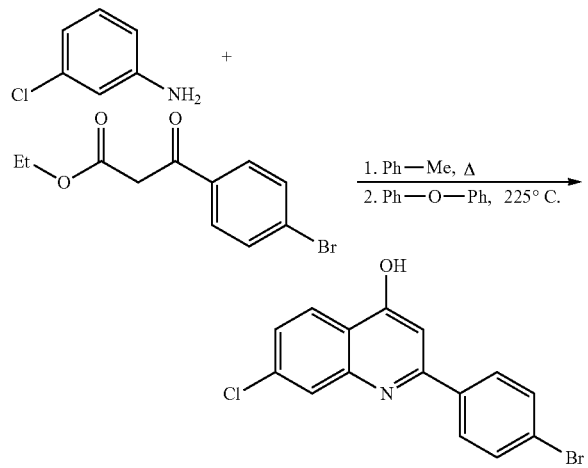

A solution of 1 g (3.69 mmol) of Ethyl 3-(4-bromo-phenyl)-3-oxopropanoate, 392 µl (3.69 mmol) of 3-chloroaniline and 35 mg (0.184 mmol) of para-toluenesulfonic acid monohydrate in 1 ml of toluene was heated for 1 h under reflux. The reaction mixture was concentrated and 7.1 ml of diphenyl ether was added before heating for 1 h at 225° C. After cooling, cyclohexane was added to the mixture to precipitate a solid; it was filtered, washed and dried to give 0.82 g of beige compound. This product was washed with dichloromethane to provide 764 mg of a white impure solid corresponding to 2-(4-bromo-phenyl)-7-chloro-4-hydroxy-quinoline. It was used in the next step without any further purification.

$^1$H NMR (300 MHz, CDCl$_3$).

VII-3/ 2-(4-bromo-phenyl)-4,7-dichloro-quinoline

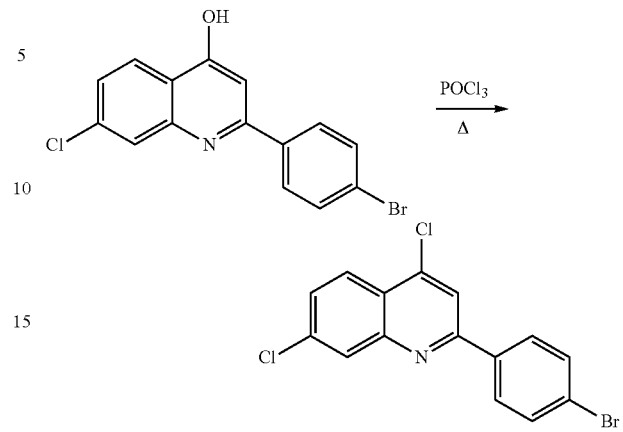

A mixture of 0.76 g (2.27 mmol) of 2-(4-bromo-phenyl)-7-chloro-4-hydroxy-quinoline, and 635 µl of phosphoryl chloride was heated for 3 h under reflux. After cooling, the solution was poured slowly into water (effervescence) and sodium bicarbonate was carefully added. The mixture was extracted with dichloromethane and the organic layer was dried over MgSO$_4$, filtered and concentrated on a rotary evaporator to give 669 mg of beige solid product. It was purified by silica gel column chromatography (petroleum ether/ethyl acetate 98:2) to give 432 mg of a white solid containing a by-product. Purification by preparative TLC gave 101 mg (yield 12% in two steps) of 2-(4-bromo-phenyl)-4,7-dichloro-quinoline.

$^1$H NMR (300 MHz, CDCl$_3$).

VII-4/ 2-(4-bromo-phenyl)-7-chloro-4-(4-N,N-diethylamino-piperidin-1-yl)quinoline (VII-4)

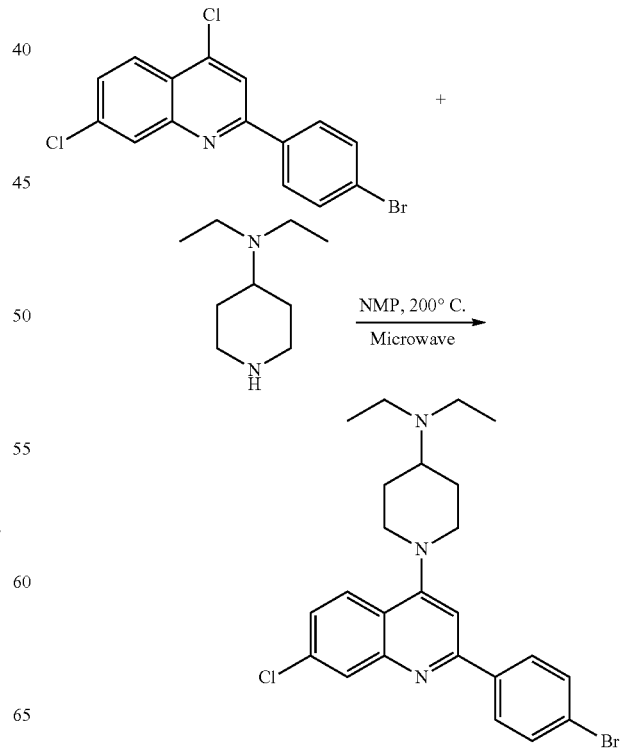

In a microwave vial were successively added, 100 mg (0.283 mmol) of 2-(4-bromo-phenyl)-4,7-dichloro-quinoline, 132 mg (0.85 mmol) of 4-diethylamino-piperidine and 2 ml of NMP. The solution was heated 30 min at 200° C. in a microwave oven and treated with a 1N NaOH aqueous solution. The mixture was extracted with ethyl acetate and the organic layer was dried over MgSO$_4$, filtered and concentrated to give an oily residue. This product was purified by silica gel column chromatography (dichloromethane/methanol 98:2) to give 94 mg (yield 74%) of orange oil corresponding to 2-(4-bromo-phenyl)-7-chloro-4-(4-N,N-diethylamino-piperidin-1-yl)quinoline.

HPLC-MS: conditions F: $t_r$=5.16 min, (ES+) $C_{24}H_{27}BrClN_3$ requires 471/473; found 472/474 [M+H].
$^1$H NMR (300 MHz, CDCl$_3$).

EXAMPLE 8

Preparation of 2-(4-bromo-phenyl)-4-(4-N,N-diethylamino-piperidin-1-yl)quinoline hydrochloride salt (VIII-6)

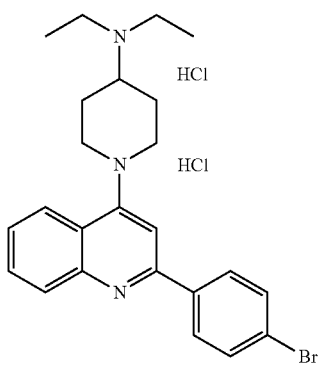 [SMILES: CCN(CC)C1CCN(c2cc(-c3ccc(Br)cc3)nc3ccccc23)CC1 ; Cl ; Cl]

VIII-1/ Benzenamine, 2-trifluoromethyl-N-[1-(4-bromo-phenyl)ethylidene]-

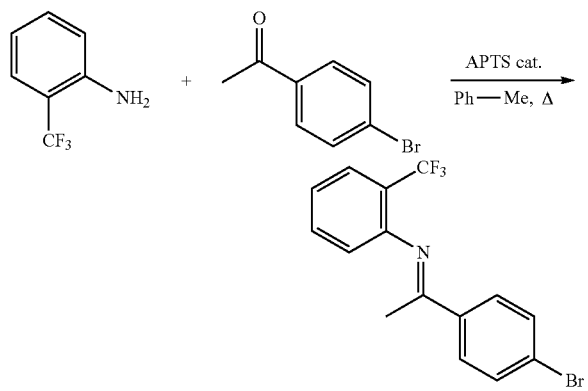

In a round bottom flask equipped with a Dean Stark apparatus was successively added under argon, 2.0 g (12.41 mmol) of 2-(trifluoromethyl)-aniline, 3.21 g (16.13 mmol) of 4'-bromoacetophenone, 60 mg of p-toluenesulfonic acid monohydrate and 60 ml of dry toluene. The mixture was heated for 8 h30 under reflux and concentrated to give 5.95 g of crude residue. It was purified by flash chromatography (Biotage SNAP Cartridge, 50 g of silica-petroleum ether/ethyl acetate 99:1) to give 2.65 g of yellow impure oil. A second flash chromatography (Biotage SNAP Cartridge, 50 g of silica-petroleum ether) gave 1.365 g (yield 32%) of crystallising yellow oil corresponding to Benzenamine, 2-trifluoromethyl-N-[1-(4-bromo-phenyl)ethylidene]-.

$^1$H NMR (300 MHz, CDCl$_3$).

VIII-2/ 2-(4-bromo-phenyl)-4-tert-butoxy-quinoline

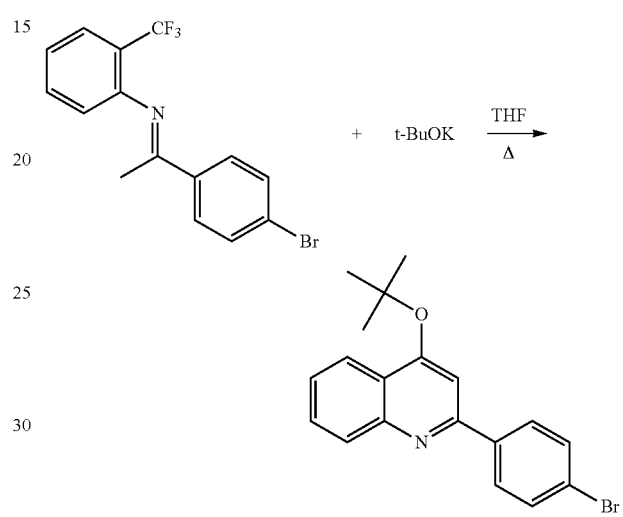

To a solution of 1.36 g (3.974 mmol) of Benzenamine, 2-trifluoromethyl-N-[1-(4-bromo-phenyl)ethylidene] in 68 ml of dry THF, 2.11 g of potassium tert-butylate were added and the mixture was stirred for 1 h under reflux. The mixture was quenched with water, both layers were separated and aqueous layer was extracted with dichloromethane. The combined organic layer was dried over MgSO$_4$, filtered and concentrated to give 1.36 g of orange oil. The crude compound was purified by a silica gel column chromatography (petroleum ether/ethyl acetate 98:2) to give 0.744 g (yield 52%) of yellow oil corresponding to 2-(4-bromo-phenyl)-4-tert-butoxy-quinoline.

HPLC-MS: conditions D: $t_r$=7.08 min, (ES+) $C_{19}H_{18}BrNO$ requires 355/357; found 356/358 [M+H].
$^1$H NMR (300 MHz, CDCl$_3$).

VIII-3/ 2-(4-bromo-phenyl)-4-hydroxy-quinoline

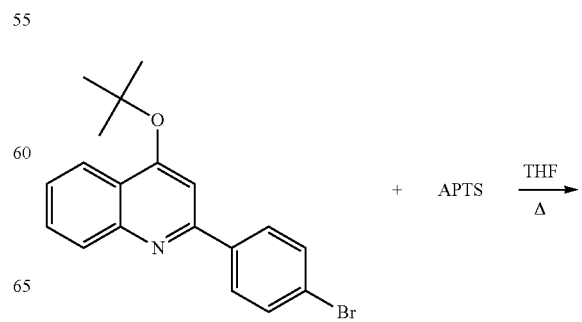

-continued

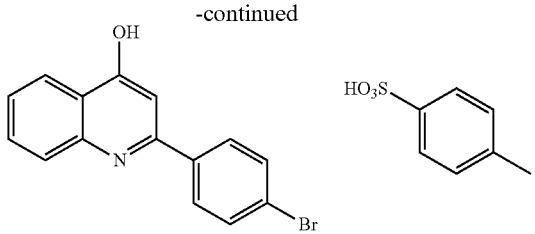

To a solution of 0.74 g (2.077 mmol) of 2-(4-bromo-phenyl)-4-tert-butoxy-quinoline in 19 ml of THF, 0.593 g of p-toluenesulfonic acid monohydrate was added and the mixture was heated for 4 h under reflux. After cooling the mixture, a white solid compound was filtered, washed with THF and dried to recover 0.810 g (yield 82%) of grey solid corresponding to the p-toluenesulfonate salt of 2-(4-bromo-phenyl)-4-hydroxy-quinoline.

HPLC-MS: conditions D: $t_r$=6.02 min, (ES+) $C_{15}H_{10}BrNO$ requires 299/301; found 300/302 [M+H].

$^1$H NMR (300 MHz, DMSO-$d_6$).

VIII-4/ 2-(4-bromo-phenyl)-4-chloro-quinoline

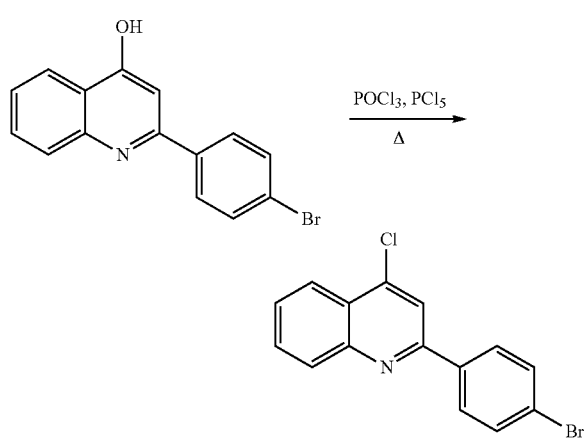

A mixture of 0.805 g (1.704 mmol) of 2-(4-bromo-phenyl)-4-hydroxy-quinoline, 8.05 ml of phosphoryl chloride and 355 mg (1.704 mmol) of phosphorus pentachloride were refluxed for 1 h under argon and the solution was poured slowly into water after cooling (effervescence) and then sodium bicarbonate was carefully added. The solid compound obtained was filtered and washed with water, then solubilized in hot ethyl acetate. The solution was dried over MgSO$_4$, filtered and concentrated on a rotary evaporator to give 576 mg of beige impure solid. The compound was purified by a silica gel column chromatography (dichloromethane 100%) to give 498 mg (yield 91%) of white solid compound corresponding to 2-(4-bromo-phenyl)-4-chloro-quinoline.

HPLC-MS: conditions D: $t_r$=11.62 min, (ES+) $C_{15}H_9BrClN$ requires 317/319; found 318/320 [M+H].

$^1$H NMR (300 MHz, CDCl$_3$).

VIII-5/ 2-(4-bromo-phenyl)-4-(4-N,N-diethylamino-piperidin-1-yl)quinolone (VIII-5)

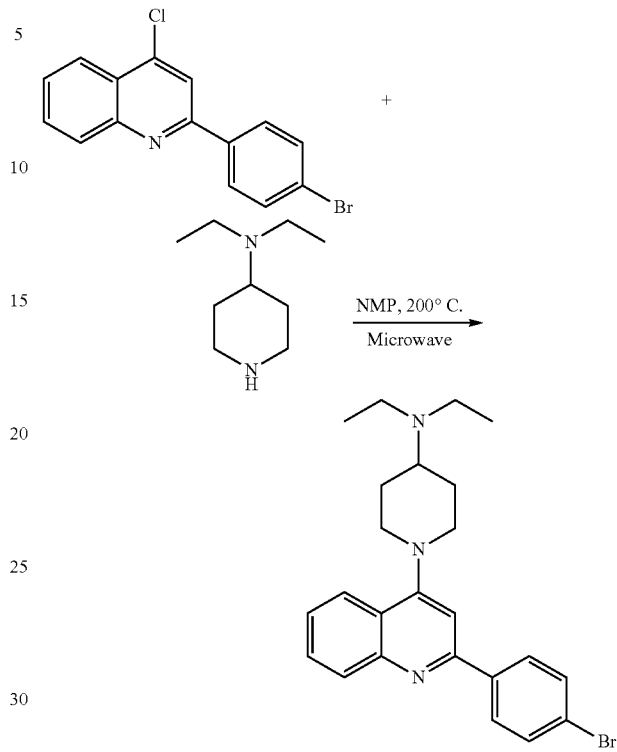

In a microwave vial were successively added, 490 mg (1.537 mmol) of 2-(4-bromo-phenyl)-4-chloro-quinoline, 490 mg (1.537 mmol) of 4-diethylamino-piperidine and 10 ml of NMP. The solution was heated for 30 min at 200° C. in a microwave oven and treated with a 1N NaOH aqueous solution. The mixture was extracted with ethyl acetate and the organic layer was dried over MgSO$_4$, filtered and concentrated to give 740 mg of an oily brown residue. This product was purified by silica gel column chromatography (dichloromethane/methanol 98:2 then 96:4) to give 477 mg (yield 70%) of a yellow solid compound corresponding to 2-(4-bromo-phenyl)-4-(4-N,N-diethylamino-piperidin-1-yl)quinoline.

HPLC-MS: conditions D: $t_r$=4.60 min, (ES+) $C_{24}H_{28}BrN_3$ requires 437/439; found 438/440 [M+H].

$^1$H NMR (300 MHz, CDCl$_3$).

VIII-6/ 2-(4-bromo-phenyl)-4-(4-N,N-diethylamino-piperidin-1-yl)-quinoline dihydrochloride (VIII-6)

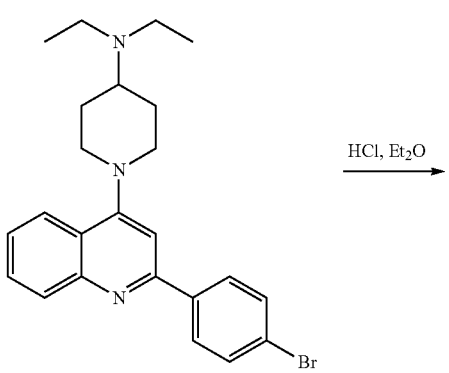

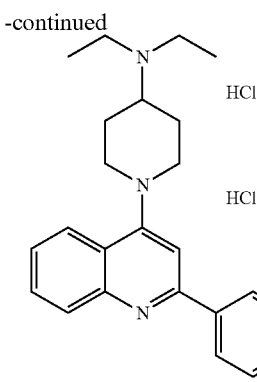

To a solution of 30 mg (0.068 mmol) of 2-(4-bromo-phenyl)-4-(4-N,N-diethylamino-piperidin-1-yl)quinoline in 200 μl of dry dichloromethane was added under argon, 140 μl (0.137 mmol) of a solution of 1N HCl in ether. The solution was stirred for 1 h at room temperature, concentrated and the residue solubilized in ethanol. Petroleum ether was added slowly to precipitate a crude solid. This product was dissolved in pure water and the solution filtered on Nalgene 0.2 μm PTFE seringue filter then freeze-dried to give 27 mg (yield 84%) of a yellow solid compound corresponding to 2-(4-bromo-phenyl)-4-(4-N,N-diethyl-amino-piperidin-1-yl)quinoline dihydrochloride.

HPLC-MS: conditions F: $t_r$=4.58 min, (ES+) $C_{24}H_{28}BrN_3$ requires 437/439; found 438/440 [M+H].

$^1$H NMR (300 MHz, DMSO-$d_6$).

$^1$H NMR (300 MHz, DMSO-$d_6$+$D_2O$).

EXAMPLE 9

Preparation of 2-(1,1'-biphenyl)-4-yl-4-(4-N,N-diethylamino-piperidin-1-yl)quinoline hydrochloride salt (IX-2)

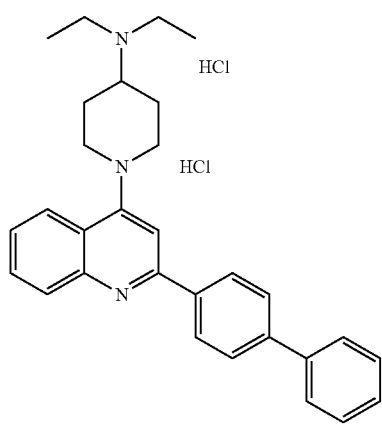 [SMILES: CCN(CC)C1CCN(c2cc(-c3ccc(-c4ccccc4)cc3)nc3ccccc23)CC1 ; Cl ; Cl]

IX-1/ 2-(1,1'-biphenyl)-4-yl-4-(4-N,N-diethylamino-piperidin-1-yl)quinoline (IX-1)

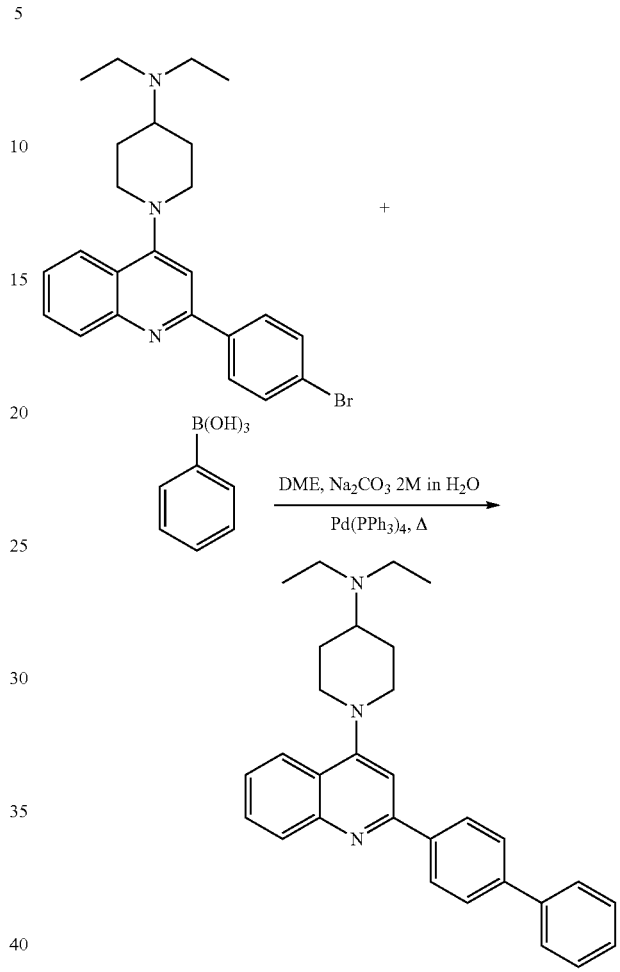

To 1 ml of 1,2-diméthoxyéthane was added successively under argon: 252 mg (0.575 mmol) of 2-(4-bromo-phenyl)-4-(4-N,N-diethylamino-piperidin-1-yl)quinoline, 76 mg (0.627 mmol) of phenylboronic acid, 20 mg (0.017 mmol) of Tetrakis(triphenylphosphine)palladium (0), then 800 μl (1.059 mmol) of a 2M $Na_2CO_3$ aqueous solution. The mixture was stirred for 4 h30 under reflux, concentrated and taken up in ethyl acetate and a 1M $Na_2CO_3$ aqueous solution. Both layers were separated and the organic layer was washed with water, dried over $MgSO_4$, filtered and concentrated to give 404 mg of brown oil. This product was purified by silica gel column chromatography (dichloromethane/methanol 95:5) to give 118 mg (yield 48%) of beige oil corresponding to 2-(1,1'-biphenyl)-4-yl-4-(4-N,N-diethyl-amino-piperidin-1-yl)quinoline.

HPLC-MS: conditions F: $t_r$=5.26 min, (ES+) $C_{30}H_{33}N_3$ requires 435; found 436 [M+H].

$^1$H NMR (300 MHz, $CDCl_3$).

IX-2/ 2-(1,1'-biphenyl)-4-yl-4-(4-N,N-diethylamino-piperidin-1-yl)quinoline dihydrochloride (IX-2)

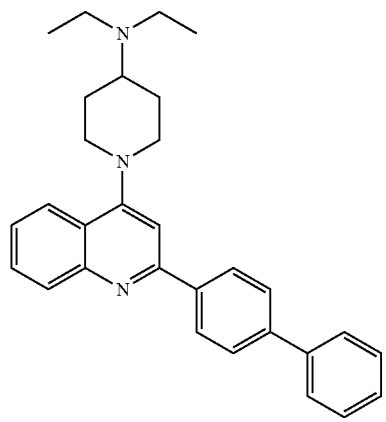

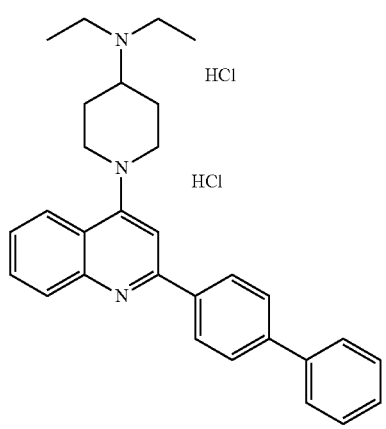

To a solution of 111 mg (0.254 mmol) of 2-(1,1'-biphenyl)-4-yl-4-(4-N,N-diethylamino-piperidin-1-yl)quinoline in 500 µl of dry dichloromethane was added under argon, 510 µl (0.509 mmol) of a solution of 1N HCl in ether. The solution was stirred for 1 h at room temperature, concentrated and the residue solubilized in dichloromethane. Petroleum ether was added slowly to precipitate a crude solid; this product was dissolved in pure water, and the solution was filtered on Nalgene 0.2 µm PTFE seringue filter then freeze-dried to give 86 mg (yield 66%) of a yellow solid corresponding to 2-(1,1'-biphenyl)-4-yl-4-(4-N,N-diethylamino-piperidin-1-yl)quinoline dihydrochloride.

HPLC-MS: conditions D: $t_r$=5.30 min, (ES+) $C_{30}H_{33}N_3$ requires 435; found 436 [M+H].

$^1$H NMR (300 MHz, DMSO-$d_6$).

$^1$H NMR (300 MHz, DMSO-$d_6$+$D_2O$).

EXAMPLE 10

Preparation of 2-(4-chloro-phenyl)-4-(4-N,N-diethylamino-piperidin-1-yl)quinoline hydrochloride salt (X-6)

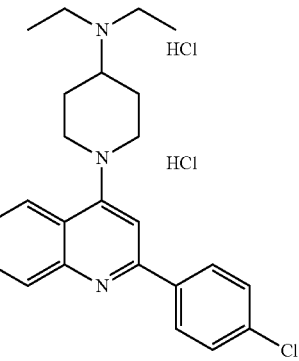

X-1/ benzenamine, 2-trifluoromethyl-N-[1-(4-chlorophenyl)ethylidene]-

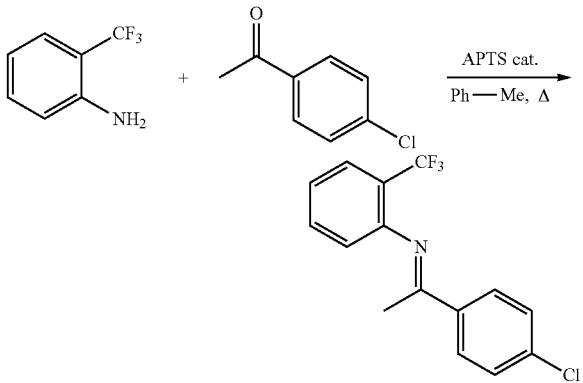

In a round bottom flask equipped with a Dean Stark apparatus was successively added under argon, 2.0 g (12.41 mmol) of 2-(trifluoromethyl)-aniline, 2.09 ml (16.13 mmol) of 4'-chloroacetophenone, 60 mg of p-toluenesulfonic acid monohydrate and 60 ml of dry toluene. The mixture was heated for 24 h under reflux and concentrated to give 4.05 g of crude orange oil. This product was purified by flash chromatography (Biotage SNAP Cartridge, 150 g of silica-petroleum ether/ethyl acetate 98:2) to give 0.94 g of orange oil. This product was then purified again by silica gel column chromatography (petroleum ether/ethyl acetate 99:1) to give 857 mg (yield 23%) of orange oil corresponding to benzenamine, 2-trifluoromethyl-N-[1-(4-chlorophenyl)ethylidene]-.

$^1$H NMR (300 MHz, CDCl$_3$).

X-2/ 2-(4-chloro-phenyl)-4-tert-butoxy-quinoline

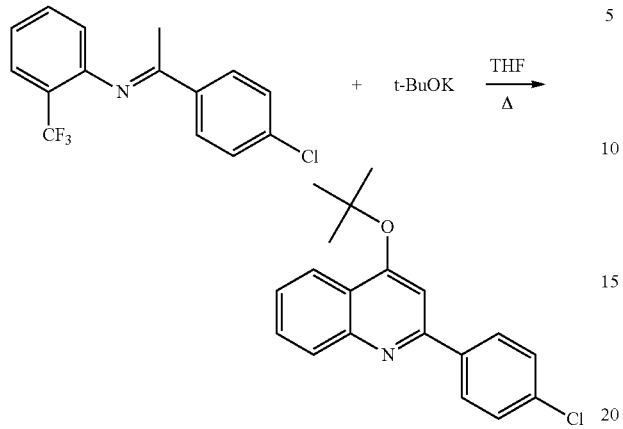

To a solution of 0.857 g (2.88 mmol) of benzenamine, 2-trifluoromethyl-N-[1-(4-chlorophenyl)ethylidene]- in 43 ml of dry THF, 1.53 g (13.53 mmol) of potassium tert-butylate was added and the mixture was stirred for 40 min under reflux. The mixture was quenched with water, both layers were separated and the aqueous layer was extracted with dichloromethane. The combined organic layers were dried over MgSO$_4$, filtered and concentrated to give 0.91 g of orange oil. The crude compound was purified by flash chromatography (Biotage SNAP Cartridge, 72 g of silica-petroleum ether/ethyl acetate 99:1) to give 249 mg (yield 27%) of orange oil corresponding to 2-(4-chloro-phenyl)-4-tert-butoxy-quinoline.

HPLC-MS: conditions D: t$_r$=6.97 min, (ES+) C$_{19}$H$_{18}$ClNO requires 311; found 312 [M+H].

$^1$H NMR (300 MHz, CDCl$_3$).

X-3/ 2-(4-chloro-phenyl)-4-hydroxy-quinoline

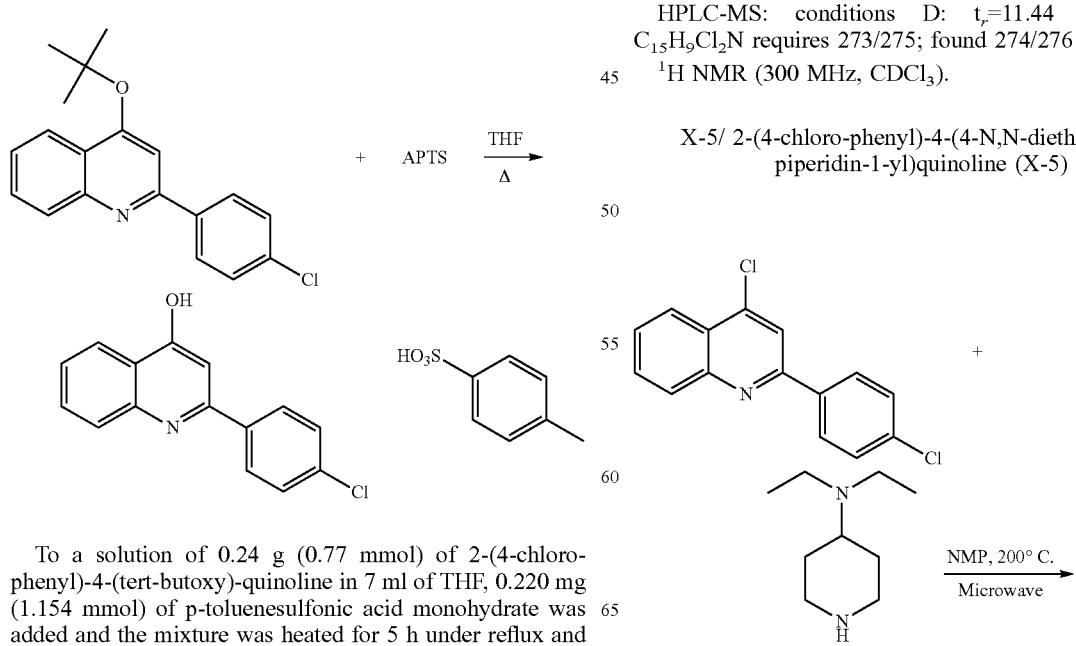

To a solution of 0.24 g (0.77 mmol) of 2-(4-chloro-phenyl)-4-(tert-butoxy)-quinoline in 7 ml of THF, 0.220 mg (1.154 mmol) of p-toluenesulfonic acid monohydrate was added and the mixture was heated for 5 h under reflux and concentrated under vacuum. 0.604 g of crude 2-(4-chloro-phenyl)-4-hydroxy-quinoline was recovered and used in the next step without any purification.

HPLC-MS: conditions D: t$_r$=5.85 min, (ES+) C$_{15}$H$_{10}$ClNO requires 255; found 256 [M+H].

$^1$H NMR (300 MHz, DMSO-d$_6$).

X-4/ 2-(4-chloro-phenyl)-4-chloro-quinoline

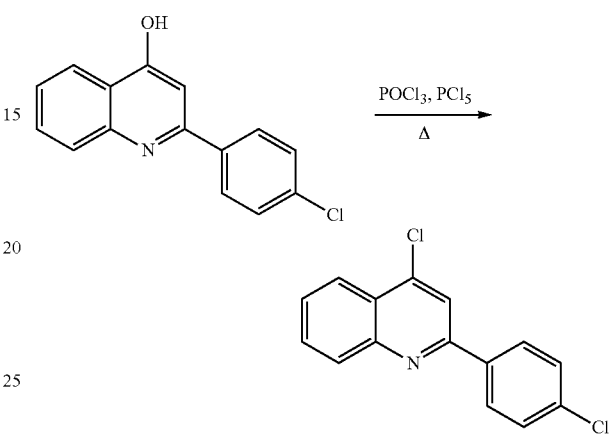

A mixture of 0.329 g (0.77 mmol) of 2-(4-chloro-phenyl)-4-hydroxy-quinoline, 3.3 ml of phosphoryl chloride and 100 mg (0.77 mmol) of phosphorus pentachloride were refluxed for 1 h under argon and the solution was poured slowly into water after cooling (effervescence) and then sodium bicarbonate was carefully added. The solid compound obtained was filtered and washed with water, then solubilized in hot ethyl acetate. The solution was dried over MgSO$_4$, filtered and concentrated on a rotary evaporator to give 506 mg of beige impure solid compound. This compound was purified by a silica gel column chromatography (dichloromethane 100%) to give 0.203 g (yield 96%) of white solid compound corresponding to 2-(4-chloro-phenyl)-4-chloro-quinoline.

HPLC-MS: conditions D: t$_r$=11.44 min, (ES+) C$_{15}$H$_9$Cl$_2$N requires 273/275; found 274/276 [M+H].

$^1$H NMR (300 MHz, CDCl$_3$).

X-5/ 2-(4-chloro-phenyl)-4-(4-N,N-diethylamino-piperidin-1-yl)quinoline (X-5)

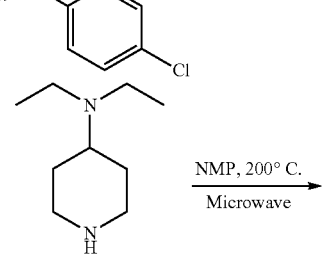

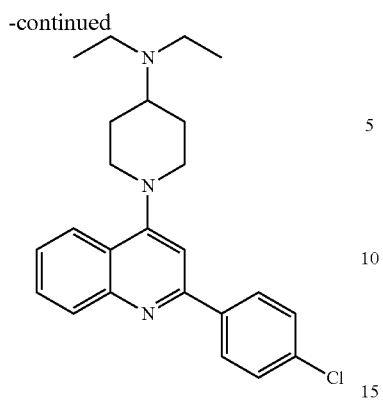

In a microwave vial was successively added, 200 mg (0.73 mmol) of 2-(4-chloro-phenyl)-4-chloro-quinoline, 342 mg (2.19 mmol) of 4-diethylamino-piperidine and 4 ml of NMP. The solution was heated for 30 min at 200° C. in a microwave oven and then treated with a 1N NaOH aqueous solution. The mixture was extracted with ethyl acetate and the organic layer dried over MgSO₄, filtered and concentrated to give 306 mg of an oily brown residue. This product was purified by silica gel column chromatography (dichloromethane/methanol 99:1 then 99:1+NH₄OH) to give 180 mg of impure orange oil. This product was then purified again by silica C18 reversed-phase column Biotage (12 g—gradient water/methanol 99:1 to methanol 100%) to give 110 mg (yield 38%) of yellow oil corresponding to 2-(4-chloro-phenyl)-4-(4-N,N-diethylamino-piperidin-1-yl)quinoline.

HPLC-MS: conditions D: $t_r$=4.43 min, (ES+) $C_{24}H_{28}ClN_3$ requires 393/395; found 394/396 [M+H].

$^1$H NMR (300 MHz, CDCl₃).

X-6/ 2-(4-chloro-phenyl)-4-(4-N,N-diethylamino-piperidin-1-yl)quinoline dihydrochloride (X-6)

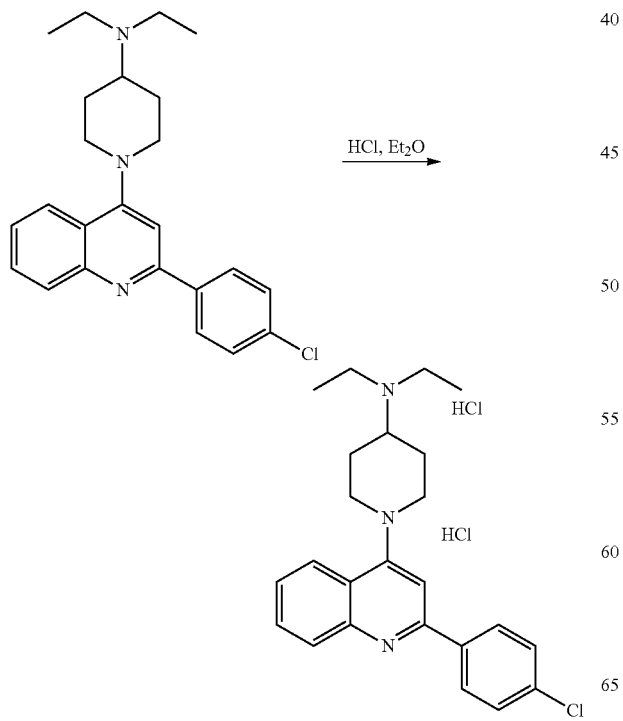

To a solution of 104 mg (0.264 mmol) of 2-(4-chloro-phenyl)-4-(4-N,N-diethylamino-piperidin-1-yl)quinoline in 400 µl of dry dichloromethane was added under argon, 528 µl (0.528 mmol) of a solution of 1N HCl in ether. The solution was stirred for 1 h at room temperature, concentrated and the residue crystallized in ethanol to give 64 mg (yield 56%) of a pale yellow solid compound corresponding to 2-(4-chloro-phenyl)-4-(4-N,N-diethylamino-piperidin-1-yl)quinoline dihydrochloride.

HPLC-MS: conditions D: $t_r$=4.52 min, (ES+) $C_{24}H_{28}ClN_3$ requires 393/395; found 394/396 [M+H].

$^1$H NMR (300 MHz, DMSO-d₆).

$^1$H NMR (300 MHz, DMSO-d₆+D₂O).

EXAMPLE 11

Preparation of 2-(1,1'-biphenyl)-4-yl-7-chloro-4-(4-N,N-diethylamino-piperidin-1-yl)quinoline hydrochloride salt (XI-2)

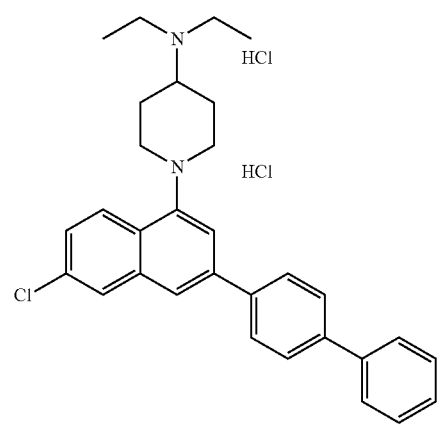 [SMILES: CCN(CC)C1CCN(c2cc(-c3ccc(-c4ccccc4)cc3)cc3cc(Cl)ccc23)CC1 ; Cl ; Cl]

XI-1/ 2-[(1,1'-biphenyl)-4-yl]-7-chloro-4-(4-N,N-diethylamino-piperidin-1-yl)quinoline (XI-1)

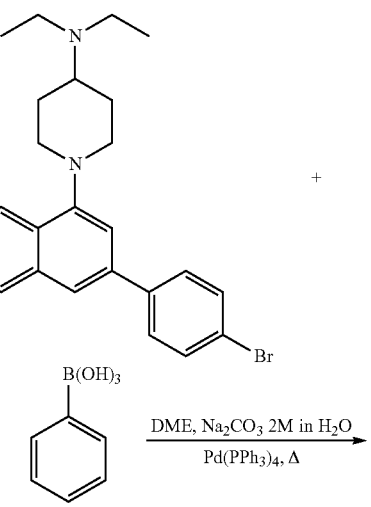

59

-continued

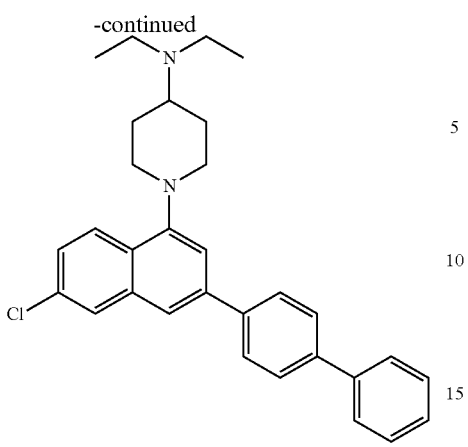

60

-continued

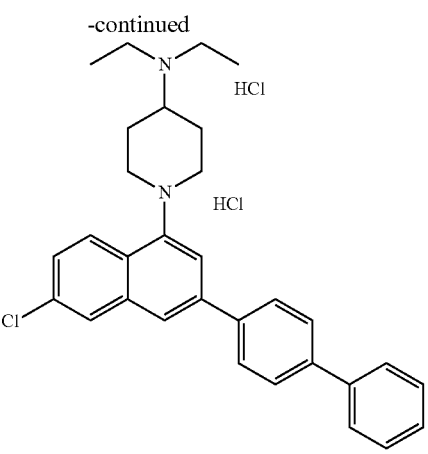

To 2 ml of 1,2-diméthoxyéthane were added successively under argon: 85 mg (0.18 mmol) of 2-(4-bromo-phenyl)-7-chloro-4-(4-N,N-diethylamino-piperidin-1-yl)quinoline (VII-4, see paragraph VII-4), 24 mg (0.197 mmol) of phenylboronic acid, 6 mg (0.0054 mmol) of Tetrakis(triphenylphosphine)palladium (0), then 252 µl (0.503 mmol) of a 2M $Na_2CO_3$ aqueous solution. The mixture was stirred for 5 h under reflux, concentrated and taken up in ethyl acetate and a 1M $Na_2CO_3$ aqueous solution. Both layers were separated and the organic layer was washed with water, dried over $MgSO_4$, filtered and concentrated to give 185 mg of brown residue. This product was purified by flash chromatography (Biotage SNAP Cartridge, 25 g of silica-dichloromethane/methanol 95:5) to give 33 mg (yield 39%) of orange oil corresponding to 2-[(1,1'-biphenyl)-4-yl]-7-chloro-4-(4-N,N-diethylamino-piperidin-1-yl)quinoline.

HPLC-MS: conditions D: $t_r$=5.84 min, (ES+) $C_{31}H_{33}ClN_2$ requires 468/470; found 469/471 [M+H].

$^1$H NMR (300 MHz, $CDL_3$).

XI-2/ 2-[(1,1'-biphenyl)-4-yl]-7-chloro-4-(4-N,N-diethylamino-piperidin-1-yl)quinoline dihydrochloride (XI-2)

To a solution of 32 mg (0.068 mmol) of 2-[(1,1'-biphenyl)-4-yl]-7-chloro-4-(4-N,N-diethylamino-piperidin-1-yl)quinoline in 200 µl of dry dichloromethane was added under argon, 137 µl (0.136 mmol) of a solution of 1N HCl in ether. The solution was stirred for 1 h at room temperature, concentrated and the residue was dissolved in pure water, and the solution filtered on Nalgene 0.2 µm PTFE seringue filter then freeze-dried to give 14.5 mg (yield 39%) of a yellow solid corresponding to 2-(1,1'-biphenyl)-4-yl-7-chloro-4-(4-N,N-diethylamino-piperidin-1-yl)quinoline dihydrochloride.

HPLC-MS: conditions D: $t_r$=5.80 min, purity 80% (ES+) $C_{31}H_{33}ClN_2$ requires 468/470; found 469/471 [M+H].

$^1$H NMR (300 MHz, DMSO-$d_6$)+impurities (purity 80%).

$^1$H NMR (300 MHz, DMSO-$d_6$+$D_2O$)+impurities (purity 80%).

EXAMPLE 12

Preparation of 2-(4-chloro-phenyl)-4-(4-N-tert-butylamino-piperidin-1-yl)quinoline hydrochloride salt (XII-4)

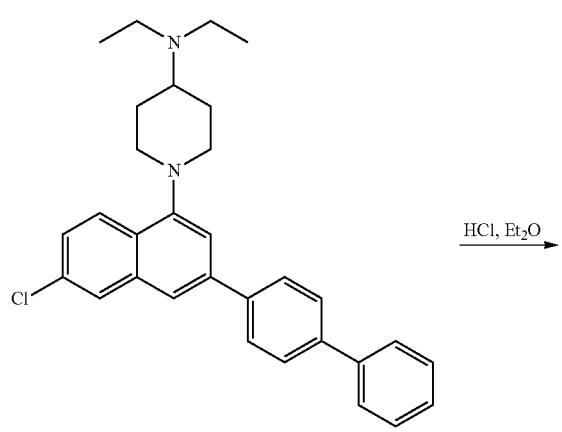

HCl, $Et_2O$ →

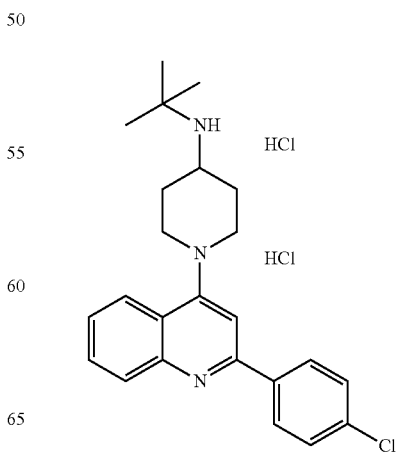

XII-1/ 2-(4-chloro-phenyl)-4-(1,4-dioxa-8-aza-spiro[4,5]dec-8-yl)quinoline

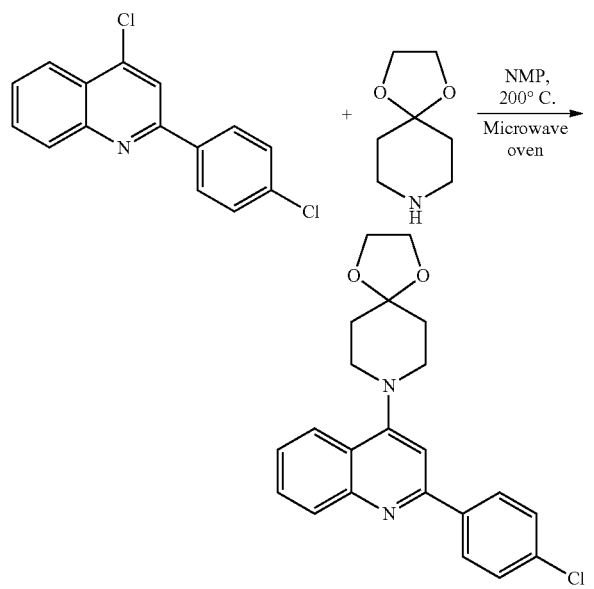

In a microwave vial was successively added: 0.4 g (1.46 mmol) of 2-(4-chloro-phenyl)-4-chloro-quinoline prepared according to the protocol described paragraph X-4, 940 µl (7.3 mmol) of 1,4-dioxa-8-azaspiro[4,8]decane and 300 µl of NMP. The solution was heated for 30 min at 200° C. in a microwave oven and treated with a 1N NaOH aqueous solution. The mixture was extracted with ethyl acetate and the organic layer was dried over MgSO$_4$, filtered and concentrated to give 1.46 g of brown oil. This product was purified by silica gel column chromatography (petroleum ether/ethyl acetate 95:5) to give 462 mg (yield 83%) of a beige solid corresponding to 2-(4-chloro-phenyl)-4-(1,4-dioxa-8-aza-spiro[4,5]dec-8-yl)quinoline.

HPLC-MS: conditions D: t$_r$=6.35 min, (ES+) C$_{22}$H$_{21}$ClN$_2$O$_2$ requires 380/382; found 381/383 [M+H].

$^1$H NMR (300 MHz, CDCl$_3$).

XII-2/ 2-(4-chloro-phenyl)-quinoline-4-yl)-piperidin-4-one

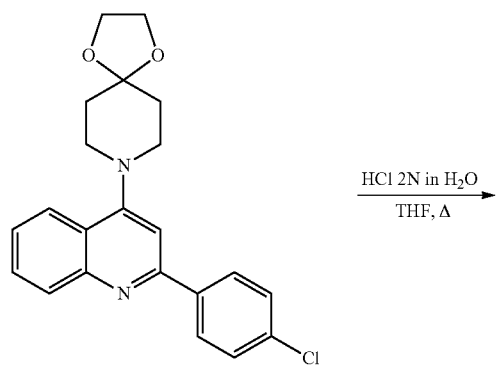

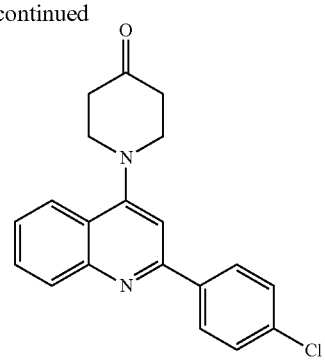

To a solution of 0.4 g (1.05 mmol) of 2-(4-chloro-phenyl)-4-(1,4-dioxa-8-aza-spiro[4,5]dec-8-yl)quinoline in 800 µl of dry tetrahydrofuran was added 2.4 ml of a 2N HCl aqueous solution. The mixture was stirred for 1 h30 under reflux, then concentrated and treated with a 1N NaOH aqueous solution. The basic mixture was extracted with dichloromethane and the organic layer was dried over MgSO$_4$, filtered and concentrated to give 299 mg of a yellow solid. The crude product was purified by silica C18 reversed-phase column Biotage (31 g—water/methanol 2:8) to give 245 mg (yield 69%) of white solid compound corresponding to 2-(4-chloro-phenyl)-quinoline-4-yl)-piperidin-4-one.

HPLC-MS: conditions D: t$_r$=5.43 min, (ES+) C$_{20}$H$_{17}$ClN$_2$O requires 336/338; found 337/339 [M+H].

$^1$H NMR (300 MHz, CDCl$_3$).

XII-3 2-(4-chloro-phenyl)-4-(4-N-tert-butylamino-piperidin-1-yl)quinoline (XII-3)

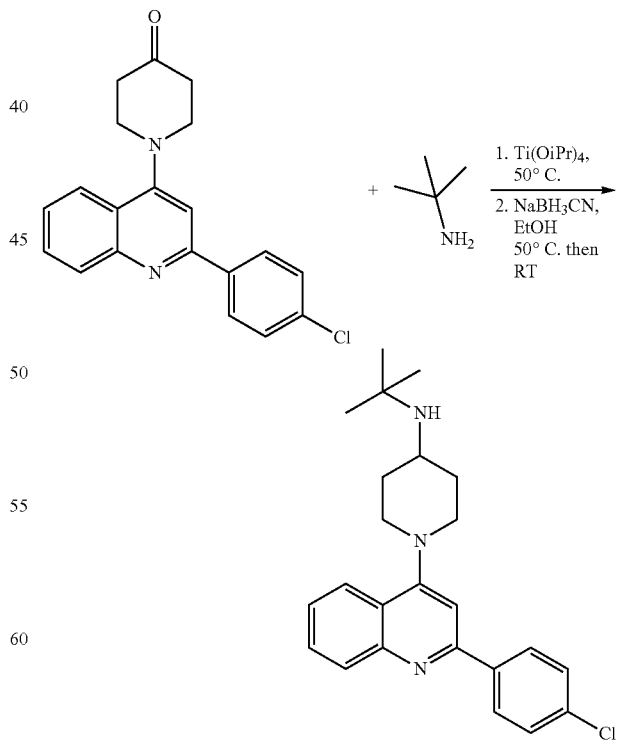

To 240 mg (0.71 mmol) of 2-(4-chloro-phenyl)-quinoline-4-yl)-piperidin-4-one were added under argon, 112 µl (1.07 mmol) of tert-butylamine and 300 μl (0.79 mmol) of titanium (IV) isopropoxide. The resulting mixture was stirred for 15 min at 50° C. The reaction mixture was cooled, diluted with 2 ml of dry ethanol and 99 mg (1.57 mmol) of sodium cyanoborohydride were added and the resulting mixture was stirred for 3 h30 at 50° C., then 20 h at room temperature. The mixture was poured into 30 ml of water, stirred for 1 h at room temperature, filtrated through a Celite® pad and the filtrate was extracted with dichloromethane. The organic layer was washed with brine, dried over MgSO$_4$, filtered and concentrated to give 287 mg of a residue. This crude product was purified by silica gel column chromatography (dichloromethane/methanol 9:1) to give 136 mg of impure yellow oil. This product was purified by silica C18 reversed-phase column Biotage (13 g—water/methanol (containing 5% of triethylamine) 3:7 to give 78 mg (yield 28%) of clear oil corresponding to 2-(4-chloro-phenyl)-4-(4-N-tert-butylamino-piperidin-1-yl)quinoline.

HPLC-MS: conditions D: t$_r$=4.67 min, (ES+) C$_{24}$H$_{28}$ClN$_3$ requires 393/395; found 394/396 [M+H].

$^1$H NMR (300 MHz, CDCl$_3$).

XII-4 2-(4-chloro-phenyl)-4-(4-N-tert-butylamino-piperidin-1-yl)quinoline dihydrochloride (XII-4)

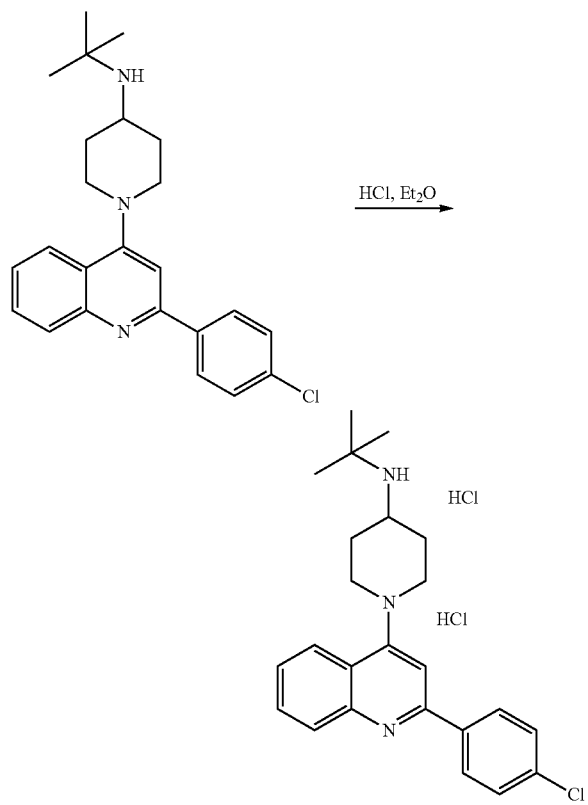

To a solution of 78 mg (0.2 mmol) of 2-(4-chloro-phenyl)-4-(4-N-tert-butylamino-piperidin-1-yl)quinoline in 300 μl of dry dichloromethane was added under argon, 400 μl (0.4 mmol) of a 1N solution of HCl in ether. The solution was stirred for 1 h at room temperature, concentrated and the residue was washed three times with ether. The crude solid was dissolved in pure water, and the solution was filtered on Nalgene 0.2 μm PTFE syringe filter and then freeze-dried to give 79 mg (yield 86%) of a yellow solid compound corresponding to 2-(4-chloro-phenyl)-4-(4-N-tert-butylamino-piperidin-1-yl)quinoline dihydrochloride.

HPLC-MS: conditions D: t$_r$=4.65 min, (ES+) C$_{24}$H$_{28}$ClN$_3$ requires 393/395; found 394/396 [M+H].

$^1$H NMR (300 MHz, DMSO-d$_6$).

$^1$H NMR (300 MHz, DMSO-d$_6$+D$_2$O).

EXAMPLE 13

Preparation of 2-(4-methyl-phenyl)-4-(4-N-tert-butylamino-piperidin-1-yl)quinoline hydrochloride salt (XIII-8)

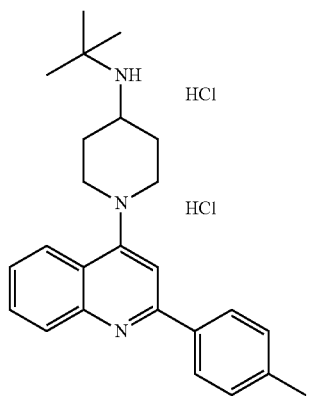 [SMILES: Cc1ccc(-c2cc(N3CCC(NC(C)(C)C)CC3)c3ccccc3n2)cc1 ; Cl ; Cl]

XIII-1/ benzenamine, 2-trifluoromethyl-N-[1-(4-methylphenyl)ethylidene]-

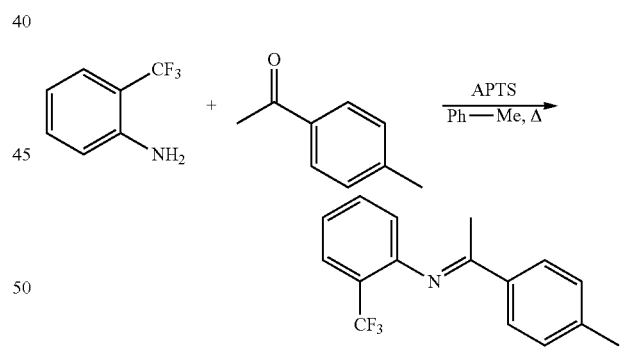

In a round bottom flask equipped with a Dean Stark apparatus was successively added under argon, 15 g (93 mmol) of 2-(trifluoromethyl)-aniline, 16 ml (121 mmol) of 4'-methylacetophenone, 500 mg of p-toluenesulfonic acid monohydrate and 400 ml of dry toluene. The mixture was heated for 48 h under reflux with azeotropic removal of water and concentrated to give 28 g of crude orange oil. This product was purified by flash chromatography (Biotage SNAP Cartridge, 340 g of silica-petroleum ether/ethyl acetate 99:1) to give 4.05 g of orange oil corresponding to benzenamine, 2-trifluoromethyl-N-[1-(4-methylphenyl)ethylidene]-.

$^1$H NMR (300 MHz, CDCl$_3$).

XIII-2/ 2-(4-methyl-phenyl)-4-(tert-butoxy)-quinoline

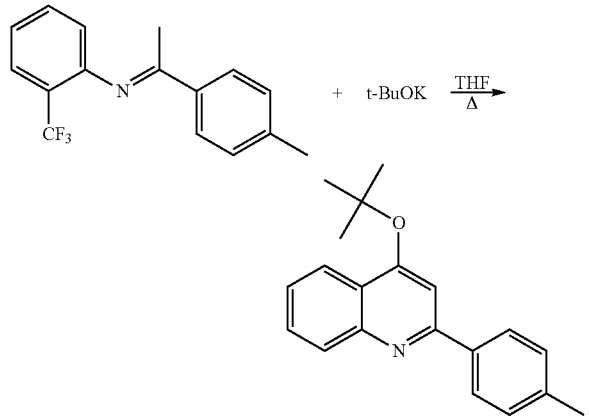

To a solution of 4.9 g (17.7 mmol) of benzenamine, 2-trifluoromethyl-N-[1-(4-methylphenyl)ethylidene]- in 100 ml of dry THF, 9.4 g (83 mmol) of potassium tert-butylate were added under argon and the mixture was stirred for 1 h30 under reflux. The mixture was quenched with water, both layers were separated and the aqueous layer was extracted with ethyl acetate. The organic layer was dried over MgSO$_4$, filtered and concentrated to give 5 g of orange oil. The crude compound was purified by flash chromatography (Biotage SNAP Cartridge, 100 g of silica-petroleum ether/ethyl acetate 99:1) to give 2.39 g (yield 7% with previous imine synthesis step) of orange oil corresponding to 2-(4-methyl-phenyl)-4-(tert-butoxy)-quinoline.

HPLC-MS: conditions D: t$_r$=6.83 min, (ES+) C$_{20}$H$_{21}$NO requires 291; found 292 [M+H].

$^1$H NMR (300 MHz, CDCl$_3$).

XIII-3/ 2-(4-methyl-phenyl)-4-hydroxy-quinoline

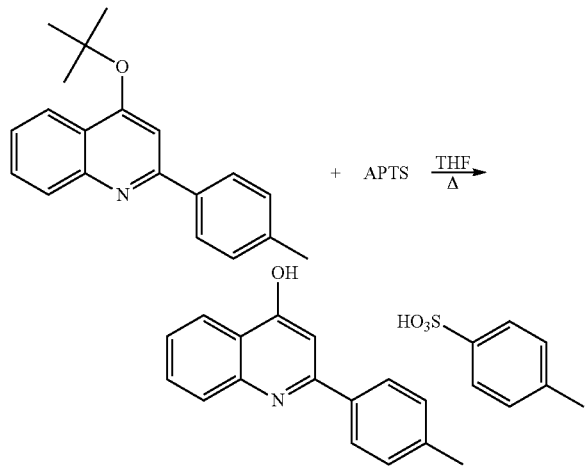

To a solution of 2.2 g (7.5 mmol) of 2-(4-methyl-phenyl)-4-(tert-butoxy)-quinoline in 40 ml of THF, 2.15 g (11.3 mmol) of p-toluenesulfonic acid monohydrate were added and the mixture was heated for 17 h under reflux and then concentrated under vacuum to precipitate the compound. The precipitate was washed with ethyl acetate to give 2.55 g (yield 83%) of white solid compound corresponding to the p-toluenesulfonate salt of 2-(4-methyl-phenyl)-4-hydroxy-quinoline.

HPLC-MS: conditions D: t$_r$=5.56 min, (ES+) C$_{16}$H$_{13}$NO requires 235; found 236 [M+H].

$^1$H NMR (300 MHz, DMSO-d$_6$).

XIII-4/ 2-(4-methyl-phenyl)-4-chloro-quinoline

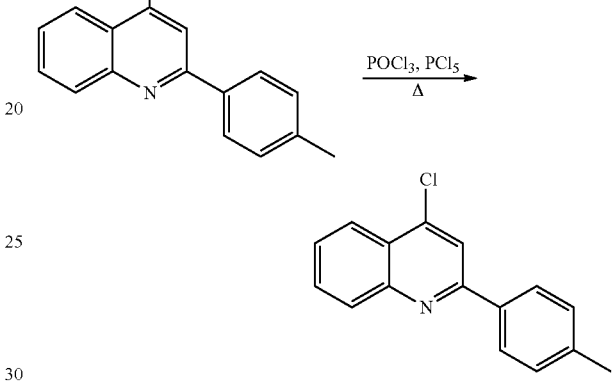

A mixture of 2.55 g (6.26 mmol) of 2-(4-methyl-phenyl)-4-hydroxy-quinoline, 20 ml of phosphoryl chloride and 1.3 g (6.26 mmol) of phosphorus pentachloride was refluxed for 2 h30 under argon and the solution was poured slowly onto water after cooling (effervescence). To neutralize the mixture, sodium bicarbonate then and successively: 1N, 5N and 10N NaOH aqueous solutions and then concentrated KOH aqueous solution were carefully added. The aqueous layer was extracted with ethyl acetate and organic layer was washed with water, dried over MgSO$_4$, filtered and concentrated on a rotary evaporator to give 2.1 g of clear oil. This compound was purified by silica gel column chromatography (cyclohexane/ethyl acetate 99:1) to give 0.879 g (yield 55%) of a white solid compound corresponding to 2-(4-methyl-phenyl)-4-chloro-quinoline.

HPLC-MS: conditions D: t$_r$=7.64 min, (ES+) C$_{16}$H$_{12}$ClN requires 253/255; found 254/256 [M+H].

$^1$H NMR (300 MHz, CDCl$_3$).

XIII-5/ 2-(4-methyl-phenyl)-4-(1,4-dioxa-8-azaspiro[4,5]dec-8-yl)quinoline

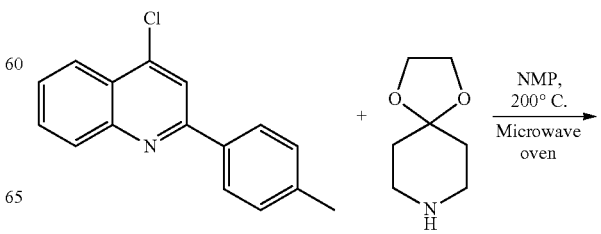

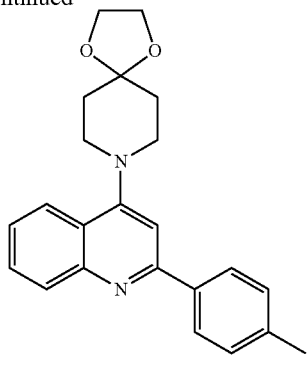

In a microwave vial was successively added: 0.4 g (1.58 mmol) of 2-(4-methyl-phenyl)-4-chloro-quinoline, 1 ml (7.88 mmol) of 1,4-dioxa-8-azaspiro[4,8]decane and 500 µl of NMP. The solution was heated for 30 min at 200° C. in a microwave oven and then treated with a 1N NaOH aqueous solution. The mixture was extracted with ethyl acetate and the organic layer dried over MgSO$_4$, filtered and concentrated to give 1.3 g of yellow oil.

This product was purified by silica gel column chromatography (petroleum ether/ethyl acetate 9:1) to give 456 mg (yield 80%) of solidified oil corresponding to 2-(4-methyl-phenyl)-4-(1,4-dioxa-8-aza-spiro[4,5]dec-8-yl)quinoline.

HPLC-MS: conditions D: t$_r$=6.59 min, (ES+) C$_{23}$H$_{24}$N$_2$O$_2$ requires 360; found 361 [M+H].
$^1$H NMR (300 MHz, CDCL$_3$).

XIII-6/ 2-(4-methyl-phenyl)-quinoline-4-yl)-piperidin-4-one

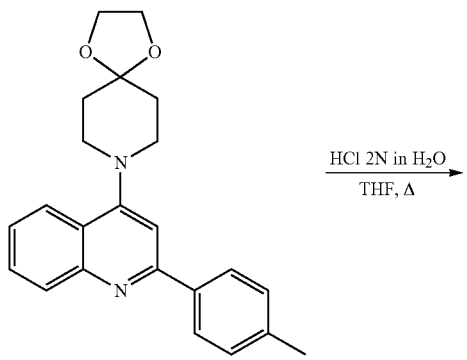

To a solution of 0.333 g (0.92 mmol) of 2-(4-methyl-phenyl)-4-(1,4-dioxa-8-aza-spiro[4,5]dec-8-yl)quinoline in 2 ml of dry tetrahydrofuran was added 2.1 ml of a 2N HCl aqueous solution. The mixture was stirred for 2 h under reflux then concentrated and treated with a 5N NaOH aqueous solution. The basic mixture was extracted with dichloromethane and the organic layer was dried over MgSO$_4$, filtered and concentrated to give 279 mg (yield 96%) of a beige solid compound corresponding to 2-(4-methyl-phenyl)-quinoline-4-yl)-piperidin-4-one.

HPLC-MS: conditions D: t$_r$=5.47 min, (ES+) C$_{21}$H$_{20}$N$_2$O requires 316; found 317 [M+H].
$^1$H NMR (300 MHz, CDCl$_3$).

XIII-7// 2-(4-methyl-phenyl)-4-(4-N-tert-butylamino-piperidin-1-yl)quinoline (XIII-7)

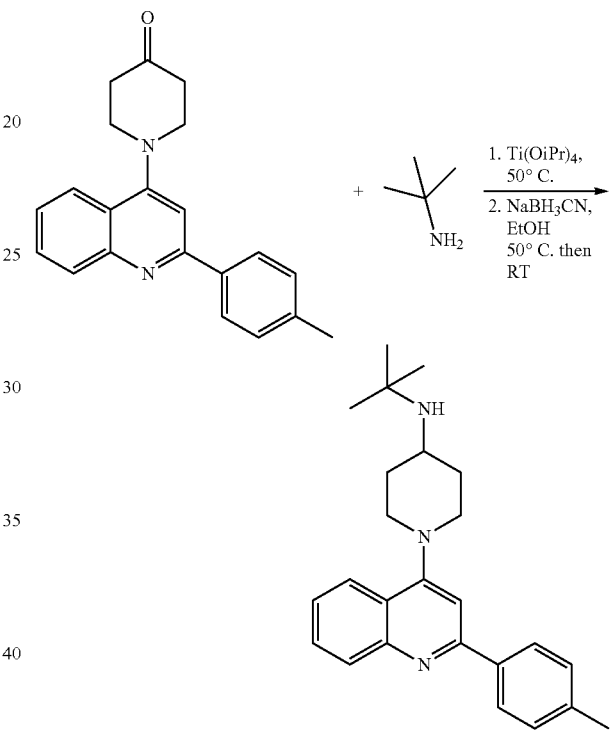

To 279 mg (0.88 mmol) of 2-(4-methyl-phenyl)-quinoline-4-yl)-piperidin-4-one were added under argon, 140 µl (1.32 mmol) of tert-butylamine and 370 µl (0.1.23 mmol) of titanium (IV) isopropoxide. The mixture was stirred for 4 h at 50° C. The reaction mixture was cooled and diluted with 2 ml of dry ethanol. Then, 122 mg (1.94 mmol) of sodium cyanoborohydride were added and the resulting mixture was stirred for 3 h30 at 50° C., and then 20 h at room temperature. The mixture was poured into 37 ml of water, stirred for 1 h at room temperature, filtrated through a Celite® pad and the filtrate was extracted with dichloromethane. The organic layer was washed with brine, dried over MgSO$_4$, filtered and concentrated to give 251 mg of a brown residue. The crude product was purified by silica gel column chromatography (dichloromethane/methanol 95:5) to give 131 mg of impure yellow oil. This product was additionally purified by silica C18 reversed-phase column Biotage (13 g—water/methanol (containing 5% of triethylamine) 3:7) to give 112 mg (yield 28%) of clear oil corresponding to 2-(4-methyl-phenyl)-4-(4-N-tert-butylamino-piperidin-1-yl)quinoline.

HPLC-MS: conditions D: t$_r$=4.55 min, (ES+) C$_{25}$H$_{31}$N$_3$ requires 373; found 374 [M+H].
$^1$H NMR (300 MHz, CDCl$_3$).

69

XIII-8/ 2-(4-methyl-phenyl)-4-(4-N-tert-butylamino-piperidin-1-yl)quinoline dihydrochloride (XIII-8)

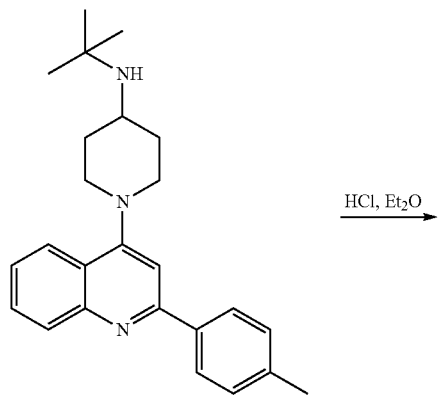

To a solution of 112 mg (0.3 mmol) of 2-(4-methyl-phenyl)-4-(4-N-tert-butylamino-piperidin-1-yl)-quinoline in 500 µl of dry dichloromethane was added under argon, 600 µl (0.6 mmol) of a 1N solution of HCl in ether. The solution was stirred for 1 h at room temperature, concentrated and the residue washed three times with ether to give 91 mg of a yellow solid. This solid was dissolved in pure water and the solution freeze-dried to give 84 mg (yield 63%) of a yellow solid compound corresponding to 2-(4-methyl-phenyl)-4-(4-N-tert-butylamino-piperidin-1-yl)-quinoline dihydrochloride.

HPLC-MS: conditions F: $t_r$=4.62 min, (ES+) $C_{25}H_{31}N_3$ requires 373; found 374 [M+H].

$^1$H NMR (300 MHz, DMSO-$d_6$).
$^1$H NMR (300 MHz, DMSO-$d_6$+$D_2O$).

EXAMPLE 14

Preparation of 2-(3,4-dichloro-phenyl)-4-(4-N-tert-butylamino-piperidin-1-yl)-quinoline hydrochloride salt (XIV-8)

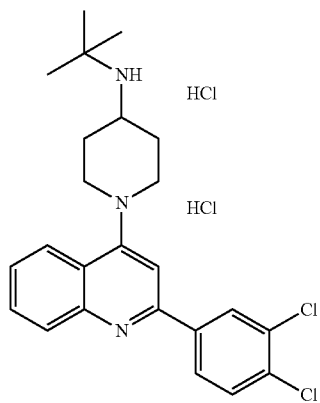 [SMILES: CC(C)(C)NC1CCN(c2cc(-c3ccc(Cl)c(Cl)c3)nc3ccccc23)CC1 ; Cl ; Cl]

70

XIV-1/ Benzenamine, 2-trifluoromethyl-N-[1-(3,4-dichlorophenyl)ethylidene]-

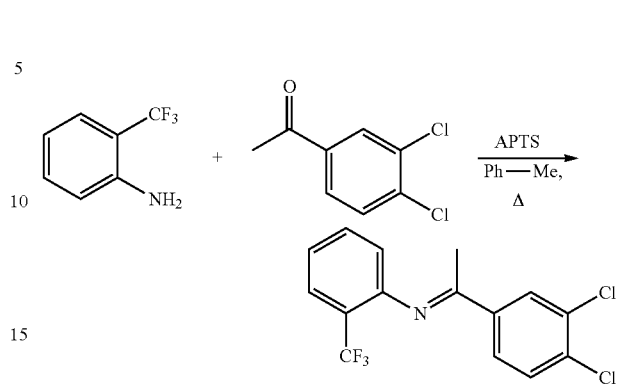

In a round bottom flask equipped with a Dean Stark apparatus was successively added under argon, 20 g (124.1 mmol) of 2-(trifluoromethyl)-aniline, 30.5 g (161.33 mmol) of 3',4'-dichloroacetophenone, 600 mg of p-toluenesulfonic acid monohydrate and 600 ml of dry toluene. The mixture was heated for 24 h under reflux with azeotropic removal of water and concentrated to give crude orange oil. This product was purified by flash chromatography (Biotage SNAP Cartridge, 340 g of silica-petroleum ether/ethyl acetate 99:1) to give 14.38 g (yield 34%) of yellow solid compound corresponding to benzenamine, 2-trifluoromethyl-N-[1-(3,4-dichlorophenyl)ethylidene]-.

$^1$H NMR (300 MHz, CDCl$_3$).

XIV-2/ 2-(3,4-dichloro-phenyl)-4-(tert-butoxy)-quinoline

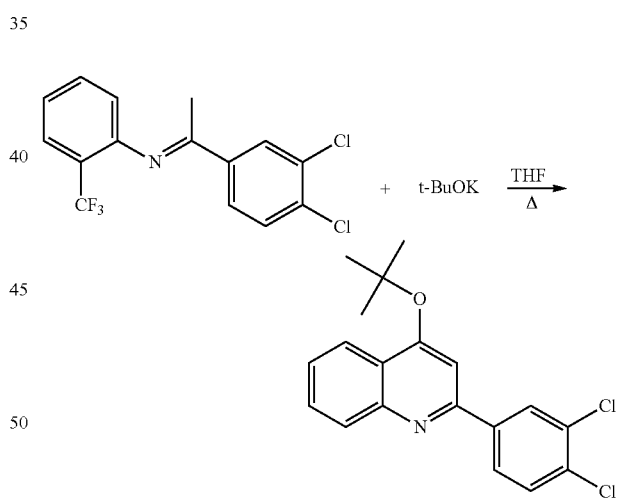

To a solution of 14.3 g (43.05 mmol) of Benzenamine, 2-trifluoromethyl-N-[1-(3,4-dichlorophenyl)ethylidene]- in 715 ml of dry THF, 22.9 g (202.4 mmol) of potassium tert-butylate were added and the mixture was stirred for 1 h under reflux. The reaction mixture was quenched with water, both layers were separated and the aqueous layer was extracted with dichloromethane. The combined organic layers were dried over MgSO$_4$, filtered and concentrated to give 15.1 g of orange oil. The crude compound was purified by flash chromatography (Biotage SNAP Cartridge, 340 g of silica-dichloromethane 100%) to give 10.04 g (yield 67%) of yellow solid compound corresponding to 2-(3,4-dichloro-phenyl)-4-(tert-butoxy)-quinoline.

HPLC-MS: conditions F: $t_r$=6.62 min, (ES+) $C_{19}H_{17}Cl_2NO$ requires 345/347; found 346/348 [M+H].
$^1$H NMR (300 MHz, CDCl$_3$).

XIV-3/ 2-(3,4-dichloro-phenyl)-4-hydroxy-quinoline

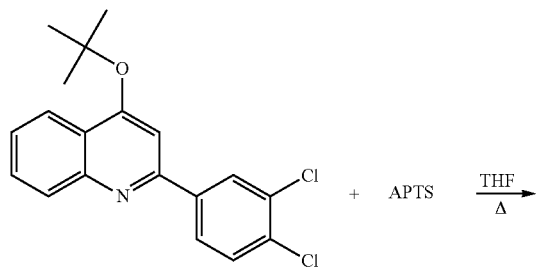

To a solution of 10.04 g (28.99 mmol) of 2-(3,4-dichloro-phenyl)-4-(tert-butoxy)-quinoline in 250 ml of THF, 8.3 g (43.49 mmol) of p-toluenesulfonic acid monohydrate were added and the mixture was heated for 4 h30 under reflux; the precipitate compound obtained after cooling was filtered and washed with THF to give 12.1 g (yield 90%) of colourless solid compound corresponding to the p-toluenesulfonate salt of 2-(3,4-dichloro-phenyl)-4-hydroxy-quinoline.

HPLC-MS: conditions D: $t_r$=6.62 min, (ES+) $Cs_{15}H_9Cl_2NO$ requires 289/291; found 290/292 [M+H].
$^1$H NMR (300 MHz, DMSO-d$_6$).

XIV-4/ 2-(3,4-dichloro-phenyl)-4-chloro-quinoline

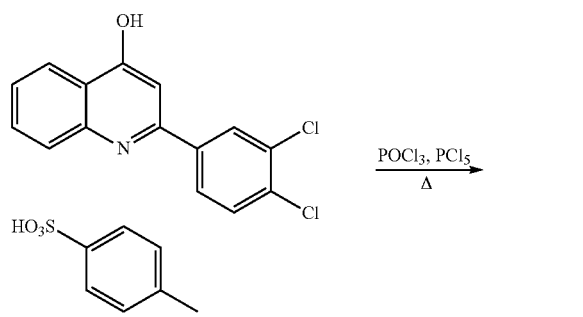

A mixture of 12.1 g (26.17 mmol) of 2-(3,4-dichloro-phenyl)-4-hydroxy-quinoline p-toluenesulfonate salt, 121 ml of phosphoryl chloride and 5.45 g (26.17 mmol) of phosphorus pentachloride was refluxed for 3 h under argon. Then, the solution was poured slowly into 1 of water after cooling (effervescence). Sodium bicarbonate and then concentrated NaOH aqueous solutions were successively and carefully added to neutralize the solution. The solid compound obtained was filtered, washed with water and dried over P$_2$O$_5$. 8.01 g (quantitative yield) of a white solid compound were recovered, corresponding to 2-(3,4-dichloro-phenyl)-4-chloro-quinoline.

$^1$H NMR (300 MHz, DMSO-d$_6$).

XIV-5/ 2-(3,4-dichloro-phenyl)-4-(1,4-dioxa-8-aza-spiro[4,5]dec-8-yl)quinoline

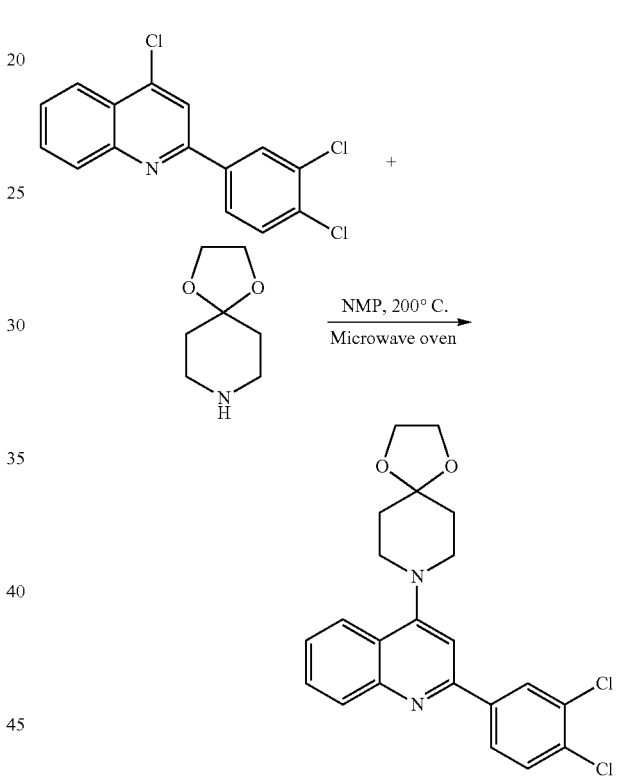

In a microwave vial was successively added: 1.00 g (3.24 mmol) of 2-(3,4-dichloro-phenyl)-4-chloro-quinoline, 1.25 ml (9.72 mmol) of 1,4-dioxa-8-azaspiro[4,8]decane and 20 ml of NMP. The solution was heated for 30 min at 200° C. in a microwave oven and then treated with a 1N NaOH aqueous solution. The mixture was extracted with ethyl acetate and the organic layer was washed with water, dried over MgSO$_4$, filtered and concentrated to give 1.54 g of brown oil. This product was purified by flash chromatography (Biotage SNAP Cartridge, 25 g of silica-dichloromethane 100%) to give 1.4 g (purity 92%) of yellow oil corresponding to 2-(3,4-dichloro-phenyl)-4-chloro-quinoline.

HPLC-MS: conditions D: $t_r$=6.96 min, (ES+) $C_{22}H_{20}Cl_2N_2O_2$ requires 414/416; found 415 [M+H], purity 92%.

$^1$H NMR (300 MHz, CDCl$_3$).

XIV-6/ 1-[2-(3,4-dichloro-phenyl)-quinoline-4-yl]-piperidin-4-one

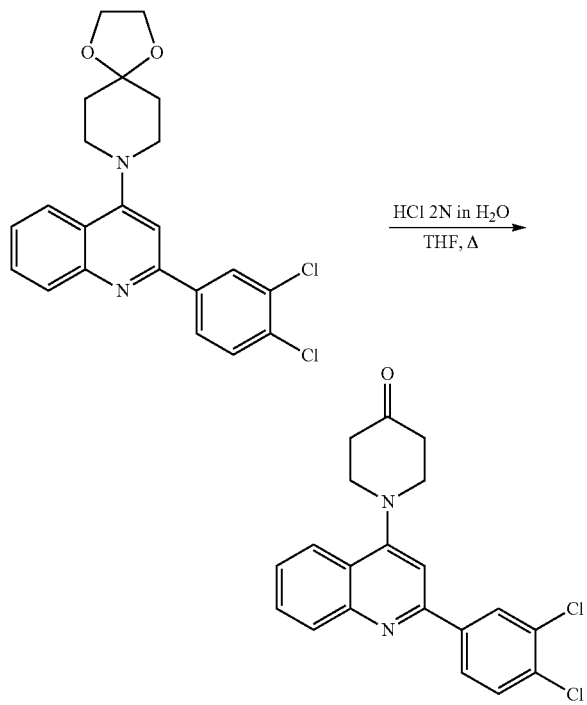

To a solution of 1.4 g (3.37 mmol) of 2-(3,4-dichloro-phenyl)-4-(1,4-dioxa-8-aza-spiro[4,5]dec-8-yl)quinoline in 2.8 ml of dry tetrahydrofuran was added 8.4 ml of a 2N HCl aqueous solution. The mixture was stirred for 2 h30 under reflux, then concentrated and treated with a 1N NaOH aqueous solution. The basic mixture was extracted with ethyl acetate and the organic layer was dried over MgSO$_4$, filtered and concentrated to give 1.34 g of yellow oil. The crude product was purified by silica gel column chromatography (dichloromethane 100%) to give 0.91 g of impure beige solid. An additionally flash chromatography (Biotage SNAP Cartridge, 25 g of silica-dichloromethane/ethyl acetate 98:2) gave 701 mg (yield 56% including previous step) of a white solid compound corresponding to 1-[2-(3,4-dichloro-phenyl)-quinoline-4-yl]-piperidin-4-one.

HPLC-MS: conditions D: $t_r$=6.06 min, (ES+) $C_{20}H_{16}Cl_2N_2O$ requires 370/372; found 371/373 [M+H].
$^1$H NMR (300 MHz, CDCl$_3$).

XIV-7/ 2-(3,4-dichloro-phenyl)-4-(4-N-tert-butylamino-piperidin-1-yl)quinoline (XIV-7)

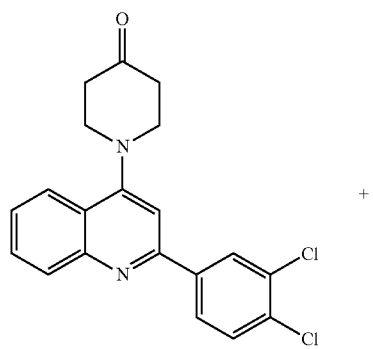

+

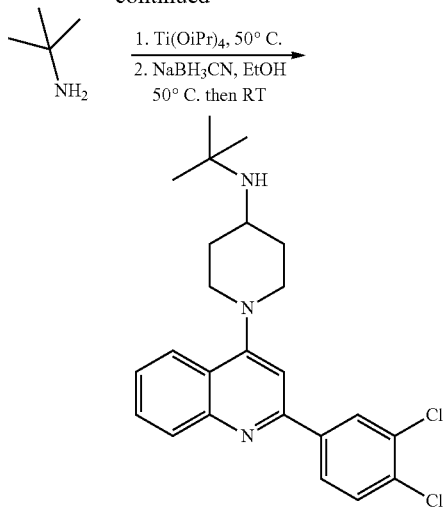

To 379 mg (1.02 mmol) of 2-(3,4-dichloro-phenyl)-quinoline-4-yl)-piperidin-4-one were added under argon, 161 µl (1.53 mmol) of tert-butylamine and 425 µl (1.428 mmol) of titanium (IV) isopropoxide. The reaction mixture was stirred for 5 h at 50° C. Then the resulting mixture was cooled, diluted with 2 ml of dry ethanol and 0.141 g (2.244 mmol) of sodium cyanoborohydride was added and the resulting reaction mixture was stirred for 24 h at 50° C. The mixture was poured onto 35 ml of water, stirred for 1 h at room temperature, filtrated through a Celite® pad and the filtrate was extracted with dichloromethane. The organic layer was washed with brine, dried over MgSO$_4$, filtered and concentrated to give 426 mg of an orange residue. This crude product was purified by silica gel column chromatography (dichloromethane/methanol 95:5) to give 173 mg (yield 39%) of clear oil corresponding to 2-(3,4-dichloro-phenyl)-4-(4-N-tert-butylamino-piperidin-1-yl)quinoline.

HPLC-MS: conditions D: $t_r$=5.01 min, (ES+) $C_{20}H_{16}Cl_2N_2O$ requires 427/429; found 428/430 [M+H].
$^1$H NMR (300 MHz, CDCl$_3$).
$^1$H NMR (300 MHz, DMSO-d$_6$).

XIV-8/ 2-(3,4-dichloro-phenyl)-4-(4-N-tert-butylamino-piperidin-1-yl)quinoline dihydrochloride (XIV-8)

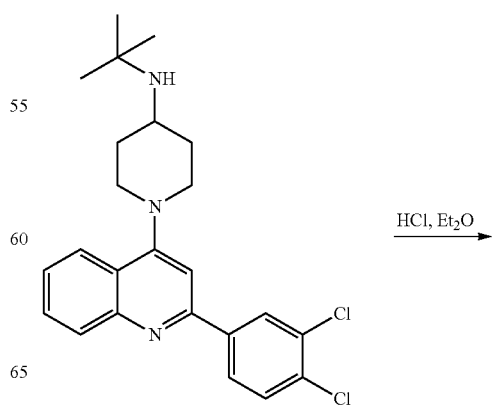

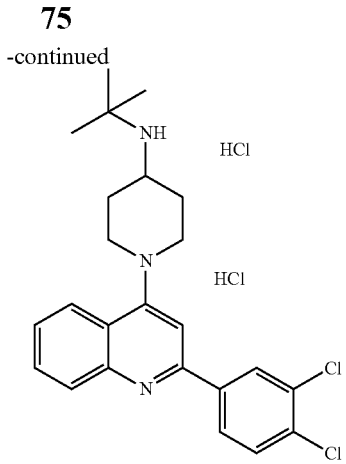

To a solution of 170 mg (0.397 mmol) of 2-(3,4-dichloro-phenyl)-4-(4-N-tert-butylamino-piperidin-1-yl)quinoline in 2 ml of dry dichloromethane was added under argon, 794 µl (0.794 mmol) of a 1N HCl solution in ether. The solution was stirred for 1 h at room temperature, concentrated and the residue triturated with dichloromethane and then petroleum ether. The compound was dissolved in pure water and a few drops of methanol. The resulting solution was filtered on Nalgene 0.2 µm PTFE syringe filter and then freeze-dried to give 160 mg (yield 86%) of a yellow solid compound corresponding to 2-(3,4-dichloro-phenyl)-4-(4-N-tert-butylamino-piperidin-1-yl)quinoline dihydrochloride.

HPLC-MS: conditions D: $t_r$=5.08 min, (ES+) $C_{20}H_{16}Cl_2N_2O$ requires 427/429; found 428/430 [M+H].
$^1$H NMR (300 MHz, DMSO-$d_6$).
$^1$H NMR (300 MHz, DMSO-$d_6$+$D_2O$).

EXAMPLE 15

Preparation of 2-(4-methoxy-phenyl)-4-(4-N-tert-butylamino-piperidin-1-yl)quinoline hydrochloride salt (XV-8)

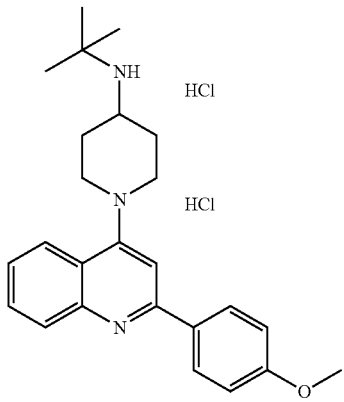 [SMILES: COc1ccc(-c2cc(N3CCC(NC(C)(C)C)CC3)c3ccccc3n2)cc1 ; Cl ; Cl]

XV-1/ Benzenamine, 2-trifluoromethyl-N-[1-(4-methoxyphenyl)ethylidene]-

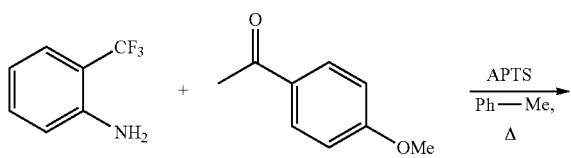

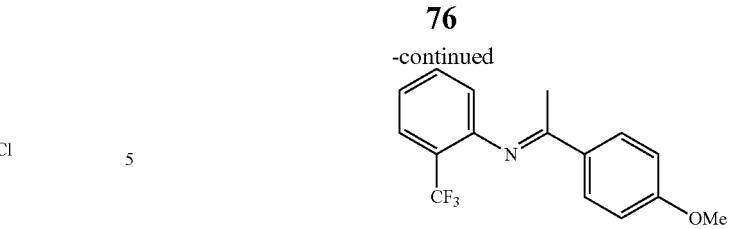

In a round bottom flask, equipped with a Dean Stark apparatus, was successively added under argon, 20 g (124.1 mmol) of 2-(trifluoromethyl)-aniline, 24 ml (161.3 mmol) of 4'-methoxyacetophenone, 670 mg of p-toluenesulfonic acid monohydrate and 500 ml of dry toluene. The mixture was heated for 18 h under reflux with azeotropic removal of water and concentrated to give 40 g of crude orange oil. This product was purified by flash chromatography (Biotage SNAP Cartridge, 340 g of silica-petroleum ether/ethyl acetate 99:1) to give 12.82 g (yield 36%) of orange oil corresponding to benzenamine, 2-trifluoromethyl-N-[1-(4-methoxyphenyl)ethylidene]-.

$^1$H NMR (300 MHz, CDCl$_3$).

XV-2/ 2-(4-methoxy-phenyl)-4-(tert-butoxy)-quinoline

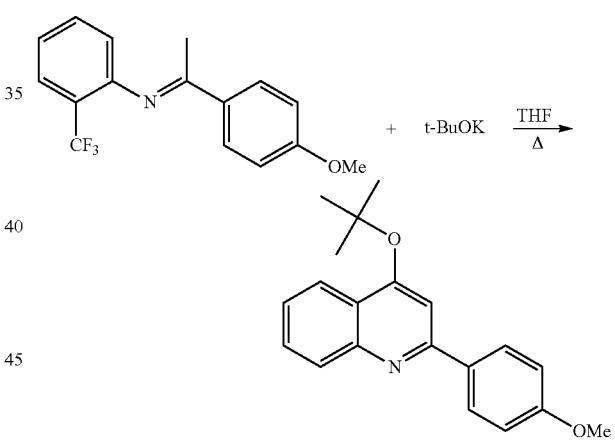

To a solution of 12.8 g (43.6 mmol) benzenamine, 2-trifluoromethyl-N-[1-(4-methoxyphenyl)ethylidene]- in 200 ml of dry THF, 23 g (205 mmol) of potassium tert-butylate were added and the mixture was stirred for 3 h under reflux. The mixture was quenched with water, both layers were separated and the aqueous layer was extracted with ethyl acetate. The combined organic layers were dried over MgSO$_4$, filtered and concentrated to give 13 g of brown oil. The crude compound was purified by flash chromatography (Biotage SNAP Cartridge, 150 g of silica-dichloromethane 100%) to give 3.8 g (yield 28%) of orange oil corresponding to 2-(4-methoxy-phenyl)-4-(tert-butoxy)-quinoline.

HPLC-MS: conditions D: $t_r$=6.75 min, (ES+) $C_{20}H_{21}NO_2$ requires 307; found 308 [M+H].
$^1$H NMR (300 MHz, CDCl$_3$).

XV-3/ 2-(4-methoxy-phenyl)-4-hydroxy-quinoline

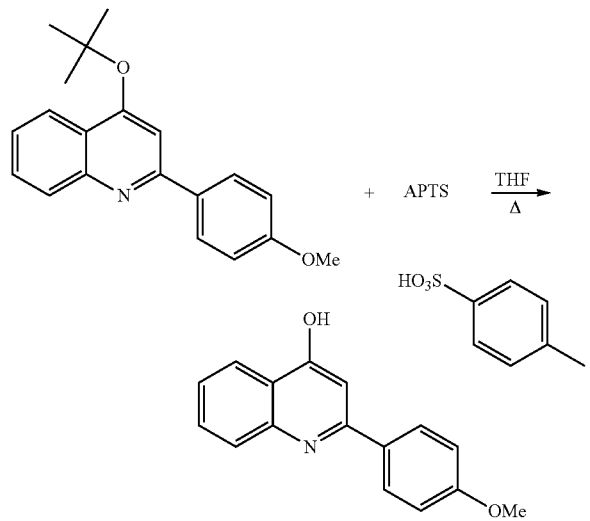

To a solution of 3.8 g (12.4 mmol) of 2-(4-methoxy-phenyl)-4-(tert-butoxy)-quinoline in 100 ml of THF was added 3.5 g (12.4 mmol) of p-toluenesulfonic acid monohydrate and the reaction mixture was heated for 24 h under reflux. After cooling, the precipitate was filtered and the solid was washed with ethyl acetate to give 3.06 g (yield 58%) of beige solid compound (purity 93%) corresponding to the p toluenesulfonate salt of 2-(4-methoxy-phenyl)-4-hydroxy-quinoline.

$^1$H NMR (300 MHz, DMSO-d$_6$).

XV-4/ 2-(4-methoxy-phenyl)-4-chloro-quinoline

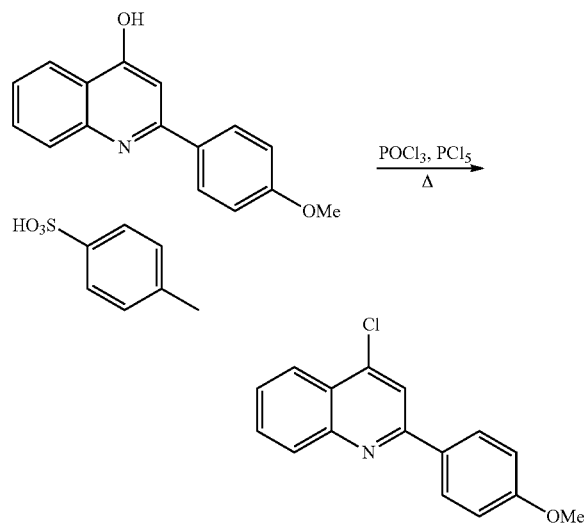

A mixture of 3.06 g (7.23 mmol) of 2-(4-methoxy-phenyl)-4-hydroxy-quinoline, 30 ml of phosphoryl chloride and 1.5 g (7.23 mmol) of phosphorus pentachloride was refluxed for 2 h under argon and the solution was poured slowly onto 200 ml of water after cooling (effervescence). Solid KOH was carefully added to neutralize the mixture (pH 7-8). The solid compound obtained was filtered and washed with water, then solubilized in dichloromethane and the solution was dried over MgSO$_4$, filtered and concentrated on a rotary evaporator to give 1.81 g (yield 93%) of a yellow solid compound corresponding to 2-(4-methoxy-phenyl)-4-chloro-quinoline.

HPLC-MS: conditions F: t$_r$=9.23 min, (ES+) C$_{16}$H$_{12}$ClNO requires 269; found 270 [M+H], purity 94%.

$^1$H NMR (300 MHz, CDCl$_3$).

XV-5/ 2-(4-methoxy-phenyl)-4-(1,4-dioxa-8-aza-spiro[4,5]dec-8-yl)quinoline

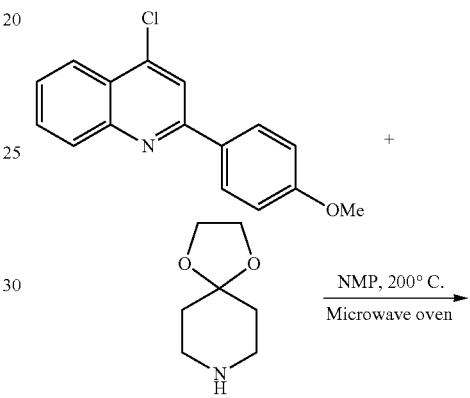

In a microwave vial was successively added: 0.6 g (2.22 mmol) of 2-(4-methoxy-phenyl)-4-chloro-quinoline, 1.4 ml (11.12 mmol) of 1,4-dioxa-8-azaspiro[4,8]decane and 500 μl of NMP. The solution was heated for 30 min at 200° C. in a microwave oven and then treated with a 1N NaOH aqueous solution. The mixture was extracted with ethyl acetate and the organic layer was dried over MgSO$_4$, filtered and concentrated to give 1.2 g of orange oil. This product was purified by flash chromatography (Biotage SNAP Cartridge, 25 g of silica-petroleum ether/ethyl acetate 9:1) to give 0.7 g (yield 83%) of colourless oil corresponding to 2-(4-methoxy-phenyl)-4-(1,4-dioxa-8-aza-spiro[4,5]dec-8-yl)quinoline.

HPLC-MS: conditions D: t$_r$=6.30 min, (ES+) C$_{23}$H$_{24}$N$_2$O$_3$ requires 376; found 377 [M+H], purity 94%.

$^1$H NMR (300 MHz, CDCl$_3$).

XV-6/ 1-[2-(4-methoxy-phenyl)-quinoline-4-yl]-piperidin-4-one

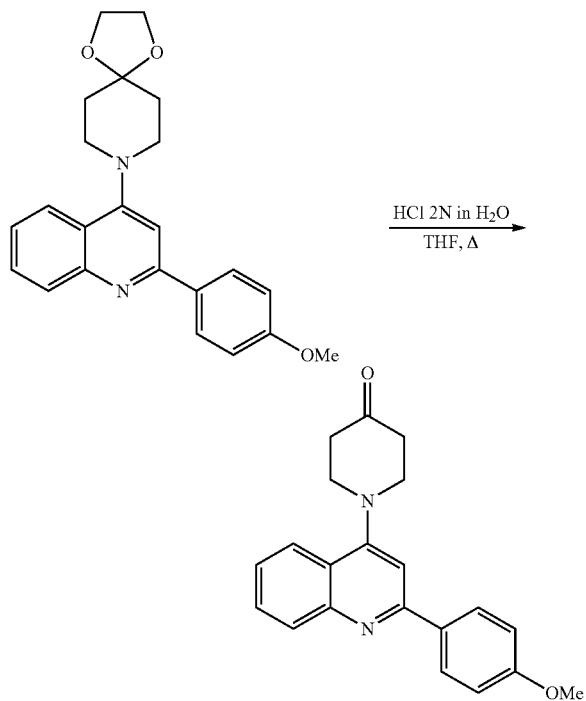

To a solution of 0.7 g (1.86 mmol) of 2-(4-methoxy-phenyl)-4-(1,4-dioxa-8-aza-spiro[4,5]dec-8-yl)quinoline in 4 ml of dry tetrahydrofuran was added 4.2 ml of a 2N HCl aqueous solution. The mixture was stirred for 1 h30 under reflux then concentrated and treated with a 1N NaOH aqueous solution. The basic mixture was extracted with dichloromethane and the organic layer was dried over MgSO$_4$, filtered and concentrated to give 560 mg of a yellow impure solid. The crude product was purified by silica gel column chromatography (petroleum ether/ethyl acetate 8:2) to give 424 mg (yield 69%) of a beige solid compound corresponding to 1-[2-(4-methoxy-phenyl)-quinoline-4-yl]-piperidin-4-one.

HPLC-MS: conditions F: $t_r$=5.30 min, (ES+) $C_{21}H_{20}N_2O_2$ requires 332; found 333 [M+H], purity 92%.

$^1$H NMR (300 MHz, CDCl$_3$).

XV-7/ 2-(4-methoxy-phenyl)-4-(4-N-tert-butylamino-piperidin-1-yl)quinoline (XV-7)

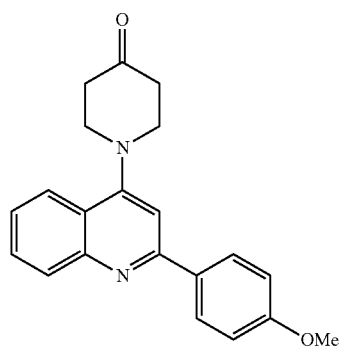

+

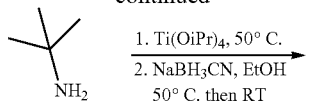

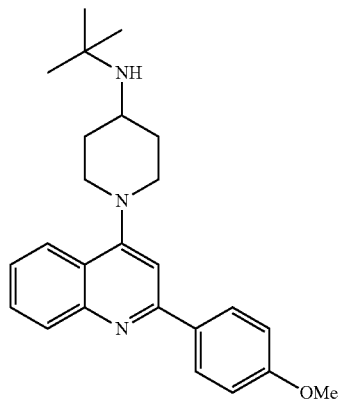

To 200 mg (0.6 mmol) of 1-[2-(4-methoxy-phenyl)-quinoline-4-yl]-piperidin-4-one were added under argon, 95 µl (0.9 mmol) of tert-butylamine and 251 µl (0.84 mmol) of titanium (IV) isopropoxide. The mixture was stirred for 5 h at 50° C. Then, the reaction mixture was cooled, diluted with 0.5 ml of dry ethanol and 83 mg (1.32 mmol) of sodium cyanoborohydride were added. The resulting mixture was stirred for 3 h30 at 50° C. and then 20 h at room temperature. The mixture was poured onto 25 ml of water, stirred for 1 h at room temperature, filtrated through a Celite® pad and the filtrate was extracted with dichloromethane. The organic layer was washed with brine, dried over MgSO$_4$, filtered and concentrated to give 227 mg of a residue. The crude product was purified by silica gel column chromatography (dichloromethane/ethyl acetate 7:3) to give 125 mg of impure yellow oil. This product was purified by silica C18 reversed-phase column Biotage (13 g—water/methanol (containing 2% of triethylamine) 3:7) to give 68 mg (yield 29%) of a white solid compound corresponding to 2-(4-methoxy-phenyl)-4-(4-N-tert-butylamino-piperidin-1-yl)quinoline.

HPLC-MS: conditions D: $t_r$=4.52 min, (ES+) $C_{25}H_{31}N_3O$ requires 389; found 390 [M+H]

$^1$H NMR (300 MHz, CDCl$_3$).

XV-8/ 2-(4-methoxy-phenyl)-4-(4-N-tert-butylamino-piperidin-1-yl)quinoline dihydrochloride (XV-8)

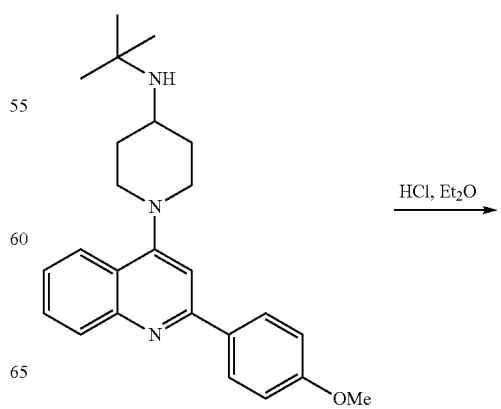

-continued

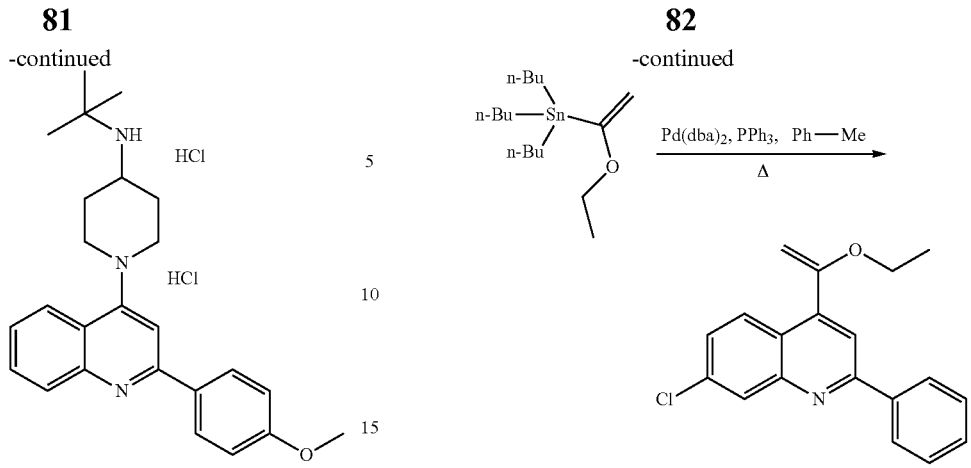

To a solution of 67 mg (0.17 mmol) of 2-(4-methoxy-phenyl)-4-(4-N-tert-butylamino-piperidin-1-yl)quinoline in 400 µl of dry dichloromethane was added under argon, 340 µl (0.34 mmol) of a 1N HCl solution in ether. The solution was stirred for 30 min at room temperature, concentrated and the solid residue was triturated with ether to give 79 mg of yellow solid. This compound was dissolved in pure water and the solution was filtered on Millipore 0.2 µm PTFE syringe filter and then freeze-dried to give 72 mg (yield 99%) of a yellow solid compound corresponding to 2-(4-methoxy-phenyl)-4-(4-N-tert-butylamino-piperidin-1-yl) quinoline dihydrochloride.

HPLC-MS: conditions D: $t_r$=4.40 min, (ES+) $C_{25}H_{31}N_3O$ requires 389; found 390 [M+H].
$^1$H NMR (300 MHz, DMSO-$d_6$).
$^1$H NMR (300 MHz, DMSO-$d_6$+$D_2O$).

EXAMPLE 16

Preparation of 7-Chloro-2-phenyl-4-{1-[4-(N,N-diethylamino)-piperidin-1-yl]-eth-1-yl}quinoline hydrochloride salt (XVI-4)

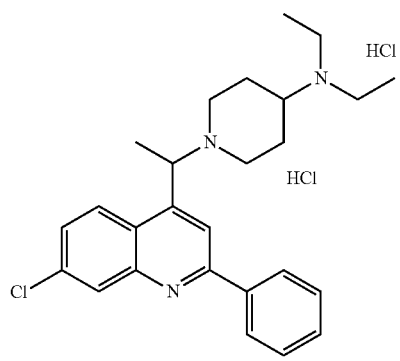 [SMILES: CCN(CC)C1CCN(C(C)c2cc(-c3ccccc3)nc3cc(Cl)ccc23)CC1 ; Cl ; Cl]

XVI-1/ 7-chloro-4-(1-ethoxy-vinyl)-2-phenyl-quinoline

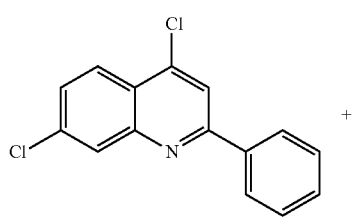

+

In a microwave vial were successively added: 0.4 g (1.46 mmol) of 4,7-dichloro-2-phenylquinoline prepared according to the protocol described paragraph II-2, 33 mg (0.06 mmol) of Bis(dibenzylideneacetone)palladium(0), 31 mg (0.12 mmol) of triphenylphosphine and 4 ml of dry toluene. The solution was stirred for 15 min at room temperature and 493 µl (1.46 mmol) of ethyl 1-(tributylstannyl)vinyl ether were added under nitrogen. The solution was heated for 3 h at 130° C. and then treated with 8 ml of a 1N HCl aqueous solution and stirred for 12 h at room temperature. The mixture was neutralized with a 1N NaOH aqueous solution, extracted with ether and the organic layer was dried over $MgSO_4$, filtered and concentrated to give 1.15 g of brown oil. This product was purified by silica gel column chromatography (petroleum ether/ethyl acetate 98:2) to give 255 mg (yield 57%) of solidified colourless oil corresponding to 7-chloro-4-(1-ethoxy-vinyl)-2-phenyl-quinoline.

HPLC-MS: conditions D: $t_r$=10.96 min, (ES+) $C_{19}H_{16}ClNO$ requires 309; found 310 [M+H].
$^1$H NMR (300 MHz, $CDCl_3$).

XVI-2/ 4-acetyl-7-chloro-2-phenyl-quinoline

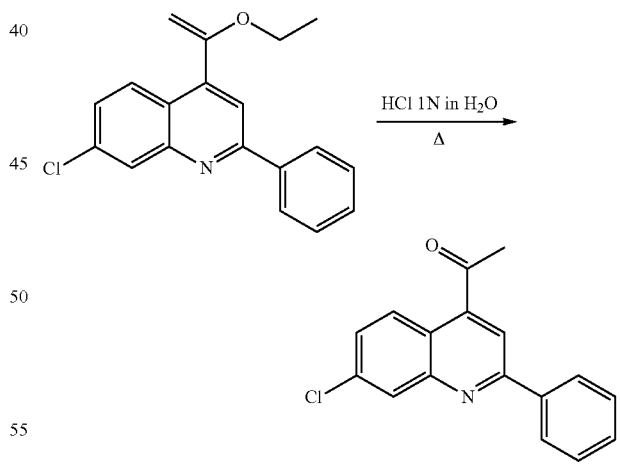

A solution of 255 mg (0.82 mmol) of 7-chloro-4-(1-ethoxy-vinyl)-2-phenyl quinoline in 5 ml of 1N HCl aqueous solution was heated for 7 h under reflux and then neutralized with a 1N NaOH aqueous solution. The aqueous layer was extracted with ether and the organic layer was dried over $MgSO_4$, filtered and concentrated to give 199 mg (yield 86%) of orange oil corresponding to 4-acetyl-7-chloro-2-phenyl-quinoline.

HPLC-MS: conditions D: $t_r$=10.18 min, (ES+) $C_{17}H_{12}ClNO$ requires 281; found 282 [M+H].
$^1$H NMR (300 MHz, $CDCl_3$).

XVI-3/ 7-chloro-2-phenyl-4-{1-[4-(N,N-diethyl-amino)-piperidin-1-yl]-eth-1-yl}quinoline (XVI-3)

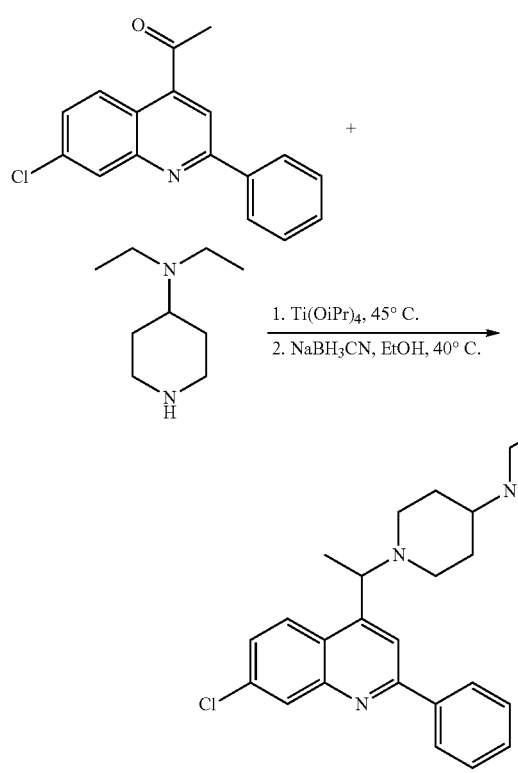

To 199 mg (0.7 mmol) of 4-acetyl-7-chloro-2-phenyl-quinoline were added a solution of 166 mg (1.06 mmol) of 4-diethylamino-piperidine in 2 ml of dichloromethane. The mixture was concentrated under vacuum and 296 μl (0.99 mmol) of titanium (IV) isopropoxide was added under nitrogen. The mixture was heated for 5 h at 45° C. Then, the reaction mixture was cooled and diluted with 4 ml of dry ethanol, and 98 mg (1.56 mmol) of sodium cyanoborohydride were added and the resulting mixture was heated for 24 h at 40° C. The mixture was poured onto 30 ml of water, stirred for 1 h at room temperature, filtrated through a Celite® pad and the filtrate was extracted with dichloromethane. The organic layer was washed with brine, dried over MgSO$_4$, filtered and concentrated to give 189 mg of yellow oil. This crude product was purified by silica C18 reversed-phase column Biotage (31 g—water/acetonitrile 7:3) to give 129 mg of impure yellow oil. This compound was additionally purified by silica gel column chromatography (dichloromethane/ethanol 95:5) to give 64 mg (yield 21%) of solidified colourless oil corresponding to 7-chloro-2-phenyl-4-{1-[4-(N,N-diethylamino)-piperidin-1-yl]-eth-1-yl}quinoline.

HPLC-MS: conditions D: t$_r$=5.80 min, (ES+) C$_{26}$H$_{32}$ClN$_3$ requires 421/423; found 422/424 [M+H].

$^1$H NMR (300 MHz, CDCl$_3$).

XVI-4/ 7-Chloro-2-phenyl-4-{1-[4-(N,N-diethyl-amino)-piperidin-1-yl]-eth-1-yl}quinoline dihydrochloride (XVI-4)

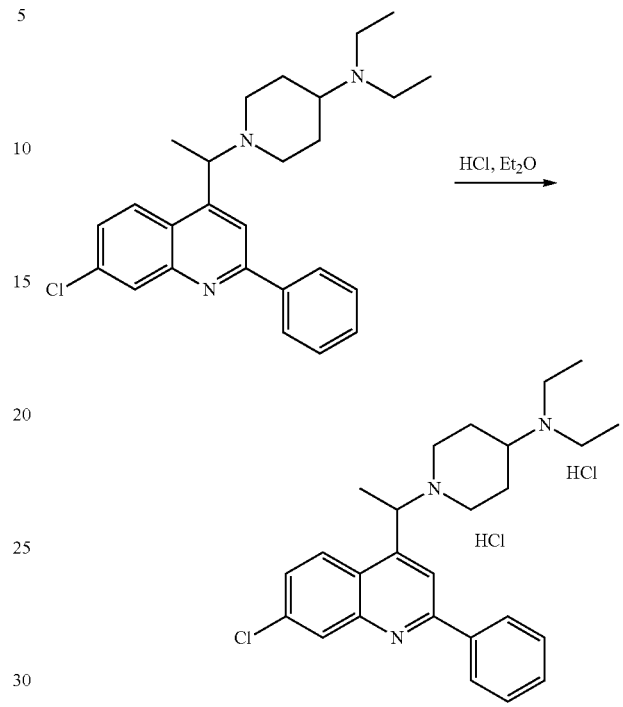

To a solution of 55 mg (0.13 mmol) of 7-chloro-2-phenyl-4-{1-[4-(N,N-diethylamino)-piperidin-1-yl]-eth-1-yl}quinoline in 500 μl of dry dichloromethane was added under argon, 400 μl (0.4 mmol) of a 1N solution of HCl in ether. The solution was stirred for 1 h at room temperature to precipitate a beige solid. The compound was filtered, washed with ether and dried to give 68 mg of a white solid. The corresponding product was dissolved in pure water, and the solution was freeze-dried to give 48.6 mg (yield 75%) of a white solid compound corresponding to 7-chloro-2-phenyl-4-{1-[4-(N,N-diethylamino)-piperidin-1-yl]-eth-1-yl}quinoline dihydrochloride.

HPLC-MS: conditions D: t$_r$=5.91 min, (ES+) C$_{26}$H$_{32}$ClN$_3$ requires 421/423; found 422/424 [M+H].

$^1$H NMR (300 MHz, DMSO-d$_6$).
$^1$H NMR (300 MHz, DMSO-d$_6$+D$_2$O).

EXAMPLE 17

Preparation of 7-Chloro-2-phenyl-4-[4-(N,N-diethylamino)-piperidin-1-ylmethyl]quinoline hydrochloride salt (XVII-6)

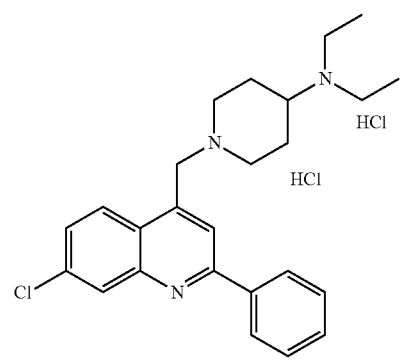 [SMILES: CCN(CC)C1CCN(Cc2cc(-c3ccccc3)nc3cc(Cl)ccc23)CC1 ; Cl ; Cl]

XVII-1/ 7-chloro-2-phenyl-quinoline-4-carboxylic acid

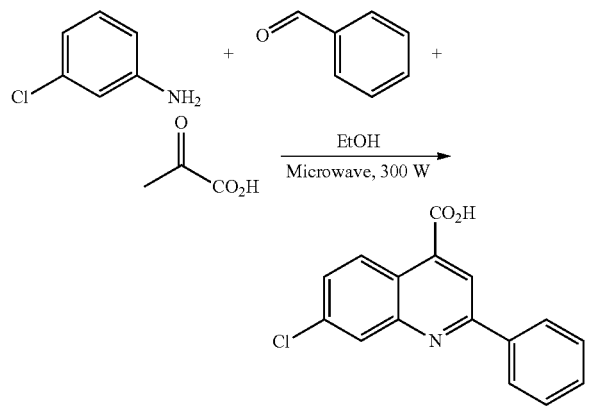

10.5 ml (98.8 mmol) of 3-chloroaniline, 9.6 ml (94.1 mmol) of benzaldehyde and 50 ml of dry ethanol were divided into 5 microwave vials. To each vial was added 1.46 ml of 20% pyruvic acid aqueous solution (7.3 ml, 103 mmol were used for the 5 vials) and the vials were treated for 1 min at 300 W in a microwave oven. All mixtures were then gathered to filter a solid. This solid was washed with ethanol and treated with a mixture of 500 ml of dichloromethane and 500 ml of a 2N NaOH aqueous solution. The organic layer was still extracted with a 2N NaOH aqueous solution. Aqueous layer was acidified with concentrated aqueous HCl and filtered to recover 9.82 g of a yellow solid. It was triturated with dichloromethane, filtered and dried to give 6.9 g (yield 23%) of a pale yellow solid compound corresponding to 7-chloro-2-phenyl-quinoline-4-carboxylic acid.

HPLC-MS: conditions D: $t_r$=9.03 min, (ES+) $C_{16}H_{10}ClNO_2$ requires 283/285; found 284/286 [M+H], (purity 91%).

$^1$H NMR (300 MHz, DMSO-$d_6$).

XVII-2/ methyl 7-chloro-2-phenyl-quinoline-4-carboxylate

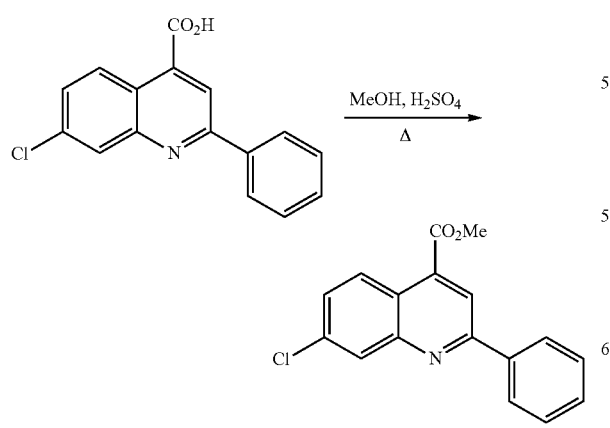

To a solution of 4.9 g (15.3 mmol) of 7-chloro-2-phenyl-quinoline-4-carboxylic acid in 80 ml of methanol was added 20 ml of concentrated $H_2SO_4$ and the mixture was heated for overnight under reflux. The reaction mixture was concentrated, treated with a mixture of ethyl acetate and water, and the organic layer was washed with an aqueous saturated solution of NaHCO$_3$, dried over MgSO$_4$, filtered and concentrated to give 3.67 g (yield 82%) of pale yellow solid corresponding to methyl 7-chloro-2-phenyl-quinoline-4-carboxylate.

$^1$H NMR (300 MHz, CDCl$_3$).

XVII-3/ 7-chloro-4-hydroxymethyl-2-phenyl-quinoline

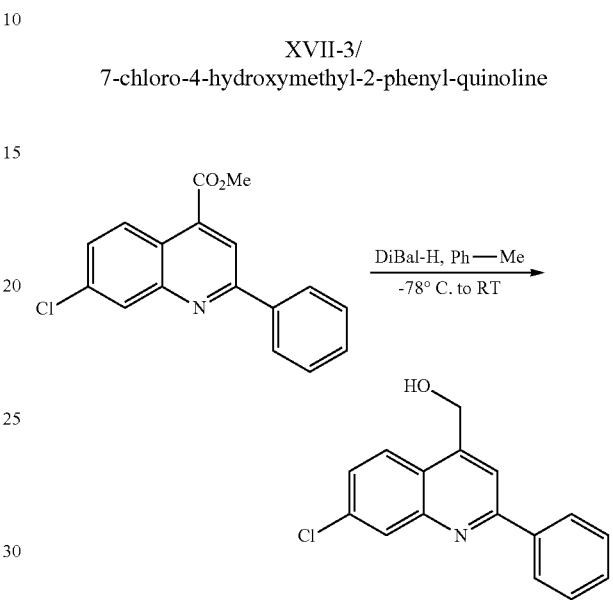

To a solution of 3.67 g (12.32 mmol) of methyl 7-chloro-2-phenyl-quinoline-4-carboxylate in 150 ml of dichloromethane was added at −78° C. under nitrogen, 12.5 ml (12.32 mmol) of Diisobutylaluminum hydride 1M in toluene and the mixture was stirred overnight at room temperature. After cooling the reaction mixture, methanol was added at 0° C. and then 25 g (7 eq.) of potassium sodium tartrate solubilized in 70 ml of water. The mixture was stirred for 1 h at room temperature and extracted with dichloromethane. The organic layer was dried over MgSO$_4$, filtered and concentrated to give 2.09 g (yield 63%) of yellow solid compound corresponding to 7-chloro-4-hydroxymethyl-2-phenyl-quinoline.

HPLC-MS: conditions D: $t_r$=6.67 min, (ES+) $C_{16}H_{12}ClNO$ requires 269/271; found 270/272 [M+H], purity 95%.

$^1$H NMR (300 MHz, CDCl$_3$).

XVII-4/ 7-chloro-2-phenyl-quinoline-4-carbaldehyde

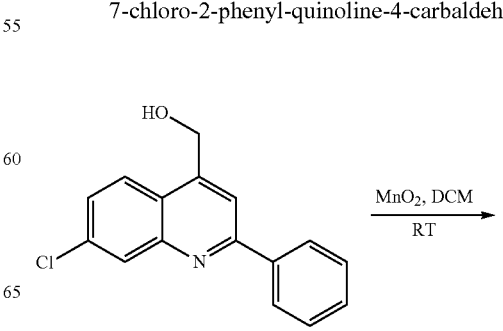

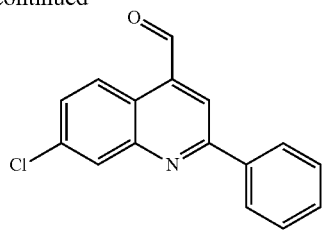

To a solution of 1.2 g (4.45 mmol) of 7-chloro-4-hydroxymethyl-2-phenyl-quinoline in 50 ml of dichloromethane was added under nitrogen, 3.87 g (44.5 mmol) of MnO$_2$. The mixture was stirred overnight at room temperature, and then filtered through a Celite® pad. The filtrate was concentrated on a rotary evaporator to give a crude residue. This crude product was purified by silica gel column chromatography (20 g—dichloromethane 100%) to give 0.97 g (yield 81%) of yellow solid compound corresponding to 7-chloro-2-phenyl-quinoline-4-carbaldehyde.

HPLC-MS: conditions D: t$_r$=10.53 min, (ES+) C$_{16}$H$_{10}$ClNO requires 267/269; found 268/270 [M+H], purity 92%.

$^1$H NMR (300 MHz, CDCl$_3$).

XVII-5/ 7-Chloro-2-phenyl-4-[4-(N,N-diethylamino)-piperidin-1-ylmethyl]quinoline (XVII-5)

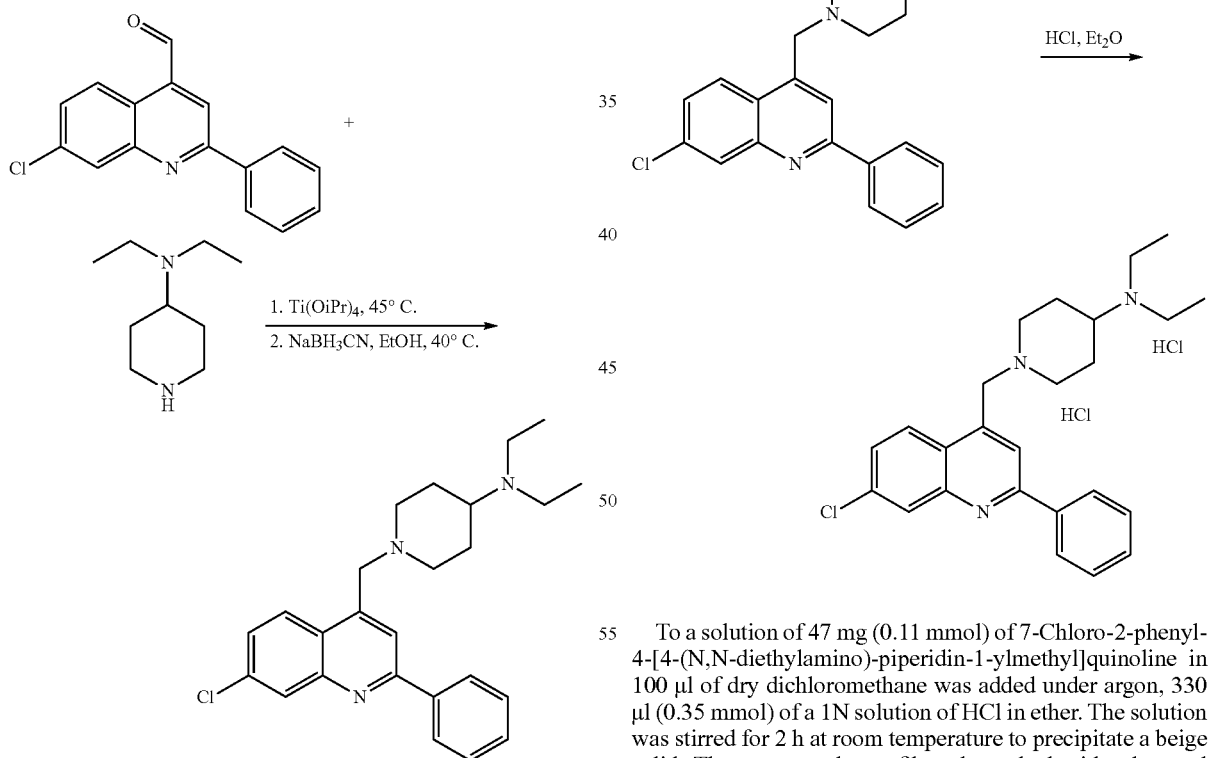

To 200 mg (0.75 mmol) of 7-chloro-2-phenyl-quinoline-4-carbaldehyde was added a solution of 175 mg (1.12 mmol) of 4-diethylamino-piperidine in 2 ml of dichloromethane. The mixture was concentrated under vacuum and 311 µl (1.05 mmol) of titanium (IV) isopropoxide were added under nitrogen. The mixture was heated for 5 h at 45° C.

Then, the reaction mixture was cooled, diluted with 4 ml of dry ethanol and 103 mg (1.64 mmol) of sodium cyanoborohydride were added and the resulting mixture was heated for 3 h at 40° C. and stirred for 12 h at room temperature. The mixture was poured onto 31 ml of water, stirred for 1 h at room temperature, filtrated through a Celite® pad and the filtrate was extracted with dichloromethane. The organic layer was washed with brine, dried over MgSO$_4$, filtered and concentrated to give 284 mg of yellow oil. This crude product was purified by silica gel column chromatography (10 g toluene/ethyl acetate 95:5 and 1% of triethylamine) to give 200 mg of impure yellow oil. An additional purification by silica gel column chromatography (10 g ethyl acetate/triethylamine 99:1) gave 47 mg of yellow oil corresponding to 7-Chloro-2-phenyl-4-[4-(N,N-diethylamino)-piperidin-1-ylmethyl]quinoline (yield 15%).

HPLC-MS: conditions D: t$_r$=5.53 min, (ES+) C$_{25}$H$_{30}$ClN$_3$ requires 407. found 408 [M+H], purity 93%.

$^1$H NMR (300 MHz, CDCl$_3$).

XVII-6/ 7-Chloro-2-phenyl-4-[4-(N,N-diethylamino)-piperidin-1-ylmethyl]quinoline dihydrochloride (XVII-6)

To a solution of 47 mg (0.11 mmol) of 7-Chloro-2-phenyl-4-[4-(N,N-diethylamino)-piperidin-1-ylmethyl]quinoline in 100 µl of dry dichloromethane was added under argon, 330 µl (0.35 mmol) of a 1N solution of HCl in ether. The solution was stirred for 2 h at room temperature to precipitate a beige solid. The compound was filtered, washed with ether and dried to give 63 mg of an impure yellow solid. It was triturated in 2 ml of hot ether to recover 38 mg of beige solid. This compound was solubilized in pure water, and the solution was filtered on Nalgene 0.2 µm PTFE syringe filter and then freeze-dried to give 32 mg (yield 58%) of a beige solid corresponding to 7-chloro-2-phenyl-4-[4-(N,N-diethylamino)-piperidin-1-ylmethyl]quinoline dihydrochloride.

HPLC-MS: conditions D: $t_r$=6.17 min, (ES+) $C_{25}H_{30}ClN_3$ requires 407; found 408 [M+H], purity 99%.
¹H NMR (300 MHz, DMSO-$d_6$). ¹H NMR (300 MHz, DMSO-$d_6$+$D_2O$).

EXAMPLE 18

Preparation of 4-[4-(N,N-diethylamino)piperidin-1-ylcarbonyl]-2-phenyl-quinoline hydrochloride salt (XVIII-2)

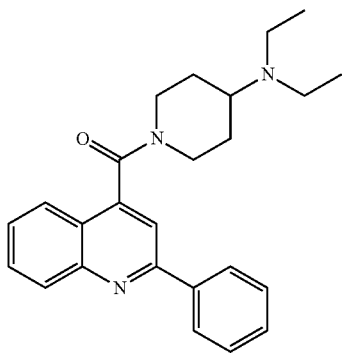 [SMILES: CCN(CC)C1CCN(C(=O)c2cc(-c3ccccc3)nc3ccccc23)CC1]

XVIII-1/ 4-[4-(N,N-diethylamino)piperidin-1-ylcarbonyl]-2-phenyl-quinoline (XVIII-1)

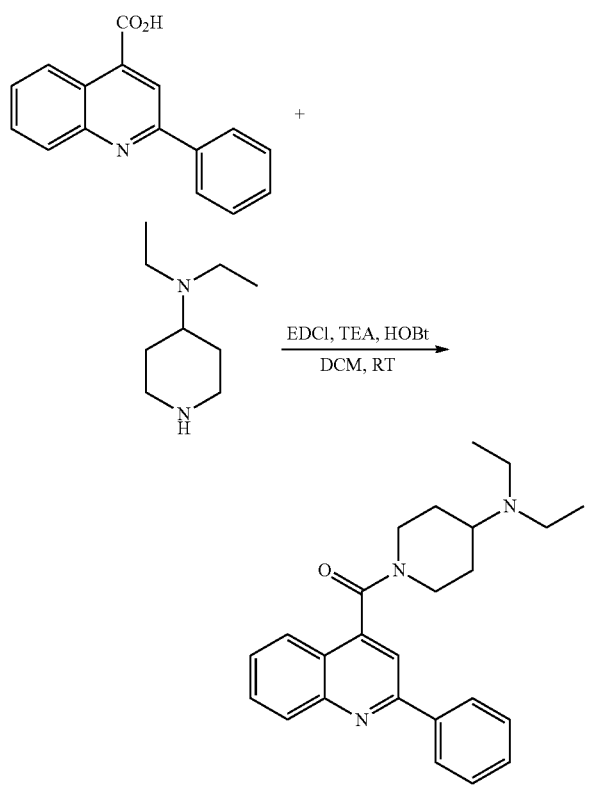

To 500 mg (2 mmol) of commercially available 2-phenyl-4-quinolinecarboxylic acid in 10 ml of dichloromethane were added 376 mg (2.41 mmol) of 4-diethylamino-piperidine, 335 µl (2.41 mmol) of triethylamine, 462 mg of (2.41 mmol) of 1-ethyl-3-(3-dimethylaminopropyl)carbodiimide and 325 mg (2.41 mmol) of hydroxybenzotriazole. The mixture was stirred overnight at room temperature and diluted with dichloromethane. The organic layer was washed with water, dried over $MgSO_4$, filtered and concentrated to give 1.11 g of yellow oil. This compound was purified by silica gel column chromatography (20 g dichloromethane then dichloromethane/ethyl acetate 1:1 then ethyl acetate 100%) to give 692 mg of impure sticky white foam. This product was additionally purified by silica C18 reversed-phase column Biotage (100 g—water/methanol 1:1) to give 565 mg of still impure pale yellow oil. This oil was solubilized in ethyl acetate and the solution was extracted with a 1N HCl aqueous solution. The aqueous layer was basified with 1N NaOH aqueous solution and the solution was extracted with ethyl acetate. The organic layer was dried over $MgSO_4$, filtered and concentrated to give 241 mg (yield 31%) of clear sticky solid corresponding to 4-[4-(N,N-diethylamino)piperidin-1-ylcarbonyl]-2-phenyl-quinoline.

HPLC-MS: conditions D: $t_r$=5.24 min, (ES+) $C_{25}H_{29}N_3O$ requires 387; found 388 [M+H], purity 99%.
¹H NMR (300 MHz, CDCl₃).

XVIII-2/ 4-[4-(N,N-diethylamino)piperidin-1-ylcarbonyl]-2-phenyl-quinoline dihydrochloride (XVIII-2)

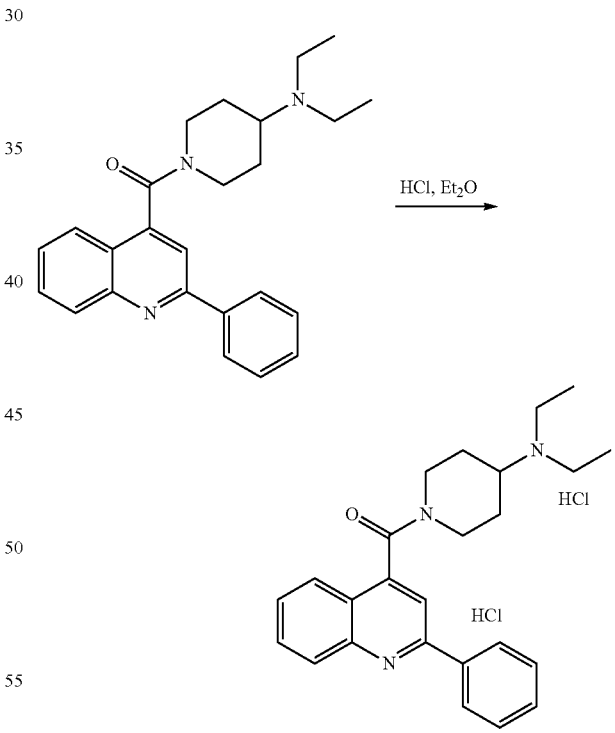

To a solution of 135 mg (0.35 mmol) of 4-[4-(N,N-diethylamino)piperidin-1-ylcarbonyl]-2-phenyl-quinoline in 5 ml of dry dichloromethane was added under nitrogen, 700 µl (0.7 mmol) of a 1N solution of HCl in ether. The solution was stirred for 2 h at room temperature and concentrated to give 164 mg of a very hygroscopic yellow solid. The compound was dissolved in pure water, and the solution freeze-dried to give 130 mg (yield 88%) of a pale yellow solid compound corresponding to 4-[4-(N,N-diethylamino)

piperidin-1-ylcarbonyl]-2-phenyl-quinoline dihydrochloride. This compound must be kept under argon.

HPLC-MS: conditions D: $t_r$=5.19 min, (ES+) $C_{25}H_{29}N_3O$ requires 387; found 388 [M+H], purity 99%.
$^1$H NMR (300 MHz, CDCl$_3$).
$^1$H NMR (300 MHz, DMSO-d$_6$).
$^1$H NMR (300 MHz, DMSO-d$_6$+D$_2$O).

Example 19

Preparation of 2-phenyl-4-{1-[4-(N,N-diethylamino) piperidin-1-yl]-eth-1-yl}quinoline hydrochloride salt (XIX-3)

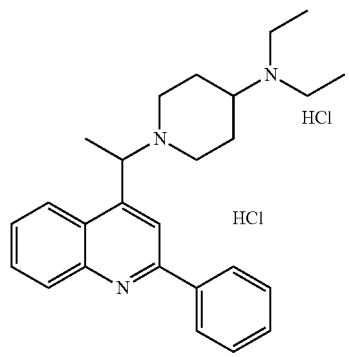 [SMILES: CCN(CC)C1CCN(C(C)c2cc(-c3ccccc3)nc3ccccc23)CC1 ; Cl ; Cl]

XIX-1/ 4-acetyl-2-phenyl-quinoline

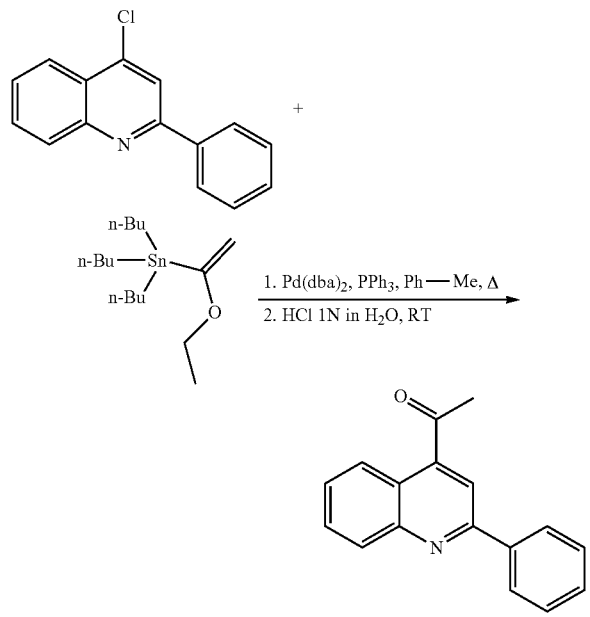

In a microwave vial was successively added: 0.5 g (2.08 mmol) of commercially available 4-chloro-2-phenylquinoline, 48 mg (0.83 mmol) of Bis(dibenzylideneacetone)palladium(0), 44 mg (0.166 mmol) of triphenylphosphine and 5 ml of dry toluene. The reaction mixture was stirred for 15 min at room temperature and 705 µl (2.08 mmol) of ethyl 1-(tributylstannyl)vinyl ether were added under nitrogen. The solution was heated for 4 h at 130° C., and then treated with 10 ml of a 1N HCl aqueous solution and stirred for 12 h at room temperature. The mixture was neutralized with a 1N NaOH aqueous solution, extracted with ether and the organic layer was dried over MgSO$_4$, filtered and concentrated to give 1.2 g of brown oil. This product was purified by silica gel column chromatography (25 g—petroleum ether/ethyl acetate 98:2) to give 283 mg (yield 55%) of yellow solid compound corresponding to 4-acetyl-2-phenyl-quinoline.

HPLC-MS: conditions D: $t_r$=8.57 min, (ES+) $C_{17}H_{13}NO$ requires 247; found 248 [M+H], purity 97%.
$^1$H NMR (300 MHz, CDCl$_3$).

XIX-2/ 2-phenyl-4-{1-[4-(N,N-diethylamino)-piperidin-1-yl]-eth-1-yl}quinoline (XIX-2)

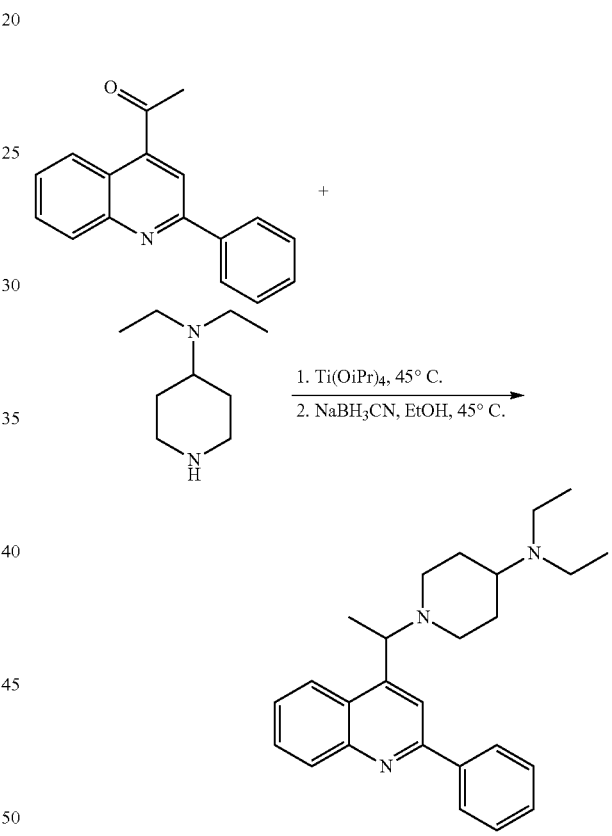

To 280 mg (1.15 mmol) of 4-acetyl-2-phenyl-quinoline were added under nitrogen, 269 mg (1.72 mmol) of 4-diethylamino-piperidine, 479 µl (1.61 mmol) of titanium (IV) isopropoxide and the mixture was heated for 2 h at 45° C. After cooling, the mixture was diluted with 4 ml of dry ethanol and 139 mg (2.53 mmol) of sodium cyanoborohydride were added and the resulting solution was heated for 4 h at 45° C. and then was stirred for 12 h at room temperature. The mixture was poured onto 30 ml of water, stirred for 1 h at room temperature, filtrated through a Celite® pad and the filtrate was extracted with dichloromethane. The organic layer was washed with brine, dried over MgSO$_4$, filtered and concentrated to give 398 mg of yellow oil. This crude compound was purified by silica gel column chromatography (dichloromethane, then dichloromethane/ethanol 95:5) to give 110 mg of impure yellow oil. This compound was additionally purified by silica C18 reversed-phase column Biotage (13 g—water/methanol 1:1 then methanol/triethylamine 99:1) to give 50 mg of yellow oil. This oil was taken up in chloroform and the organic layer washed with a few drops of 1N NaOH aqueous solution, dried over MgSO$_4$, filtered and concentrated to give 33 mg (yield 7%) of clear yellow oil corresponding to 2-phenyl-4-{1-[4-(N,N-diethylamino)-piperidinyl]-eth-1-yl}quinoline. This oil was used directly in the next step.

HPLC-MS: conditions D: t$_r$=4.75 min, (ES+) C$_{26}$H$_{33}$N$_3$ requires 387; found 388 [M+H], purity 87%.

$^1$H NMR (300 MHz, CDCl$_3$).

XIX-3/ 2-phenyl-4-{1-[4-(N,N-diethylamino)piperidin-1-yl]-eth-1-yl}quinoline dihydrochloride (XIX-3)

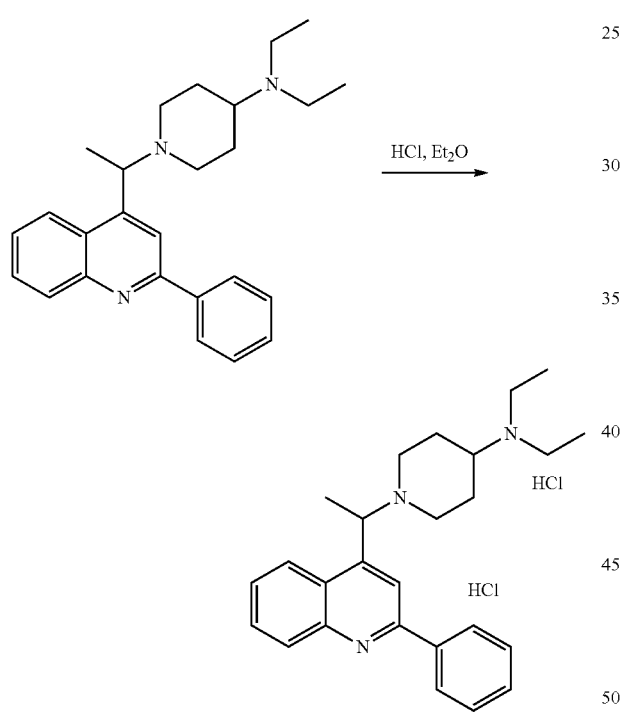

To a solution of 27 mg (0.07 mmol) of 2-phenyl-4-{1-[4-(N,N-diethylamino)-piperidinyl]-eth-1-yl}quinoline in 1 ml of dry dichloromethane was added under nitrogen, 210 μl (0.21 mmol) of a 1N solution of HCl in ether. The solution was stirred for 2 h at room temperature and concentrated to give 37 mg of a yellow solid. The compound was dissolved in pure water, and the solution freeze-dried to give 29 mg (yield 90%) of a pale yellow solid compound corresponding to 2-phenyl-4-{1-[4-(N,N-diethylamino)-piperidinyl]-eth-1-yl}quinoline dihydrochloride.

HPLC-MS: conditions D: t$_r$=4.85 min, (ES+) C$_{26}$H$_{33}$N$_3$ requires 387; found 388 [M+H], purity 98%.

$^1$H NMR (300 MHz, DMSO-d$_6$).

$^1$H NMR (300 MHz, DMSO-d$_6$+D$_2$O).

Example 20

Preparation of 2-phenyl-4-[4-(N,N-diethylamino)-piperidin-1-ylmethyl]quinoline hydrochloride salt (XX-5)

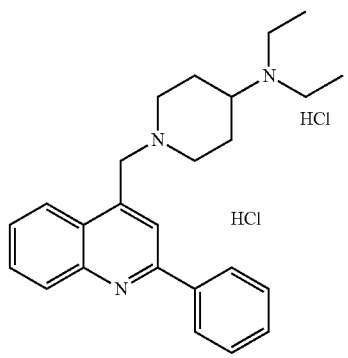 [SMILES: CCN(CC)C1CCN(Cc2cc(-c3ccccc3)nc3ccccc23)CC1 ; Cl ; Cl]

XX-1/ methyl 2-phenyl-quinoline-4-carboxylate

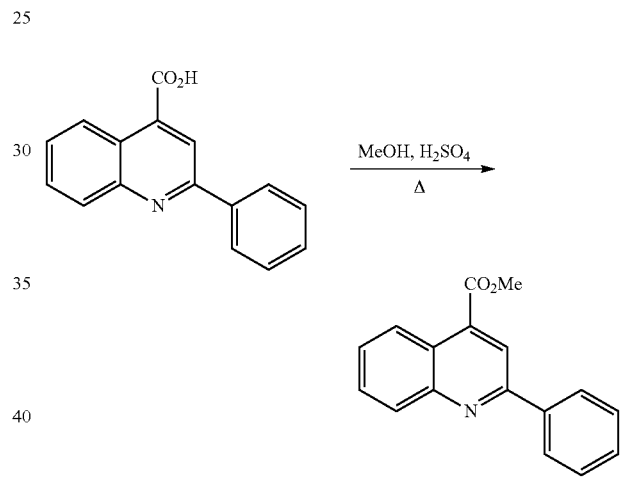

To a solution of 2 g (8 mmol) of commercially available 2-phenyl-4-quinolinecarboxylic acid in 20 ml of methanol was added 0.5 ml of concentrated H$_2$SO$_4$ and the mixture was heated overnight under reflux. The reaction mixture was concentrated, treated with a mixture of ethyl acetate and water, and then the organic layer was washed with a saturated NaHCO$_3$ aqueous solution, dried over MgSO$_4$, filtered and concentrated to give 2.1 g (quantitative yield) of yellow oil corresponding to methyl 2-phenyl-quinoline-4-carboxylate.

$^1$H NMR (300 MHz, CDCl$_3$).

XX-2/ 4-hydroxymethyl-2-phenyl-quinoline

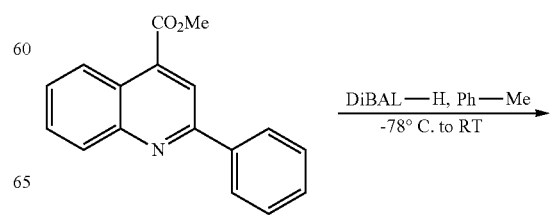

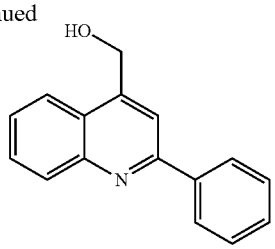

To a solution of 2.1 g (8 mmol) of methyl 2-phenyl-quinoline-4-carboxylate in 50 ml of dichloromethane was added at −78° C. under nitrogen, 12 ml (12 mmol) of Diisobutylaluminium hydride 1M in toluene and the mixture was stirred for one night at room temperature. After cooling the mixture, methanol was added at 0° C., and then 15 g (7 eq.) of potassium sodium tartrate dissolved in 50 ml of water. The mixture was stirred for 1 h at room temperature and extracted with dichloromethane. The organic layer was dried over MgSO$_4$, filtered and concentrated to give 2.01 g of yellow oil (quantitative yield) corresponding to 4-hydroxymethyl-2-phenyl-quinoline.

HPLC-MS: conditions D: t$_r$=4.39 min, (ES+) C$_{16}$H$_{13}$NO requires 235; found 236 [M+H], purity 95%.

$^1$H NMR (300 MHz, CDCl$_3$).

XX-3/ 2-phenyl-quinoline-4-carbaldehyde

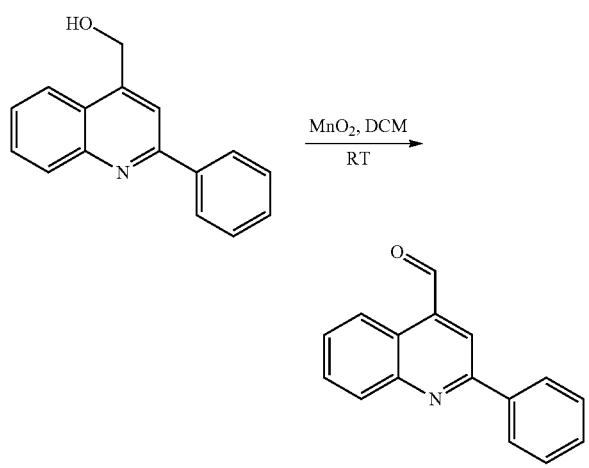

To a solution of 2.01 g (8.5 mmol) of 4-hydroxymethyl-2-phenyl-quinoline in 50 ml of dichloromethane was added under nitrogen, 7.4 g (85 mmol) of MnO$_2$. The mixture was stirred for one night at room temperature, filtered through a Celite® pad and the filtrate concentrated on a rotary evaporator to give 1.48 g of a crude residue. This product was purified by silica gel column chromatography (50 g—petroleum ether 100% then petroleum ether/ethyl acetate 9:1) to give 1.4 g of impure yellow oil. This oil was additionally purified by silica C18 reversed-phase column Biotage (120 g—water/methanol 1:1 then methanol 100%) to give 835 mg (yield 42%) of orange oil corresponding to 2-phenyl-quinoline-4-carbaldehyde.

$^1$H NMR (300 MHz, CDCl$_3$).

XX-4/ 2-phenyl-4-[4-(N,N-diethylamino)-piperidin-1-ylmethyl]quinoline (XX-4)

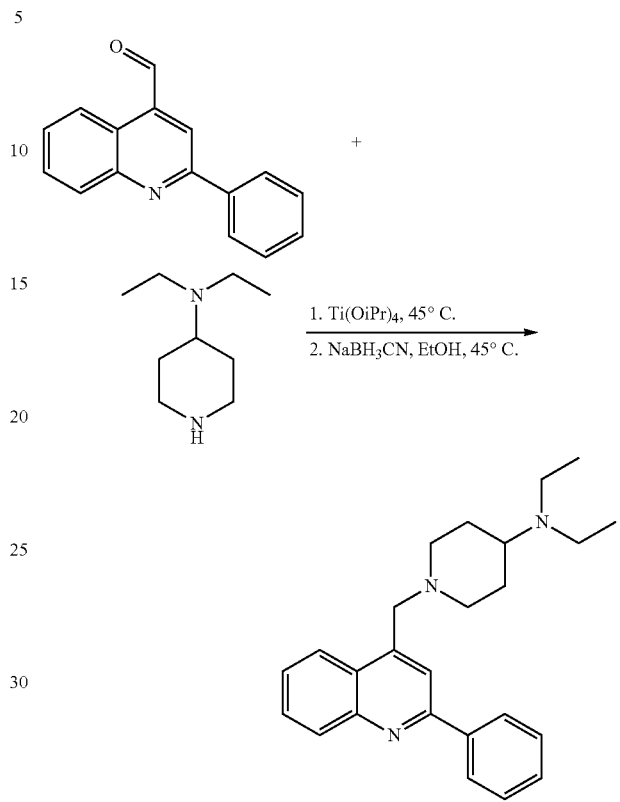

To 400 mg (1.71 mmol) of 2-phenyl-quinoline-4-carbaldehyde were added under nitrogen, 402 mg (2.57 mmol) of 4-diethylamino-piperidine and 712 μl (2.39 mmol) of titanium (IV) isopropoxide. The mixture was heated for 2 h at 45° C. Then, the reaction mixture was cooled, diluted with 5 ml of dry ethanol, and 236 mg (3.76 mmol) of sodium cyanoborohydride were added and the resulting mixture was heated for 4 h at 45° C. and stirred for 12 h at room temperature. The reaction mixture was poured onto 40 ml of water, stirred for 1 h at room temperature, filtrated trough a Celite® pad and the filtrate was extracted with dichloromethane. The organic layer was washed with brine, dried over MgSO$_4$, filtered and concentrated to give 815 mg of yellow oil. This crude product was purified by silica gel column chromatography (25 g from dichloromethane 100% to dichloromethane/ethanol 9:2) to give 202 mg of impure yellow oil. An additional purification of this oil by silica C18 reversed-phase column Biotage (31 g—water/methanol from water 100% to methanol 100%) gave 161 mg of still impure yellow oil. This oil was taken up in a solution of 1N HCl in water; the aqueous layer was washed with dichloromethane, basified with a 1N NaOH aqueous solution and extracted with dichloromethane. The organic layer was dried over MgSO$_4$, filtered and concentrated to give 95 mg (yield 15%) of clear yellow oil corresponding to 2-phenyl-4-[4-(N,N-diethylamino)-piperidin-1-ylmethyl]quinoline.

HPLC-MS: conditions D: t$_r$=4.59 min, (ES+) C$_{25}$H$_{31}$N$_3$ requires 373; found 374 [M+H], purity 99%.

$^1$H NMR (300 MHz, CDCl$_3$).

XX-5/ 2-phenyl-4-[4-(N,N-diethylamino)-piperidin-1-ylmethyl]quinoline dihydrochloride (XX-5)

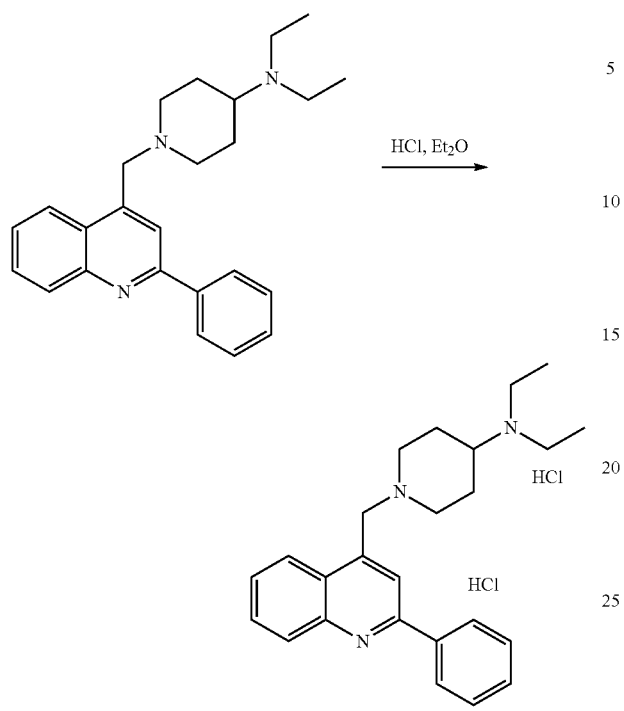

To a solution of 73 mg (0.2 mmol) of 2-phenyl-4-[4-(N,N-diethylamino)-piperidin-1-ylmethyl]quinoline in 5 ml of dry dichloromethane was added under argon, 600 µl (0.6 mmol) of a 1N solution of HCl in ether. The solution was stirred for 2 h at room temperature and concentrated to obtain a solid residue. The compound was triturated with hot ether and dried to give 100 mg of a yellow solid. This solid was solubilized in pure water, and the solution was filtered on Millipore 0.2 µm PTFE syringe filter and then freeze-dried to give 76 mg (yield 85%) of a yellow solid compound corresponding to 2-phenyl-4-[4-(N,N-diethylamino)-piperidin-1-ylmethyl]quinoline dihydrochloride.

HPLC-MS: conditions F: $t_r$=4.62 min, (ES+) $C_{25}H_{31}N_3$ requires 373; found 374 [M+H], purity 99%.

$^1$H NMR (300 MHz, DMSO-$d_6$).
$^1$H NMR (300 MHz, DMSO-$d_6$+$D_2O$).

Example 21

Preparation of 2-phenyl-4-{1-[4-(benzyl-(phenethyl)-amino)-piperidinyl]-eth-1-yl}quinoline hydrochloride salt (XXI-4)

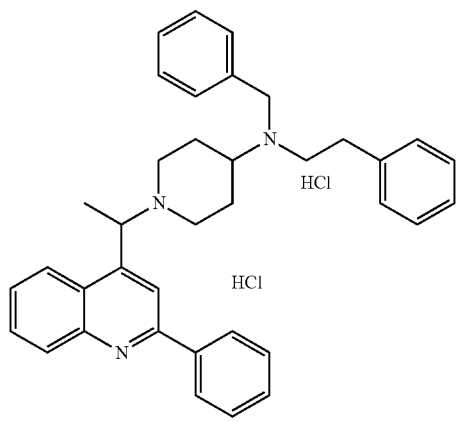 [SMILES: CC(c1cc(-c2ccccc2)nc2ccccc12)N1CCC(N(CCc2ccccc2)Cc2ccccc2)CC1 ; Cl ; Cl]

XXI-1/ N-tert-butyloxycarbonyl-4-[benzyl-(phenethyl)amino]-piperidine

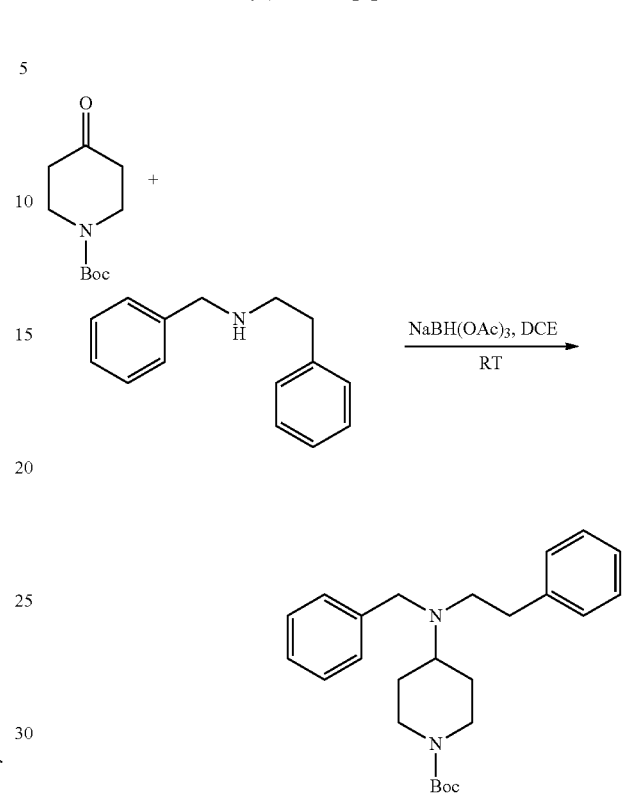

To 200 mg (1.0 mmol) of N-tert-butyloxycarbonylpiperidine-4-one were successively added under argon, 253 µl (1.2 mmol) of N-benzyl-2-phenethylamine, 361 mg (1.7 mmol) of sodium triacetoxyborohydride and 4 ml of 1,2-dichloroethane. The mixture was stirred for one night at room temperature and then concentrated and taken up in ethyl acetate. The organic solution was washed with a saturated solution of sodium bicarbonate, dried over MgSO$_4$, filtered and concentrated to give 640 mg of orange oil. This crude product was purified by silica gel column chromatography (25 g gradient: from dichloromethane 100% to dichloromethane/ethyl acetate 95:5) to give 338 mg (yield 85%) of yellow oil corresponding to N-tert-butyloxycarbonyl-4-[benzyl-(phenethyl)amino]-piperidine.

$^1$H NMR (300 MHz, CDCl$_3$).

XXI-2/ 4-[benzyl-(phenethyl)amino]-piperidine

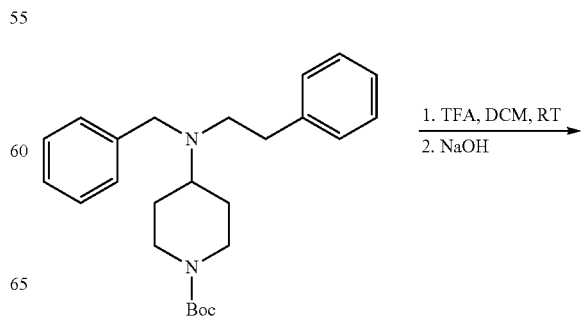

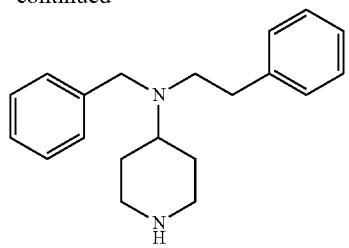

To a solution of 330 mg (0.836 mmol) of N-tert-butyloxycarbonyl-4-[benzyl-(phenethyl)amino]-piperidine in 6.6 ml of dry dichloromethane was added under argon, 642 µl (8.36 mmol) of trifluoroacetic acid and the solution was stirred for 5 h at room temperature. The mixture was quenched with a 1N NaOH aqueous solution and extracted with dichloromethane. The organic layer was dried over MgSO$_4$, filtered and concentrated to give 245 mg (yield 99%) of orange oil corresponding to 4-[benzyl-(phenethyl)amino]-piperidine.

$^1$H NMR (300 MHz, CDCl$_3$).

XXI-3/ 2-phenyl-4-{1-{4-[benzyl(phenethyl)amino]-piperidin-1-yl}-eth-1-yl}quinoline (XXI-3)

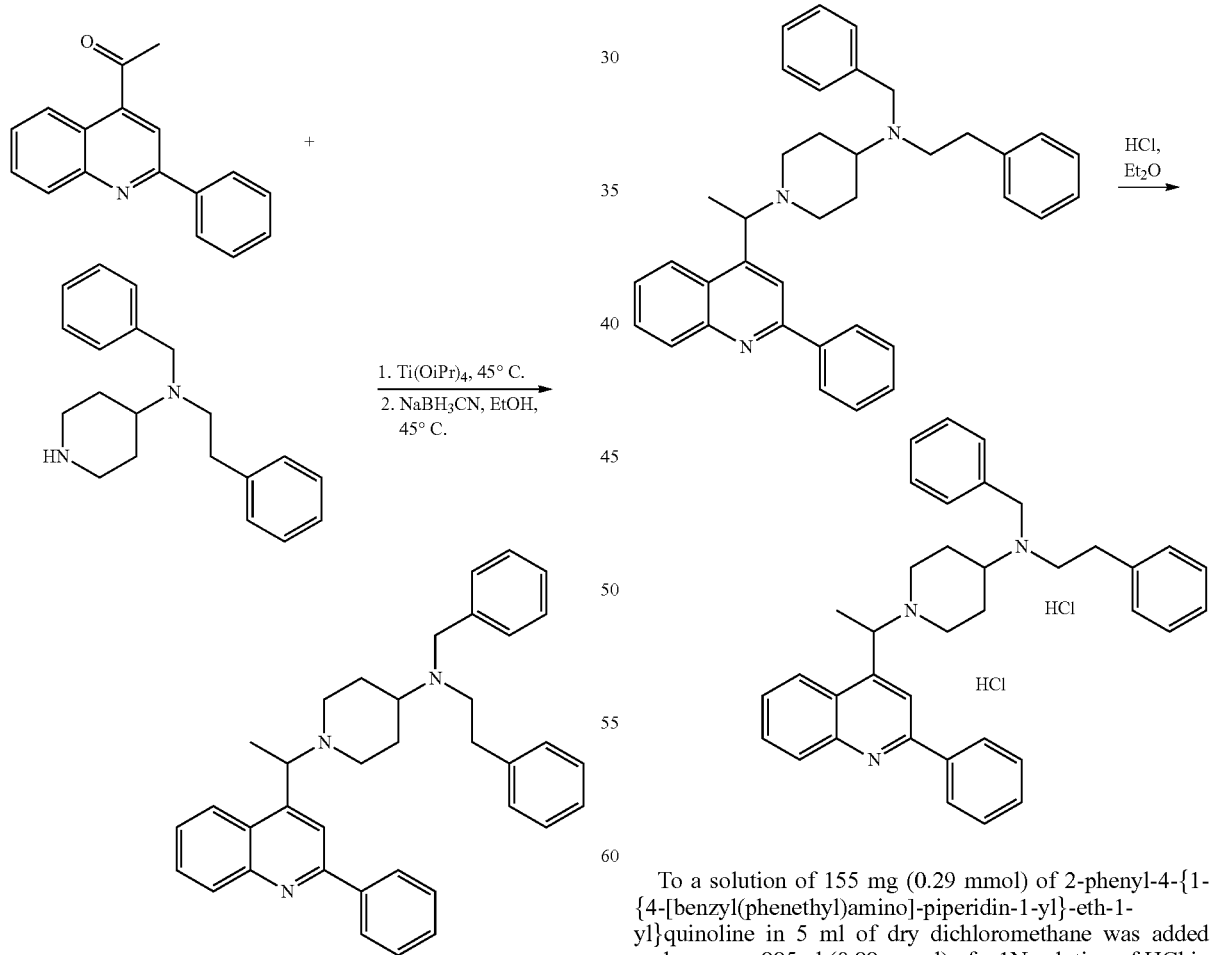

To 135 mg (0.545 mmol) of 4-acetyl-2-phenyl quinoline (prepared according to the process described paragraph XIX-1) were added under argon, 241 mg (0.818 mmol) of 4-[benzyl-(phenethyl)amino]-piperidine, 227 µl (0.764 mmol) of titanium (IV) isopropoxide and the mixture was heated for 5 h at 45° C. After cooling, the mixture was diluted with 1.1 ml of dry ethanol and 76 mg (1.2 mmol) of sodium cyanoborohydride were added and the resulting reaction mixture was heated for 48 h at 45° C. The mixture was poured onto 20 ml of water, stirred for 1 h at room temperature, filtrated through a Celite® pad and the filtrate was extracted with dichloromethane. The organic layer was washed with brine, dried over MgSO$_4$, filtered and concentrated to give 465 mg of yellow oil. This crude compound was purified by silica gel column chromatography (20 g—dichloromethane/ethyl acetate 9:1) to give 158 mg (yield 55%) of yellow oil corresponding to 2-phenyl-4-{1-{4-[benzyl(phenethyl)amino]-piperidin-1-yl}-eth-1-yl}quinoline.

HPLC-MS: conditions D: $t_r$=6.44 min, (ES+) $C_{37}H_{39}N_3$ requires 525; found 526 [M+H], purity 99%.

$^1$H NMR (300 MHz, DMSO-d$_6$).

XXI-4/ 2-phenyl-4-{1-{4-[benzyl(phenethyl)amino]-piperidin-1-yl}-eth-1-yl}quinoline dihydrochloride (XXI-4)

To a solution of 155 mg (0.29 mmol) of 2-phenyl-4-{1-{4-[benzyl(phenethyl)amino]-piperidin-1-yl}-eth-1-yl}quinoline in 5 ml of dry dichloromethane was added under argon, 885 µl (0.88 mmol) of a 1N solution of HCl in ether. The solution was stirred for 1 h at room temperature and concentrated to obtain a solid residue. The compound was triturated with hot dichloromethane, petroleum ether and then solubilized in pure water. The resulting solution was filtered on Nalgene 0.2 μm PTFE syringe filter and then freeze-dried to give 143 mg (yield 81%) of a yellow solid compound corresponding to 2-phenyl-4-{1-{4-[benzyl (phenethyl)amino]-piperidin-1-yl}-eth-1-yl}quinoline dihydrochloride.

HPLC-MS: conditions D: $t_r$=6.39 min, (ES+) $C_{37}H_{39}N_3$ requires 525; found 526 [M+H], purity 98%.

$^1$H NMR (300 MHz, DMSO-$d_6$).

$^1$H NMR (300 MHz, DMSO-$d_6$+$D_2O$).

Example 22

Preparation of 2-phenyl-4-{1-[(1,4'-bipiperidin)-1'-yl]-eth-1-yl}quinoline hydrochloride salt (XXII-4)

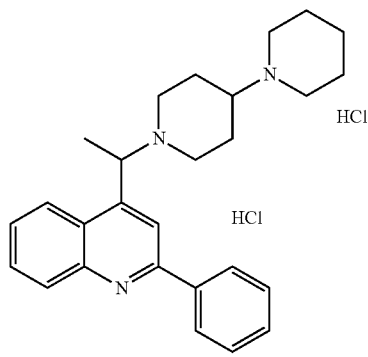 [SMILES: CC(c1cc(-c2ccccc2)nc2ccccc12)N1CCC(N2CCCCC2)CC1 ; Cl ; Cl]

XXII-1/ 2-phenyl-4-{1-(1,4-dioxa-8-aza-spiro[4,5]dec-8-yl)-eth-1-yl}quinoline

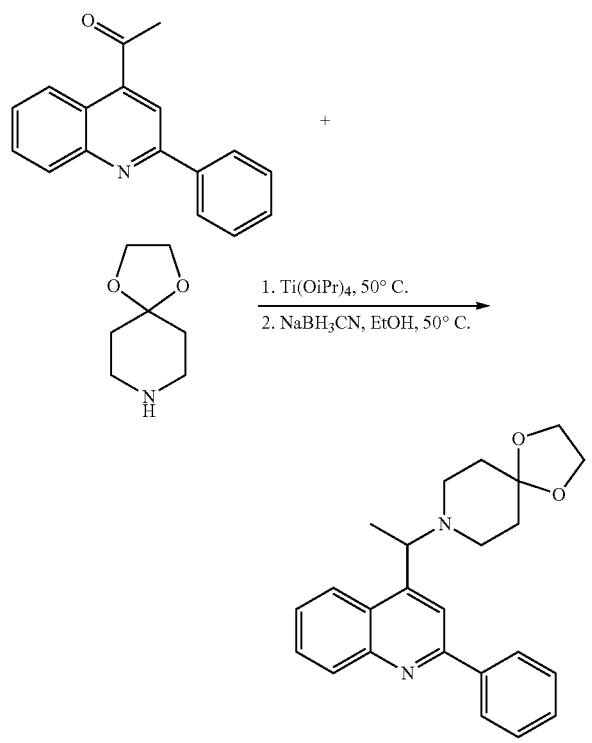

To 430 mg (1.738 mmol) of 4-acetyl-2-phenyl-quinoline (prepared according to the process described paragraph XIX-1) were added under argon, 335 μl (2.6 mmol) of 1,4-dioxa-8-azaspiro[4,8]decane, 725 μl (2.43 mmol) of titanium (IV) isopropoxide and the reaction mixture was heated for 4 h at 50° C. After cooling, the mixture was diluted with 3.5 ml of dry ethanol and 240 mg (3.82 mmol) of sodium cyanoborohydride were added and the resulting reaction mixture was heated for 5 h at 50° C. The mixture was poured onto 60 ml of water, stirred for 1 h at room temperature, filtrated through a Celite® pad and the filtrate was extracted with dichloromethane. The organic layer was washed with brine, dried over MgSO$_4$, filtered and concentrated to give 770 mg of brown oil. This crude compound was purified by silica gel column chromatography (10 g—gradient from dichloromethane 100% to dichloromethane/ethyl acetate 95:5) to give 316 mg of impure yellow foam. This compound was additionally purified by silica gel column chromatography (10 g—dichloromethane/ethyl acetate 9:1) to give 271 mg (yield 41%) of yellow oil corresponding to 2-phenyl-4-{1-(1,4-dioxa-8-aza-spiro[4,5]dec-8-yl)-eth-1-yl}quinoline.

HPLC-MS: conditions D: $t_r$=5.92 min, (ES+) $C_{24}H_{26}N_2O_2$ requires 374; found 375 [M+H], purity 99%.

$^1$H NMR (300 MHz, CDCl$_3$).

XXII-2/ 2-phenyl-4-[1-(4-oxo-piperidin-1-yl)-eth-1-yl]quinoline

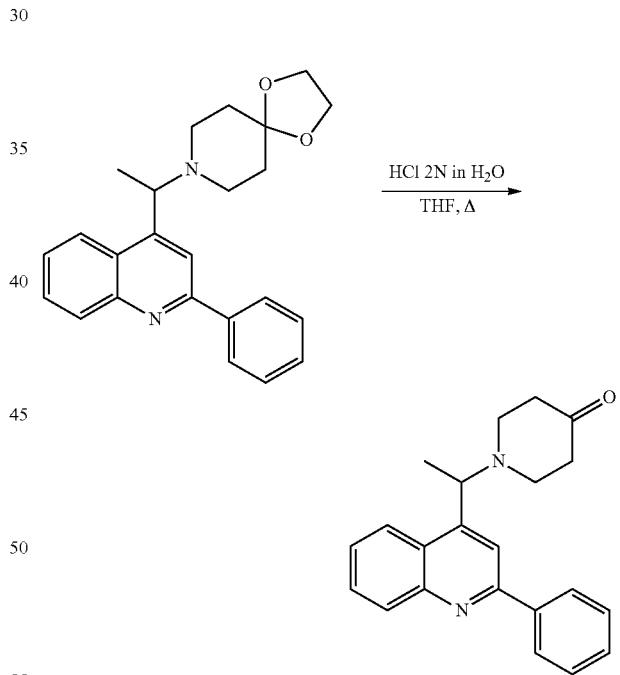

To a solution of 270 mg (0.72 mmol) of 2-phenyl-4-{1-(1,4-dioxa-8-aza-spiro[4,5]dec-8-yl)-eth-1-yl}quinoline in 540 μl of dry tetrahydrofuran was added 1.7 ml of a 2N HCl aqueous solution. The mixture was heated for 2 h under reflux and then treated with a 1N NaOH aqueous solution. The basic mixture was extracted with ethyl acetate and the organic layer was dried over MgSO$_4$, filtered and concentrated to give 235 mg (quantitative yield) of colourless oil corresponding to 2-phenyl-4-[1-(4-oxo-piperidin-1-yl)-eth-1-yl]quinoline.

$^1$H NMR (300 MHz, CDCl$_3$).

XXII-3/ 2-phenyl-4-{1-[(1,4'-bipiperidin)-1'-yl]-eth-1-yl}quinoline (XXII-3)

XXII-4/ 2-phenyl-4-{1-[(1,4'-bipiperidin)-1'-yl]-eth-1-yl}quinoline dihydrochloride (XXII-4)

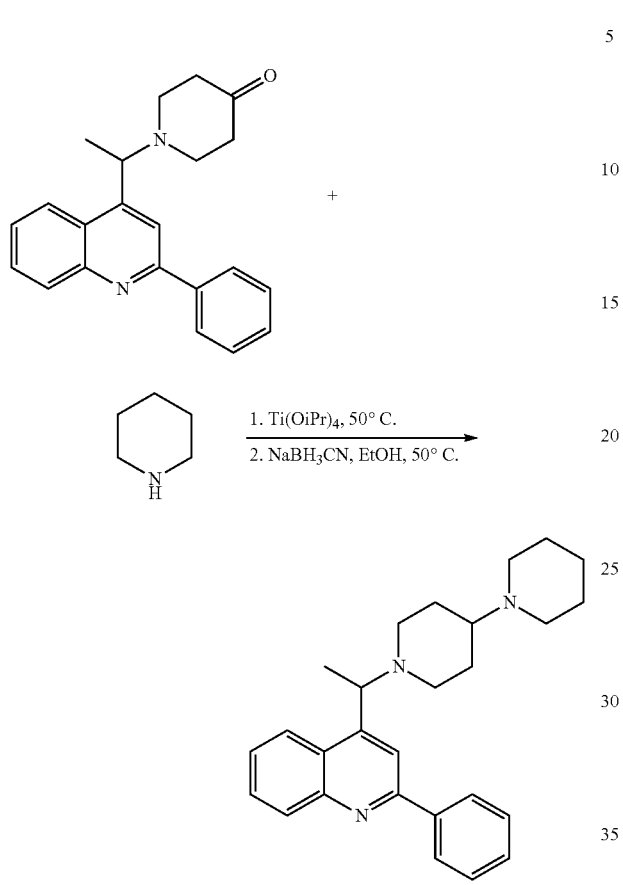

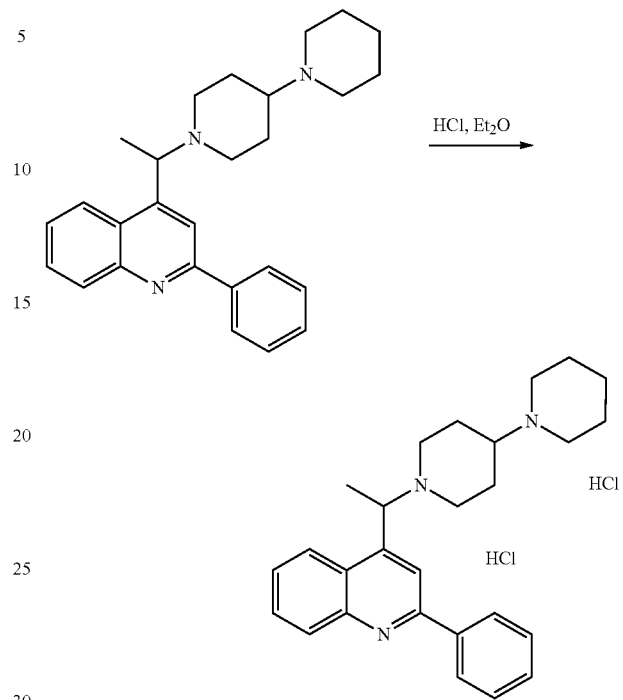

To 110 mg (0.33 mmol) of 2-phenyl-4-[1-(4-oxo-piperidin-1-yl)-eth-1-yl]quinoline were added under argon, 50 μl (0.5 mmol) of piperidine, 139 μl (0.466 mmol) of titanium (IV) isopropoxide and the mixture was heated for 5 h at 50° C. After cooling, the mixture was diluted with 660 μl of dry ethanol and 46 mg (0.732 mmol) of sodium cyanoborohydride were added and the solution heated for 12 h at 50° C. The mixture was poured onto 12 ml of water, stirred for 1 h at room temperature, then filtrated through a Celite® pad and the filtrate was extracted with dichloromethane. The organic layer was washed with brine, dried over $MgSO_4$, filtered and concentrated to give 245 mg of orange oil. This crude compound was purified by silica gel column chromatography (10 g—dichloromethane/methanol 95:5 then 9:1) to give 87 mg of impure yellow oil. This product was additionally purified by silica gel column chromatography (5 g—dichloromethane/methanol 96:4 and a few drops of $NH_4OH$) to give 33 mg (yield 24%) of colourless oil corresponding to 2-phenyl-4-{1-[(1,4'-bipiperidin)-1'-yl]-eth-1-yl}quinoline.

HPLC-MS: conditions D: $t_r$=4.85 min, (ES+) $C_{27}H_{33}N_3$ requires 399; found 400 [M+H], purity 98%.

$^1$H NMR (300 MHz, $CDCl_3$).

To a solution of 33 mg (0.082 mmol) of 2-phenyl-4-{1-[(1,4'-bipiperidin)-1'-yl]-eth-1-yl}quinoline in 1 ml of dry dichloromethane was added under argon, 250 μl (0.248 mmol) of a 1N solution of HCl in ether. The solution was stirred for 1 h at room temperature and concentrated to obtain a solid residue that was triturated with petroleum ether and ether. The residue was then solubilized in pure water, the solution was filtered on Nalgene 0.2 μm PTFE syringe filter and then freeze-dried to give 23 mg (yield 58%) of an orange solid compound corresponding to 2-phenyl-4-{1-[(1,4'-bipiperidin)-1'-yl]-eth-1-yl}quinoline dihydrochloride.

HPLC-MS: conditions D: $t_r$=4.80 min, (ES+) $C_{27}H_{33}N_3$ requires 399; found 400 [M+H], purity >99%.

$^1$H NMR (300 MHz, DMSO-$d_6$).
$^1$H NMR (300 MHz, DMSO-$d_6$+$D_2O$).

Example 23

Preparation of 2-phenyl-4-{1-[4-N-tert-butylamino-piperidin-1-yl]-eth-1-yl}quinoline hydrochloride salt (XXIII-2)

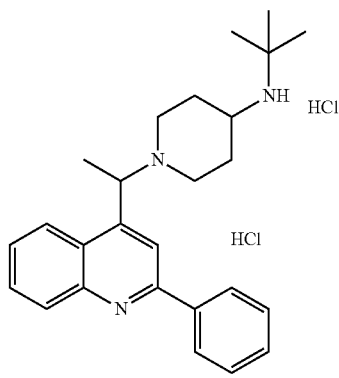 [SMILES: CC(c1cc(-c2ccccc2)nc2ccccc12)N1CCC(NC(C)(C)C)CC1 ; Cl ; Cl]

XXIII-1/ 2-phenyl-4-{1-[4-N-tert-butylamino-piperidinyl]-eth-1-yl}quinoline (XXIII-1)

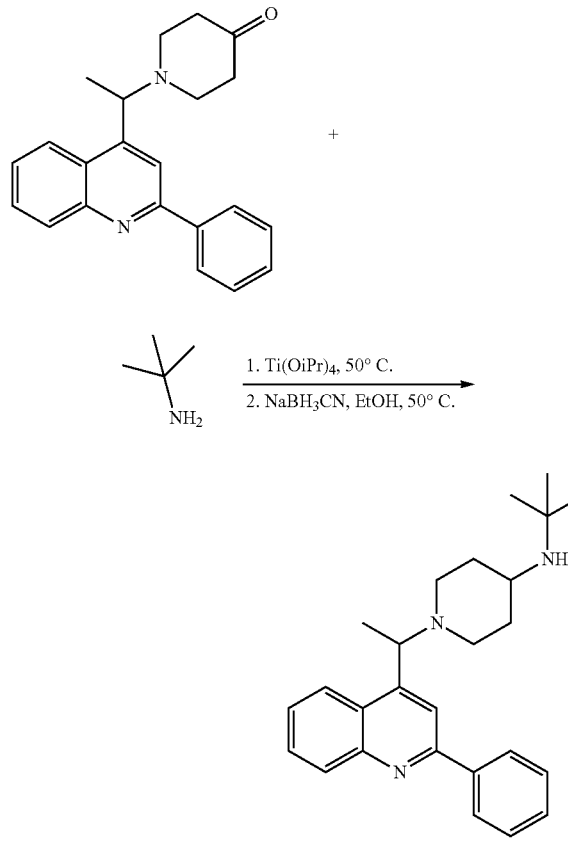

To 130 mg (0.393 mmol) of 2-phenyl-4-[1-(4-oxo-piperidin-1-yl)-eth-1-yl]quinoline, prepared according to the process described in paragraph XXII-2, were added under argon, 62 μl (0.59 mmol) of tert-butylamine, 164 μl (0.55 mmol) of titanium (IV) isopropoxide and the mixture was heated for 6 h at 50° C. After cooling, the mixture was diluted with 0.8 ml of dry ethanol and 55 mg (0.865 mmol) of sodium cyanoborohydride were added. The resulting solution was heated for 3 h30 at 50° C. and overnight at room temperature. The mixture was poured onto 13 ml of water, stirred for 1 h at room temperature, filtrated through a celite pad and the filtrate was extracted with dichloromethane. The organic layer was washed with brine, dried over MgSO$_4$, filtered and concentrated to give 122 mg of orange oil. This crude compound was purified by silica gel column chromatography (10 g—gradient from dichloromethane 100% to dichloromethane/methanol 9:1) to give 57 mg (yield 37%) of colourless oil corresponding to 2-phenyl-4-{1-[4-N-tert-butylamino-piperidinyl]-eth-1-yl}quinoline.

HPLC-MS: conditions D: t$_r$=4.93 min, (ES+) C$_{26}$H$_{33}$N$_3$ requires 387; found 388 [M+H], purity >99%.

$^1$H NMR (300 MHz, CDCl$_3$).

XXIII-2/ 2-phenyl-4-{1-[4-N-tert-butylamino-piperidinyl]-eth-1-yl}quinoline dihydrochloride (XXIII-2)

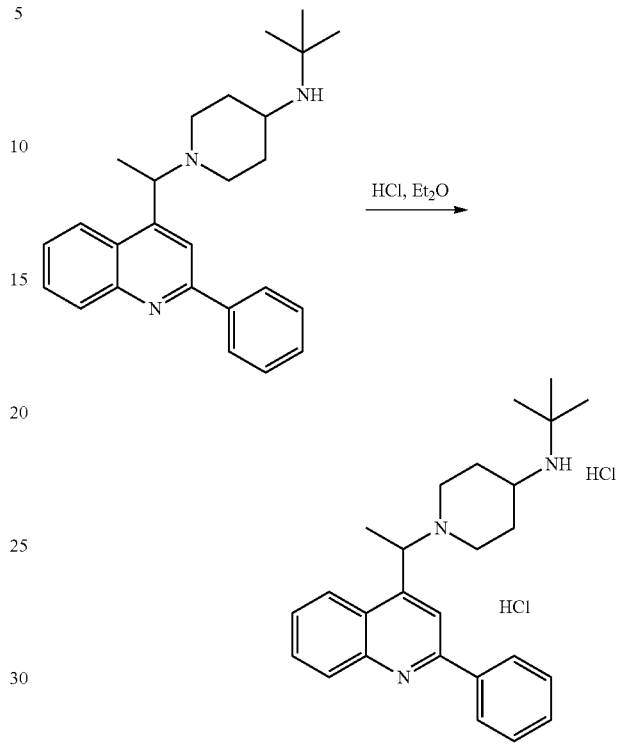

To a solution of 53 mg (0.137 mmol) of 2-phenyl-4-{1-[4-N-tert-butylamino-piperidinyl]-eth-1-yl}quinoline in 1 ml of dry dichloromethane was added under argon, 410 μl (0.41 mmol) of a 1N solution of HCl in ether. The solution was stirred for 1 h at room temperature and concentrated to obtain a solid residue that was triturated with dichloromethane and then petroleum ether. The solid residue was solubilized in pure water and the solution was filtered on Nalgene 0.2 μm PTFE syringe filter and then freeze-dried to give 53 mg (85%) of a white solid corresponding to 2-phenyl-4-{1-[4-N-tert-butylamino-piperidinyl]-eth-1-yl}quinoline dihydrochloride.

HPLC-MS: conditions D: t$_r$=4.92 min, (ES+) C$_{26}$H$_{33}$N$_3$ requires 387; found 388 [M+H], purity >99%.

$^1$H NMR (300 MHz, DMSO-d$_6$).
$^1$H NMR (300 MHz, DMSO-d$_6$+D$_2$O).

Example 24

Preparation of 2-(2-naphtyl)-4-{1-[4-(N,N-diethylamino)-piperidin-1-yl]-eth-1-yl}quinoline hydrochloride salt (XXIV-3)

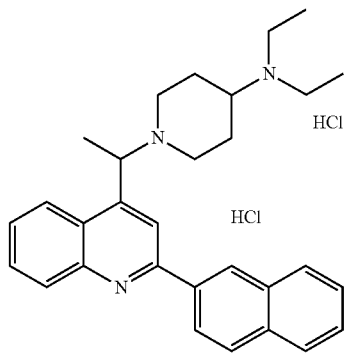 [SMILES: CCN(CC)C1CCN(C(C)c2cc(-c3ccc4ccccc4c3)nc3ccccc23)CC1 ; Cl ; Cl]

XXIV-1/ 2-(2-naphtyl)-4-acetyl-quinoline

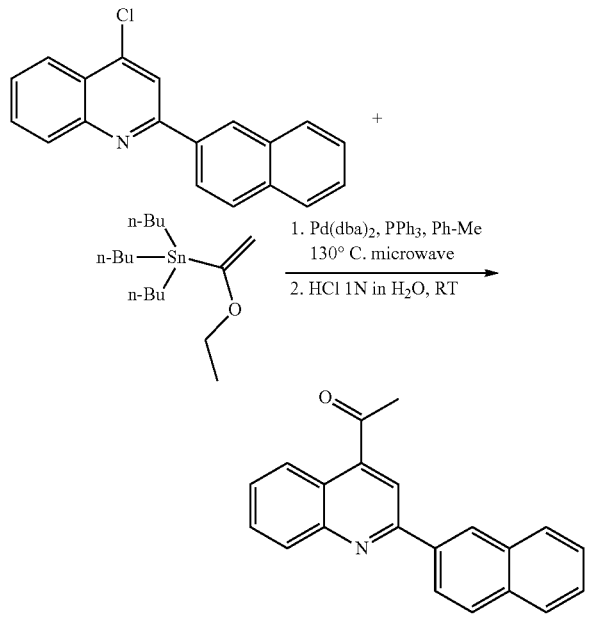

In a microwave vial was successively added under argon: 130 mg (0.45 mmol) of 2-(2-naphtyl)-4-chloro-quinoline prepared according to the protocol described in the paragraph VI-4, 10 mg (0.018 mmol) of Bis(dibenzylideneacetone)palladium(0), 9 mg (0.036 mmol) of triphenylphosphine and 2 ml of dry toluene. The resulting solution was stirred for 15 min at room temperature and 152 μl (0.45 mmol) of ethyl 1-(tributylstannyl)vinyl ether were added under argon. The solution was heated for 16 h at 130° C. in the microwave oven and treated with 5 ml of a 1N HCl aqueous solution and stirred for 3 days at room temperature. The mixture was neutralized with a 1N NaOH aqueous solution, extracted with ethyl acetate and the organic layer was dried over MgSO$_4$, filtered and concentrated to give 294 mg of yellow oil. This product was taken up in 9 ml of THF and 9 ml of a 1N HCl aqueous solution was added. The mixture was stirred for 48 h at room temperature and neutralized with a 1N NaOH aqueous solution. The aqueous layer was extracted with dichloromethane and organic layer dried over MgSO$_4$, filtered and concentrated to give 278 mg of brown oil. This crude compound was purified by silica gel column chromatography (10 g—cyclohexane/ethyl acetate 9:1) to give 68 mg (yield 51%) of yellow oil corresponding to 2-(2-naphtyl)-4-acetyl-quinoline.

HPLC-MS: conditions D: t$_r$=9.77 min, (ES+) C$_{21}$H$_{15}$NO requires 297; found 298 [M+H], purity 93%.

$^1$H NMR (300 MHz, CDCl$_3$).

XXIV-2/ 2-(2-naphtyl)-4-{1-[4-(N,N-diethylamino)-piperidin-1-yl]-eth-1-yl}quinoline (XXIV-2)

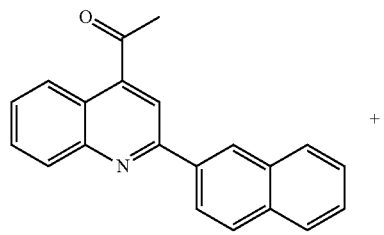

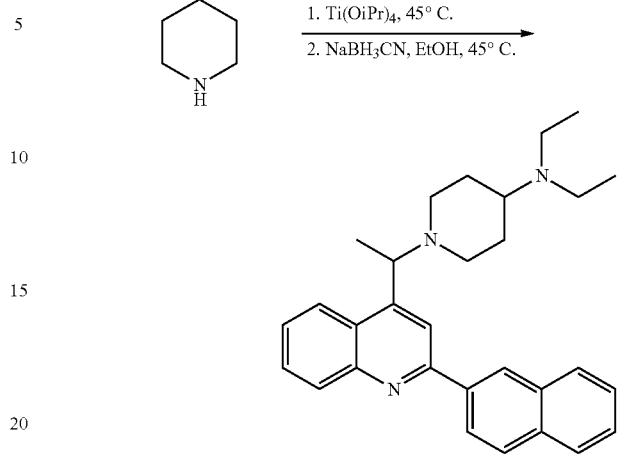

To 65 mg (0.22 mmol) of 2-(2-naphtyl)-4-acetyl-quinoline were added 41 mg (0.26 mmol) of 4-diethylamino-piperidine. Under nitrogen, 144 μl (0.484 mmol) of titanium (IV) isopropoxide were added and the mixture was heated for 4 h at 45° C. Then, the reaction mixture was cooled, diluted with 1 ml of dry ethanol, and 19 mg (0.31 mmol) of sodium cyanoborohydride were added. The resulting mixture was heated for 4 h at 45° C. and stirred for 12 h at room temperature. The mixture was poured onto 10 ml of water, stirred for 1 h at room temperature, filtrated through a Celite® pad and the filtrate was extracted with dichloromethane. The organic layer was washed with brine, dried over MgSO$_4$, filtered and concentrated to give 152 mg of orange oil. This product was purified by silica gel column chromatography (dichloromethane/ethanol 9:1) to give 34 mg (yield 35%) of yellow oil corresponding to 2-(2-naphtyl)-4-{1-[4-(N,N-diethylamino)-piperidin-1-yl]-eth-1-yl}quinoline.

HPLC-MS: conditions D: t$_r$=6.20 min, (ES+) C$_{30}$H$_{35}$N$_3$ requires 437; found 438 [M+H].

$^1$H NMR (300 MHz, CDCl$_3$).

$^1$H NMR (300 MHz, CD$_3$OD).

XXIV-3/ 2-(2-naphtyl)-4-{1-[4-(N,N-diethylamino)-piperidin-1-yl]-eth-1-yl}quinoline dihydrochloride (XXIV-3)

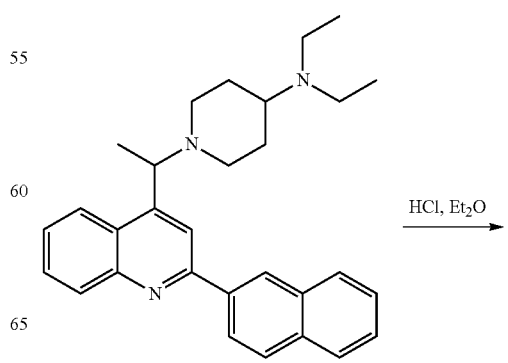

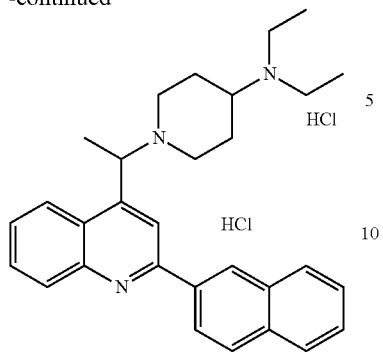

To a solution of 34 mg (0.077 mmol) of 2-(2-naphtyl)-4-{1-[4-(N,N-diethylamino)-piperidinyl]-eth-1-yl}quinoline in 1 ml of dry dichloromethane was added under argon, 233 μl (0.233 mmol) of a 1N solution of HCl in ether. The solution was stirred for 2 h at room temperature and concentrated to obtain a solid residue that was triturated with ether. A yellow solid compound (32 mg) was recovered and solubilized in pure water. The solution was filtered on Millipore 0.2 μm PTFE syringe filter and then freeze-dried to give 21 mg (yield 54%) of a yellow solid compound corresponding to 2-(2-naphtyl)-4-{1-[4-(N,N-diethylamino)-piperidin-1-yl]-eth-1-yl}quinoline dihydrochloride.

HPLC-MS: conditions D: $t_r$=5.89 min, (ES+) $C_{30}H_{35}N_3$ requires 437; found 438 [M+H], purity >95%.

$^1$H NMR (300 MHz, DMSO-$d_6$).
$^1$H NMR (300 MHz, DMSO-$d_6$+$D_2O$).

Example 25

Preparation of 2-phenyl-4-{2-[4-(N,N-diethyl-amino)-piperidin-1-yl]-propan-2-yl}quinoline trifluoroacetate salt (XXV-6)

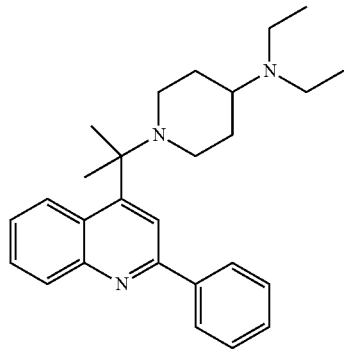 [SMILES: CCN(CC)C1CCN(C(C)(C)c2cc(-c3ccccc3)nc3ccccc23)CC1]

XXV-1/ 2-phenyl-4-quinolinecarboxamide

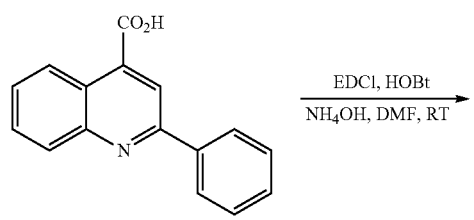

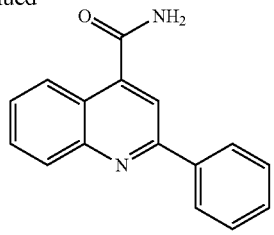

To a solution of 5 g (20 mmol) of commercially available 2-phenyl-quinoline-4-carboxylic acid in 50 ml of DMF was added 3.83 g (20 mmol) of 1-ethyl-3-(3-dimethylaminopropyl)carbodiimide and 2.97 g (22 mmol) of Hydroxybenzotriazole. The mixture was stirred for 30 min at room temperature and 25 ml of concentrated NH$_4$OH aqueous solution were added. After stirring 36 h at room temperature, the mixture was concentrated on a rotary evaporator and the residue was extracted with a mixture of ethyl acetate and water. The organic layer was washed with water, dried over MgSO$_4$, filtered and concentrated to give 3.42 g of a pale yellow solid compound corresponding to 2-phenyl-quinoline-4-carboxamide. This compound was used in the next step without any further purification.

$^1$H NMR (300 MHz, DMSO-$d_6$).

XXV-2/ 2-phenyl-quinoline-carbonitrile

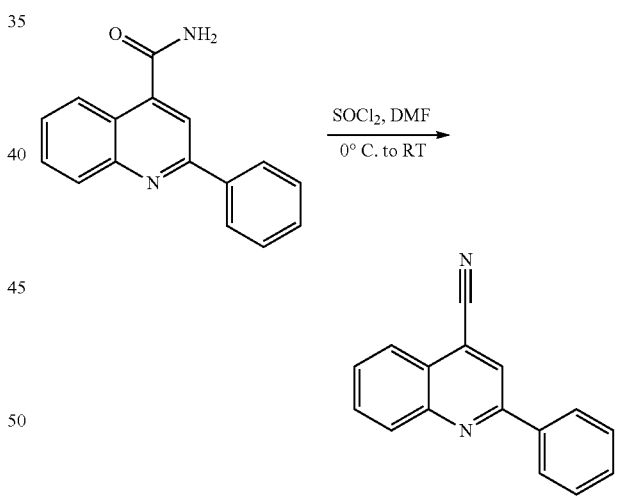

To a solution of 3.42 g (13.7 mmol) of 2-phenyl-quinoline-4-carboxamide in 40 ml of DMF, were added 6.14 ml of thionyl chloride at 0° C. under argon. The mixture was stirred for one night at room temperature then poured onto cold water. The precipitate was filtered, washed with water, taken up in toluene and the organic layer was concentrated to dryness on a rotary evaporator to give 1.69 g (yield 53%) of a yellow solid compound corresponding to 2-phenyl-quinoline-4-carbonitrile. The resulting compound was used in the next step without any further purification.

$^1$H NMR (300 MHz, DMSO-$d_6$).

XXV-3/ 2-phenyl-4-(2-aminopropan-2-yl)-quinoline

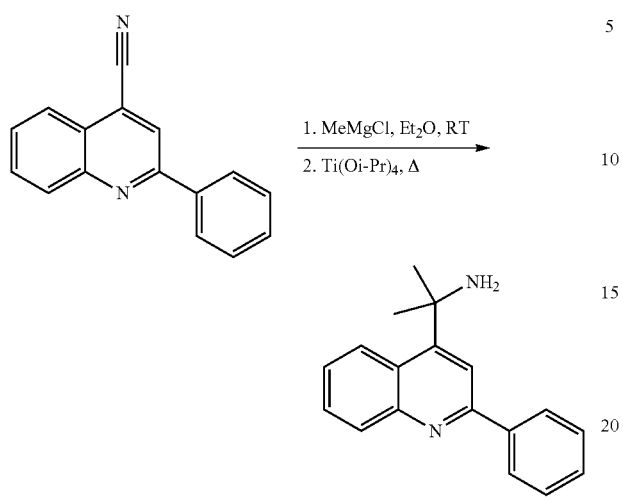

To a suspension of 1.48 g (6.43 mmol) of 2-phenyl-quinoline-4-carbonitrile in 30 ml of ether was added 6.4 ml (19.3 mmol) of a 3M solution of methyl magnesium chloride and the mixture was stirred for 30 min at room temperature. Then, 1.9 ml (6.43 mmol) of titanium (IV) isopropoxide was added and the mixture was heated 4 days under reflux. After cooling, the reaction mixture was quenched and filtered through a Celite® pad and concentrated. The residue was taken up in dichloromethane and 1N NaOH aqueous solution. The organic layer was washed with water, dried over MgSO$_4$, filtered and concentrated to give 0.82 g of a crude oil. This product was purified by silica gel column chromatography (50 g—gradient from cyclohexane/ethyl acetate 9:1 to ethyl acetate 100%) to give 152 mg (yield 9%) of a yellow solid compound corresponding to 2-phenyl-4-(2-aminopropan-2-yl)-quinoline.

$^1$H NMR (300 MHz, DMOS—d$_6$).

XXV-4/ Methyl iodide salt of N-benzyl-4-piperidone

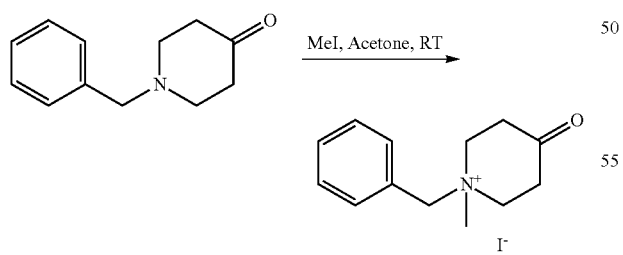

To a solution of 101 μl (0.57 mmol) of N-benzyl-4-piperidone in 1 ml of acetone was added under argon at room temperature, 42 μl (0.68 mmol) of methyl iodide. The precipitate was filtered, washed with acetone and dried under vacuum. The white solid (189 mg) corresponding to the methyl iodide salt of N-benzyl-4-piperidone was used directly in the next step without further purification.

XXV-5/ 2-phenyl-4-[2-(4-oxo-piperidin-1-yl)propan-2-yl]quinoline

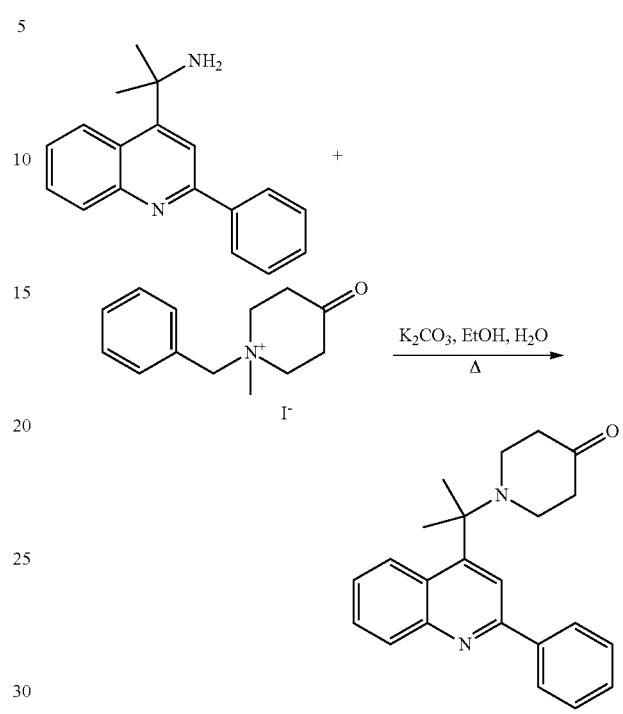

To a solution of 150 mg (0.57 mmol) of 2-phenyl-4-(2-aminopropan-2-yl)-quinoline in 1 ml of dry ethanol were successively added 8 mg (0.057 mmol) of K$_2$CO$_3$, and then 189 mg (0.57 mmol) of the methyl iodide salt of N-benzyl-4-piperidone in solution in 0.5 ml of water. This mixture was heated for 3 h under reflux and taken up in ethyl acetate and water. The organic layer was washed with water, dried over MgSO$_4$, filtered and concentrated to give 280 mg of yellow oil. This product was purified by silica gel column chromatography (10 g—gradient from cyclohexane/ethyl acetate 9:1 to 5:5) to give 83 mg (yield 13%) of yellow solid compound corresponding to 2-phenyl-4-[2-(4-oxo-piperidin-1-yl)propan-2-yl]quinoline.

HPLC-MS: conditions D: t$_r$=6.36 min, (ES+) C$_{23}$H$_{24}$N$_2$O requires 344; found 345 [M+H].

$^1$H NMR (300 MHz, CDCl$_3$).

XXV-6/ 2-phenyl-4-{2-[4-(N,N-diethylamino)-piperidin-1-yl]-propan-2-yl}quinoline trifluoroacetate salt (XXV-6)

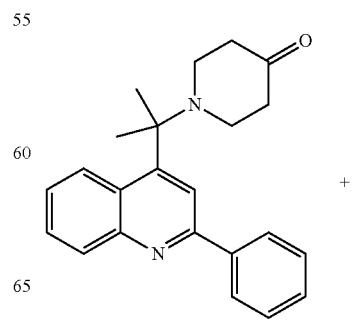

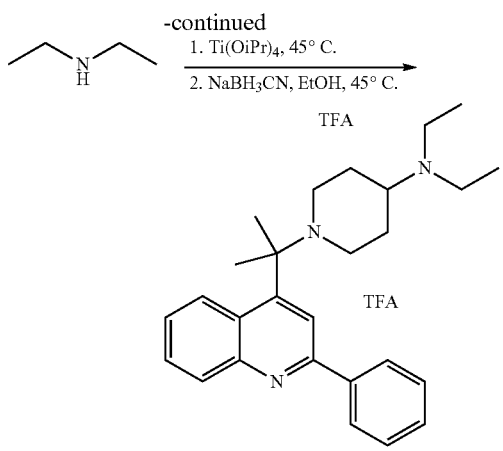

To 20 mg (0.06 mmol) of 2-phenyl-4-[2-(4-oxo-piperidin-1-yl)propan-2-yl]quinoline were added 0.5 ml (a large excess) of diethylamine and 39 μl (0.132 mmol) of titanium (IV) isopropoxide and the resulting mixture was heated for 4 h at 45° C. After cooling, the mixture was diluted with 0.5 ml of dry ethanol and 5.28 mg (0.084 mmol) of sodium cyanoborohydride were added. The solution was heated for 4 h at 45° C. and then stirred for 12 h at room temperature. The mixture was poured onto 10 ml of water, stirred for 1 h at room temperature, filtrated through a Celite® pad and the filtrate was extracted with dichloromethane. The organic layer was washed with brine, dried over MgSO$_4$, filtered and concentrated to give 22 mg of brown solid. This crude compound was purified by semi preparative HPLC-MS to recover 2.2 mg of yellow oil (yield 5%) corresponding to the trifluoro acetate salt of 2-phenyl-4-{2-[4-(N,N-diethyl-amino)-piperidin-1-yl]-propan-2-yl}quinoline.

HPLC-MS: conditions F: t$_r$=5.19 min, (ES+) C$_{27}$H$_{35}$N$_3$ requires 401; found 402 [M+H], purity 96%.

$^1$H NMR (300 MHz, D$_2$O).

Example 26

Preparation of 7-chloro-2-phenyl-4-[4-(N,N-diethyl-aminomethyl)-piperidin-1-yl]-quinoline hydrochloride salt (XXVI-4)

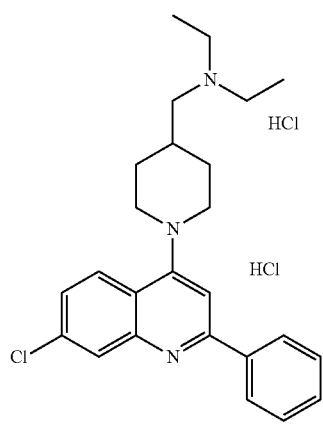 [SMILES: CCN(CC)CC1CCN(c2cc(-c3ccccc3)nc3cc(Cl)ccc23)CC1 ; Cl ; Cl]

XXVI-1/ N-tert-butyloxycarbonyl-4-(N,N-diethyl-aminomethyl)piperidine

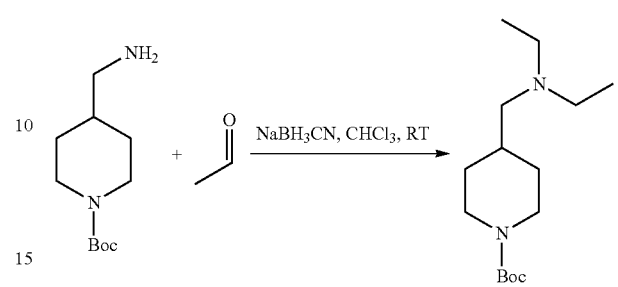

To a solution of 0.5 g (2.33 mmol) of N-tert-butyloxycarbonyl-4-(aminomethyl)piperidine in 5 ml of dry chloroform was successively added under argon, 1.32 ml (23.3 mmol) of acetaldehyde and 440 mg (7 mmol) of sodium cyanoborohydride. The reaction mixture was stirred for 40 min at room temperature, and then neutralized with acetic acid, stirred for 1 h at room temperature and concentrated. The residue was taken up in a 2N NaOH aqueous solution and extracted with dichloromethane. The organic layer was washed with water, dried over MgSO$_4$, filtered and concentrated to give 779 mg of yellow oil. This crude product was purified by silica gel column chromatography (25 g—gradient from dichloromethane 100% to dichloromethane/methanol+1% NH$_4$OH, 9:1) to give 236 mg (yield 37%) of yellow oil corresponding to N-tert-butyloxycarbonyl-4-(N,N-diethylaminomethyl)piperidine.

HPLC-MS: conditions D: t$_r$=4.89 min, (ES+) C$_{15}$H$_{30}$N$_2$O$_2$ requires 270; found 271 [M+H].

$^1$H NMR (300 MHz, CDCl$_3$).

XXVI-2/ 4-(N,N-diethylaminomethyl)piperidine

A solution of 230 mg (0.85 mmol) of N-tert-butyloxycarbonyl-4-(N,N-diethylaminomethyl)piperidine in 2 ml of a 4M solution of HCl in dioxane was stirred for 4 h at room temperature, then concentrated and taken up in a mixture of a 1N NaOH aqueous solution and dichloromethane. The organic layer was washed with water, dried over MgSO$_4$, filtered and concentrated to give 153 mg of colourless oil corresponding to 4-(N,N-diethylaminomethyl)piperidine.

$^1$H NMR (300 MHz CDCl$_3$).

XXVI-3/ 7-chloro-2-phenyl-4-[4-(N,N-diethylaminomethyl)-piperidin-1-yl]quinoline (XXVI-3)

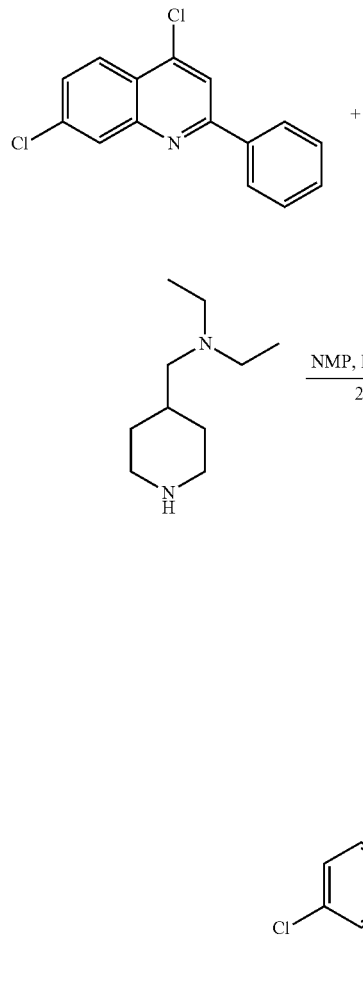

In a microwave vial was successively added, 80 mg (0.3 mmol) of 4 4,7-dichloro-2-phenylquinoline (obtained according to the protocol described in paragraph II-2), 153 mg (0.9 mmol) of 4-(N,N-diethylaminomethyl)-1-piperidine and 1 ml of NMP. The solution was heated for 1 h at 200° C. in a microwave oven and then treated with a 1N NaOH aqueous solution. The mixture was extracted with dichloromethane and the organic layer was dried over $MgSO_4$, filtered and concentrated to give 672 mg of an oily residue. It was purified by silica gel column chromatography (25 g—gradient from dichloromethane 100% to dichloromethane/methanol 9:1) to provide 139 mg of impure brown oil. This product was taken up in a 1N NaOH aqueous solution and the aqueous layer was extracted with toluene. The organic layer was washed with water, dried over $MgSO_4$, filtered and concentrated to give 28 mg (yield 23%) of pale brown oil corresponding to 7-chloro-2-phenyl-4-[4-(N,N-diethylaminomethyl)-piperidin-1-yl]quinoline.

HPLC-MS: conditions D: $t_r$=4.75 min, (ES+) $C_{25}H_{30}ClN_3$ requires 407; found 408 [M+H], purity 98%.

$^1$H NMR (300 MHz, $CDCl_3$).

XXVI-4/ 7-chloro-2-phenyl-4-[4-(N,N-diethylaminomethyl)-piperidin-1-yl]quinoline dihydrochloride (XXVI-4)

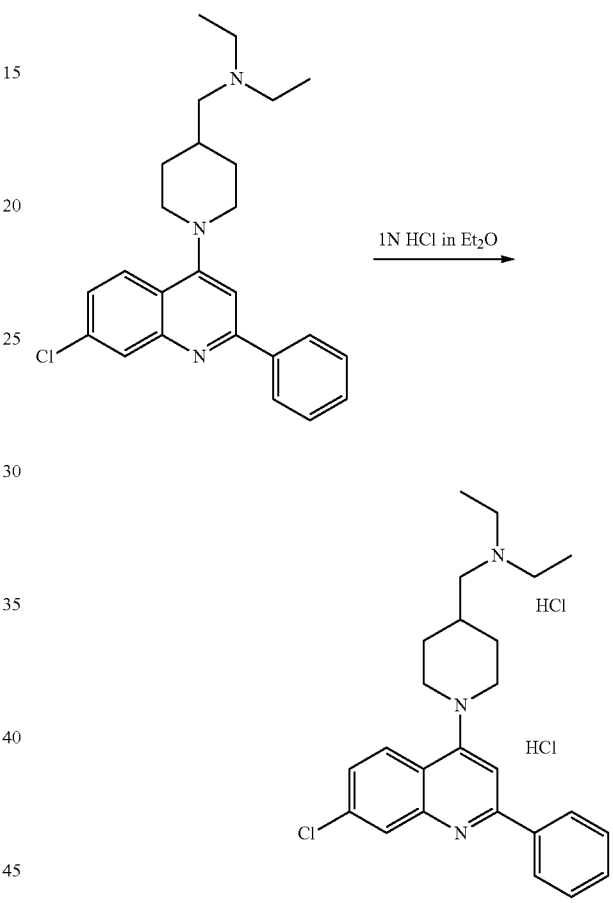

To a solution of 25 mg (0.061 mmol) of 7-chloro-2-phenyl-4-[4-(N,N-diethylaminomethyl)-piperidin-1-yl]quinoline in 2 ml of dry dichloromethane was added under argon, 122 μl (0.122 mmol) of a 1N solution of HCl in ether. This solution was stirred for 2 h at room temperature and concentrated to obtain a solid residue that was triturated with ether. 24 mg of a yellow solid compound were recovered and solubilized in pure water. The solution was filtered on Millipore 0.2 μm PTFE syringe filter and freeze-dried to give 20 mg (yield 74%) of a pale yellow solid compound corresponding to 7-chloro-2-phenyl-4-[4-(N,N-diethylaminomethyl)-piperidin-1-yl]quinoline dihydrochloride.

HPLC-MS: conditions D: $t_r$=4.70 min, (ES+) $C_{25}H_{30}ClN_3$ requires 407; found 408 [M+H], purity >99%.

$^1$H NMR (300 MHz, DMSO-$d_6$ and DMSO-$d_6$+$D_2O$).

Example 27

Preparation of 2-phenyl-4-[4-(N,N-diethylaminomethyl)-piperidin-1-yl]quinoline hydrochloride salt (XXVII-2)

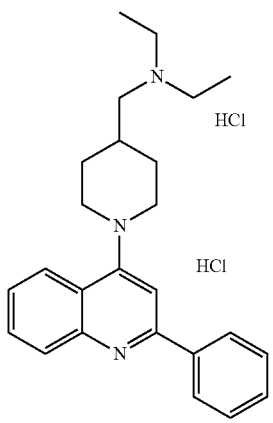 [SMILES: CCN(CC)CC1CCN(c2cc(-c3ccccc3)nc3ccccc23)CC1 ; Cl ; Cl]

XXVII-1/ 2-phenyl-4-[4-(N,N-diethylaminomethyl)-piperidin-1-yl]quinoline (XXVII-1)

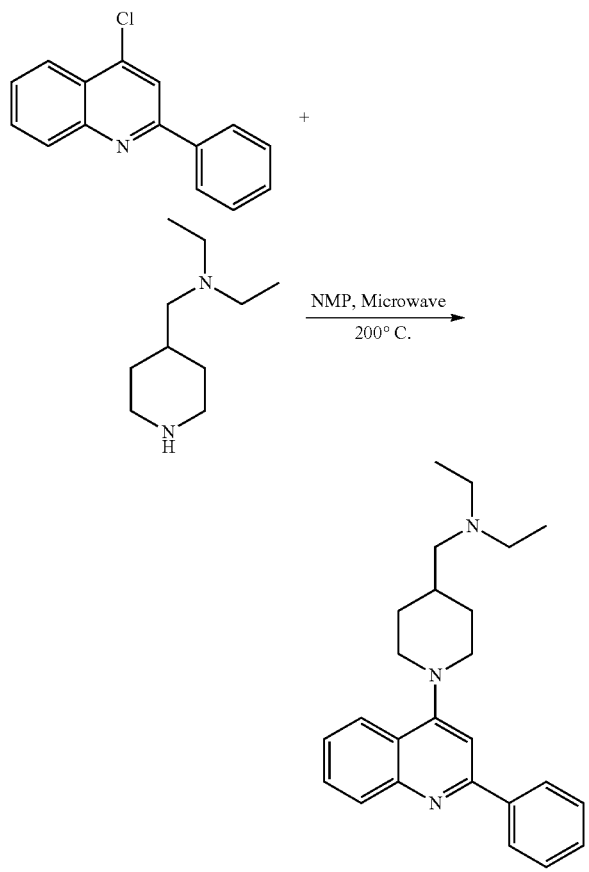

In a microwave vial was successively added, 211 mg (0.88 mmol) of commercially available 4-chloro-2-phenylquinoline, 450 mg (2.64 mmol) of 4-(N,N-diethylaminomethyl)-piperidine and 2 ml of NMP. The solution was heated for 1 h at 200° C. in a microwave oven and then treated with a 1N NaOH aqueous solution. The mixture was extracted with dichloromethane and the organic layer was dried over MgSO$_4$, filtered and concentrated to give 1.02 g of a brown oily residue. The crude product was purified by silica gel column chromatography (25 g—dichloromethane 100% then ethyl acetate 100%) to give 586 mg of impure yellow oil. This product was taken up in a 1N NaOH aqueous solution and the mixture was extracted with toluene. The organic layer was washed with water, dried over MgSO$_4$, filtered and concentrated to give 170 mg (yield 52%) of yellow oil corresponding to 2-phenyl-4-[4-(N,N-diethylaminomethyl)-piperidin-1-yl]quinoline.

HPLC-MS: conditions D: t$_r$=4.35 min, (ES+) C$_{25}$H$_{31}$N$_3$ requires 373; found 374 [M+H], purity 97%.

$^1$H NMR (300 MHz, CDCl$_3$).

XXVII-2/ 2-phenyl-4-[4-(N,N-diethylaminomethyl)-piperidin-1-yl]quinoline dihydrochloride (XXVII-2)

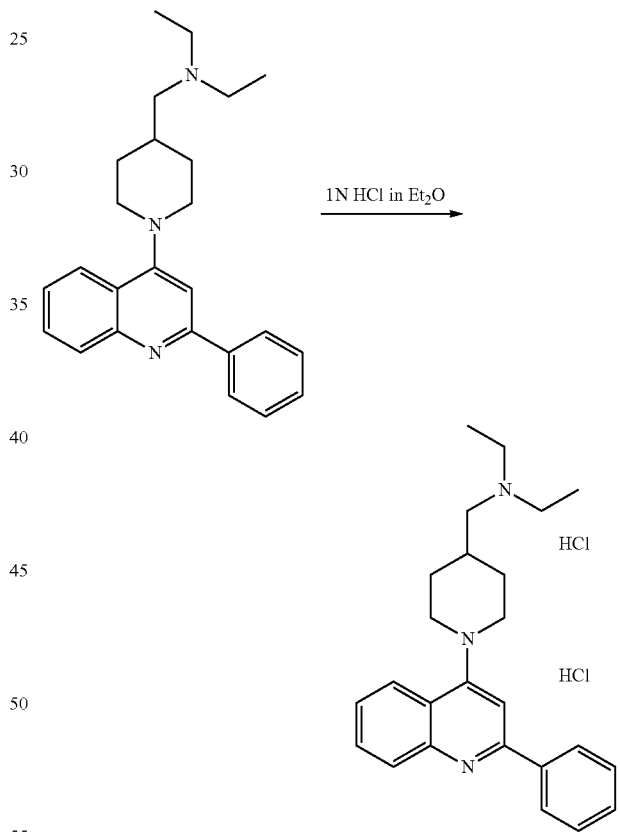

To a solution of 160 mg (0.428 mmol) of 2-phenyl-4-[4-(N,N-diethylaminomethyl)-piperidin-1-yl]quinoline in 5 ml of dry dichloromethane was added under argon, 857 μl (0.857 mmol) of a 1N solution of HCl in ether. The solution was stirred for 2 h at room temperature and concentrated to obtain a yellow solid that was triturated with ether. The solid compound was solubilized in pure water, filtered on Millipore 0.2 μm PTFE syringe filter and freeze-dried to provide 150 mg (yield 79%) of a pale yellow solid compound corresponding to 2-phenyl-4-[4-(N,N-diethylaminomethyl)-piperidin-1-yl]quinoline dihydrochloride.

HPLC-MS: conditions D: $t_r$=4.33 min, (ES+) $C_{25}H_{31}N_3$ requires 373; found 374 [M+H], purity >99%.

$^1$H NMR (300 MHz, DMSO-$d_6$ and DMSO-$d_6$+$D_2O$).

Example 28

Preparation of 7-chloro-2-phenyl-4-[(N-benzylpiperidin-4-yl)-amino]quinoline hydrochloride salt: (XXVIII-2)

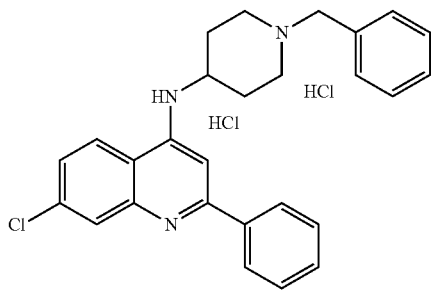 [SMILES: Clc1ccc2c(NC3CCN(Cc4ccccc4)CC3)cc(-c3ccccc3)nc2c1 ; Cl ; Cl]

XXVIII-1/ 7-chloro-2-phenyl-4-[(N-benzylpiperidin-4-yl)-amino]quinoline (XXVIII-1)

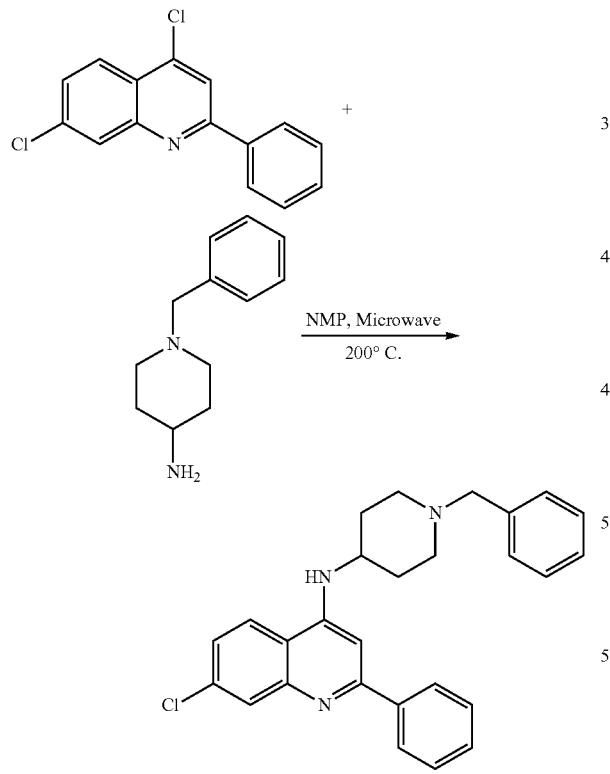

In a microwave vial was successively added, 370 mg (1.35 mmol) of 44,7-dichloro-2-phenylquinoline obtained according to the protocol described in paragraph II-2, 2.8 ml (13.5 mmol) of 1-benzyl-4-aminopiperidine and 0.5 ml of NMP. The solution was heated for 1 h at 200° C. in a microwave oven and then treated with a 1N NaOH aqueous solution. The mixture was extracted with ethyl acetate and the organic layer was washed with water, dried over MgSO$_4$, filtered and concentrated to provide 3.4 g of an oily residue. The crude product was purified by silica gel column chromatography (20 g—gradient from dichloromethane 100% to dichloromethane/ethanol 95:5) to give 599 mg of brown oil. This product was additionally purified by silica C18 reversed-phase column Biotage (31 g—gradient from water/methanol 7:3 to methanol 100%) to give a brown solid compound that was triturated with petroleum ether to give 239 mg (yield 41%) of a beige solid compound corresponding to 7-chloro-2-phenyl-4-[(N-benzylpiperidin-4-yl)-amino]quinoline.

HPLC-MS: conditions D: $t_r$=5.33 min, (ES+) $C_{27}H_{26}ClN_3$ requires 427/429; found 428/430 [M+H], purity 96%.

$^1$H NMR (300 MHz, DMSO-$d_6$).

XXVIII-2/ 7-chloro-2-phenyl-4-[(N-benzylpiperidin-4-yl)-amino]quinoline dihydrochloride: (XXVIII-2)

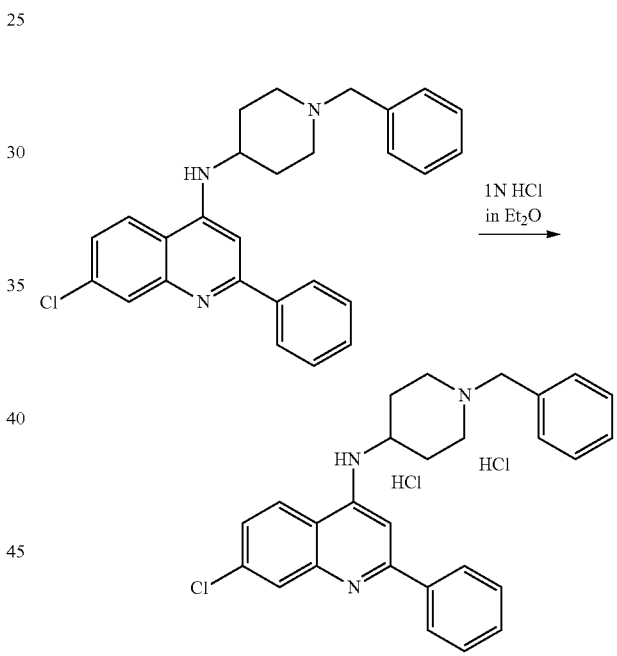

To a solution of 120 mg (0.28 mmol) of 7-chloro-2-phenyl-4-[(N-benzylpiperidin-4-yl)-amino]quinoline in 0.3 ml of dry dichloromethane was added under nitrogen, 600 μl (0.56 mmol) of a 1N solution of HCl in ether. The solution was stirred for 1 h at room temperature and filtered to recover a yellow solid that was triturated with ether. This compound was solubilized in pure water, filtered on Millipore 0.2 μm PTFE syringe filter and freeze-dried to give 63 mg (yield 45%) of a white solid compound corresponding to 7-chloro-2-phenyl-4-[(N-benzylpiperidin-4-yl)-amino]quinoline dihydrochloride.

HPLC-MS: conditions D: $t_r$=5.23 min, (ES+) $C_{27}H_{26}ClN_3$ requires 427/429; found 428/430 [M+H], purity >95%.

$^1$H NMR (DMSO-$d_6$ and DMSO-$d_6$+$D_2O$).

Example 29

Preparation of 7-chloro-2-phenyl-4-[N-methyl-N—(N-benzylpiperidin-4-yl)-amino]quinoline dihydrochloride: (XXIX-2)

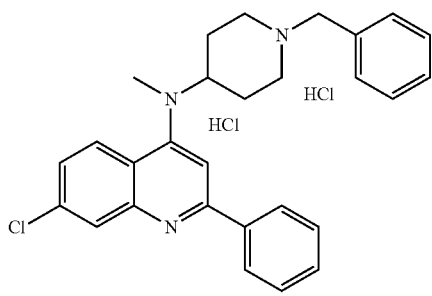 [SMILES: CN(c1cc(-c2ccccc2)nc2cc(Cl)ccc12)C1CCN(Cc2ccccc2)CC1 ; Cl ; Cl]

XXIX-1/ 7-chloro-2-phenyl-4-[N-methyl-N—(N-benzylpiperidin-4-yl)-amino]quinoline (XXIX-1)

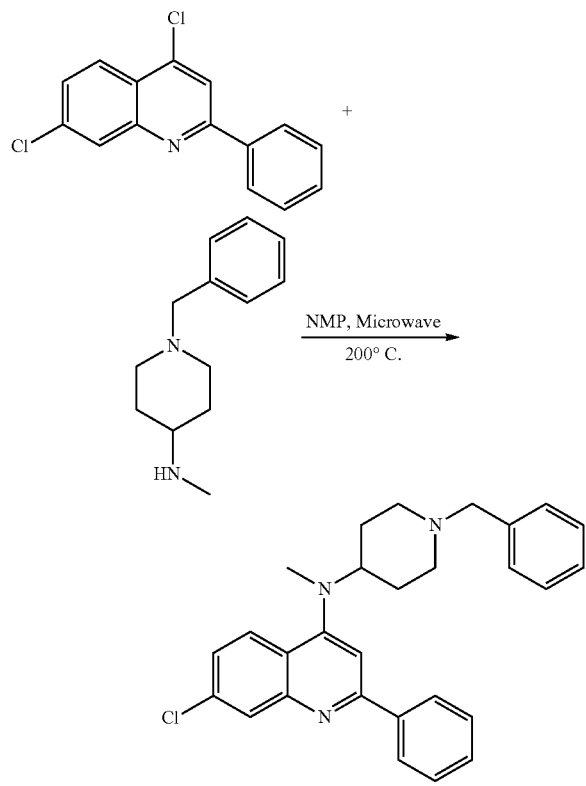

In a microwave vial was successively added, 300 mg (1.1 mmol) of 4,7-dichloro-2-phenylquinoline (prepared according to the protocol described in paragraph II-2), 1.12 g (5.5 mmol) of 1-benzyl-4-(N-methyl-amino)piperidine and 1 ml of NMP. The resulting reaction mixture was heated for 7 h at 200° C. in a microwave oven and then treated with a 1N NaOH aqueous solution. The mixture was extracted with ethyl acetate and the organic layer was dried over MgSO$_4$, filtered and concentrated to give 1.9 g of brown oil. This oil was purified by silica gel column chromatography (20 g—toluene/ethyl acetate 9:1+1% triethylamine) to give 606 mg of impure yellow oil. This product was additionally purified according to the slightly modified previous conditions (10 g of silica gel—toluene/ethyl acetate 95:5 without triethylamine) to give 318 mg of impure yellow oil. A new purification using silica C18 reversed-phase column Biotage (31 g—water/methanol 1:1+1% triethylamine) gave 186 mg (yield 38%) of yellow oil corresponding to 7-chloro-2-phenyl-4-[N-methyl-N—(N-benzylpiperidin-4-yl)-amino]quinoline.

HPLC-MS: conditions F: $t_r$=5.03 min, (ES+) $C_{28}H_{28}ClN_3$ requires 441/443; found 442/444 [M+H], purity >99%.

$^1$H NMR (300 MHz, CDCl$_3$).

XXIX-2/ 7-chloro-2-phenyl-4-[N-methyl-N—(N-benzylpiperidin-4-yl)-amino]quinoline dihydrochloride (XXIX-2)

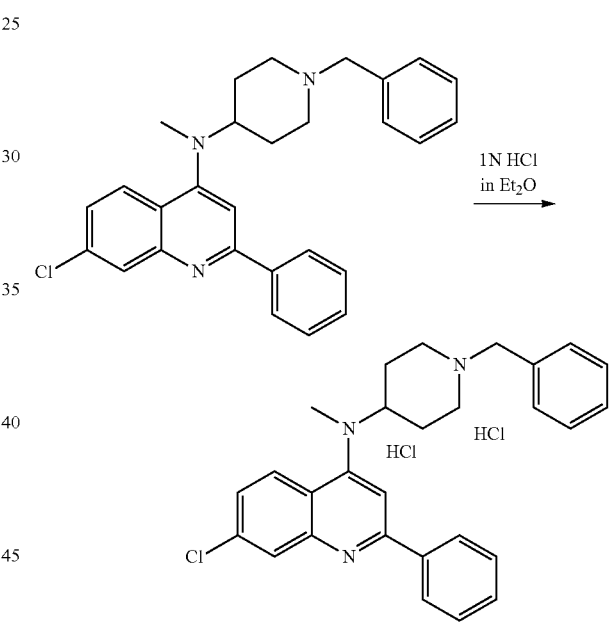

To a solution of 162 mg (0.37 mmol) of 7-chloro-2-phenyl-4-[N-methyl-N—(N-benzylpiperidin-4-yl)-amino]quinoline in 0.5 ml of dry dichloromethane was added under argon, 730 μl (0.73 mmol) of a 1N solution of HCl in ether. The solution was stirred for 1 h at room temperature and filtered to recover 185 mg of a yellow solid that was triturated with ether. The compound was solubilized in pure water, filtered on Millipore 0.2 μm PTFE syringe filter and freeze-dried to give 154 mg (yield 88%) of a yellow solid compound corresponding to 7-chloro-2-phenyl-4-[N-methyl-N—(N-benzylpiperidin-4-yl)-amino]quinoline dihydrochloride.

HPLC-MS: conditions D: $t_r$=5.09 min, (ES+) $C_{28}H_{28}ClN_3$ requires 441/443; found 442/444 [M+H], purity 98%.

$^1$H NMR (300 MHz, DMSO-d$_6$ and DMSO-d$_6$+D$_2$O).

Example 30

Preparation of 7-chloro-2-phenyl-4-[N-methyl-N—(N-1-phenylethyl-piperidin-4-yl)-amino]quinoline hydrochloride salt (XXX-3)

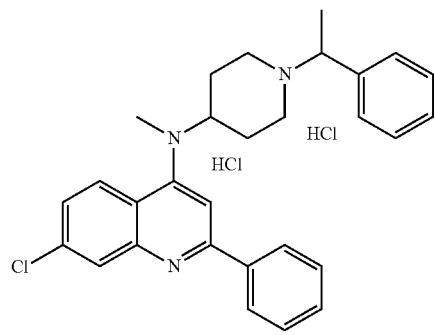 [SMILES: CC(c1ccccc1)N1CCC(N(C)c2cc(-c3ccccc3)nc3cc(Cl)ccc23)CC1 ; Cl ; Cl]

XXX-1/ 1-(1-phenylethyl)-4-(N-methylamino)-piperidine

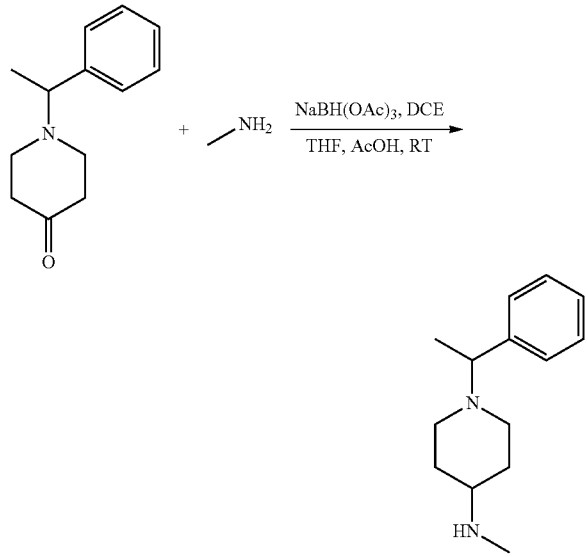

To a solution of 4.3 g (21.15 mmol) of 1-(1-phenylethyl)-piperidin-4-one in 20 ml of 1,2-dichloroethane was successively added under nitrogen, 10.6 ml (21.15 mmol) of a 2M solution of methylamine in THF, 1.26 ml of acetic acid and 4.5 g (21.16 mmol) of sodium triacetoxyborohydride. The resulting mixture was stirred overnight at room temperature, and then concentrated and taken up in ethyl acetate. The organic solution was washed with a saturated aqueous solution of sodium bicarbonate, dried over MgSO$_4$, filtered and concentrated to give 4 g of brown oil. This crude product was purified by silica gel column chromatography (100 g dichloromethane/methanol+1% of triethylamine, 9:1) to give 2.56 g (yield 55%) of brown oil corresponding to 1-(1-phenylethyl)-4-(N-methylamino)-piperidine.

HPLC-MS: conditions D: t$_r$=2.46 min, (ES+) C$_{14}$H$_{22}$N$_2$ requires 218; found 219 [M+H].

$^1$H NMR (300 MHz, CDCl$_3$).

XXX-2/ 7-chloro-2-phenyl-4-[N-methyl-N—(N-1-phenylethyl-piperidin-4-yl)-amino]quinoline (XXX-2)

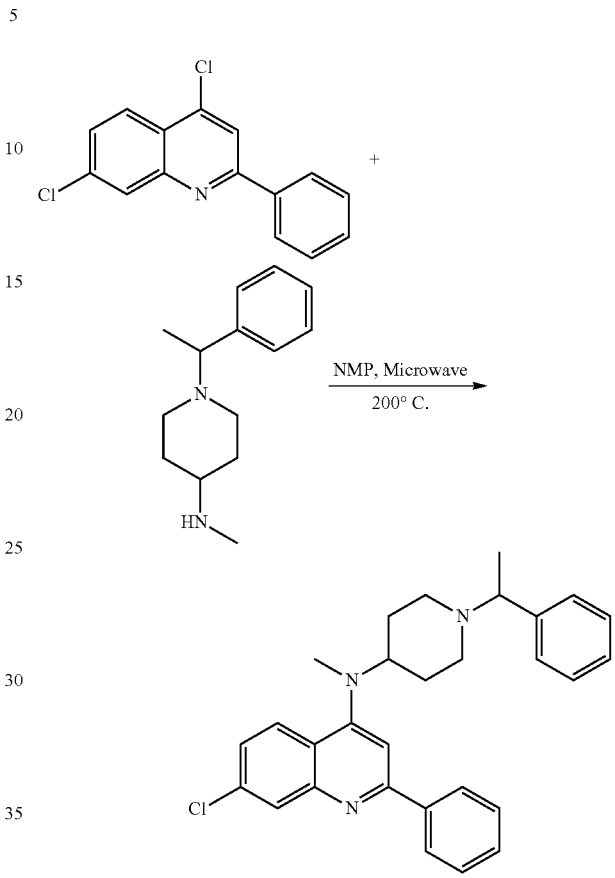

In a microwave vial was successively added, 250 mg (0.92 mmol) of 4,7-dichloro-2-phenylquinoline (prepared according to the protocol described in paragraph II-2), 1 g (4.58 mmol) of 1-(1-phenylethyl)-4-(N-methylamino)-piperidine and 0.5 ml of NMP. The resulting solution was heated for 8 h at 200° C. in a microwave oven and then treated with a 1N NaOH aqueous solution. The mixture was extracted with ethyl acetate and the organic layer was dried over MgSO$_4$, filtered and concentrated to give 1.29 g of brown oil. This compound was purified by silica gel column chromatography (20 g—dichloromethane/ethyl acetate 9:1) to give 424 mg of impure brown oil. This product was additionally purified by silica C18 reversed-phase column Biotage (31 g—water/methanol 1:1 then water/methanol+1% triethylamine, 1:9) to give 182 mg of a mixture of oil and solid. This mixture was taken up in a 1N NaOH aqueous solution and the aqueous layer was extracted with chloroform. The organic layer was dried over MgSO$_4$, filtered and concentrated to give 176 mg of yellow oil that was triturated with petroleum ether to precipitate a pasty solid. A new purification using silica gel column chromatography (5 g—petroleum ether then dichloromethane/ethanol 9:1) gave 145 mg (yield 35%) of yellow oil corresponding to 7-chloro-2-phenyl-4-[N-methyl-N—(N-1-phenylethyl-piperidin-4-yl)-amino]quinoline.

HPLC-MS: conditions F: t$_r$=5.19 min, (ES+) C$_{29}$H$_{30}$ClN$_3$ requires 455/457; found 456/458 [M+H].

$^1$H NMR (300 MHz, CDCl$_3$).

XXX-3/ 7-chloro-2-phenyl-4-[N-methyl-N—(N-1-phenylethyl-piperidin-4-yl)-amino]quinoline (XXX-3)

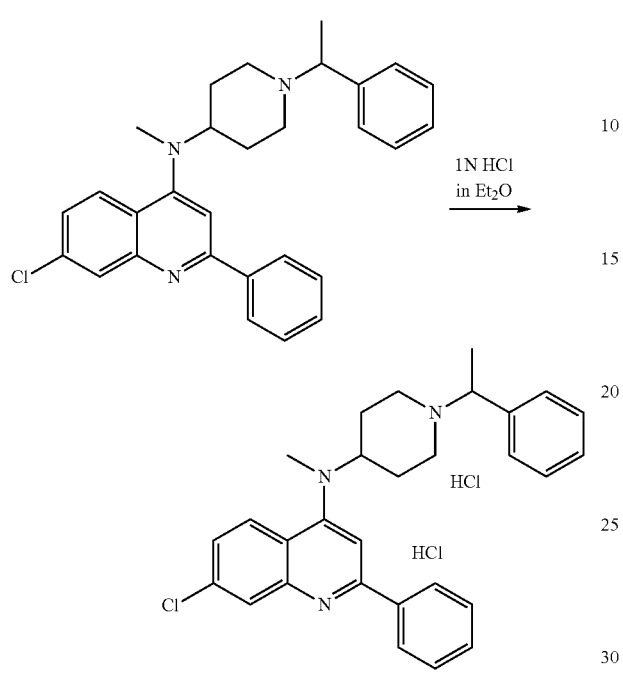

To a solution of 145 mg (0.32 mmol) of 7-chloro-2-phenyl-4-[N-methyl-N—(N-1-phenylethyl-piperidin-4-yl)-amino]quinoline in 0.5 ml of dry dichloromethane was added under argon, 640 μl (0.64 mmol) of a 1N solution of HCl in ether. The solution was stirred for 1 h30 at room temperature and filtered to recover 131 mg of a yellow solid that was triturated with ether. The solid compound was solubilized in pure water, filtered on Millipore 0.2 μm PTFE syringe filter and freeze-dried to give 117.2 mg (yield 75%) of a yellow solid compound corresponding to 7-chloro-2-phenyl-4-[N-methyl-N—(N-1-phenylethyl-piperidin-4-yl)-amino]quinoline dihydrochloride.

HPLC-MS: conditions D: $t_r$=5.17 min, (ES+) $C_{29}H_{30}ClN_3$ requires 455/457; found 456/458 [M+H].

$^1$H NMR (300 MHz, DMSO-$d_6$ and DMSO-$d_6$+$D_2O$).

Example 31

Preparation of 2-phenyl-4-[N-methyl-N—(N-1-phenylethyl-piperidin-4-yl)-amino]quinoline hydrochloride salt (XXXI-2)

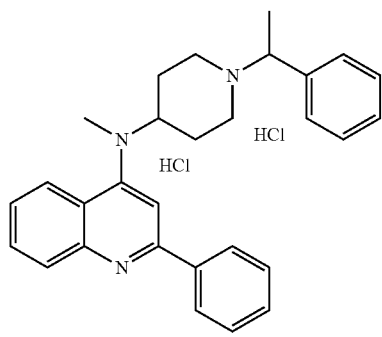 [SMILES: CC(c1ccccc1)N1CCC(N(C)c2cc(-c3ccccc3)nc3ccccc23)CC1 ; Cl ; Cl]

XXXI-1/ 2-phenyl-4-[N-methyl-N—(N-1-phenylethyl-piperidin-4-yl)-amino]quinoline (XXXI-1)

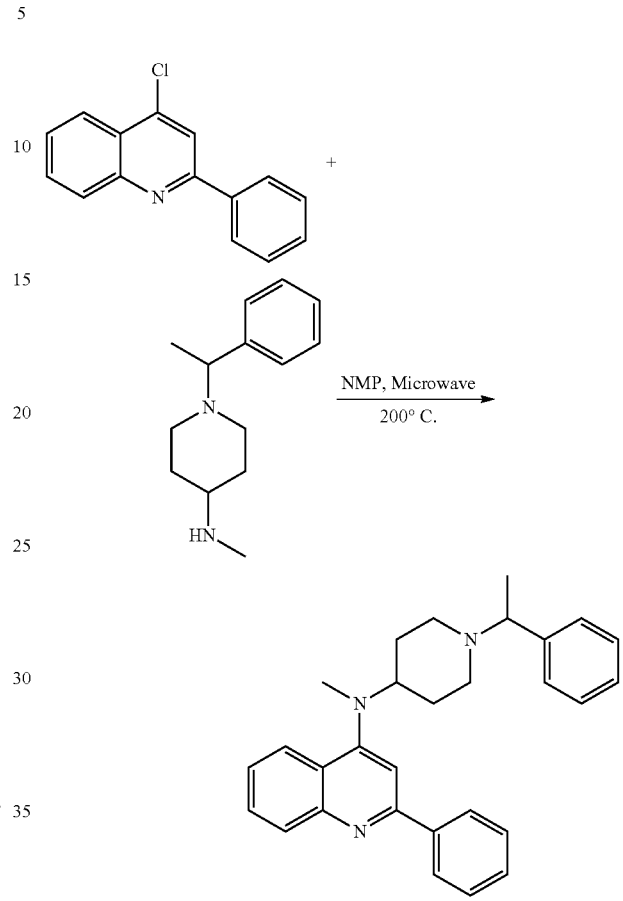

In a microwave vial was successively added, 200 mg (0.83 mmol) of 4-chloro-2-phenylquinoline, 911 mg (4.17 mmol) of 1-(1-phenylethyl)-4-(N-methylamino)-piperidine and 0.5 ml of NMP. The resulting solution was heated for 8 h at 200° C. in a microwave oven and then treated with a 1N NaOH aqueous solution. The mixture was extracted with ethyl acetate and the organic layer was dried over MgSO$_4$, filtered and concentrated to give 1.14 g of brown oil. This compound was purified by silica gel column chromatography (20 g—dichloromethane/acetone+0.5% triethylamine, 99:1) to provide 180 mg of white oil. This product was taken up in a 1N NaOH aqueous solution and the aqueous layer was extracted with toluene. The organic layer was dried over MgSO$_4$, filtered and concentrated to give 123 mg (yield 35%) of colourless oil corresponding to 2-phenyl-4-[N-methyl-N—(N-1-phenylethyl-piperidin-4-yl)-amino]quinoline.

HPLC-MS: conditions D: $t_r$=4.94 min, (ES+) $C_{29}H_{31}N_3$ requires 421; found 422 [M+H], purity 97%.

$^1$H NMR (300 MHz, CD$_3$OD).

127

XXXI-2/ 2-phenyl-4-[N-methyl-N—(N-1-phenyl-ethyl-piperidin-4-yl)-amino]quinoline dihydrochloride (XXXI-2)

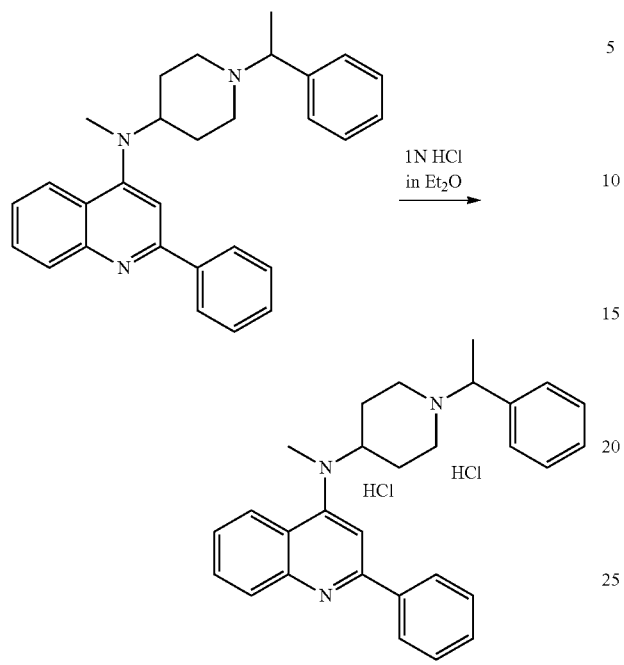

To a solution of 123 mg (0.29 mmol) of 2-phenyl-4-[N-methyl-N—(N-1-phenylethyl-piperidin-4-yl)-amino]quinoline in 0.5 ml of dry dichloromethane was added under argon 580 µl (0.58 mmol) of a 1N solution of HCl in ether. The solution was stirred for 1 h30 at room temperature and the solid was filtered and triturated with ether to give 122 mg of a beige solid. The solid compound was solubilized in pure water, filtered on Millipore 0.2 µm PTFE syringe filter and freeze-dried to provide 113 mg (yield 78%) of a pale yellow solid compound corresponding to 2-phenyl-4-[N-methyl-N—(N-1-phenylethyl-piperidin-4-yl)-amino]quinoline dihydrochloride.

HPLC-MS: conditions D: $t_r$=4.93 min, (ES+) $C_{29}H_{31}N_3$ requires 421; found 422 [M+H], purity 98%.

$^1$H NMR (300 MHz, DMSO-$d_6$ and DMSO-$d_6$+$D_2O$).

Example 32

Preparation of N-(1-benzylpiperidin-4-yl)-7-chloro-2-phenylquinoline-4-carboxamide hydrochloride salt (XXXII-2)

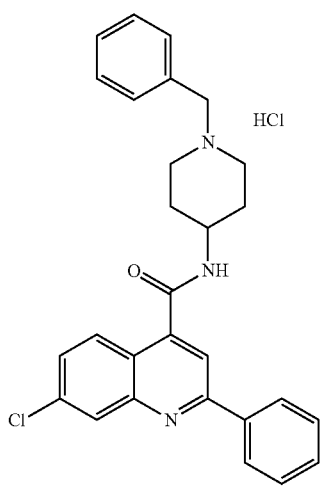 [SMILES: O=C(NC1CCN(Cc2ccccc2)CC1)c1cc(-c2ccccc2)nc2cc(Cl)ccc12 ; Cl]

128

XXXII-1/ N-(1-benzylpiperidin-4-yl)-7-chloro-2-phenylquinoline-4-carboxamide (XXXII-1)

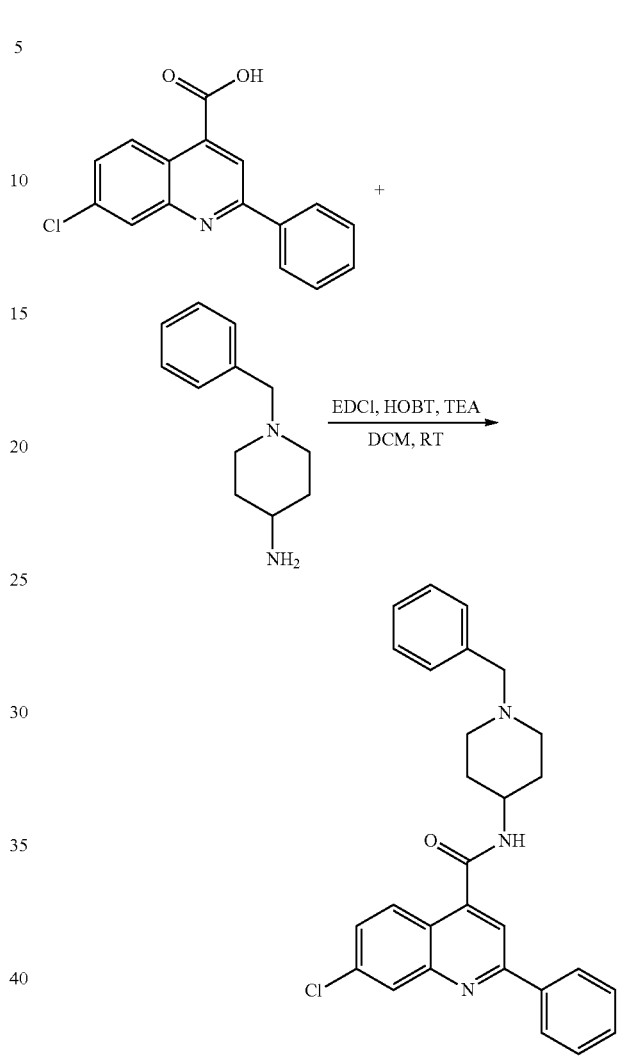

To a solution of 205 mg (0.722 mmol) of 7-chloro-2-phenyl-4-quinolinecarboxylic acid (prepared according to the protocol described paragraph XVII-1) in 5 ml of dry dichloromethane was successively added under argon, 152 µl (1.084 mmol) of triethylamine, 166 mg of (0.867 mmol) of 1-ethyl-3-(3-dimethylaminopropyl)carbodiimide and 117 mg (0.867 mmol) of hydroxybenzotriazole. After stirring for 30 min at room temperature, 176 µl (0.867 mmol) of 1-benzyl-4-aminopiperidine were added and the resulting reaction mixture was stirred for 24 h at room temperature and then diluted with dichloromethane. The organic layer was washed with water, dried over MgSO$_4$, filtered and concentrated to give 0.93 g of a beige solid product. This compound was purified by silica gel column chromatography (20 g—dichloromethane/ethyl acetate 8:2) to give 223 mg (yield 67%) of a white solid compound corresponding to N-(1-benzylpiperidin-4-yl)-7-chloro-2-phenylquinoline-4-carboxamide.

HPLC-MS: conditions D: $t_r$=7.14 min, (ES+) $C_{28}H_{26}ClN_3O$ requires 455; found 456 [M+H], purity 97%.

$^1$H NMR (300 MHz, DMSO-$d_6$).

XXXII-2/ N-(1-benzylpiperidin-4-yl)-7-chloro-2-phenylquinoline-4-carboxamide hydrochloride (XXXII-2)

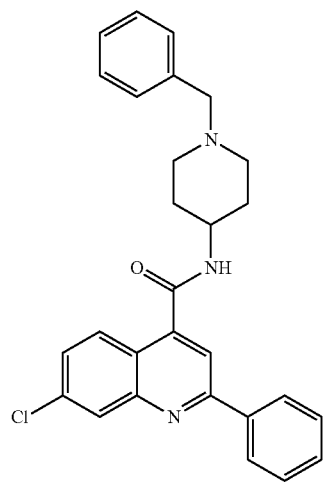

1N HCl in Et₂O

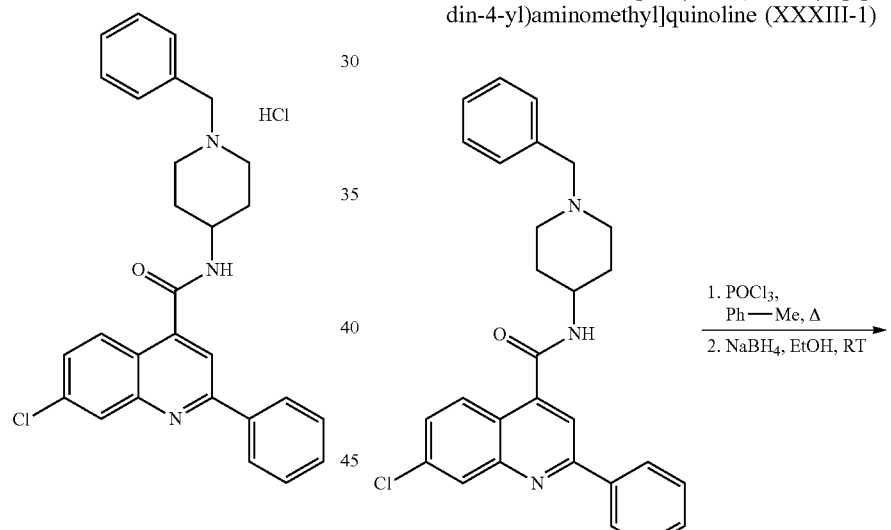

To a solution of 144 mg (0.316 mmol) of N-(1-benzylpiperidin-4-yl)-7-chloro-2-phenylquinoline-4-carboxamide in 0.5 ml of dry dichloromethane was added under argon, 632 µl (0.63 mmol) of a 1N solution of HCl in ether. The solution was stirred for 1 h at room temperature and the precipitate was filtered and triturated with dichloromethane. 140 mg of a yellow solid product were recovered and solubilized in pure water. The resulting solution was filtered on Millipore 0.2 µm PTFE syringe filter and freeze-dried to provide 129 mg (yield 77%) of a pale yellow solid compound corresponding to N-(1-benzylpiperidin-4-yl)-7-chloro-2-phenylquinoline-4-carboxamide hydrochloride.

HPLC-MS: conditions D: $t_r$=7.18 min, (ES+) $C_{28}H_{26}ClN_3O$ requires 455; found 456 [M+H], purity 99%.

¹H NMR (300 MHz, DMSO-$d_6$ and DMSO-$d_6$+$D_2O$).

Example 33

Preparation of 7-chloro-2-phenyl-4-[(N-benzyl-piperidin-4-yl)aminomethyl]quinoline hydrochloride salt (XXXIII-2)

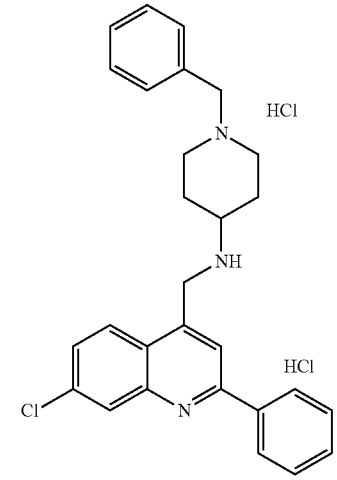 [SMILES: Clc1ccc2c(CNC3CCN(Cc4ccccc4)CC3)cc(-c3ccccc3)nc2c1 ; Cl ; Cl]

XXXIII-1/ 7-chloro-2-phenyl-4-[(N-benzyl-piperidin-4-yl)aminomethyl]quinoline (XXXIII-1)

1. POCl₃, Ph—Me, Δ
2. NaBH₄, EtOH, RT

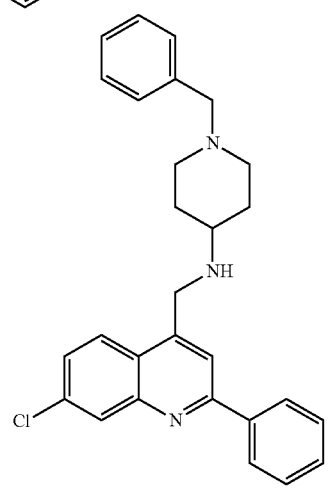

To a solution of 116 mg (0.254 mmol) of N-(1-benzylpiperidin-4-yl)-7-chloro-2-phenylquinoline-4-carboxamide (prepared according to the protocol described in paragraph XXXII-1) in 6 ml of dry toluene was added under argon, 48 µl (0.508 mmol) of phosphoryl chloride. The mixture was heated for 52 h under reflux and then cooled before addition of 6 ml of ethanol and 39 mg (1.017 mmol) of sodium borohydride. This resulting mixture was stirred for 3 days at room temperature, and then quenched with water. The resulting mixture was extracted with dichloromethane and the organic layer was washed with water, dried over MgSO$_4$, filtered and concentrated to give 162 mg of orange oil. This compound was purified by silica gel column chromatography (10 g—dichloromethane/methanol 98:2 then 96:4) to give 42 mg of yellow oil that was triturated with ether to give 18 mg (yield 28%) of solidified oil corresponding to 7-chloro-2-phenyl-4-[(N-benzyl-piperidin-4-yl)aminomethyl]quinoline.

HPLC-MS: conditions D: t$_r$=5.89 min, (ES+) C$_{28}$H$_{28}$ClN$_3$ requires 441; found 442 [M+H], purity >95%.
$^1$H NMR (300 MHz, CDCl$_3$).

XXXIII-2/ 7-chloro-2-phenyl-4-[(N-benzyl-piperidin-4-yl)aminomethyl]quinoline dihydrochloride (XXXIII-2)

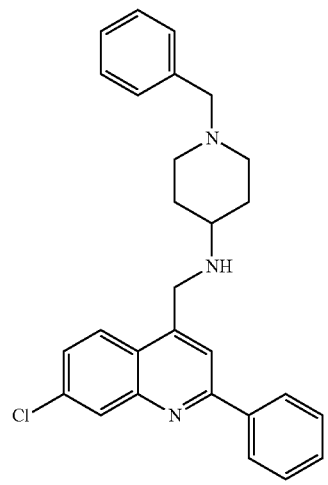

To a solution of 24 mg (0.054 mmol) of 7-chloro-2-phenyl-4-[(N-benzyl-piperidin-4-yl)aminomethyl]quinoline in 0.5 ml of dry dichloromethane was added under argon, 204 µl (0.2 mmol) of a 1N solution of HCl in ether. The resulting solution was stirred for 1 h at room temperature, and then concentrated. The residue was solubilized in hot ethanol and ether was then added to precipitate a solid compound. This product was filtered, solubilized in pure water, and then the solution was filtered on Nalgene 0.2 µm PTFE syringe filter and freeze-dried to give 12 mg (yield 40%) of a beige solid compound corresponding to 7-chloro-2-phenyl-4-[(N-benzyl-piperidin-4-yl)aminomethyl]quinoline dihydrochloride.

HPLC-MS: conditions D: t$_r$=5.84 min, (ES+) C$_{28}$H$_{28}$ClN$_3$ requires 441; found 442 [M+H], purity 97%.
$^1$H NMR (300 MHz, DMSO-d$_6$ and DMSO-d$_6$+D$_2$O).

Example 34

Preparation of 2-phenyl-4-{1-[(N-benzyl-piperidin-4-yl)amino]-eth-1-yl}quinoline hydrochloride salt (XXXIV-2)

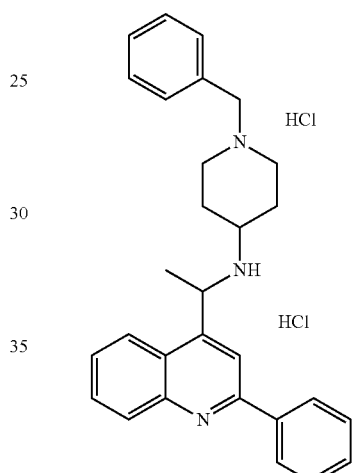

XXXIV-1/ 2-phenyl-4-{1-[(N-benzyl-piperidin-4-yl)amino]-eth-1-yl}quinoline (XXXIV-1)

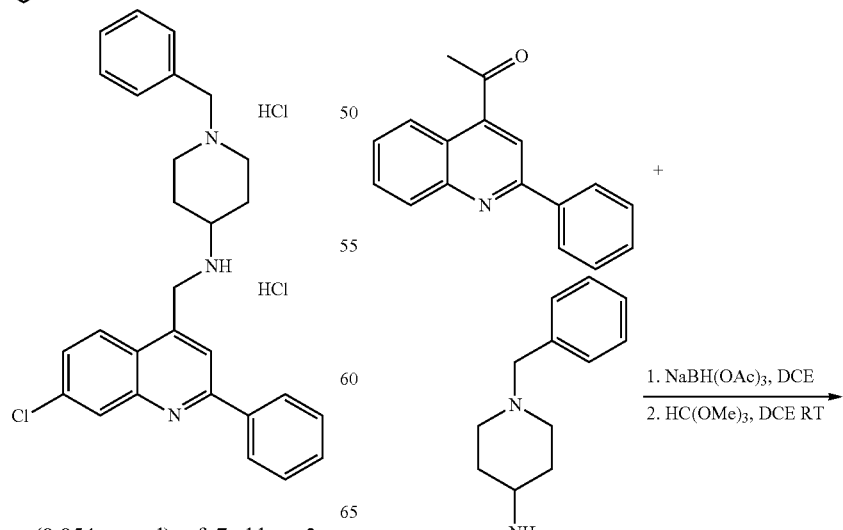

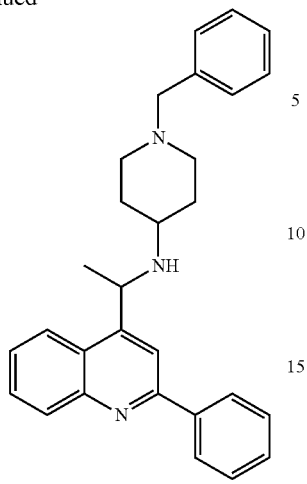

To 262 mg (1.06 mmol) of 4-acetyl-2-phenyl-quinoline (prepared as described in paragraph XIX-1) were added under nitrogen, 260 µl (1.27 mmol) of 1-benzyl-4-aminopiperidine, 382 mg (1.8 mmol) of sodium triacetoxyborohydride and 5 ml of 1,2-dichloroethane. After stirring for 12 h at room temperature, the reaction was not complete; therefore sodium triacetoxyborohydride and trimethyl orthoformate (1 eq. each) were added and the reaction mixture was additionally stirred overnight at room temperature. The mixture was concentrated and taken up in ethyl acetate. The organic layer was washed with a saturated solution of sodium bicarbonate, dried over MgSO$_4$, filtered and concentrated to give 505 mg of yellow oil. This crude product was purified by silica gel column chromatography (25 g—dichloromethane/methanol 95:5) to provide 182 mg of impure oil that was additionally purified by silica gel column chromatography (10 g—toluene/ethyl acetate 95:5+1% triethylamine) to give 90 mg of yellow oil containing an impurity. A new purification by silica gel column chromatography (5 g—ethyl acetate 100%) gave 37 mg (yield 8%) of colourless oil corresponding to 2-phenyl-4-{1-[(N-benzyl-piperidin-4-yl)amino]-eth-1-yl}quinoline.

HPLC-MS: conditions D: t$_r$=5.15 min, (ES+) C$_{29}$H$_{31}$N$_3$ requires 421; found 422 [M+H], purity 99%.

$^1$H NMR (300 MHz, CD$_3$OD).

XXXIV-2/ 2-phenyl-4-{1-[(N-benzyl-piperidin-4-yl)amino]-eth-1-yl}quinoline dihydrochloride (XXXIV-2)

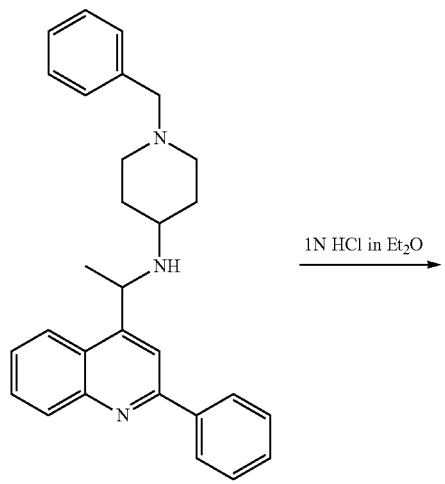

1N HCl in Et$_2$O →

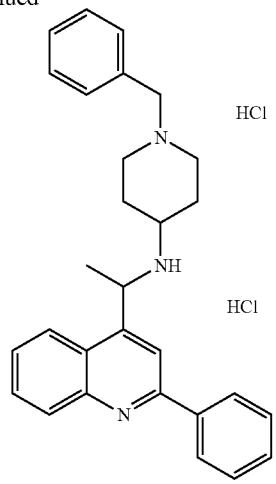

To a solution of 37 mg (0.09 mmol) of 2-phenyl-4-{1-[(N-benzyl-piperidin-4-yl)amino]-eth-1-yl}quinoline in 300 µl of dry dichloromethane was added under argon 260 µl (0.26 mmol) of a 1N solution of HCl in ether. The solution was stirred for 1 h at room temperature to form a precipitate. The solid was filtered, solubilized in pure water and the solution was filtered on Nalgene 0.2 µm PTFE syringe filter and then freeze-dried to give 25.5 mg (yield 59%) of a beige solid compound corresponding to 2-phenyl-4-{1-[(N-benzyl-piperidin-4-yl)amino]-eth-1-yl}quinoline dihydrochloride.

HPLC-MS: conditions D: t$_r$=5.18 min, (ES+) C$_{29}$H$_{31}$N$_3$ requires 421; found 422 [M+H], purity 99%.

$^1$H NMR (300 MHz, DMSO-d$_6$ and DMSO-d$_6$+D$_2$O).

Example 35

Preparation of 7-chloro-2-phenyl-4-{1-[(N-benzyl-piperidin-4-yl)amino]-eth-1-yl}quinoline hydrochloride salt (XXXV-2)

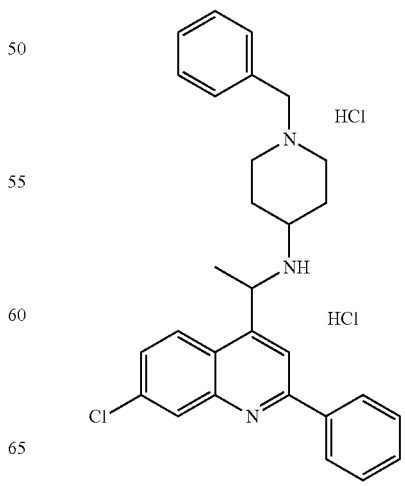

XXXV-1/ 7-chloro-2-phenyl-4-{1-[(N-benzyl-piperidin-4-yl)amino]-eth-1-yl}quinoline (XXXV-1)

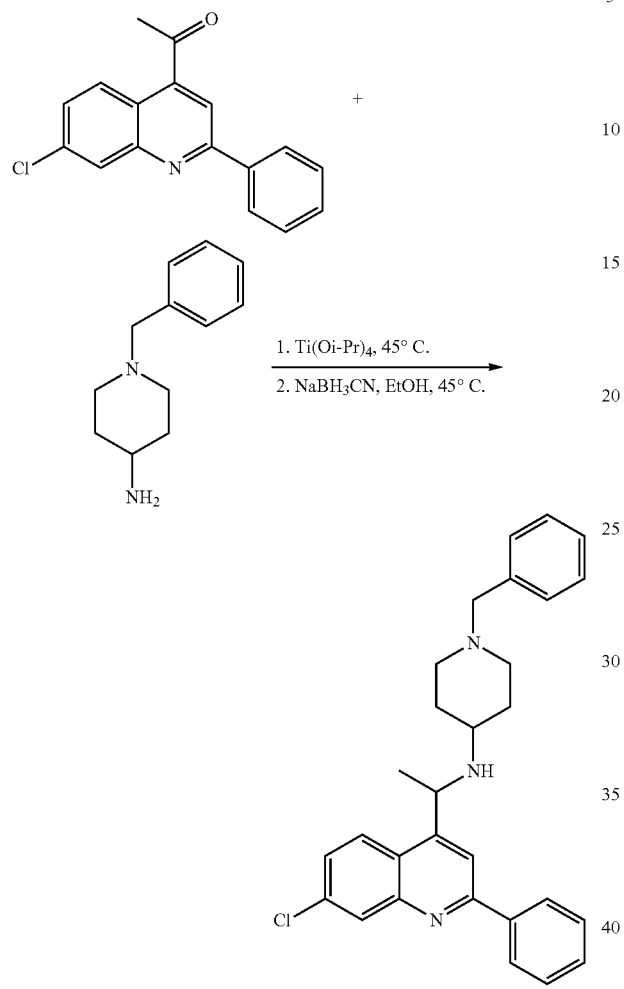

To 133 mg (0.47 mmol) of 4-acetyl-7-chloro-2-phenyl-quinoline (prepared according to the protocol described in paragraph XVI-2) were added a solution of 144 µl (0.71 mmol) of 1-benzyl-4-aminopiperidine in 2 ml of dichloromethane. The mixture was concentrated under vacuum and 197 µl (0.66 mmol) of titanium (IV) isopropoxide were added under argon. The mixture was heated for 4 h30 at 45° C. Then, the reaction mixture was cooled, diluted with 2 ml of dry ethanol and 65 mg (1.04 mmol) of sodium cyanoborohydride were added. The resulting reaction mixture was heated for 4 h at 45° C. and then 14 h at room temperature. The mixture was poured onto 20 ml of water, stirred for 1 h at room temperature, filtered through a Celite® pad and the filtrate was extracted with dichloromethane. The organic layer was washed with brine, dried over MgSO₄, filtered and concentrated to give 375 mg of brown oil. This crude product was purified by silica gel column chromatography (ethyl acetate/ethanol 95.5:0.5) to give 140 mg of impure brown oil that was additionally purified by silica gel column chromatography (Biotage 9 g—ethyl acetate 100%). A new yellow oil (65 mg) containing an impurity was recovered, that was purified by silica C18 reversed-phase column Biotage (4 g—water/methanol+10% triethylamine, 25:75).

Two fractions: 15 mg (purity 91%—LCMS M+1=456/458) and 16 mg (purity 88%—LCMS M+1=456/458), corresponding to 7-chloro-2-phenyl-4-{1-[(N-benzyl-piperidin-4-yl)amino]-eth-1-yl}quinoline, were recovered and gathered to be treated in the next step.

HPLC-MS: conditions D: $t_r$=6.09 min, (ES+) $C_{29}H_{30}ClN_3$ requires 455/457; found 456/458 [M+H].

$^1$H NMR (300 MHz, CD₃OD).

XXXV-2/ 7-chloro-2-phenyl-4-{1-[(N-benzyl-piperidin-4-yl)amino]-eth-1-yl}quinoline dihydrochloride (XXXV-2)

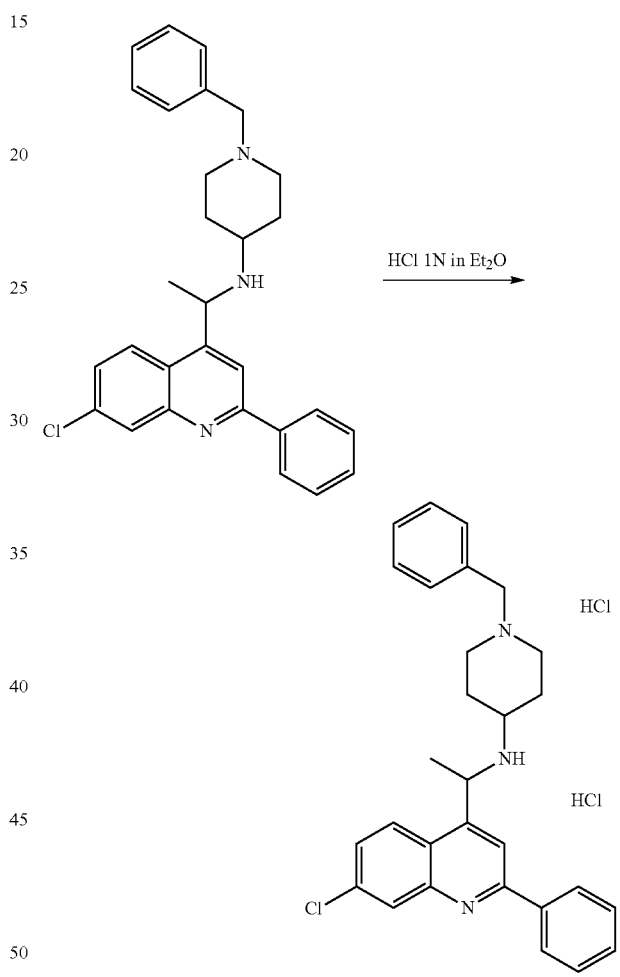

To a solution of 30 mg (0.07 mmol) of 7-chloro-2-phenyl-4-{1-[(N-benzyl-piperidin-4-yl)amino]-eth-1-yl}quinoline in 0.1 ml of dry dichloromethane was added under argon, 200 µl (0.2 mmol) of a 1N solution of HCl in ether. The solution was stirred for 1 h30 at room temperature to form a precipitate. The precipitate was filtered, washed with ether, solubilized in pure water and the solution was filtered on Nalgene 0.2 µm PTFE syringe filter and then freeze-dried to give 23 mg (yield 66%) of a beige solid compound corresponding to 7-chloro-2-phenyl-4-{1-[(N-benzyl-piperidin-4-yl)amino]-eth-1-yl}quinoline dihydrochloride.

HPLC-MS: conditions D: $t_r$=6.16 min, (ES+) $C_{29}H_{30}ClN_3$ requires 455/457; found 456/458 [M+H], purity 97%.

$^1$H NMR (300 MHz, DMSO-d₆ and DMSO-d₆+D₂O).

Example 36

Preparation of N¹,N¹-dimethyl-N²-(2-naphthalen-2-yl-quinoline-4-yl)-ethane-1,2-diamine hydrochloride salt (XXXVI-2)

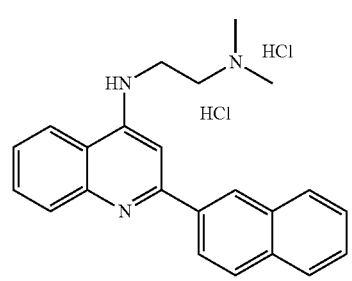 [SMILES: CN(C)CCNc1cc(-c2ccc3ccccc3c2)nc2ccccc12 ; Cl ; Cl]

XXXVI-1/ N¹,N¹-dimethyl-N²-(2-naphthalen-2-yl-quinoline-4-yl)-ethane-1,2-diamine (XXXVI-1)

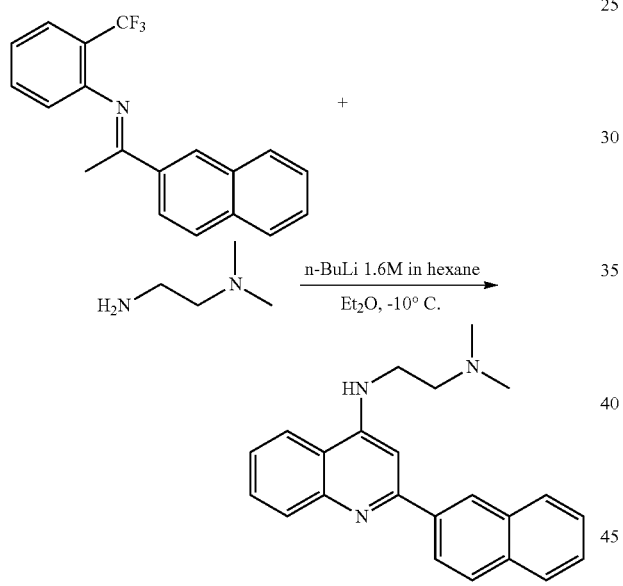

To a solution of 1.65 ml (15.19 mmol) of N¹,N¹-dimethylethylenediamine in 29 ml of dry ether, was added at −10° C. under nitrogen, 9.49 ml (15.19 mmol) of a 1.6 M solution of n-butyllithium in hexane. The reaction mixture was stirred for 20 min at −10° C. and a solution of 0.952 g (3.04 mmol) of benzenamine, 2-trifluoromethyl-N-[1-(2-naphthalenyl)ethylidene]- (prepared according to the protocol described in paragraph VI-1) in 9 ml of dry ether was added. After stirring for 45 min at −10° C., the mixture was quenched with cold water and extracted with dichloromethane. The organic layer was washed with water, dried over MgSO₄, filtered and concentrated to give 1.01 g of brown oil. This compound was purified by silica gel column chromatography (cyclohexane/ethanol/triethylamine 9:0.5:0.5) to give 368 mg (yield 35%) of yellow oil corresponding to N¹,N¹-dimethyl-N²-(2-naphthalen-2-yl-quinoline-4-yl)-ethane-1,2-diamine.

HPLC-MS: conditions D: $t_r$=4.30 min, (ES+) $C_{23}H_{23}N_3$ requires 341; found 342 [M+H].

¹H NMR (300 MHz, DMSO-d₆).

XXXVI-2/ N¹,N¹-dimethyl-N²-(2-naphthalen-2-yl-quinoline-4-yl)-ethane-1,2-diamine dihydrochloride (XXXVI-2)

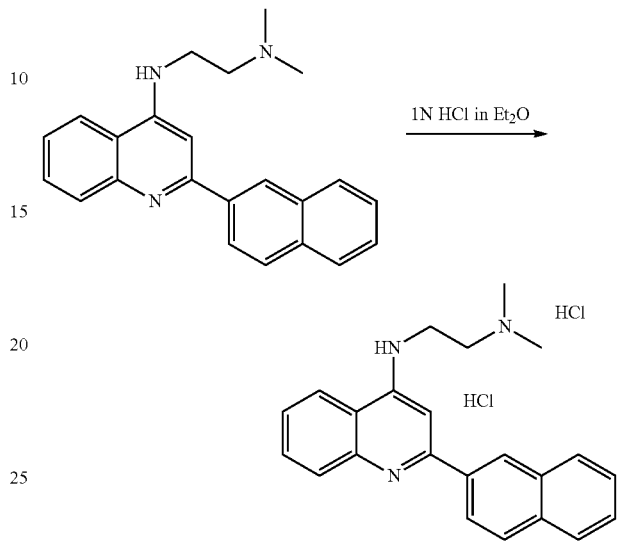

To a solution of 52 mg (0.152 mmol) of N¹,N¹-dimethyl-N²-(2-naphthalen-2-yl-quinoline-4-yl)-ethane-1,2-diamine in a mixture of 0.5 ml of dry dichloromethane and 1 ml of dry ether, was added under nitrogen, 1 ml of a 1N solution of HCl in ether. The solution was stirred for 1 h30 at room temperature to form a brown precipitate that was filtered and washed with ether to give 63 mg (quantitative yield) of a brown solid compound corresponding to N¹,N¹-dimethyl-N²-(2-naphthalen-2-yl-quinoline-4-yl)-ethane-1,2-diamine dihydrochloride.

HPLC-MS: conditions D: $t_r$=4.62 min, (ES+) $C_{23}H_{23}N_3$ requires 341; found 342 [M+H], purity 99%.

¹H NMR (300 MHz, DMSO-d₆ and DMSO-d₆+D₂O).

Example 37

Preparation of N¹,N¹,N²-trimethyl-N²-(2-naphthalen-2-yl-quinoline-4-yl)-ethane-1,2-diamine hydrochloride salt (XXXVII-2)

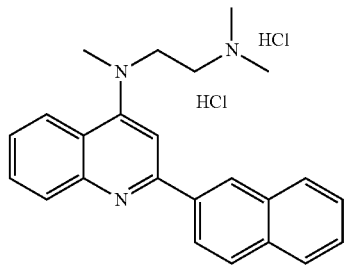 [SMILES: CN(C)CCN(C)c1cc(-c2ccc3ccccc3c2)nc2ccccc12 ; Cl ; Cl]

XXXVII-1/ N$^1$,N$^1$,N$^2$-trimethyl-N$^2$-(2-naphthalen-2-yl-quinoline-4-yl)-ethane-1,2-diamine (XXXVII-1)

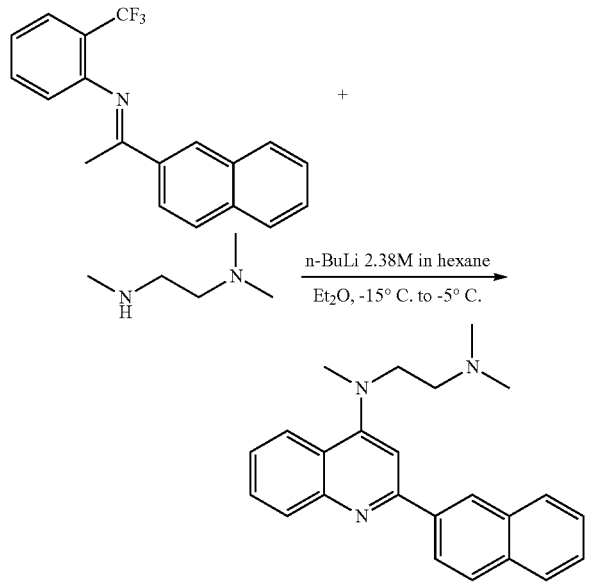

To a solution of 1.14 ml (9.08 mmol) of N$^1$,N$^1$,N$^2$-trimethylethylenediamine in 20 ml of dry ether were added at −15° C. under argon, 3.81 ml (9.08 mmol) of a 2.38 M solution of n-butyllithium in hexane. The mixture was stirred for 15 min at −15° C. and a solution of 0.712 g (2.27 mmol) of benzenamine, 2-trifluoromethyl-N-[1-(2-naphthalenyl)ethylidene]- (prepared according to the protocol described in paragraph VI-1) in 10 ml of dry ether was added. After stirring for 2 h between −15° C. and −5° C., the mixture was quenched with cold water and then extracted with ether. The organic layer was washed with water, dried over MgSO$_4$, filtered and concentrated to give brown oil. This compound was purified by silica C18 reversed-phase column Biotage (31 g—gradient from acetonitrile/water 3:7 to 7:3) to give 101 mg (yield 12%) of yellow oil corresponding to N$^1$,N$^1$,N$^2$-trimethyl-N$^2$-(2-naphthalen-2-yl-quinoline-4-yl)-ethane-1,2-diamine.

HPLC-MS: conditions D: t$_r$=4.66 min, (ES+) C$_{24}$H$_{25}$N$_3$ requires 355; found 356 [M+H].

$^1$H NMR (300 MHz, CDCl$_3$).

XXXVII-2/ N$^1$,N$^1$,N$^2$-trimethyl-N$^2$-(2-naphthalen-2-yl-quinoline-4-yl)-ethane-1,2-diamine dihydrochloride (XXXVII-2)

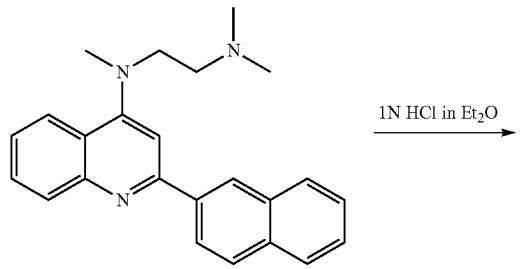

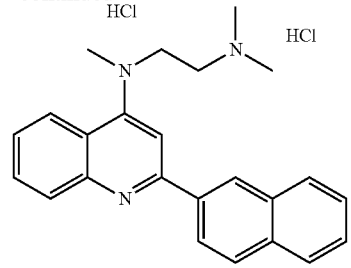

To a solution of 95 mg (0.267 mmol) of N$^1$,N$^1$,N$^2$-trimethyl-N$^2$-(2-naphthalen-2-yl-quinoline-4-yl)-ethane-1,2-diamine in 2 ml of dry dichloromethane was added under nitrogen, 610 μl of a 1N solution of HCl in ether. The solution was stirred for 2 h at room temperature to give a gummy precipitate. This precipitate was triturated with ether and the yellow solid was filtered, solubilized in pure water, the solution was filtered on Nalgene 0.2 μm PTFE syringe filter and freeze-dried to give 52 mg (yield 45%) of a pale yellow solid compound corresponding to N$^1$,N$^1$,N$^2$-trimethyl-N$^2$-(2-naphthalen-2-yl-quinoline-4-yl)-ethane-1,2-diamine dihydrochloride.

HPLC-MS: conditions F: t$_r$=4.77 min, (ES+) C$_{24}$H$_{25}$N$_3$ requires 355; found 356 [M+H], purity 98%.

$^1$H NMR (300 MHz, DMSO-d$_6$).

Example 38

Preparation N$^1$,N$^1$,N$^2$-trimethyl-N$^2$-(2-phenyl-7-chloro-quinoline-4-ylmethyl)-ethane-1,2-diamine hydrochloride salt (XXXVIII-2)

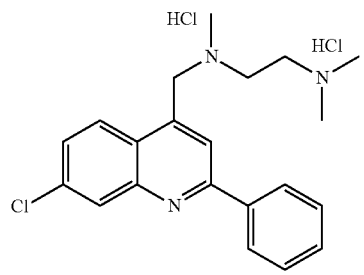 [SMILES: CN(C)CCN(C)Cc1cc(-c2ccccc2)nc2cc(Cl)ccc12 ; Cl ; Cl]

XXXVIII-1/ N$^1$,N$^1$,N$^2$-trimethyl-N$^2$-(2-phenyl-7-chloro-quinoline-4-ylmethyl)-ethane-1,2-diamine (XXXVIII-1)

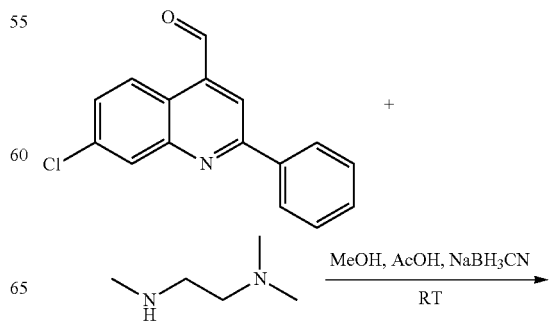

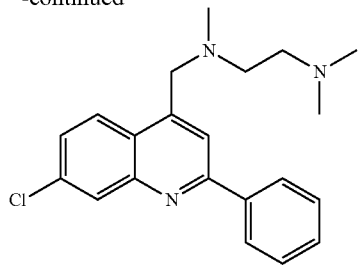

To a solution of 200 mg (0.75 mmol) of 7-chloro-2-phenyl-quinoline-4-carbaldehyde (obtained according to the protocol described in the paragraph XVII-4) in 10 ml of dry methanol was added 104 μl (0.82 mmol) of $N^1,N^1,N^2$-trimethylethylenediamine and 3 drops of acetic acid. After stirring for 2 h at room temperature, 57 mg (0.9 mmol) of sodium cyanoborohydride were added and the resulting mixture was stirred for 14 h at room temperature under nitrogen. The reaction mixture was poured onto 30 ml of water containing 10% of sodium bicarbonate, and the aqueous layer was extracted with dichloromethane. The organic layer was washed with brine, dried over MgSO₄, filtered and concentrated to give 262 mg of yellow oil. This product was purified by silica gel column chromatography (25 g—gradient from dichloromethane 100% to dichloromethane/ethyl acetate 9:1) to give 144 mg of impure yellow oil. This product was additionally purified by silica gel column chromatography (10 g—elution with petroleum ether then chloroform/ethanol 9:1 then ethanol/triethylamine 99:1) to give 108 mg of impure yellow oil. A new purification by silica C18 reversed-phase column Biotage (5.5 g—gradient from water/methanol 1:1 to 0:1) gave 63 mg (yield 24%) of pale yellow oil corresponding to $N^1,N^1,N^2$-trimethyl-$N^2$-(2-phenyl-7-chloro-quinoline-4-ylmethyl)-ethane-1,2-diamine.

HPLC-MS: conditions D: $t_r$=6.07 min, (ES+) $C_{21}H_{24}ClN_3$ requires 353; found 354 [M+H], purity 98%.
$^1$H NMR (300 MHz, CDCl₃).

XXXVIII-2/ $N^1,N^1,N^2$-trimethyl-$N^2$-(2-phenyl-7-chloro-quinoline-4-ylmethyl)-ethane-1,2-diamine dihydrochloride (XXXVIII-2)

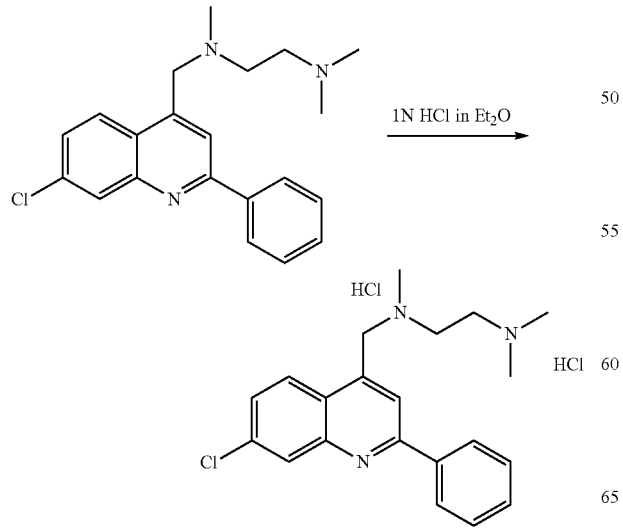

To a solution of 60 mg (0.17 mmol) of $N^1,N^1,N^2$-trimethyl-$N^2$-(2-phenyl-7-chloro-quinoline-4-ylmethyl)-ethane-1,2-diamine in 4 ml of dry dichloromethane was added under nitrogen, 340 μl of a 1N solution of HCl in ether. The solution was stirred for 2 h at room temperature and concentrated under vacuum to give a residue that was triturated with ether. The yellow solid was filtered, solubilized in pure water and the solution was filtered on Nalgene 0.2 μm PTFE syringe filter then freeze-dried to give 65 mg of a pale yellow solid compound. This product was solubilized in ethanol and the solution was treated with petroleum ether to precipitate 40 mg (yield 55%) of a white solid compound corresponding to $N^1,N^1,N^2$-trimethyl-$N^2$-(2-phenyl-7-chloro-quinoline-4-ylmethyl)-ethane-1,2-diamine dihydrochloride.

HPLC-MS: conditions D: $t_r$=6.14 min, (ES+) $C_{21}H_{24}ClN_3$ requires 353; found 354 [M+H], purity >95%.
$^1$H NMR (300 MHz, DMSO-d₆ and D₂O).

Example 39

Preparation of $N^1,N^1,N^3$-trimethyl-$N^3$-[2-(naphthalen-2-yl)-quinoline-4-yl]-propane-1,3-diamine hydrochloride salt (XXXIX-2)

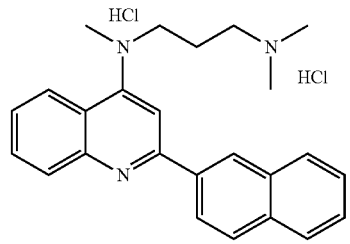 [SMILES: Cl ; CN(C)CCCN(C)c1cc(-c2ccc3ccccc3c2)nc2ccccc12 ; Cl]

XXXIX-1/ $N^1,N^1,N^3$-trimethyl-$N^3$-[2-(naphthalen-2-yl)-quinoline-4-yl]-propane-1,3-diamine (XXXIX-1)

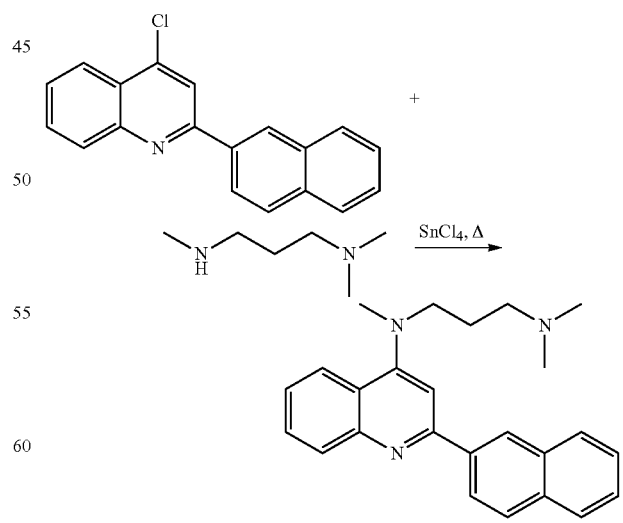

To a mixture of 185 mg (0.638 mmol) of 2-(2-naphtyl)-4-chloro-quinoline (obtained according to the protocol described in the paragraph VI-4) and 3.1 g (26.81 mmol) of $N^1,N^1,N^3$-trimethylpropane-1,3-diamine was added under argon, 150 μl (1.277 mmol) of Tin (IV) chloride. The mixture was heated for 14 h under reflux and then quenched with a 1N NaOH aqueous solution. The resulting mixture was extracted with ethyl acetate and the organic layer was washed with water, dried over MgSO₄, filtered and concentrated to give 545 mg of brown oil. This compound was purified by silica gel column chromatography (20 g—gradient from dichloromethane/methanol 98:2 to 97:3) to give 125 mg of impure yellow oil. This product was triturated with petroleum ether to give 109 mg (yield 46%) of orange oil corresponding to $N^1,N^1,N^3$-trimethyl-$N^3$-[2-(naphthalen-2-yl)-quinoline-4-yl]-propane-1,3-diamine.

HPLC-MS: conditions D: $t_r$=4.78 min, (ES+) $C_{25}H_{27}N_3$ requires 369; found 370 [M+H], purity 94%.

$^1$H NMR (300 MHz, CDCl₃).

XXXIX-2/ $N^1,N^1,N^3$-trimethyl-$N^3$-[2-(naphthalen-2-yl)-quinoline-4-yl]-propane-1,3-diamine dihydrochloride (XXXIX-2)

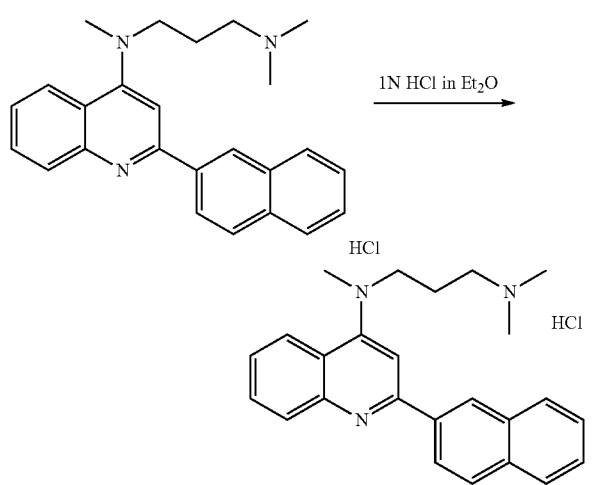

To a solution of 95 mg (0.26 mmol) of $N^1,N^1,N^3$-trimethyl-$N^3$-[2-(naphthalen-2-yl)-quinoline-4-yl]-propane-1,3-diamine in 4 ml of dry dichloromethane was added under argon, 526 μl of a 1N solution of HCl in ether. The solution was stirred for 1 h at room temperature and concentrated under vacuum to give a residue. This residue was solubilized in ethanol and petroleum ether was added to the solution to precipitate a yellow solid product. This solid product was filtered, solubilized in pure water and the solution was filtered on Nalgene 0.2 μm PTFE syringe filter then freeze-dried to give 84 mg of an impure yellow solid. This compound was triturated with dichloromethane and the solid compound recovered by filtration was solubilized in pure water and freeze-dried to give 62 mg (yield 53%) of yellow solid compound corresponding to $N^1,N^1,N^3$-trimethyl-$N^3$-[2-(naphthalen-2-yl)-quinoline-4-yl]-propane-1,3-diamine dihydrochloride.

HPLC-MS: conditions D: $t_r$=4.75 min, (ES+) $C_{25}H_{27}N_3$ requires 369; found 370 [M+H], purity 89% UV—99% DEDL.

$^1$H NMR (300 MHz, DMSO-d₆ and DMSO-d₆+D₂O).

Example 40

Preparation of $N^1,N^1$-dimethyl-$N^3$-(2-phenylquinoline-4-yl)propane-1,3-diamine trifluoroacetate salt (XL-2)

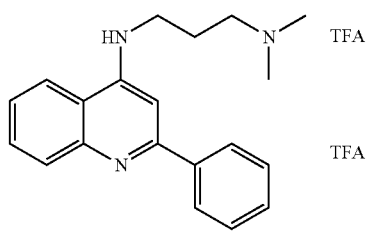 [SMILES: CN(C)CCCNc1cc(-c2ccccc2)nc2ccccc12]

XL-1/ Benzenamine,2-trifluoromethyl-N-(1-phenyl-ethylidene)-

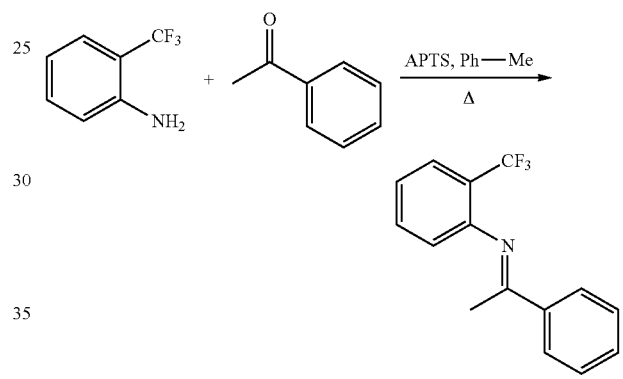

In a round bottom flask equipped with a Dean Stark apparatus was successively added, under nitrogen, 5 g (31.03 mmol) of 2-trifluoromethyl-aniline, 4.85 g (40.34 mmol) of acetophenone, 150 mg of p-toluenesulfonic acid monohydrate and 150 ml of dry toluene.

The mixture was heated 14 h under reflux and concentrated to give 5.95 g of crude residue. It was purified by distillation with a bulb to bulb Kugelrohr apparatus to give 2.34 g (yield 28%) of yellow oil corresponding to benzenamine, 2-trifluoromethyl-N-(1-phenylethylidene)-.

$^1$H NMR (300 MHz, DMSO-d₆).

XL-2/ $N^1,N^1$-dimethyl-$N^3$-(2-phenylquinoline-4-yl) propane-1,3-diamine trifluoroacetate salt (XL-2)

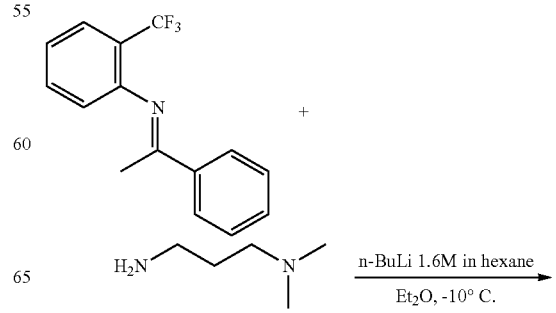

-continued

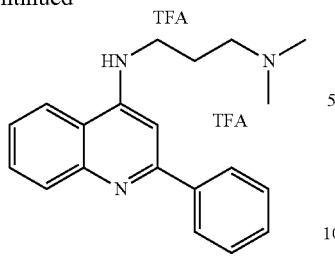

To a solution of 5.6 ml (44.4 mmol) of $N^1,N^1$-dimethyl-propane-1,3-diamine in 93 ml of dry ether, was added at −10° C. under nitrogen, 28 ml (44.4 mmol) of a 1.6 M solution of n-butyllithium in hexane. The mixture was stirred for 2 h at −10° C. and a solution of 2.34 g (8.88 mmol) of benzenamine, 2-trifluoromethyl-N-(1-phenylethylidene)- in 17 ml of dry ether was added. After stirring for 1 h at −10° C., the mixture was quenched with cold water and extracted with dichloromethane. The organic layer was washed with water, dried over MgSO$_4$, filtered and concentrated to give 3.14 g of brown oil. This product was purified by silica gel column chromatography (150 g—cyclohexane/ethanol/triethylamine 9:0.5:0.5) to recover a small fraction (79.5 mg) of impure yellow oil. This compound was purified by semi preparative HPLC to give 32 mg (yield 1%) of yellow oil corresponding to the trifluoro acetate salt of $N^1,N^1$-dimethyl-$N^3$-(2-phenylquinoline-4-yl)propane-1,3-diamine.

HPLC-MS: conditions E: $t_r$=12.54 min, (ES+) $C_{20}H_{23}N_3$ requires 305; found 306 [M+H], purity >99%.

$^1$H NMR (300 MHz, CDCl$_3$, DMSO-d$_6$ and DMSO-d$_6$+D$_2$O).

Example 41

Preparation of $N^1,N^1$-dimethyl-$N^3$-(2-phenylquinoline-4-yl)propane-1,3-diamine hydrochloride salt (XL-2)

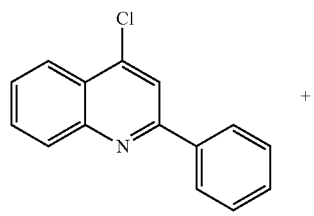

XLI-1/ $N^1,N^1$-dimethyl-$N^3$-(2-phenylquinoline-4-yl)propane-1,3-diamine (XLI-1)

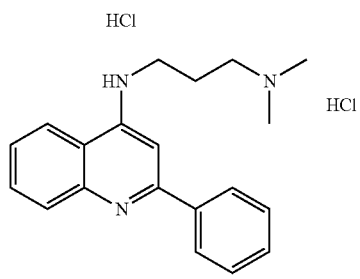 [SMILES: Cl ; CN(C)CCCNc1cc(-c2ccccc2)nc2ccccc12 ; Cl]

-continued

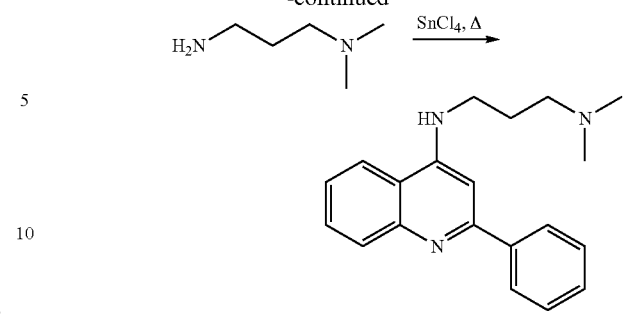

To a mixture of 500 mg (2.09 mmol) of 4-chloro-2-phenylquinoline and 11 ml (87.8 mmol) of $N^1,N^1$-dimethylpropane-1,3-diamine was added under argon, 99 µl (0.84 mmol) of Tin (IV) chloride. The mixture was heated for 28 h under reflux. Since the reaction was not complete, 99 µl of Tin (IV) chloride were still added and the reaction mixture was heated for 3 days under reflux. The reaction was quenched with 100 ml of water and the resulting mixture was extracted with ethyl acetate. The combined organic layers were washed with water, dried over MgSO$_4$, filtered and concentrated to provide a residue that was purified by silica gel column chromatography (20 g—gradient from dichloromethane/methanol 98:2 to 95:5 (+1% NH$_4$OH) to give 553 mg (yield 86%) of yellow oil corresponding to $N^1,N^1$-dimethyl-$N^3$-(2-phenylquinoline-4-yl)propane-1,3-diamine.

HPLC-MS: conditions D: $t_r$=3.90 min, (ES+) $C_{20}H_{23}N_3$ requires 305; found 306 [M+H], purity 97%.

$^1$H NMR (300 MHz, CDCl$_3$).

XLI-2/ $N^1,N^1$-dimethyl-$N^3$-(2-phenylquinoline-4-yl)propane-1,3-diamine dihydrochloride (XLI-2)

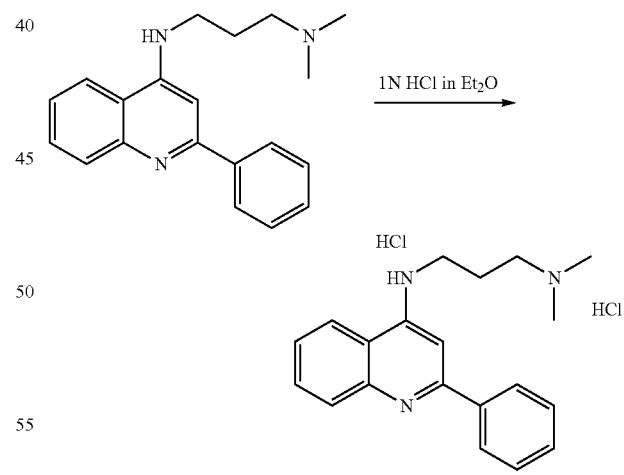

To a solution of 515 mg (1.687 mmol) of $N^1,N^1$-dimethyl-$N^3$-(2-phenylquinoline-4-yl)propane-1,3-diamine in 20 ml of dry dichloromethane was added under nitrogen, 3.4 ml of a 1N solution of HCl in ether. The solution was stirred for 1 h at room temperature and concentrated under vacuum to give a residue that was triturated with dichloromethane. The yellow solid was filtered, solubilized in pure water and the solution was filtered on Nalgene 0.2 µm PTFE syringe filter then freeze-dried to give 559 mg (yield 87%) of a beige solid compound corresponding to $N^1,N^1$-dimethyl-$N^3$-(2-phenylquinoline-4-yl)propane-1,3-diamine dihydrochloride.

HPLC-MS: conditions E: $t_r$=12.37 min, (ES+) $C_{20}H_{23}N_3$ requires 305; found 306 [M+H], purity 97%.

$^1$H NMR (300 MHz, DMSO-$d_6$ and DMSO-$d_6$+$D_2O$).

Example 42

Preparation of $N^1,N^1$-dimethyl-$N^3$-[2-(naphtalen-2-yl)quinoline-4-yl]propane-1,3-diamine hydrochloride salt (XLII-2)

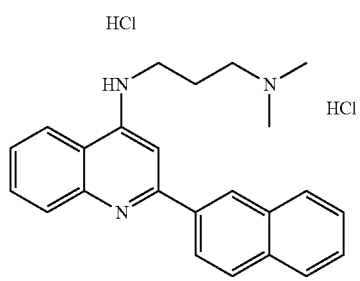 [SMILES: Cl ; CN(C)CCCNc1cc(-c2ccc3ccccc3c2)nc2ccccc12 ; Cl]

XLII-1/ $N^1,N^1$-dimethyl-$N^3$-[2-(naphtalen-2-yl)quinoline-4-yl]propane-1,3-diamine (XLII-1)

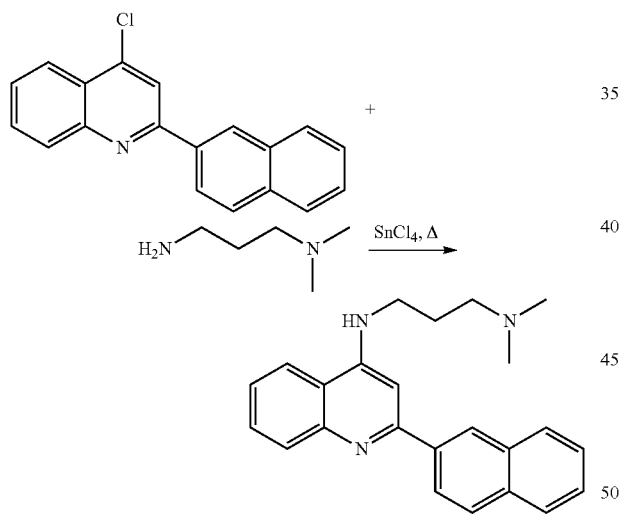

To a mixture of 109 mg (0.38 mmol) of 2-(2-naphtyl)-4-chloro-quinoline (obtained according to the protocol described in the paragraph VI-4) and 2 ml (15.9 mmol) of $N^1,N^1$-dimethylpropane-1,3-diamine, was added under argon 18 μl (0.15 mmol) of Tin (IV) chloride. The resulting reaction mixture was heated for 24 h under reflux. Since the reaction was not complete, 40 μl of Tin (IV) chloride were still added, and the resulting reaction mixture was heated for 8 h under reflux. Then, the reaction was quenched with 20 ml of water and the corresponding mixture was extracted with ethyl acetate and the combined organic layer were washed with water, dried over $MgSO_4$, filtered and concentrated to give a residue. This residue was purified by silica C18 reversed-phase column Biotage (17 g—gradient from acetonitrile/water 2:8 to 100% water) to give 39 mg (yield 28%) of yellow oil corresponding to $N^1,N^1$-dimethyl-$N^3$-[2-(naphtalen-2-yl)quinoline-4-yl]propane-1,3-diamine.

HPLC-MS: conditions D: $t_r$=4.65 min, (ES+) $C_{24}H_{25}N_3$ requires 355; found 356 [M+H], purity 98%.

$^1$H NMR (300 MHz, CDCl$_3$).

XLII-2/ $N^1,N^1$-dimethyl-$N^3$-[2-(naphtalen-2-yl)quinoline-4-yl]propane-1,3-diamine dihydrochloride (XLII-2)

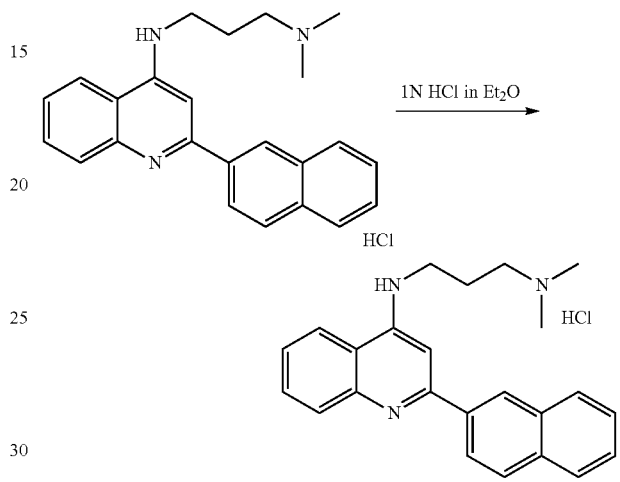

To a solution of 39 mg (0.11 mmol) of $N^1,N^1$-dimethyl-$N^3$-[2-(naphtalen-2-yl)quinoline-4-yl]propane-1,3-diamine in 1 ml of dry dichloromethane was added under nitrogen, 230 μl of a 1N solution of HCl in ether. After stirring for 1 h at room temperature, the precipitate was filtered and washed with dichloromethane. The yellow solid product was then triturated with ether to provide 17 mg (yield 36%) of a beige solid compound corresponding to $N^1,N^1$-dimethyl-$N^3$-[2-(naphtalen-2-yl)quinoline-4-yl]propane-1,3-diamine dihydrochloride.

HPLC-MS: conditions D: $t_r$=4.79 min, (ES+) $C_{24}H_{25}N_3$ requires 355; found 356 [M+H], purity 97%.

$^1$H NMR (300 MHz, DMSO-$d_6$ and DMSO-$d_6$+$D_2O$).

Example 43

Preparation of N-[3-(dimethylamino)propyl]-7-chloro-2-phenylquinoline-4-carboxamide hydrochloride salt (XLIII-2)

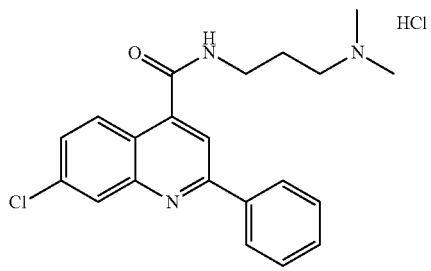 [SMILES: CN(C)CCCNC(=O)c1cc(-c2ccccc2)nc2cc(Cl)ccc12 ; Cl]

XLIII-1/ N-[3-(dimethylamino)propyl]-7-chloro-2-phenylquinoline-4-carboxamide (XLIII-1)

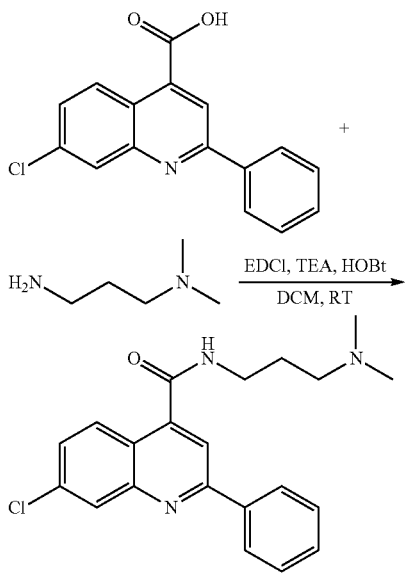

To a solution of 375 mg (1.321 mmol) of 7-chloro-2-phenyl-4-quinolinecarboxylic acid (prepared according to the protocol described paragraph XVII-1) in 10 ml of dry dichloromethane was successively added under argon, 297 µl (1.98 mmol) of triethylamine, 304 mg of (1.585 mmol) of 1-ethyl-3-(3-dimethylaminopropyl)carbodiimide and 214 mg (1.585 mmol) of hydroxybenzotriazole. After stirring for 30 min at room temperature, 199 µl (1.585 mmol) of $N^1,N^1$-dimethylpropane-1,3-diamine were added and the resulting reaction mixture was stirred for 2 days at room temperature and then diluted with dichloromethane. The organic layer was washed with water, dried over $MgSO_4$, filtered and concentrated to give 762 mg of a pasty yellow solid product. This compound was purified by silica gel column chromatography (20 g—gradient from dichloromethane/methanol 96:4 to 9:1) to give 310 mg of yellow foam. This product was additionally purified by silica gel column chromatography (20 g—gradient from dichloromethane/methanol 95:5 to 9:1) to give 190 mg (yield 39%) of a beige solid compound corresponding to N-[3-(dimethylamino)propyl]-7-chloro-2-phenylquinoline-4-carboxamide.

HPLC-MS: conditions D: $t_r$=6.26 min, (ES+) $C_{21}H_{22}ClN_3O$ requires 367; found 368 [M+H], purity 98%.
$^1$H NMR (300 MHz, CDCl$_3$).

XLIII-2/ N-[3-(dimethylamino)propyl]-7-chloro-2-phenylquinoline-4-carboxamide hydrochloride (XLIII-2)

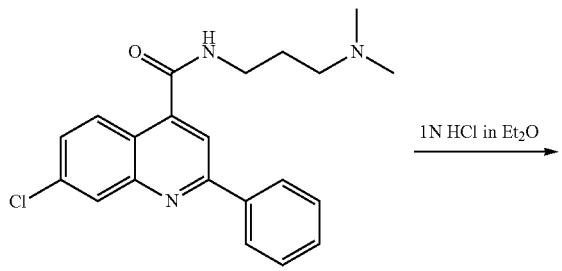

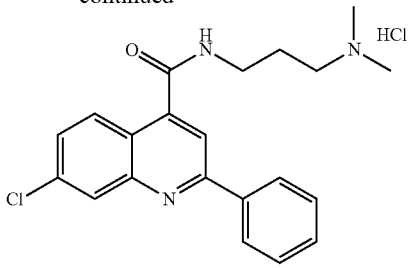

To a solution of 20 mg (0.054 mmol) of N-[3-(dimethylamino)propyl]-7-chloro-2-phenylquinoline-4-carboxamide in 0.5 ml of dry dichloromethane was added under nitrogen, 107 µl of a 1N solution of HCl in ether. The solution was stirred for 1 h at room temperature and concentrated under vacuum to give a residue that was triturated with ether. The yellow solid product was filtered, solubilized in pure water and the solution was filtered on Nalgene 0.2 µm PTFE syringe filter then freeze-dried to give 21 mg (yield 87%) of a pale beige solid compound corresponding to N-[3-(dimethylamino)propyl]-7-chloro-2-phenylquinoline-4-carboxamide hydrochloride.

HPLC-MS: conditions D: $t_r$=6.37 min, (ES+) $C_{21}H_{22}ClN_3O$ requires 367; found 368 [M+H], purity >99%.
$^1$H NMR (300 MHz, DMSO-d$_6$).

Example 44

Preparation of $N^1,N^1$-dimethyl-$N^3$-(7-chloro-2-phenylquinoline-4-ylmethyl)-propane-1,3-diamine hydrochloride salt (XLIV-2)

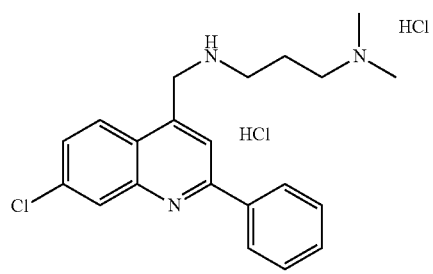 [SMILES: CN(C)CCCNCc1cc(-c2ccccc2)nc2cc(Cl)ccc12 ; Cl ; Cl]

XLIV-1/ $N^1,N^1$-dimethyl-$N^3$-(7-chloro-2-phenylquinoline-4-ylmethyl)-propane-1,3-diamine (XLIV-1)

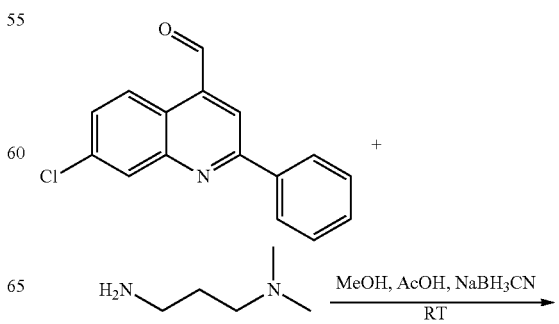

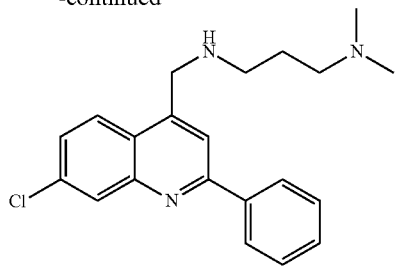

To a solution of 200 mg (0.75 mmol) of 7-chloro-2-phenyl-quinoline-4-carbaldehyde (prepared according to the protocol described in paragraph XVII-4) in 10 ml of dry methanol, were added 104 μl (0.82 mmol) of $N^1,N^1$-dimethylpropane-1,3-diamine and 3 drops of acetic acid. After stirring for 5 h at room temperature, 57 mg (0.9 mmol) of sodium cyanoborohydride were added and the mixture was stirred for 14 h at room temperature under argon. The reaction mixture was poured onto 30 ml of water containing 10% of sodium bicarbonate, and then the aqueous layer was extracted with dichloromethane. The organic layer was washed with brine, dried over $MgSO_4$, filtered and concentrated to give 280 mg of brown oil. This product was purified by silica gel column chromatography (10 g—gradient from dichloromethane 100% to dichloromethane/ethyl acetate 95:5) to give 193 mg of impure orange oil. This product was additionally purified by silica gel column chromatography (5 g—gradient from dichloromethane/methanol 95:5 to 9:1, then dichloromethane/methanol+1% $NH_4OH$, 9:1) to give 127 mg (yield 48%) of orange oil corresponding to $N^1,N^1$-dimethyl-$N^3$-(7-chloro-2-phenylquinoline-4-ylmethyl)-propane-1,3-diamine.

HPLC-MS: conditions D: $t_r$=5.19 min, (ES+) $C_{21}H_{24}ClN_3$ requires 353; found 354 [M+H], purity >95%.
$^1$H NMR (300 MHz, $CDCl_3$).
$^1$H NMR (300 MHz, DMSO-$d_6$).

XLIV-2/ $N^1,N^1$-dimethyl-$N^3$-(7-chloro-2-phenylquinoline-4-ylmethyl)-propane-1,3-diamine dihydrochloride (XLIV-2)

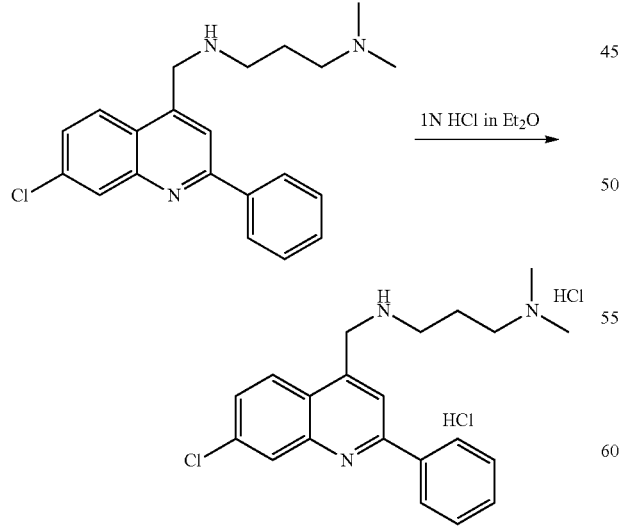

To a solution of 112 mg (0.316 mmol) of $N^1,N^1$-dimethyl-$N^3$-(7-chloro-2-phenylquinoline-4-ylmethyl)-propane-1,3-diamine in 5 ml of dry dichloromethane was added under argon, 950 μl of a 1N solution of HCl in ether. The solution was stirred for 1 h at room temperature and concentrated under vacuum to give a solid compound. It was purified by recrystallization in ethanol, then solubilized in pure water and the solution was filtered on nalgene 0.2 μm PTFE syringe filter then freeze-dried to provide 78 mg (yield 53%) of a pale yellow solid compound corresponding to $N^1,N^1$-dimethyl-$N^3$-(7-chloro-2-phenylquinoline-4-ylmethyl)-propane-1,3-diamine dihydrochloride.

HPLC-MS: conditions D: $t_r$=5.45 min, (ES+) $C_{21}H_{24}ClN_3$ requires 353; found 354 [M+H], purity >99%.
$^1$H NMR (300 MHz, DMSO-$d_6$ and DMSO-$d_6$+$D_2O$).

Example 45

Preparation of 2-phenyl-4-{1-[4-(morpholino)-piperidinyl]-eth-1-yl}quinoline hydrochloride salt (XLV-1)

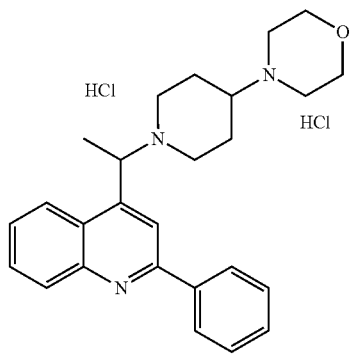 [SMILES: CC(c1cc(-c2ccccc2)nc2ccccc12)N1CCC(N2CCOCC2)CC1 ; Cl ; Cl]

XLV-1/ 2-phenyl-4-{1-[4-(morpholino)-piperidinyl]-eth-1-yl}quinoline hydrochloride salt (XLV-1)

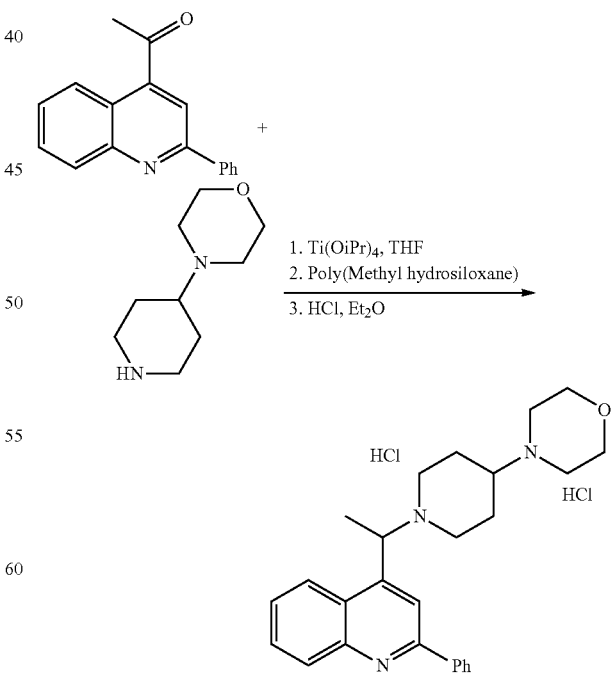

To a solution of 400 mg (1.61 mmol) of 4-acetyl-2-phenyl quinoline (prepared according to the protocol described for example in paragraph XIX-1) in 20 ml of THF was added under argon, 293 mg (1.61 mmol) of 4-morpholinopiperidine and 0.63 mL (2.1 mmol) of Titanium (IV) isopropoxide. The reaction mixture was stirred at RT for 1 h and a solution of 0.183 mL (3.22 mmol) of poly (methyl hydrosiloxane) in 6 ml of THF was added. The resulting reaction mixture was stirred at RT for 20 h. After completion of the reaction monitored by TLC [MeOH: CHCl₃ (1:9), 4-acetyl-2-phenyl quinoline Rf-0.95, 2-phenyl-4-{1-[4-(morpholino)-piperidinyl]-eth-1-yl}quinoline (free base) Rf-0.5], the reaction was carefully quenched with 30 ml of a 3N NaOH aqueous solution (a vigorous gas evolution occurred at the beginning) and the mixture was stirred for 20 min. The aqueous layer was extracted with AcOEt (2×30 mL) and the combined organic layers were washed with brine (30 mL), dried over anhydrous Na₂SO₄, filtered and evaporated under vacuum. The crude residue was purified by flash column chromatography using MeOH:CHCl₃ (0.5:9.5) to elute 2-phenyl-4-{1-[4-(morpholino)-piperidinyl]-eth-1-yl}quinoline (free base). The 2-phenyl-4-{1-[4-(morpholino)-piperidinyl]-eth-1-yl}quinoline (free base) was diluted with diethyl ether and the solution was treated with 10 ml of HCl in diethyl ether at 5° C. The resulting solution was then stirred for 1 h to precipitate a white solid compound. The solid compound was filtered off and washed with hexane to offer 2-phenyl-4-{1-[4-(morpholino)-piperidinyl]-eth-1-yl}quinoline dihydrochloride (180 mg, yield 24% overall 2 steps) as an off-white solid.

HPLC: conditions A: $t_r$=1.90 min, purity >99%, $C_{26}H_{31}N_3O$ requires 401; found 402 [M+H].

HPLC: conditions C: $t_r$=1.50 min, purity >99%, $C_{26}H_{31}N_3O$ requires 401.2467; found 402.2542 [M+H].

¹H NMR (400 MHz, DMSO-d₆) 11.91 (bs, 1H), 11.21 (bs, 1H), 9.02 (s, 1H), 8.47 (m, 3H), 8.22 (m, 1H), 7.89 (t, 1H, J=7.6 Hz), 7.32 (t, 1H, J=7.6 Hz), 7.58 (m, 3H), 5.50 (m, 1H), 4.16 (m, 1H), 3.95 (m, 2H), 3.81 (m, 2H), 3.35 (m, 4H), 3.21 (m, 1H), 3.17 (m, 2H), 3.07 (m, 1H), 2.44 (m, 2H), 2.14 (m, 2H), 1.87 (d, 3H, J=6.8 Hz).

¹³C NMR (100 MHz, D₂O) 154.99, 151.15, 138.96, 135.46, 133.15, 130.63, 130.35, 129.59, 128.90, 125.50, 123.70, 121.64, 120.38, 63.59, 59.66, 49.83, 49.64, 49.02, 23.53, 17.18

Example 46

Preparation of 2-phenyl-4-{1-[4-(N,N-diethyl-amino)-piperidinyl]-eth-1-yl}quinoline hydrochloride salt (XIX-3) According to a One Pot Enamine Synthesis-reduction Procedure)

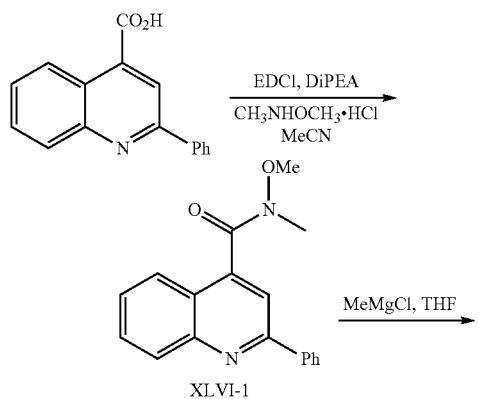

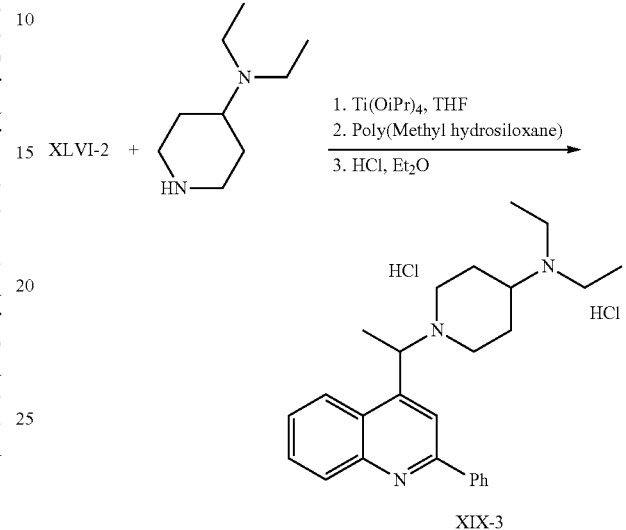

XLVI-1/
N-methoxy-N-methyl-2-phenylquinoline-4-carboxamide

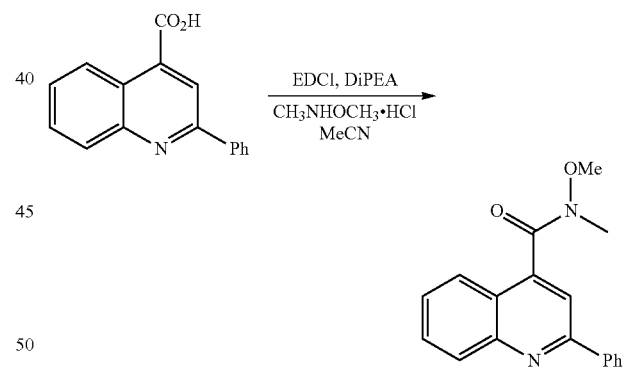

To a solution of 5.0 g (20.0 mmol) of 2-phenyl-quinoline-4-carboxylic acid in 50 ml of acetonitrile was added 1.17 g (12 mmol) of N,O-dimethylhydroxylamine hydrochloride, 2.30 g (12 mmol) of EDCI.HCl, 2.1 mL (12 mmol) of DiPEA and the reaction mixture was stirred for 20 h at room temperature. After completion of the reaction, the solvent was evaporated under vacuum. The residue was dissolved in DCM (100 mL) and the solution was washed with 50 ml of 1N HCl aqueous solution and 50 ml of 1N NaOH aqueous solution. The organic layer was dried over anhydrous Na₂SO₄, filtered and evaporated under vacuum to give 1.5 g (crude product) of N-methoxy-N-methyl-2-phenylquinoline-4-carboxamide. The crude product was carried to the next step without further purification.

XLVI-2/ 4-acetyl-2-phenyl quinoline

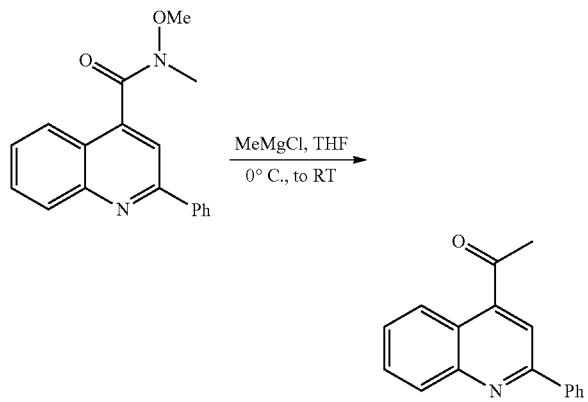

To a solution of 1.5 g (5.13 mmol) of crude N-methoxy-N-methyl-2-phenylquinoline-4-carboxamide in 30 ml of THF was added slowly at 0° C. methyl magnesium chloride (3 Molar solution in THF, 5 mL, 15 mmol) and the resulting reaction mixture was stirred for 5 h at RT. After completion of the reaction monitored by TLC [AcOEt/Hexane 2:8], carboxamide Rf-0.1, ketone Rf-0.7], the reaction mixture was quenched with 50% aq. AcOH (20 mL), diluted with 50 ml of water and then extracted with 2×50 mL of AcOEt. The combined organic layers were washed with 50 ml of brine and dried over anhydrous $Na_2SO_4$, filtered and evaporated under vacuum. The crude residue was purified by flash column chromatography (AcOEt/Hexane 2:8), to give 1 g (yield 50%) of a light solid yellow solid compound corresponding to 4-acetyl-2-phenyl quinoline.

$R_f$ 0.7 (Petroleum ether/AcOEt 8:2)

HPLC: conditions A: $t_r$=3.28 min, purity >98%, (ES+) $C_{17}H_{14}NO$ requires 247; found 248 [M+H].

$^1$H NMR (400 MHz, $CDCl_3$) 8.42 (d, 1H, J=8.4 Hz), 8.22 (d, 1H, J=8.4 Hz), 8.19-8.16 (m, 3H), 8.07 (s, 1H), 7.76 (td, 1H, J=8.2 Hz, J'=1.2 Hz), 7.59-7.49 (m, 4H), 2.82 (s, 3H).

XLVI-3/ 2-phenyl-4-{1-[4-(N,N-diethylamino)-piperidinyl]-eth-1-yl}quinoline dihydrochloride (XIX-3)

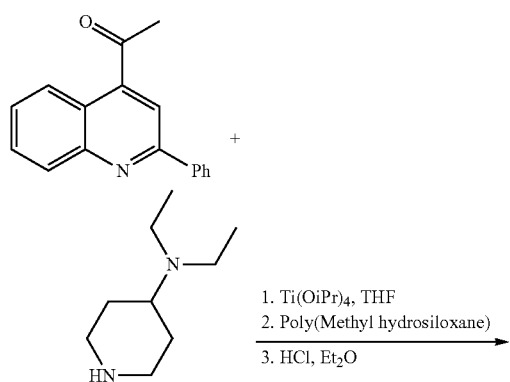

-continued

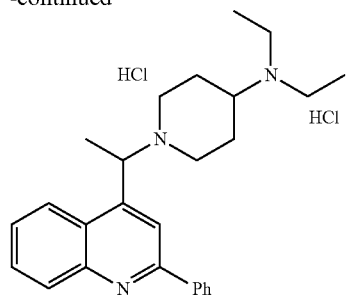

To a solution of 400 mg (1.61 mmol) of 4-acetyl-2-phenyl quinoline in 20 ml of THF was added 252 mg (1.61 mmol) of 4-diethylaminopiperidine, 0.63 mL (2.1 mmol) of Titanium (IV) isopropoxide and the resulting reaction mixture was stirred at room temperature for 1 h. Then a solution of 0.183 mL (3.22 mmol) of poly-(methyl hydrosiloxane) in 6 ml of THF was added and the resulting reaction mixture was stirred at room temperature for 20 h. After completion of the reaction monitored by TLC [MeOH/$CHCl_3$ 1:9), methyl ketone Rf-0.95, XIX-2 (XIX-3 free base form) Rf-0.2] the reaction was carefully quenched with 30 ml of a 3N NaOH aqueous solution (a vigorous gas evolution occurred at the beginning) and the resulting mixture was stirred for 20 min. The aqueous layer was then extracted with 2×30 ml of AcOEt and the combined organic layers were washed with 30 ml of brine, dried over anhydrous $Na_2SO_4$, filtered and evaporated under vacuum. The crude residue was purified by flash column chromatography (MeOH/$CHCl_3$ 1:9) to elute XIX-2 (XIX-3 free base form). The XIX-2 (XIX-3 free base form) was diluted with diethyl ether and the solution was treated with 10 ml of HCl in diethyl ether at 5° C. The solution was then stirred for 1 h to precipitate a white solid compound. The solid was filtered off and washed with hexane to give 170 mg (yield 23% overall 3 steps) of an off-white solid corresponding to 2-phenyl-4-{1-[4-(N,N-diethylamino)-piperidinyl]-eth-1-yl}quinoline dihydrochloride.

HPLC: conditions A: $t_r$=1.95 min, purity >98%, $C_{26}H_{33}N_3$ requires 387; found 388 [M+H].

HPLC: conditions C: $t_r$=1.43 min, purity >98%, $C_{26}H_{33}N_3$ requires 387.2674; found 388.2748 [M+H].

$^1$H NMR (400 MHz, DMSO-$d_6$): 11.86 (bs, 1H), 10.01 (bs, 1H), 8.93 (s, 1H), 8.43 (m, 3H), 8.17 (d, 1H, J=8.4 Hz), 7.87 (t, 1H, J=8.0 Hz), 7.71 (t, 1H, J=7.6 Hz), 7.55 (m, 3H), 5.44 (m, 1H), 4.10 (m, 1H), 3.49 (m, 1H), 3.31-3.01 (m, 7H), 2.65 (m, 1H), 2.48 (m, 1H), 2.38 (m, 1H), 2.20 (m, 1H), 1.88 (m, 3H), 1.22 (m, 6H).

$^{13}$C NMR (100 MHz, $CD_3OD$): 157.04, 154.85, 140.65, 137.04, 134.91, 132.35, 132.05, 131.52, 131.11, 127.62, 126.51, 123.22, 62.05, 57.91, 53.04, 51.8, 47.26, 25.25, 24.86, 19.44, 10.93.

Example 47

Preparation of 2-phenyl-4-{1-[4-(N,N-diethyl-amino)-piperidinyl]-eth-1-yl}quinoline hydrochloride salt (XIX-3) According to an Enamine Intermediate Synthesis, Followed by a Catalytic Reduction

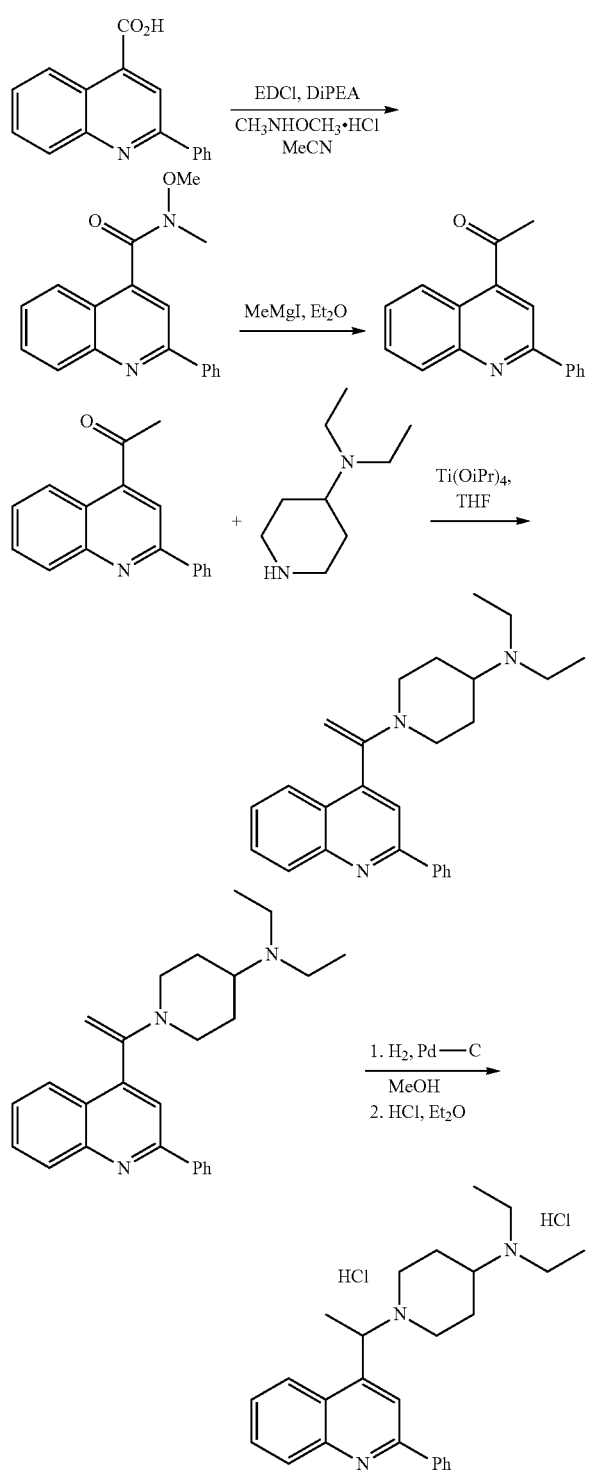

XLVII-1/ N-methoxy-N-methyl-2-phenylquinoline-4-carboxamide

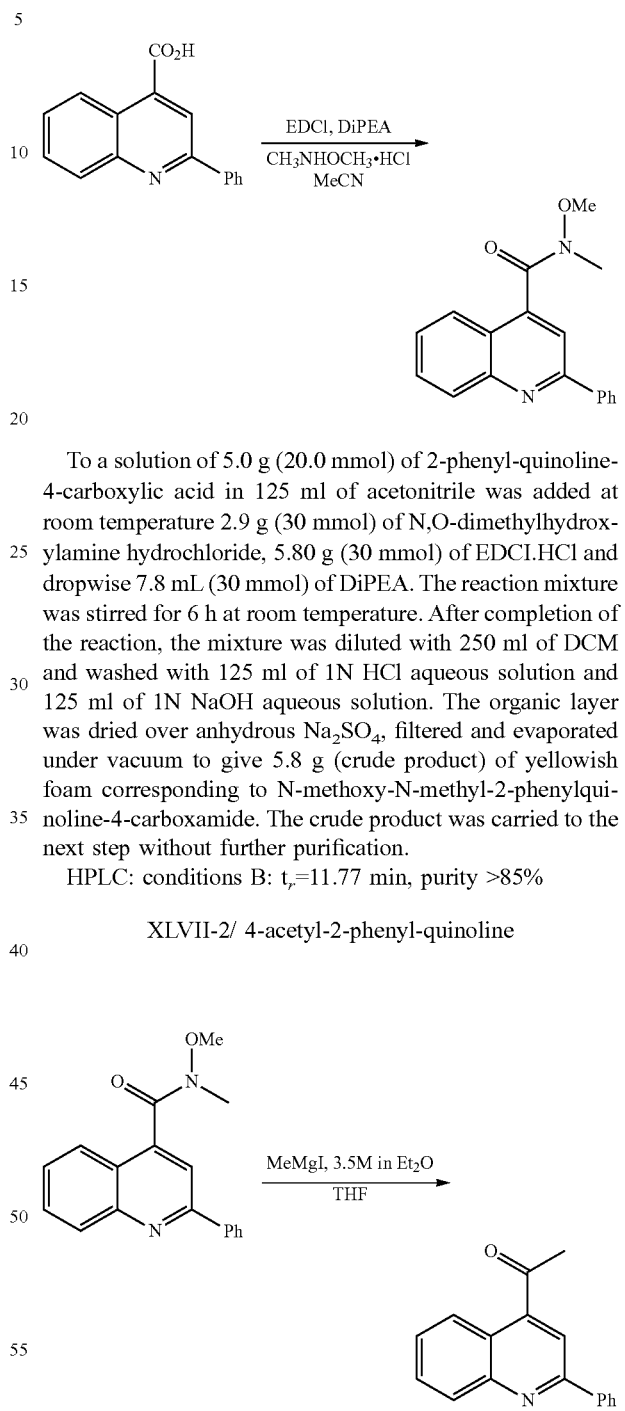

To a solution of 5.0 g (20.0 mmol) of 2-phenyl-quinoline-4-carboxylic acid in 125 ml of acetonitrile was added at room temperature 2.9 g (30 mmol) of N,O-dimethylhydroxylamine hydrochloride, 5.80 g (30 mmol) of EDCl.HCl and dropwise 7.8 mL (30 mmol) of DiPEA. The reaction mixture was stirred for 6 h at room temperature. After completion of the reaction, the mixture was diluted with 250 ml of DCM and washed with 125 ml of 1N HCl aqueous solution and 125 ml of 1N NaOH aqueous solution. The organic layer was dried over anhydrous $Na_2SO_4$, filtered and evaporated under vacuum to give 5.8 g (crude product) of yellowish foam corresponding to N-methoxy-N-methyl-2-phenylquinoline-4-carboxamide. The crude product was carried to the next step without further purification.

HPLC: conditions B: $t_r$=11.77 min, purity >85%

XLVII-2/ 4-acetyl-2-phenyl-quinoline

To a solution of 3.8 g (13 mmol) of N-methoxy-N-methyl-2-phenylquinoline-4-carboxamide in 76 ml of THF was added slowly Methyl magnesium iodide 5 mL (52.5 mmol, 3.5 Molar solution in $Et_2O$,) during 20 min at −10° C. (exotherm+7° C.). Then, the resulting reaction mixture was stirred at room temperature for 5 h. The reaction was quenched with 50 ml of a 50% AcOH aqueous solution, diluted with 120 ml of water and extracted with 2×125 ml of AcOEt. The combined organic layers were washed with 100 ml of brine, dried over anhydrous $Na_2SO_4$, filtered and evaporated under vacuum to give 4.4 g of a yellow solid. The crude residue was purified by flash column chromatography (gradient elution from Petroleum ether/AcOEt 95:5 to 90:10) to give 2.7 g (yield 84% for 2 steps) of a light yellow solid corresponding to 4-acetyl-2-phenyl-quinoline.

$R_f$ 0.4 (Petroleum ether-AcOEt 8/2).

HPLC: conditions B: $t_r$=12.65 min, purity >99%.

$^1$H NMR (400 MHz, $CDCl_3$) 8.42 (dd, 1H, J=8.5 Hz, J'=5 Hz), 8.23 (d, 1H, J=8.3 Hz), 8.18 (d, 2H, J=6.7 Hz), 8.06 (s, 1H), 7.77 (td, 1H, J=8.3 Hz, J'=1.3 Hz), 7.56 (m, 4H), 2.81 (s, 3H).

XLVII-3/ 2-phenyl-4-{1-[4-(N,N-diethylamino)-piperidin-1-yl]-vinyl}quinoline

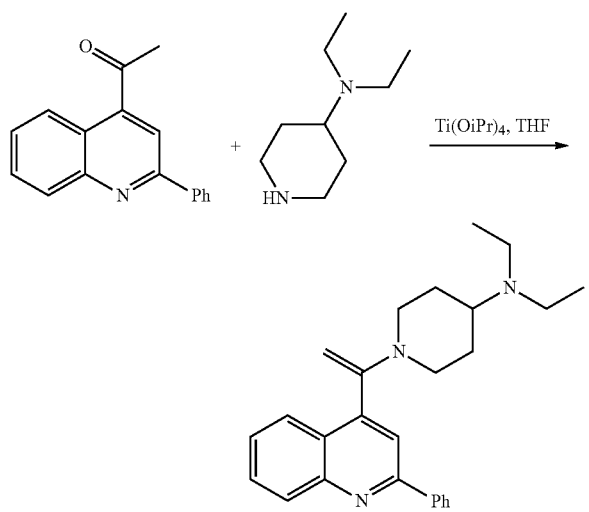

To a solution of 2.7 g (10.92 mmol) of 4-acetyl-2-phenyl quinoline in 135 ml of THF was added 1.9 ml (10.92 mmol) of 4-diethylaminopiperidine, 4.2 mL (14.2 mmol) of Titanium (IV) isopropoxide and the reaction mixture was stirred at room temperature overnight. Then, the reaction was carefully quenched with 200 ml of a 3N NaOH aqueous solution (a vigorous gas evolution occurred at the beginning). The aqueous layer was extracted with 3×200 ml of AcOEt and the combined organic layers were washed with 100 ml of brine, dried over anhydrous $Na_2SO_4$, filtered and evaporated under vacuum to give 3.8 g (crude; yield 90%) of a yellowish oil corresponding to 2-phenyl-4-{1-[4-(N,N-diethylamino)-piperidin-1-yl]-vinyl}quinoline. The crude product was carried to the next step without further purification.

$^1$H NMR (400 MHz, $CDCl_3$) crude product with representative enamine proton 8.43-8.38 (m, 1H), 8.23-8.16 (m, 3H), 7.86 (s, 1H), 7.68 (m, 1H), 7.56-7.44 (m, 4H), 4.41 (s, 1H), 4.22 (s, 1H), 3.32 (bd, 1H, J=12 Hz), 2.63-2.51 (m, 8H), 1.74 (m, 2H), 1.60-1.43 (m, 2H), 1.07-0.90 (m, 6H).

XLVII-4/ 2-phenyl-4-{1-[4-(N,N-diethylamino)-piperidinyl]-eth-1-yl}quinoline dihydrochloride (XIX-3)

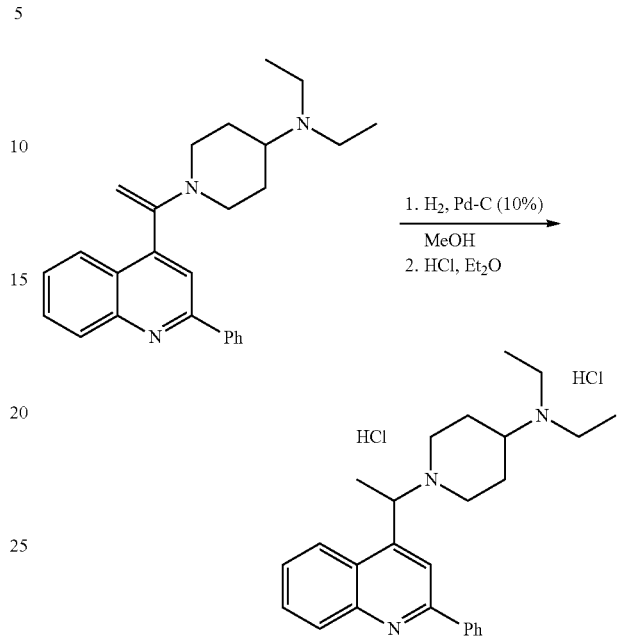

To a solution of 1.9 g (4.90 mmol) of 2-phenyl-4-{1-[4-(N,N-diethylamino)-piperidin-1-yl]-vinyl}quinoline in 25 ml of MeOH was added 190 mg of Pd/C 10% wet, then hydrogen was bubbled at room temperature and under atmospheric pressure for 2 hours. The reaction mixture was filtered off through a Celite® pad and the cake was washed with MeOH. The filtrate was evaporated to dryness under vacuum to give 2.3 g of yellowish oil. The crude residue was purified by flash column chromatography (gradient elution from $CHCl_3$/MeOH 100:0 to 85:15) to give 1.13 g of yellowish oil. The purified product was dissolved in $Et_2O$ and 25 ml of a solution of HCl in $Et_2O$ was added dropwise at 0° C. The mixture was stirred at 0° C. for 2 h to precipitate a solid product. This solid product was filtered off and washed with ether to give 1.2 g (yield 53% overall 2 steps) of a white solid compound corresponding to 2-phenyl-4-{1-[4-(N,N-diethylamino)piperidin-1-yl]-eth-1-yl}quinoline dihydrochloride.

$R_f$ 0.37 ($CHCl_3$-MeOH 9/1).

HPLC: conditions B: $t_r$=10.09 min, purity >99%.

HPLC: conditions C: $t_r$=1.60 min, purity >99%, $C_{26}H_{33}N_3$ requires 387.2674; found 388.2749 [M+H].

$^1$H NMR (400 MHz, DMSO-$d_6$): 12.62 & 12.26 (bs, 1H), 11.07 & 10.89 (bs, 1H), 10.68 (bs, 1H,), 9.31 & 9.14 (s, 1H), 8.84 & 8.52 (m, 3H), 8.38 (d, 1H, J=8.3 Hz), 7.94 (t, 1H, J=7.3 Hz), 7.77 (t, 1H, J=7.5 Hz), 7.60 (m, 3H), 5.70 & 5.54 (m, 1H), 4.13 (m, 1H), 3.58 (m, 1H), 3.32 (m, 2H), 3.10 (m, 5H), 2.59 (d, 1H, J=12.3 Hz), 2.41 (d, 1H, J=11.8 Hz), 2.25 (d, 1H, J=10.8 Hz), 2.09 (d, 1H, J=12 Hz), 1.88 & 1.82 (d, 3H, J=6 Hz), 1.27 (m, 6H).

$^{13}$C NMR (75 MHz, $CD_3OD$): 156.93, 154.83, 140.61, 136.86, 134.91, 132.09, 132.07, 131.29, 131.05, 127.50, 126.03, 123.10, 61.93, 57.72, 51.73, 51.32, 46.94, 24.92, 24.68, 19.01, 10.58.

Example 48

Preparation of 2-phenyl-4-{1-[4-(N,N-diethyl-amino)-piperidinyl]-eth-1-yl}quinoline hydrochloride salt (XIX-3) According to a Still Coupling and Hydride Reduction of Enamine Intermediate

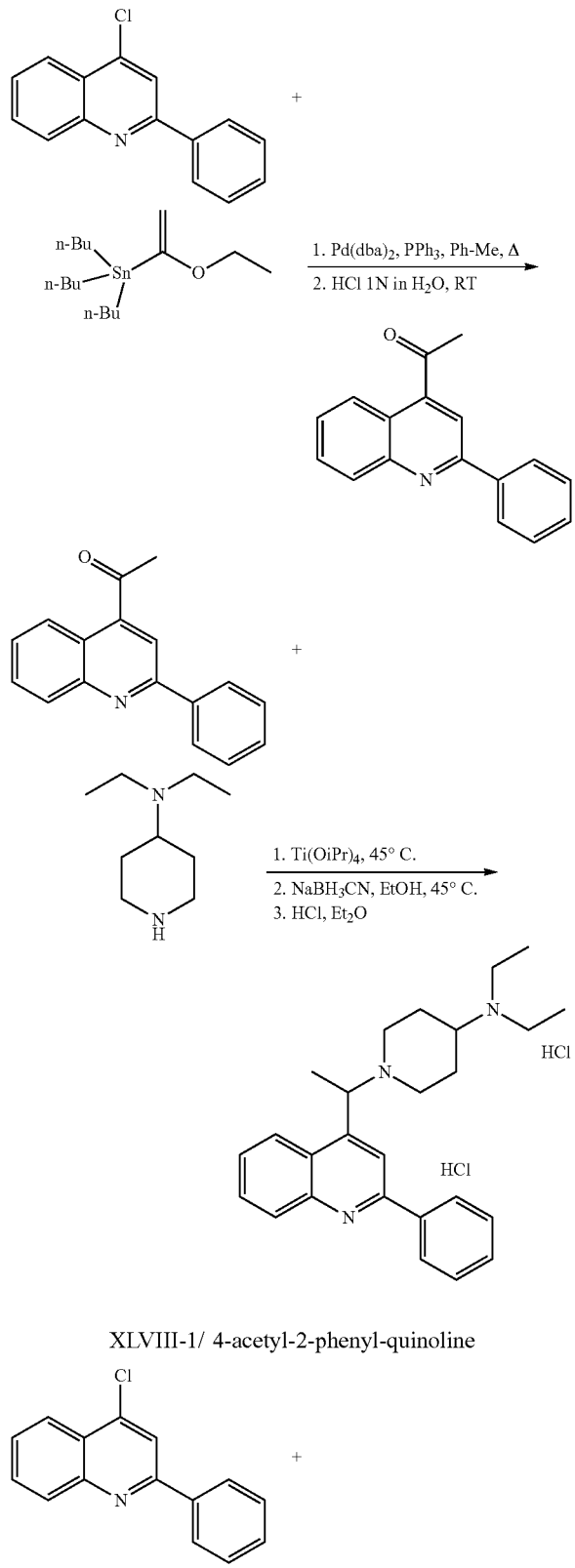

XLVIII-1/ 4-acetyl-2-phenyl-quinoline

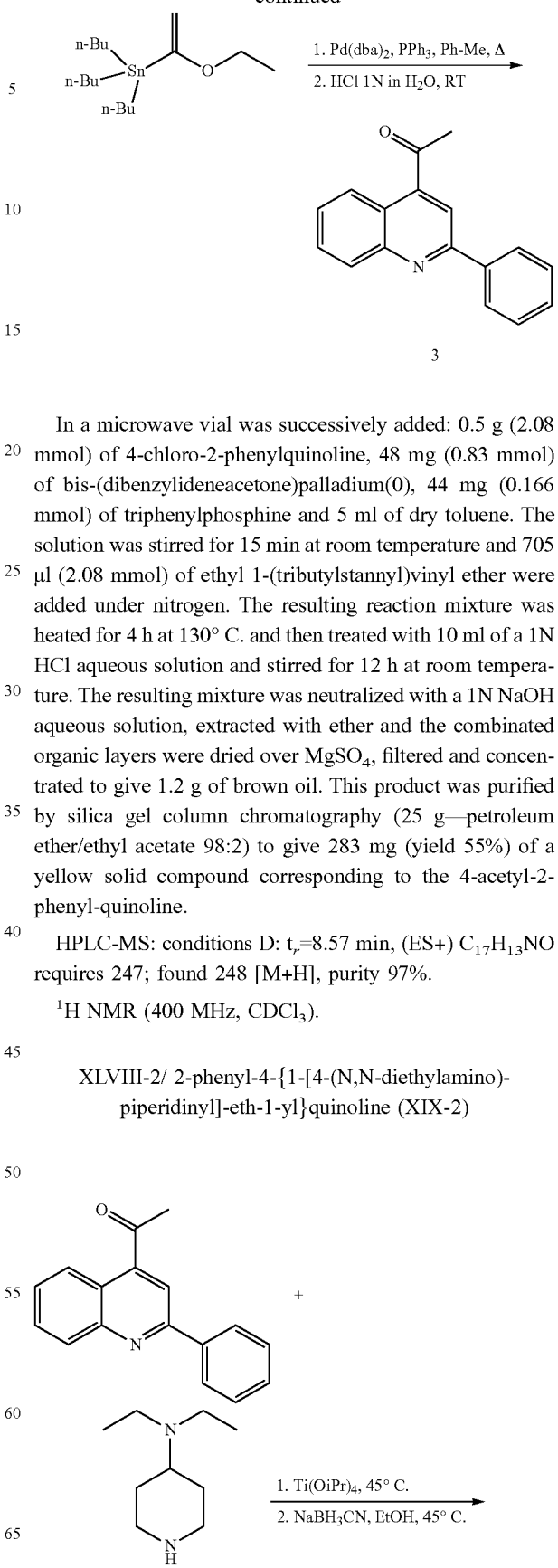

In a microwave vial was successively added: 0.5 g (2.08 mmol) of 4-chloro-2-phenylquinoline, 48 mg (0.83 mmol) of bis-(dibenzylideneacetone)palladium(0), 44 mg (0.166 mmol) of triphenylphosphine and 5 ml of dry toluene. The solution was stirred for 15 min at room temperature and 705 µl (2.08 mmol) of ethyl 1-(tributylstannyl)vinyl ether were added under nitrogen. The resulting reaction mixture was heated for 4 h at 130° C. and then treated with 10 ml of a 1N HCl aqueous solution and stirred for 12 h at room temperature. The resulting mixture was neutralized with a 1N NaOH aqueous solution, extracted with ether and the combinated organic layers were dried over $MgSO_4$, filtered and concentrated to give 1.2 g of brown oil. This product was purified by silica gel column chromatography (25 g—petroleum ether/ethyl acetate 98:2) to give 283 mg (yield 55%) of a yellow solid compound corresponding to the 4-acetyl-2-phenyl-quinoline.

HPLC-MS: conditions D: $t_r$=8.57 min, (ES+) $C_{17}H_{13}NO$ requires 247; found 248 [M+H], purity 97%.

$^1$H NMR (400 MHz, $CDCl_3$).

XLVIII-2/ 2-phenyl-4-{1-[4-(N,N-diethylamino)-piperidinyl]-eth-1-yl}quinoline (XIX-2)

-continued

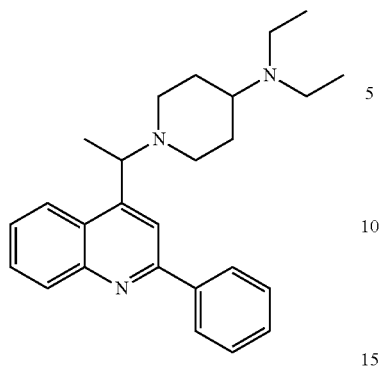

To 280 mg (1.15 mmol) of 4-acetyl-2-phenyl quinoline were added under nitrogen, 269 mg (1.72 mmol) of 4-diethylaminopiperidine, 479 μl (1.61 mmol) of titanium (IV) isopropoxide and the reaction mixture was heated for 2 h at 45° C. After cooling, the mixture was diluted with 4 ml of dry ethanol and 139 mg (2.53 mmol) of sodium cyanoborohydride were added and the resulting solution was heated for 4 h at 45° C. and then stirred for 12 h at room temperature. The mixture was poured onto 30 ml of water, stirred for 1 h at room temperature, filtrated through a Celite® pad and the filtrate was extracted with dichloromethane. The combinated organic layers was washed with brine, dried over MgSO$_4$, filtered and concentrated to give 398 mg of yellow oil. This crude product was purified by silica gel column chromatography (dichloromethane, then dichloromethane/ethanol 95:5) to give 110 mg of impure yellow oil. This compound was additionally purified by silica C18 reversed-phase column Biotage (13 g—water/methanol 1:1 then methanol/triethylamine 99:1) to give 50 mg of yellow oil. This oil was taken up in chloroform and the organic layer washed with a few drops of 1N NaOH aqueous solution, then dried over MgSO$_4$, filtered and concentrated to give 33 mg (yield 7%) of clear yellow oil corresponding to 2-phenyl-4-{1-[4-(N,N-diethylamino)-piperidinyl]-eth-1-yl}quinoline.

HPLC-MS: conditions D: t$_r$=4.75 min, (ES+) C$_{26}$H$_{33}$N$_3$ requires 387; found 388 [M+H], purity 87%.

$^1$H NMR (400 MHz, CDCl$_3$).

XLVIII-3/ 2-phenyl-4-{1-[4-(N,N-diethylamino)-piperidinyl]-eth-1-yl}quinoline dihydrochloride (XIX-3)

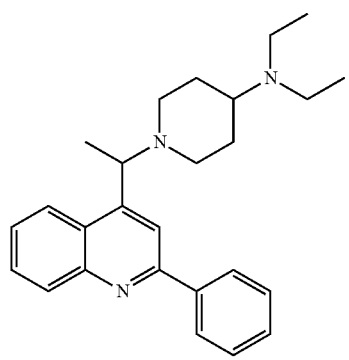

-continued

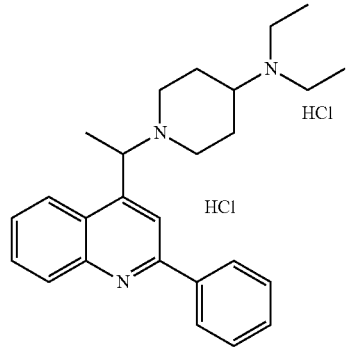

To a solution of 27 mg (0.07 mmol) of 2-phenyl-4-{1-[4-(N,N-diethylamino)-piperidinyl]-eth-1-yl}quinoline in 1 ml of dry dichloromethane was added under nitrogen, 210 μl (0.21 mmol) of a 1N solution of HCl in ether. The resulting solution was stirred for 2 h at room temperature and concentrated to give 37 mg of a yellow solid. The compound was dissolved in pure water, and the solution was freeze-dried to give 29 mg (yield 90%) of a pale yellow solid compound corresponding to 2-phenyl-4-{1-[4-(N,N-diethylamino)-piperidinyl]-eth-1-yl}quinoline dihydrochloride.

HPLC-MS: conditions D: t$_r$=4.85 min, (ES+) C$_{26}$H$_{33}$N$_3$ requires 387; found 388 [M+H], purity 98%.

$^1$H NMR (400 MHz, DMSO-d$_6$).
$^1$H NMR (400 MHz, DMSO-d$_6$+D$_2$O).

Example 49

Preparation of 2-phenyl-4-{1-[4-(N,N-diethylamino)-piperidin-1-yl]-eth-1-yl}quinoline hydrochloride salt (XIX-3) According to a One Pot Reductive Amination/Hydrure Reduction

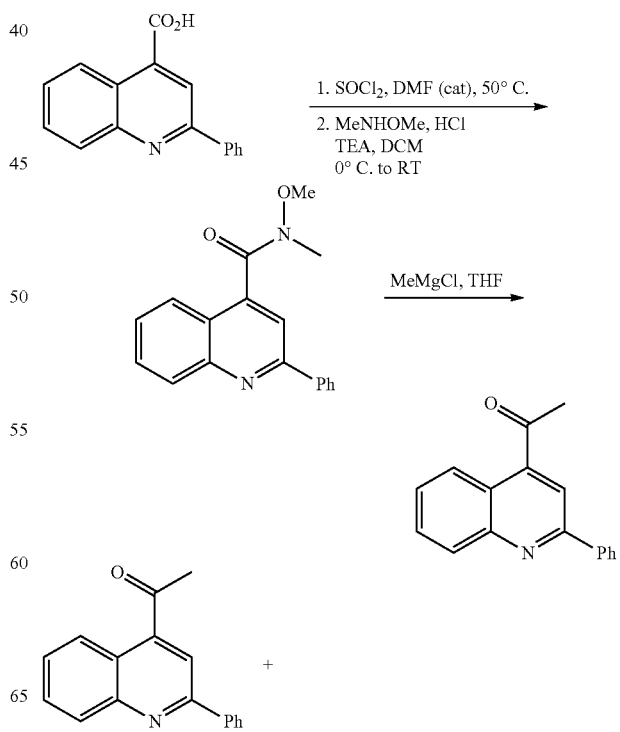

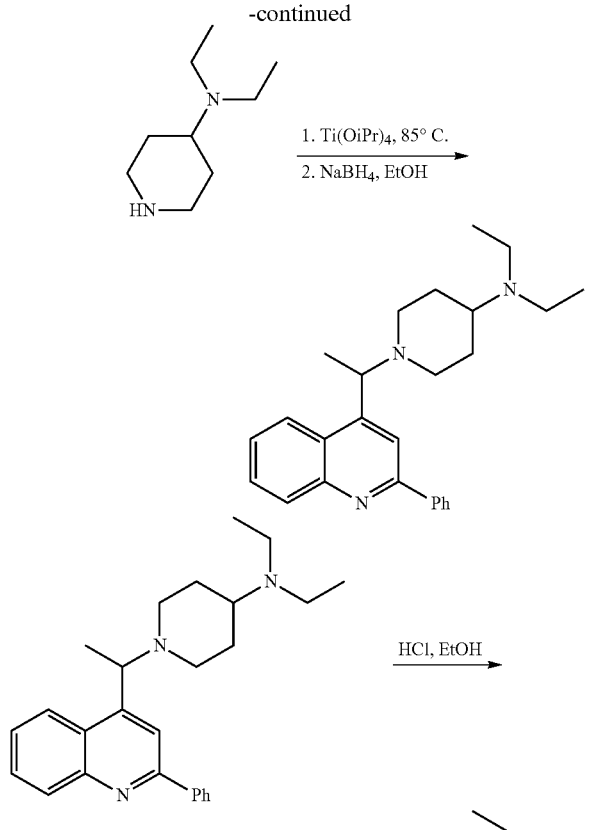

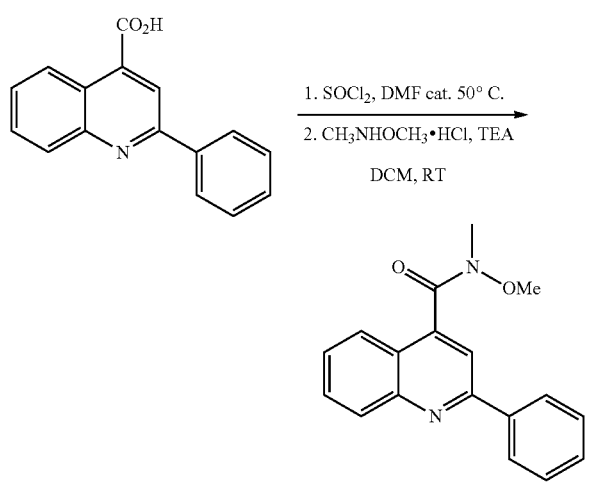

XLIX-1/
N-methoxy-N-methyl-2-phenylquinoline-4-carboxamide

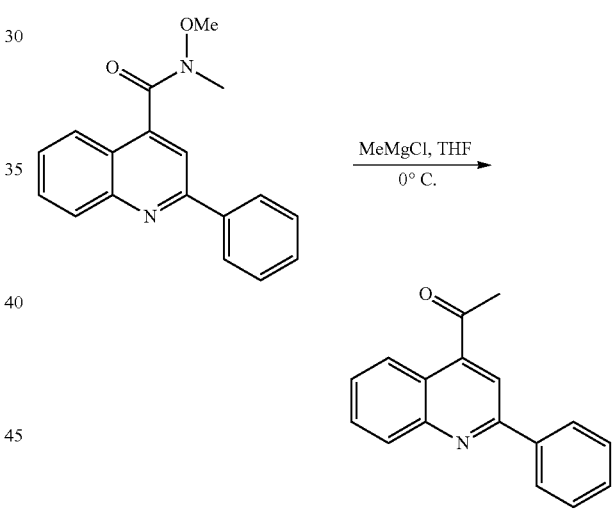

To a solution of 60.0 g (241 mmol) of 2-phenyl-quinoline-4-carboxylic acid in 300 ml (4.135 mol) of thionyl chloride was added at room temperature a catalytic amount of N,N-dimethylformamide (5 drops). Then, the reaction mixture was warmed to 50° C. and stirred for 3 h. After completion of the reaction, the reaction mixture was concentrated to dryness. The residue was suspended in 300 ml of DCM, concentrated to dryness and dried under vacuum to give 76 g of a yellow solid corresponding to 2-phenylquinoline-4-carbonyl chloride. The residue was dissolved in 1200 ml of DCM and was added portionwise at 0° C. 35.20 g (360.9 mmol) of Weinreb amine hydrochloride and dropwise over 45 min 125 ml (896.8 mmol) of TEA. The reaction mixture was warmed to room temperature and stirred overnight. Then, the reaction was quenched between 5-15° C. by addition of 60.0 ml of water. The aqueous layer was extracted with DCM. The combinated organic layers were washed with brine, dried over anhydrous $Na_2SO_4$, filtered and evaporated under vacuum to give 70.6 g (yield=97%) of a yellow solid corresponding to N-methoxy-N-methyl-2-phenylquinoline-4-carboxamide. This product was carried to the next step without further purification.

$^1$H NMR (400 MHz, $CDCl_3$).

XLIX-2/ 4-acetyl-2-phenyl-quinoline

To a solution of 70.6 g (241.5 mmol) of N-methoxy-N-methyl-2-phenylquinoline-4-carboxamide in 800 ml of THF was added slowly at 0° C. a Methyl magnesium chloride 3.0 M solution in THF 160 mL (480 mmol). Then, the resulting reaction mixture was stirred at 0-5° C. for 2.5 h. The reaction was quenched at 0° C., by carefully addition of 60 ml of a saturated aqueous solution of $NH_4Cl$, 50 ml of water and 1000 ml of EtOAc (pH=9). The aqueous layer was extracted with EtOAc. The combined organic layers were washed with water, then brine and dried over anhydrous $Na_2SO_4$, filtered and evaporated under vacuum. The crude residue was purified by cake on silica gel (elution cyclohexane/AcOEt 90:10) to give 51.5 g (yield 85%) of a yellow solid corresponding to 4-acetyl-2-phenyl-quinoline.

HPLC-MS: conditions G: $t_r$=2.76 min, (ES+) $C_{17}H_{13}NO$ requires 247; found 248 [M+H], purity 99.1%.

$^1$H NMR (400 MHz, $CDCl_3$).

XLIX-3/ 2-phenyl-4-{1-[4-(N,N-diethylamino)-piperidinyl]-eth-1-yl}quinoline (XIX-2)

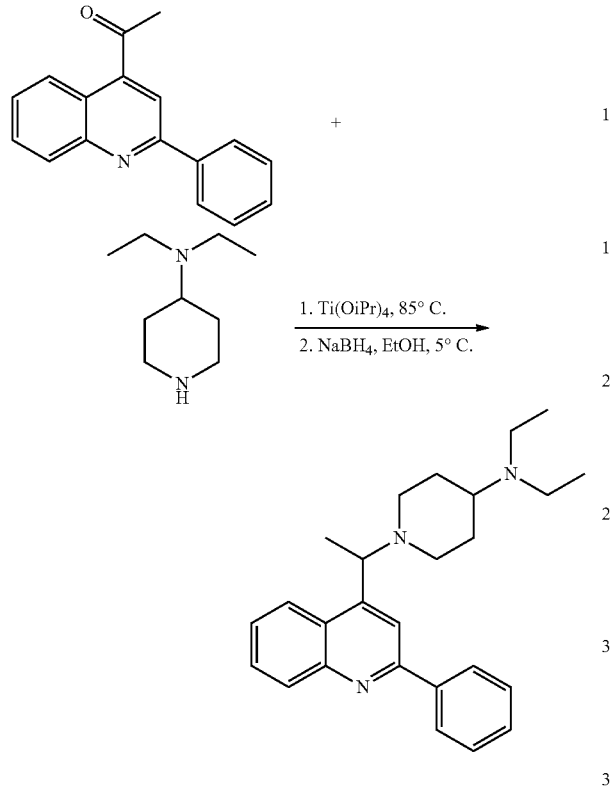

XLIX-4/ 2-phenyl-4-{1-[4-(N,N-diethylamino)-piperidin-1-yl]-eth-1-yl}quinoline dihydrochloride (XIX-3)

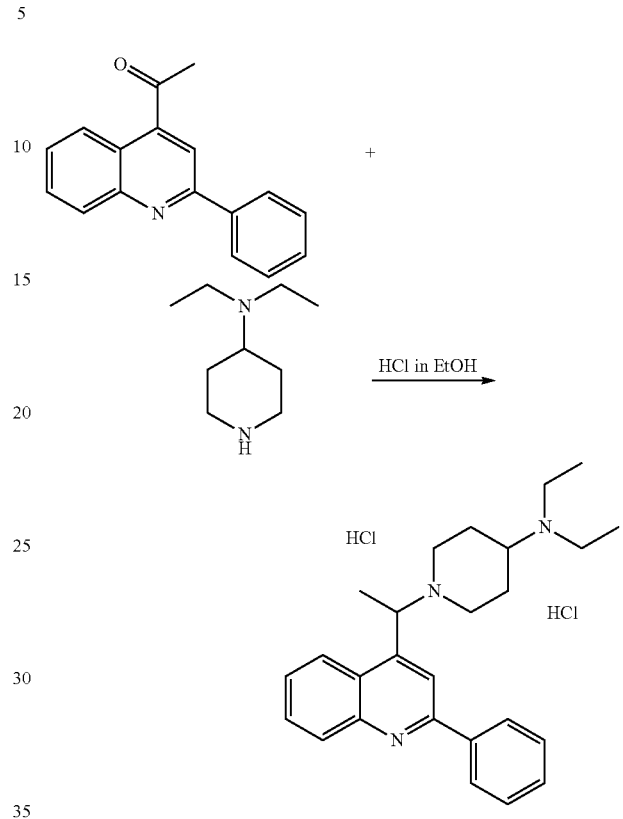

To 15.60 g (63.08 mmol) of 4-acetyl-2-phenyl quinoline was added dropwise 9.82 g (62.84 mmol) of 4-diethylaminopiperidine and 37.0 mL (125.0 mmol) of Titanium (IV) isopropoxide. The resulting reaction mixture was warmed to 85° C. and stirred for 3 h. Then, the reaction mixture was cooled down to 0-5° C. diluted with 320 ml of EtOH and 7.49 g (198.0 mmol) of sodium borohydride was carefully portionwise added between 5-15° C. The reaction mixture was warmed to room temperature and stirred overnight. Then, the reaction was carefully quenched with 100 ml of MeOH and concentrated to dryness. The residue was redissolved in 400 ml of EtOAc and 400 ml of a saturated aqueous solution of NaHCO$_3$. The mixture was stirred for 15 min and then filtrated through a Celite® pad. The cake was washed with EtOAc and the aqueous layer was extracted with EtOAc. The combinated organic layers were washed with brine, dried over anhydrous Na$_2$SO$_4$, filtered and evaporated under vacuum.

The crude product was purified by cake on silica gel (gradient elution from cyclohexane/EtOAc from 90:10 to 70:30:5+0.5% v/v TEA) to give 18.81 g (yield 77%) of yellow oil corresponding to 2-phenyl-4-{1-[4-(N,N-diethylamino)-piperidin-1-yl]-vinyl}quinoline.

HPLC-MS: conditions G: t$_r$=1.74 min, (ES+) C$_{17}$H$_{13}$NO requires 247; found 248 [M+H], purity 99.7%.

$^1$H NMR (400 MHz, CDCl$_3$).

$^{13}$C NMR (400 MHz, CDCl$_3$).

To a solution of 9.68 g (24.98 mmol) of 2-phenyl-4-{1-[4-(N,N-diethylamino)-piperidin-1-yl]-eth-1-yl}quinoline in 100 ml of Et$_2$O was added dropwise at 0° C. 68 ml of a 2.2 M solution of HCl in Et$_2$O. The resulting solution was stirred for 2 h at room temperature to precipitate a white solid. The resulting solid product was filtered off, washed with Et$_2$O and dried under high vacuum to give 7.37 g (yield 64.1%) of a white solid compound corresponding to 2-phenyl-4-{1-[4-(N,N-diethylamino)piperidin-1-yl]-eth-1-yl}quinoline dihydrochloride.

HPLC-MS: conditions G: t$_r$=1.74 min, (ES+) C$_{26}$H$_{33}$N$_3$ requires 387; found 388 [M+H], purity >99%.

$^1$H NMR (400 MHz, D$_2$O).

Example 50

Preparation of 2-(4-chloro-phenyl)-4-(4-N-tert-butylamino-piperidin-1-yl)quinoline hydrochloride salt (XII-4) Using a Convergent Synthesis

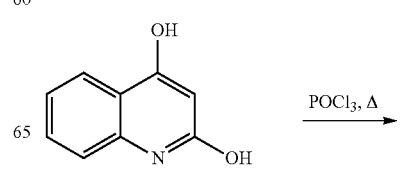

-continued

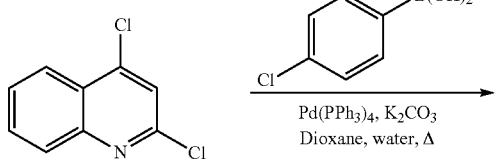

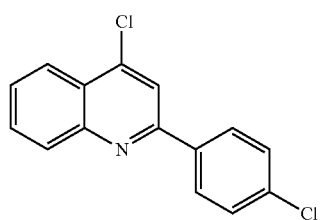

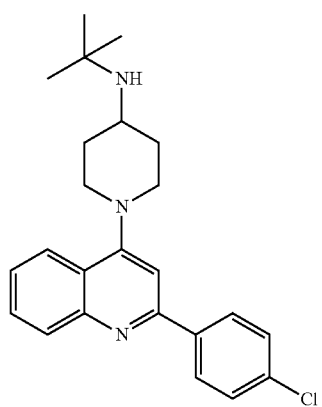

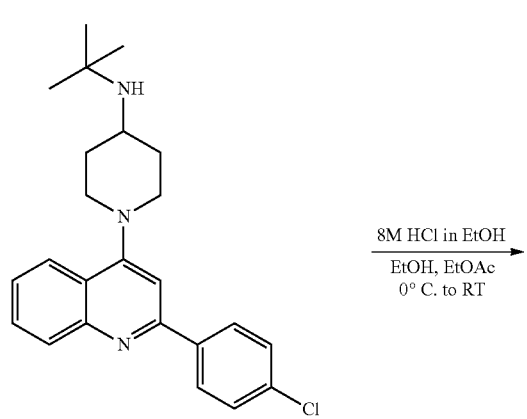

-continued

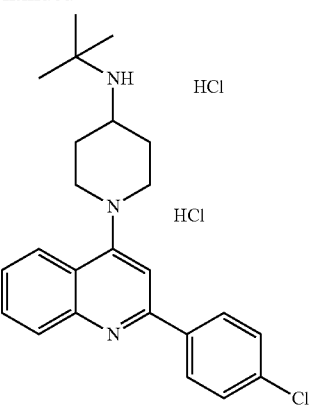

L-1/ 2,4-dichloroquinoline

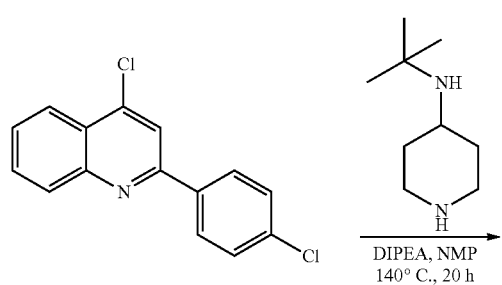 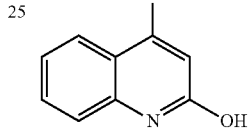

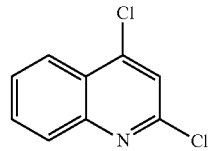

A solution of 50.0 g (0.310 mol) of quinoline-2,4-diol in 250 mL of phosphoryl chloride was warmed to reflux and stirred for 18 h. The reaction mixture was cooled down to room temperature and concentrated to dryness. The residue was coevaporated twice with 500 mL of toluene. The residue was dissolved in 500 mL of dichloromethane and hydrolyzed carefully at 0° C. with 500 mL of water. The aqueous layer was extracted with 500 mL of dichloromethane. The combined organic layers were washed with 500 mL of water, dried over anhydrous $Na_2SO_4$, filtered and evaporated under vacuum to give 57.0 g (93%) of a brown solid corresponding to 2,4-dichloroquinoline. This product was carried to the next step without further purification.

HPLC-MS: conditions H: $t_r$=2.71 min, (ES+) $C_9H_5Cl_2N$ requires 197; found 198 [M+H], purity 94.6%.

$^1$H NMR (400 MHz, $CDCl_3$).

L-2/ 4-chloro-2-(4-chlorophenyl)-quinoline

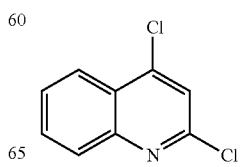 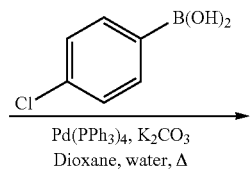

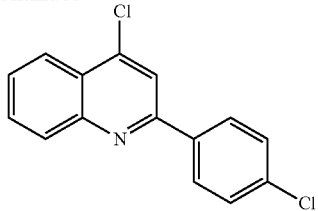

To a solution of 28.8 g (145 mmol) of 2,4-dichloroquinoline and 25.0 g (160 mmol) of 4-chlorophenylboronic acid in 350 mL of 1,4-dioxane, at room temperature, was added 120 mL of 5.4 M K$_2$CO$_3$ aqueous solution. The reaction mixture was degazed for 20 minutes with nitrogen. Then, 8.4 g (7.3 mmol) of tetrakis(triphenylphosphine)palladium were added and the mixture was warmed to reflux and stirred for 20 hours. The reaction mixture was cooled down to room temperature and poured into 350 mL of a 5% NaCl aqueous solution. The layers were separated and the aqueous layer was extracted with dichloromethane. The combined organic layers were washed with water, dried over anhydrous Na$_2$SO$_4$, filtered and evaporated under vacuum to give 49.6 g of crude product. The residue was purified by silica gel column chromatography (Cyclohexane/EtOAc 98:2) to give 40.5 g of an off-white solid corresponding to a mixture of 4-chloro-2-(4-chlorophenyl)quinoline and 2,4-bis(4-chlorophenyl)quinoline (72.7% of 4-chloro-2-(4-chlorophenyl)quinoline according to UPLC analysis at 260 nm). The mixture was used in the next step without further purification.

HPLC-MS: conditions H: t$_r$=4.05 min, (ES+) C$_{15}$H$_9$Cl$_2$N requires 273; found 274 [M+H], purity 72.7%.

$^1$H NMR (300 MHz, CDCl$_3$).

L-3/ 2-(4-chloro-phenyl)-4-(4-N-tert-butylamino-piperidin-1-yl)quinoline

To a solution of 20.7 g of the above mixture of 4-chloro-2-(4-chlorophenyl)quinoline and 4-bis(4-chlorophenyl)quinoline and 14.2 g (90.6 mmol) of 4-(tert-butylamino)piperidine in 100 mL of NMP, at room temperature, was added dropwise 9.6 mL (113 mmol) of DIPEA. The reaction mixture was warmed to 140° C. and stirred for 20 hours. After cooling down to room temperature, 400 mL of 1 M NaOH aqueous solution and 200 mL of ethyl acetate were added. The aqueous layer was extracted with ethyl acetate. The combined organic layers were dried over anhydrous Na$_2$SO$_4$, filtered and evaporated under vacuum to give 34.3 g of crude product. The residue was purified by silica gel column chromatography (dichloromethane/methanol 95:5 to 90:10) to give a first fraction of 16.6 g as a brown oil containing the expected product contaminated with 30% w/w of residual NMP, and a second fraction of 5.6 g of a white solid corresponding to 2-(4-chloro-phenyl)-4-(4-N-tert-butylamino-piperidin-1-yl)quinoline (19% from 2,4-dichloroquinoline). The first fraction was triturated in a mixture of DCM-iPr$_2$O, filtered off and dried under vacuum to give 5.2 g (yield 18% from 2,4-dichloroquinoline) of a white solid corresponding to 2-(4-chloro-phenyl)-4-(4-N-tert-butylamino-piperidin-1-yl)quinoline.

HPLC-MS: conditions G: t$_r$=1.38 min, (ES+) C$_{24}$H$_{28}$ClN$_3$ requires 393; found 394 [M+H], purity 94.8%.

$^1$H NMR (300 MHz, CDCl$_3$).

L-4/ 2-(4-chloro-phenyl)-4-(4-N-tert-butylamino-piperidin-1-yl)quinoline dihydrochloride

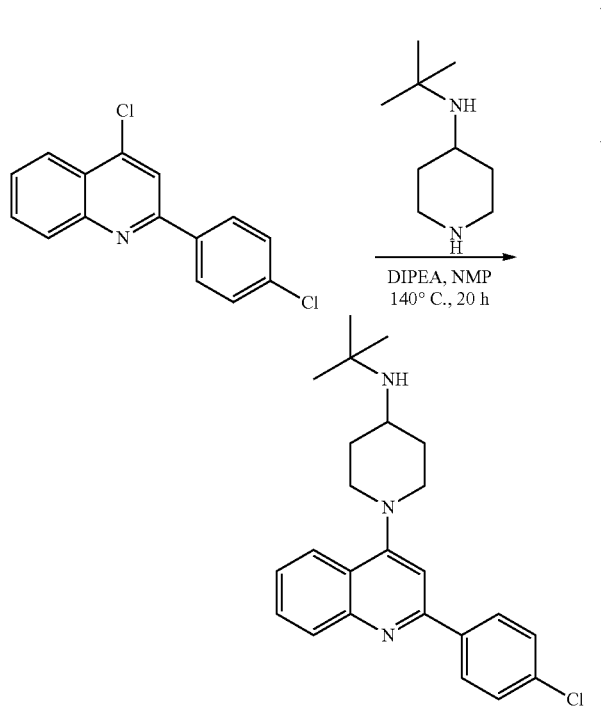

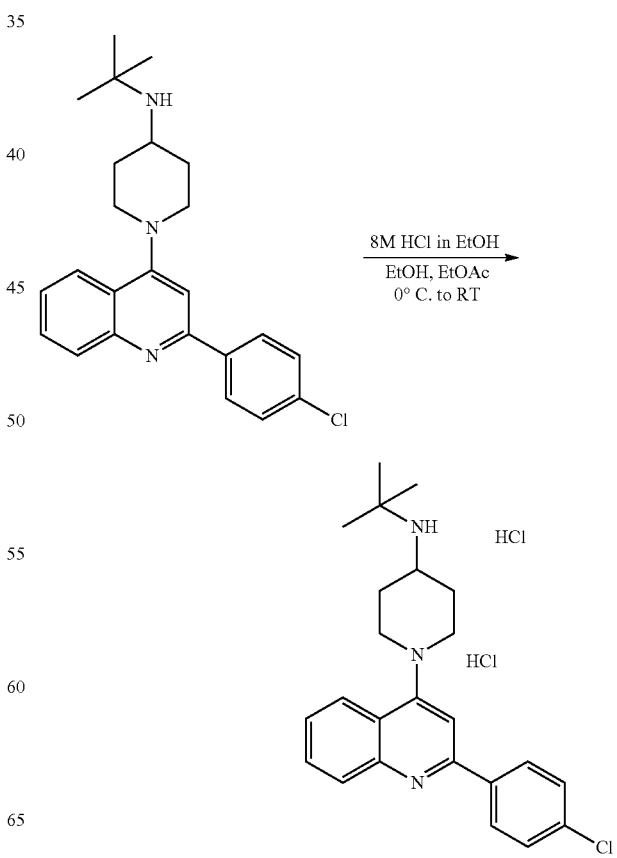

To a solution of 9.78 g (24.8 mmol) of 2-(4-chlorophenyl)-4-(4-N-tert-butylamino-piperidin-1-yl)quinoline in 150 mL of ethanol and 50 mL of ethyl acetate, at 0° C., was added dropwise 7.8 ml (62.4 mmol) of a 8.0 M solution of HCl in ethanol. The reaction mixture was stirred at 0° C. for 30 minutes and 10 minutes at room temperature. The precipitate was filtered, washed with ethanol and dried under high vacuum to give 8.8 g (yield 76%) of tert-Butyl-{1-[2-(4-chlorophenyl)-quinolin-4-yl]-piperidin-4-yl}-amine dihydrochloride as a pale yellow solid.

HPLC-MS: conditions G: $t_r$=1.22 min, (ES+) $C_{24}H_{28}ClN_3$ requires 393; found 394 [M+H], purity 99.8%.

$^1$H NMR (300 MHz, DMSO-$d_6$).

Example 51

Cell Proliferation Assay in A-375, HCT-116 and MOLM-14 Cell Lines at 10 µM

The human melanoma cell line A375 and colorectal carcinoma cell line HCT-116 were cultured in Dulbecco's modified Eagle's medium supplemented with 10% fetal bovine serum and 1% Penicillin-Streptomycin. The human leukemia cell line MOLM-14 was cultured in Minimum Essential Medium Alpha Medium supplemented with 10% Fetal Bovine Serum and 1% Penicillin-Streptomycin. All the cell lines were maintained at 37° C. with 5% $CO_2$.

Briefly, adherent cells, A375 and HCT-116 cells were respectively plated at 800 or 5,000 cells per well onto 96-well plates in 90 µL of media per well and were allowed to grow overnight before the assay.

For MOLM-14 cell line, which grows in suspension, 30,000 cells were plated onto 96-well plates immediately before the assay.

Compounds were added at different concentrations to each well, and cell cultures were incubated for 72 h. Vehicle (DMSO or $H_2O$) was used as a control, and all compounds were tested in a constant percentage of vehicle. Cell outgrowth was measured using for adherent cells CellTiter 95® Aqu$_{eous}$ One Solution Cell Proliferation Assay (Promega) and for cell suspension, Sulforhodamine B colorimetric assay as described in Vichai et al. (Vichai, V. and Kirtikara, K. Nat. Protoc. 2006 (1) 1112-1116). Absorbance was measured using an Infinite F200 Pro or Sunrise TECAN plate reader.

In each experiment, each point represents the average of two replicates in cell culture.

Results are presented in Table 1 below for concentrations of 10 µM of tested compounds.

TABLE 1

| | | Cell viability observed at 10 µM on A-375, HCT-116 and MOLM-14 AML cell lines | | | |
|---|---|---|---|---|---|
| | | | Cell viability observed at 10 µM$^a$ | | |
| Entry | ID | Structures | A375 | HCT-116 | MOLM-14 |
| 1 | I-3 | *[structure: 4-(4-diethylamino-piperidin-1-yl)-2-phenylquinoline]* | − | − | + |
| 2 | I-4 | *[structure: 4-(4-diethylamino-piperidin-1-yl)-2-phenylquinoline · 2 HCl]* | − | − | + |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 3 | II-4 | 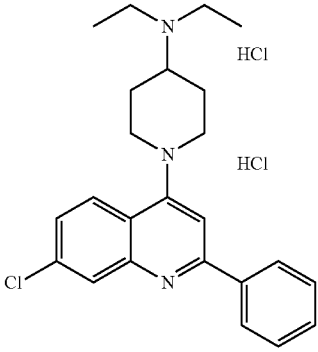 [SMILES: CCN(CC)C1CCN(c2cc(-c3ccccc3)nc3cc(Cl)ccc23)CC1 ; Cl ; Cl] | ++++ | +++ | + |
| 4 | III-4 | 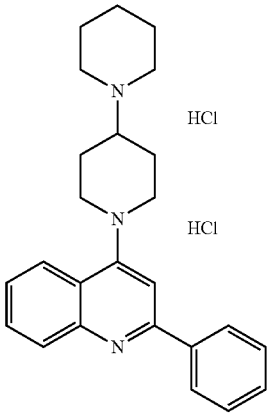 [SMILES: c1ccc(-c2cc(N3CCC(N4CCCCC4)CC3)c3ccccc3n2)cc1 ; Cl ; Cl] | − | − | + |
| 5 | IV-2 | 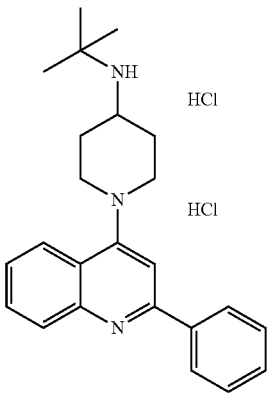 [SMILES: CC(C)(C)NC1CCN(c2cc(-c3ccccc3)nc3ccccc23)CC1 ; Cl ; Cl] | ++ | + | +++ |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 6 | V-2 | 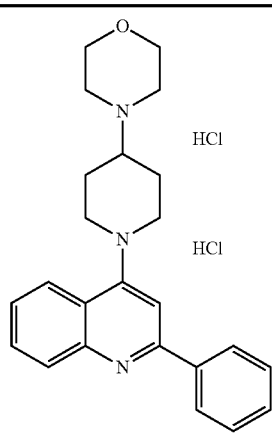 | − | − | + |
| 7 | VI-6 | 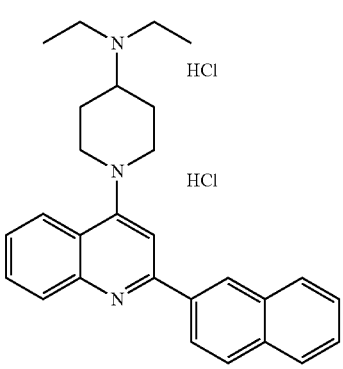 [SMILES: CCN(CC)C1CCN(c2cc(-c3ccc4ccccc4c3)nc3ccccc23)CC1 ; Cl ; Cl] | ++++ | ++++ | ++++ |
| 8 | VII-4 | 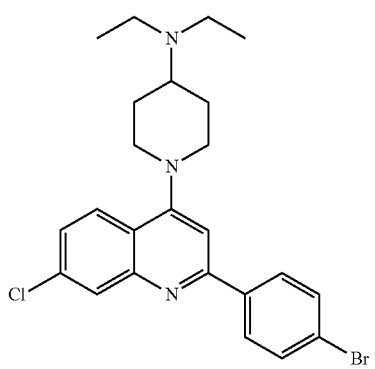 [SMILES: CCN(CC)C1CCN(c2cc(-c3ccc(Br)cc3)nc3cc(Cl)ccc23)CC1] | ND | ND | ND |
| 9 | VIII-6 | 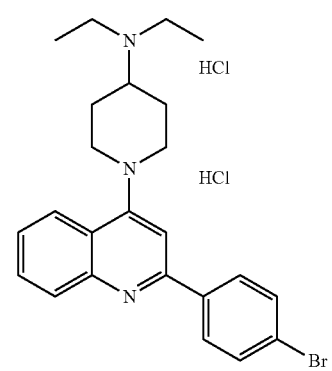 [SMILES: CCN(CC)C1CCN(c2cc(-c3ccc(Br)cc3)nc3ccccc23)CC1 ; Cl ; Cl] | ++++ | ++++ | +++ |

TABLE 1-continued

Cell viability observed at 10 μM on A-375, HCT-116 and MOLM-14 AML cell lines

| Entry | ID | Structures | Cell viability observed at 10 μM[a] | | |
|---|---|---|---|---|---|
| | | | A375 | HCT-116 | MOLM-14 |
| 10 | IX-2 | 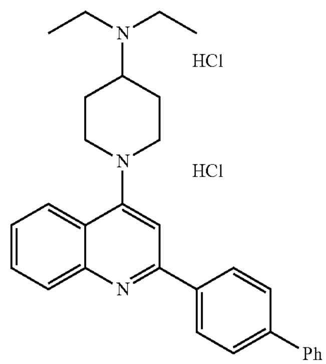 [SMILES: CCN(CC)C1CCN(c2cc(-c3ccc(-c4ccccc4)cc3)nc3ccccc23)CC1 ; Cl ; Cl] | ++++ | ++++ | ++++ |
| 11 | X-6 | 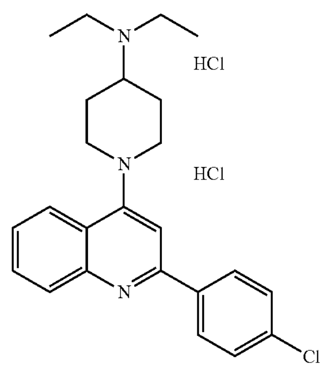 [SMILES: CCN(CC)C1CCN(c2cc(-c3ccc(Cl)cc3)nc3ccccc23)CC1 ; Cl ; Cl] | ++++ | ++++ | ++ |
| 12 | XI-2 | 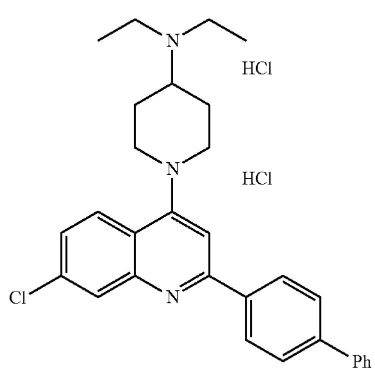 [SMILES: CCN(CC)C1CCN(c2cc(-c3ccc(-c4ccccc4)cc3)nc3cc(Cl)ccc23)CC1 ; Cl ; Cl] | ND | ND | ND |
| 13 | XII-4 | 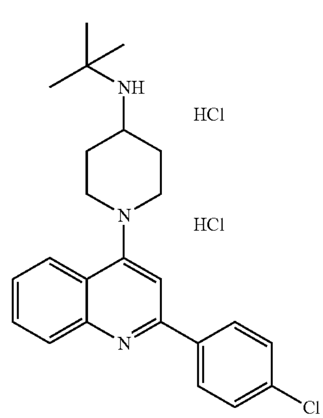 [SMILES: CC(C)(C)NC1CCN(c2cc(-c3ccc(Cl)cc3)nc3ccccc23)CC1 ; Cl ; Cl] | ++++ | ++++ | ++++ |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 14 | XIII-8 | 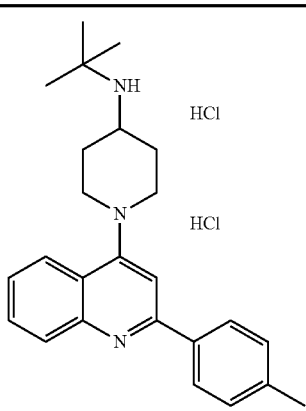 | ++++ | ++++ | ++++ |
| 15 | XIV-8 | 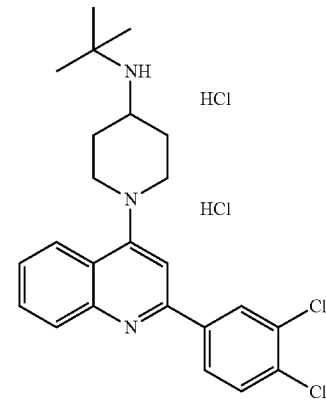 [SMILES: CC(C)(C)NC1CCN(c2cc(-c3ccc(Cl)c(Cl)c3)nc3ccccc23)CC1 ; Cl ; Cl] | ++++ | ++++ | ++++ |
| 16 | XV-8 | 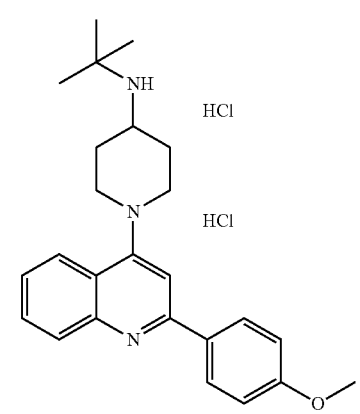 [SMILES: COc1ccc(-c2cc(N3CCC(NC(C)(C)C)CC3)c3ccccc3n2)cc1 ; Cl ; Cl] | +++ | − | ++++ |

TABLE 1-continued

Cell viability observed at 10 μM on A-375, HCT-116 and MOLM-14 AML cell lines

| Entry | ID | Structures | Cell viability observed at 10 μM[a] | | |
|---|---|---|---|---|---|
| | | | A375 | HCT-116 | MOLM-14 |
| 17 | XVI-4 | 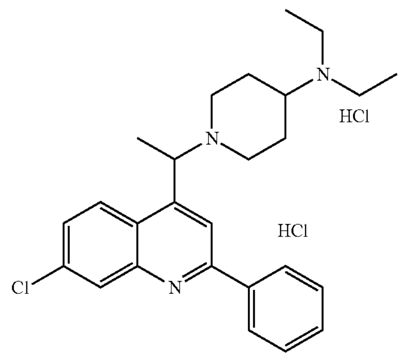 [SMILES: CCN(CC)C1CCN(C(C)c2cc(-c3ccccc3)nc3cc(Cl)ccc23)CC1 ; Cl ; Cl] | ++++ | ++++ | ++++ |
| 18 | XVII-6 | 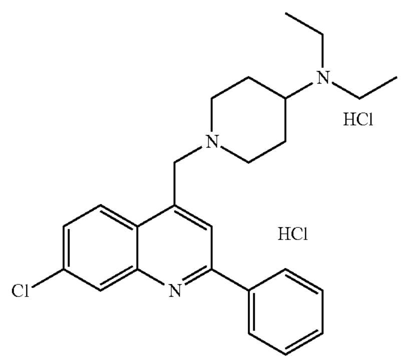 [SMILES: CCN(CC)C1CCN(Cc2cc(-c3ccccc3)nc3cc(Cl)ccc23)CC1 ; Cl ; Cl] | ++++ | ++++ | ++++ |
| 19 | XVIII-2 | 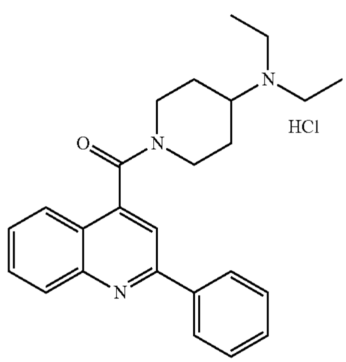 [SMILES: CCN(CC)C1CCN(C(=O)c2cc(-c3ccccc3)nc3ccccc23)CC1 ; Cl] | – | – | – |
| 20 | XIX-3 | 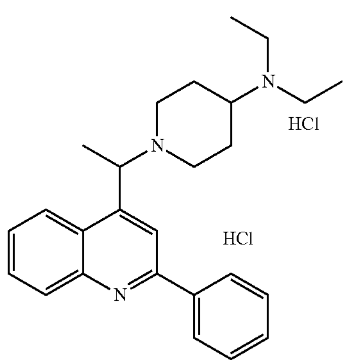 [SMILES: CCN(CC)C1CCN(C(C)c2cc(-c3ccccc3)nc3ccccc23)CC1 ; Cl ; Cl] | ++++ | +++ | +++ |

TABLE 1-continued

Cell viability observed at 10 μM on A-375, HCT-116 and MOLM-14 AML cell lines

| Entry | ID | Structures | Cell viability observed at 10 μM[a] | | |
|---|---|---|---|---|---|
| | | | A375 | HCT-116 | MOLM-14 |
| 21 | XX-5 | | + | − | ++ |
| 22 | XXI-4 | | − | − | − |
| 23 | XXII-4 | | ND | ND | ND |
| 24 | XXIII-2 | | ++++ | +++ | ++++ |

TABLE 1-continued
Cell viability observed at 10 μM on A-375, HCT-116 and MOLM-14 AML cell lines
| Entry | ID | Structures | Cell viability observed at 10 μM$^a$ | | |
|---|---|---|---|---|---|
| | | | A375 | HCT-116 | MOLM-14 |
| 25 | XXIV-3 | 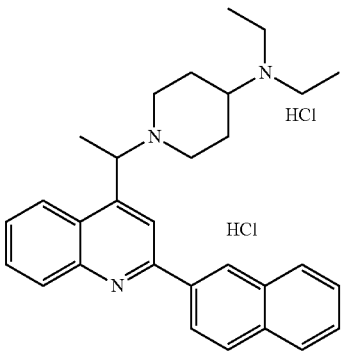 [SMILES: CCN(CC)C1CCN(C(C)c2cc(-c3ccc4ccccc4c3)nc3ccccc23)CC1 ; Cl ; Cl] | ++++ | ++++ | ++++ |
| 26 | XXV-6 | 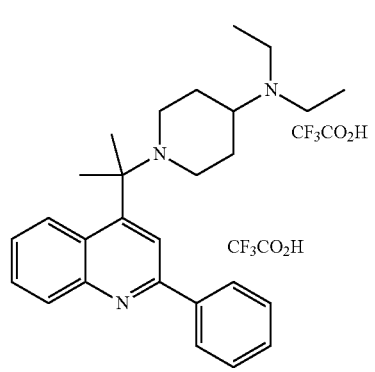 [SMILES: CCN(CC)C1CCN(C(C)(C)c2cc(-c3ccccc3)nc3ccccc23)CC1 ; "CF3CO2H" ; "CF3CO2H"] | ND | ND | ND |
| 27 | XXVI-4 | 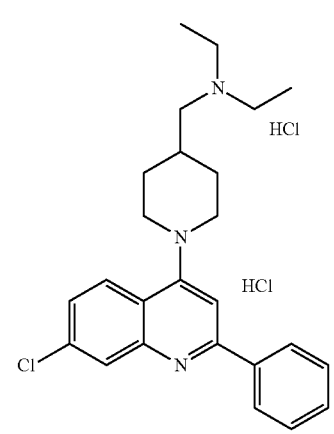 [SMILES: CCN(CC)CC1CCN(c2cc(-c3ccccc3)nc3cc(Cl)ccc23)CC1 ; Cl ; Cl] | − | − | − |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 28 | XXVII-2 | 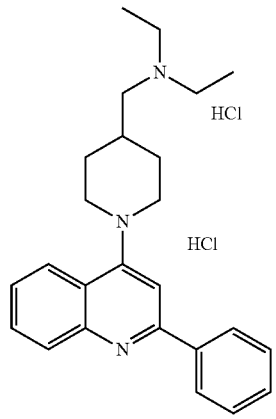 [SMILES: CCN(CC)CC1CCN(c2cc(-c3ccccc3)nc3ccccc23)CC1 ; Cl ; Cl] | +++ | − | ++ |
| 29 | XXVIII-2 | 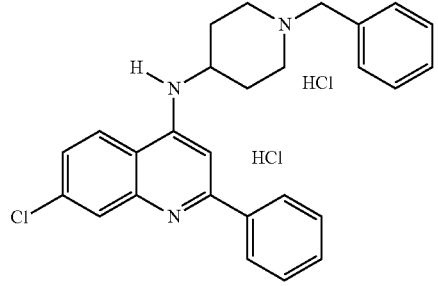 [SMILES: Clc1ccc2c(NC3CCN(Cc4ccccc4)CC3)cc(-c3ccccc3)nc2c1 ; Cl ; Cl] | ++++ | ++++ | ++++ |
| 30 | XXIX-2 | 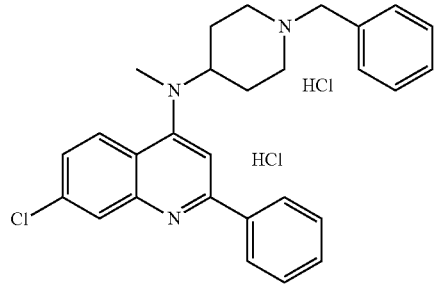 [SMILES: CN(c1cc(-c2ccccc2)nc2cc(Cl)ccc12)C1CCN(Cc2ccccc2)CC1 ; Cl ; Cl] | − | − | − |
| 31 | XXX-2 | 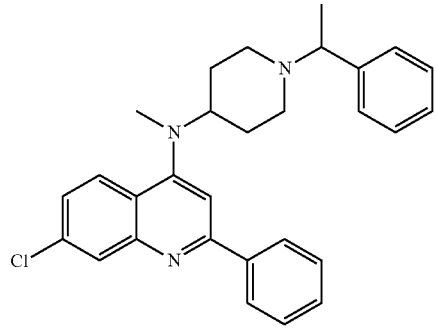 [SMILES: CC(c1ccccc1)N1CCC(N(C)c2cc(-c3ccccc3)nc3cc(Cl)ccc23)CC1] | − | − | + |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 32 | XXXI-2 | 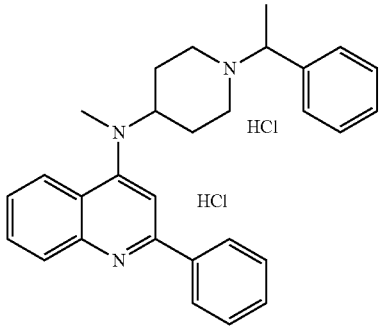 [SMILES: CC(c1ccccc1)N1CCC(N(C)c2cc(-c3ccccc3)nc3ccccc23)CC1 ; Cl ; Cl] | – | – | – |
| 33 | XXXII-2 | 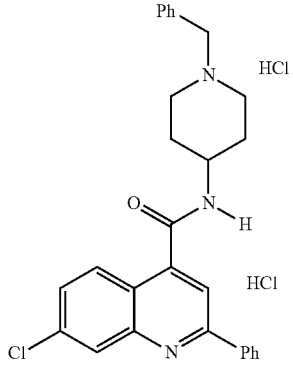 [SMILES: O=C(NC1CCN(Cc2ccccc2)CC1)c1cc(-c2ccccc2)nc2cc(Cl)ccc12 ; Cl ; Cl] | – | – | ++ |
| 34 | XXXIII-2 | 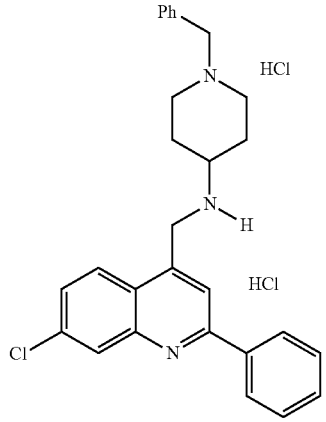 [SMILES: Clc1ccc2c(CNC3CCN(Cc4ccccc4)CC3)cc(-c3ccccc3)nc2c1 ; Cl ; Cl] | ++ | +++ | ++ |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 35 | XXXIV-2 | 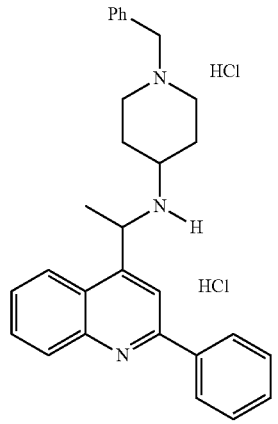 [SMILES: CC(NC1CCN(Cc2ccccc2)CC1)c1cc(-c2ccccc2)nc2ccccc12 ; Cl ; Cl] | ++++ | +++ | ++ |
| 36 | XXXV-2 | 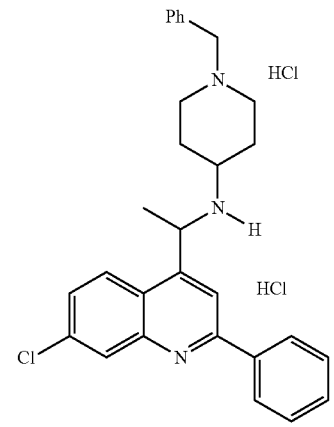 [SMILES: CC(NC1CCN(Cc2ccccc2)CC1)c1cc(-c2ccccc2)nc2cc(Cl)ccc12 ; Cl ; Cl] | − | − | − |
| 37 | XXXVI-2 | 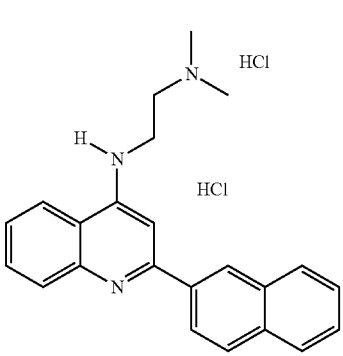 [SMILES: CN(C)CCNc1cc(-c2ccc3ccccc3c2)nc2ccccc12 ; Cl ; Cl] | ND | ND | ND |
| 38 | XXXVII-2 | 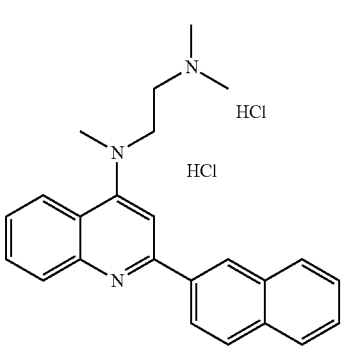 [SMILES: CN(C)CCN(C)c1cc(-c2ccc3ccccc3c2)nc2ccccc12 ; Cl ; Cl] | ++ | − | ++ |

TABLE 1-continued
Cell viability observed at 10 μM on A-375, HCT-116 and MOLM-14 AML cell lines
| Entry | ID | Structures | Cell viability observed at 10 μM[a] | | |
|---|---|---|---|---|---|
| | | | A375 | HCT-116 | MOLM-14 |
| 39 | XXXVIII-2 | 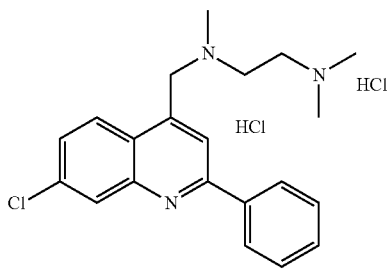 [SMILES: CN(C)CCN(C)Cc1cc(-c2ccccc2)nc2cc(Cl)ccc12 ; Cl ; Cl] | ++++ | ++++ | ++ |
| 40 | XXXIX-2 | 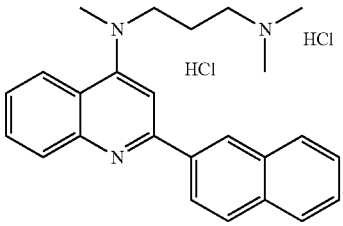 [SMILES: CN(C)CCCN(C)c1cc(-c2ccc3ccccc3c2)nc2ccccc12 ; Cl ; Cl] | ++++ | ++++ | ++++ |
| 41 | XL-2 | 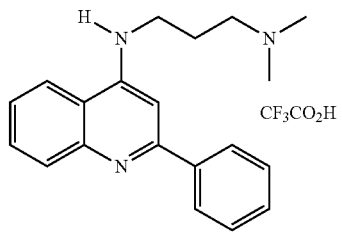 | ++++ | +++ | ++++ |
| 42 | XLI-2 | 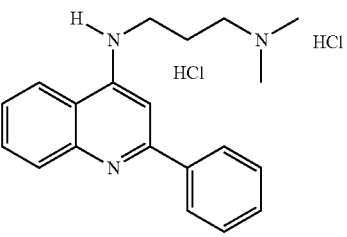 [SMILES: CN(C)CCCNc1cc(-c2ccccc2)nc2ccccc12 ; Cl ; Cl] | ++++ | +++ | ++++ |
| 43 | XLII-2 | 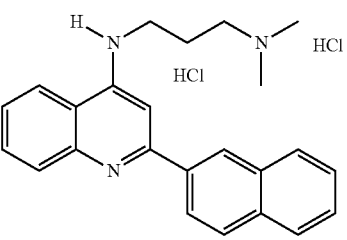 [SMILES: CN(C)CCCNc1cc(-c2ccc3ccccc3c2)nc2ccccc12 ; Cl ; Cl] | ++++ | ++++ | ++++ |

TABLE 1-continued
Cell viability observed at 10 μM on A-375, HCT-116 and MOLM-14 AML cell lines
| Entry | ID | Structures | Cell viability observed at 10 μM$^a$ | | |
|---|---|---|---|---|---|
| | | | A375 | HCT-116 | MOLM-14 |
| 44 | XLIII-2 | 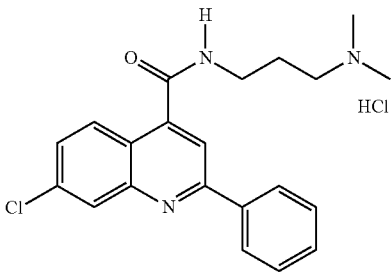 [SMILES: CN(C)CCCNC(=O)c1cc(-c2ccccc2)nc2cc(Cl)ccc12 ; Cl] | ++++ | − | + |
| 45 | XLIV-2 | 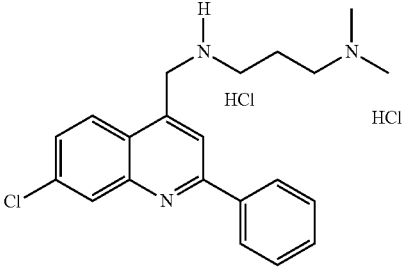 [SMILES: CN(C)CCCNCc1cc(-c2ccccc2)nc2cc(Cl)ccc12 ; Cl ; Cl] | ++++ | ++++ | ++++ |
| 46 | XLV-1 | 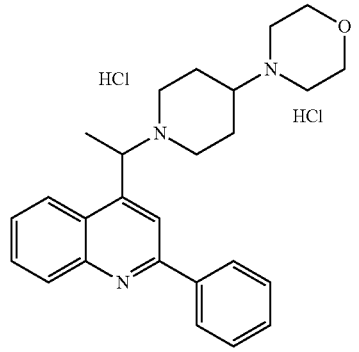 [SMILES: CC(c1cc(-c2ccccc2)nc2ccccc12)N1CCC(N2CCOCC2)CC1 ; Cl ; Cl] | ND | ND | ND |

Example 52

Structure Activity Relationships of Cell Proliferation Assay in A-375, HCT-116 and MOLM-14 Cell Lines Compounds of General Formula (I'):

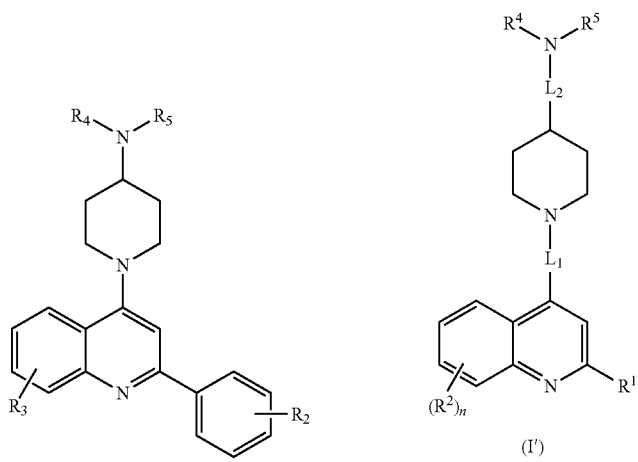

| ID | $R_2$ | $R_3$ | $R_4$ | $R_5$ | Cell viability[a] A375 | HCT-116 | MOLM-14 |
|---|---|---|---|---|---|---|---|
| I-3 | H | H | $C_2H_5$ | $C_2H_5$ | − | − | + |
| I-4 | H | H | $C_2H_5$ | $C_2H_5$ | − | − | + |
| II-4 | H | 7-Cl | $C_2H_5$ | $C_2H_5$ | ++++ | +++ | + |
| III-4 | H | H | —$(CH_2)_5$— | | − | − | + |
| IV-2 | H | H | $C(CH_3)_3$ | H | ++ | + | +++ |
| V-2 | H | H | —$(CH_2)_2$—O—$(CH_2)_2$— | | − | − | + |
| VI-6 | 2-Naphtyl | H | $C_2H_5$ | $C_2H_5$ | ++++ | ++++ | ++++ |
| VII-4 | 4-Br | 7-Cl | $C_2H_5$ | $C_2H_5$ | ND | ND | ND |
| VIII-6 | 4-Br | H | $C_2H_5$ | $C_2H_5$ | ++++ | +++ | +++ |
| IX-2 | 4-$C_6H_5$ | H | $C_2H_5$ | $C_2H_5$ | ++++ | ++++ | ++++ |
| X-6 | 4-Cl | H | $C_2H_5$ | $C_2H_5$ | ++++ | ++++ | ++ |
| XI-2 | 4-$C_6H_5$ | 7-Cl | $C_2H_5$ | $C_2H_5$ | ND | ND | ND |
| XII-4 | 4-Cl | H | $C(CH_3)_3$ | H | ++++ | ++++ | ++++ |
| XIII-8 | 4-$CH_3$ | H | $C(CH_3)_3$ | H | ++++ | ++++ | ++++ |
| XIV-8 | 3,4-$Cl_2$ | H | $C(CH_3)_3$ | H | ++++ | ++++ | ++++ |
| XV-8 | 4-$OCH_3$ | H | $C(CH_3)_3$ | H | +++ | − | ++++ |

[a] % of cell viability remaining after a dose of 10 μM, ND: not determined.

Compounds of General Formula (I'):

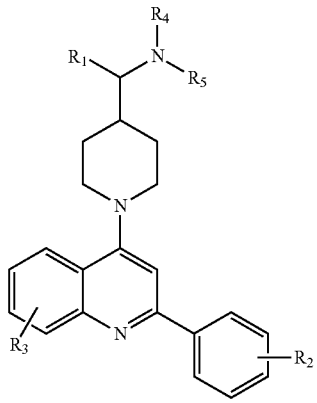

| ID | R1 | R2 | R3 | R4 | R5 | A375 | HCT-116 | MOLM-14 |
|---|---|---|---|---|---|---|---|---|
| XXVI-4 | H | H | 7-Cl | $C_2H_5$ | $C_2H_5$ | − | − | − |
| XXVII-2 | H | H | H | $C_2H_5$ | $C_2H_5$ | +++ | − | ++ |

Cell viability[a]

[a] % of cell viability remaining after a dose of 10 μM

Compounds of General Formula (I"):

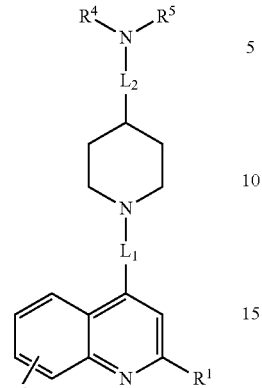

| ID | R1 | R2 | R3 | R4 | R5 | A375 | HCT-116 | MOLM-14 |
|---|---|---|---|---|---|---|---|---|
| XVI-4 | $CH_3$ | H | 7-Cl | $C_2H_5$ | $C_2H_5$ | ++++ | ++++ | ++++ |
| XVII-6 | H | H | 7-Cl | $C_2H_5$ | $C_2H_5$ | ++++ | ++++ | ++++ |
| XVIII-2 | =O | H | H | $C_2H_5$ | $C_2H_5$ | − | − | − |
| XIX-3 | $CH_3$ | H | H | $C_2H_5$ | $C_2H_5$ | ++++ | +++ | +++ |
| XX-5 | H | H | H | $C_2H_5$ | $C_2H_5$ | + | − | ++ |
| XXI-4 | $CH_3$ | H | H | $CH_2$—Ph | $(CH_2)_2$—Ph | − | − | − |
| XXII-4 | $CH_3$ | H | H | —$(CH_2)_5$— | | ND | ND | ND |
| XXIII-2 | $CH_3$ | H | H | $C(CH_3)_3$ | H | ++++ | +++ | ++++ |
| XXIV-3 | $CH_3$ | 2-Naphtyl | H | $C_2H_5$ | $C_2H_5$ | ++++ | ++++ | ++++ |
| XXV-6 | Gem $CH_3$ | H | H | $C_2H_5$ | $C_2H_5$ | ND | ND | ND |
| XLV-1 | CH3 | H | H | —$(CH_2)_2$—O—$(CH_2)_2$— | | ND | ND | ND |

[a] % of cell viability remaining after a dose of 10 μM

Compounds of General Formula (I″):

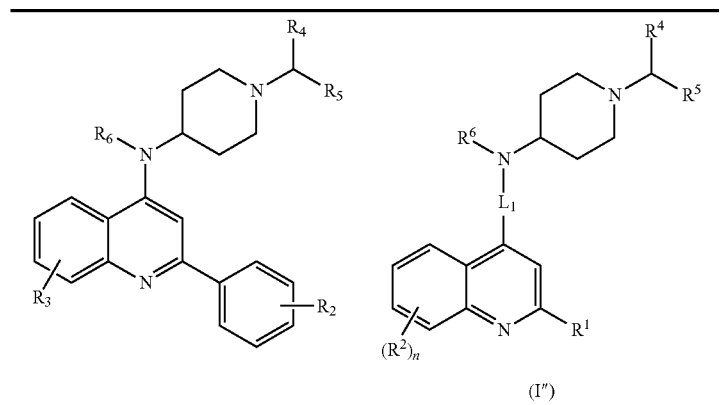

| ID | R2 | R3 | R4 | R5 | R6 | Cell viability[a] | | |
|---|---|---|---|---|---|---|---|---|
| | | | | | | A375 | HCT-116 | MOLM-14 |
| XXVIII-2 | H | 7-Cl | H | $C_6H_5$ | H | ++++ | ++++ | ++++ |
| XXIX-2 | H | 7-Cl | H | $C_6H_5$ | $CH_3$ | − | − | − |
| XXX-2 | H | 7-Cl | $CH_3$ | $C_6H_5$ | $CH_3$ | − | − | + |
| XXXI-2 | H | H | $CH_3$ | $C_6H_5$ | $CH_3$ | − | − | − |

[a] % of cell viability remaining after a dose of 10 μM

Compounds of General Formula (I″):

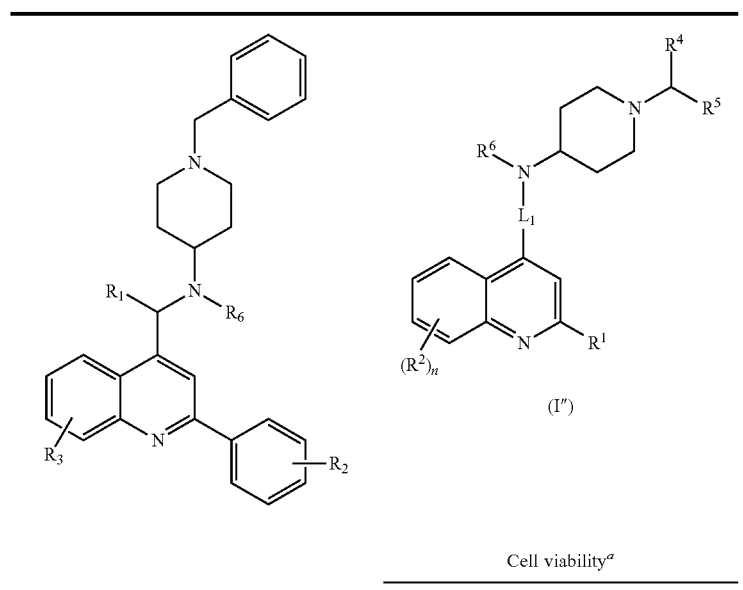

| ID | $R_1$ | $R_2$ | $R_3$ | $R_6$ | Cell viability[a] | | |
|---|---|---|---|---|---|---|---|
| | | | | | A375 | HCT-116 | MOLM-14 |
| XXXII-2 | =O | H | 7-Cl | H | − | − | ++ |
| XXXIII-2 | H | H | 7-Cl | H | ++ | +++ | ++ |
| XXXIV-2 | $CH_3$ | H | H | H | ++++ | +++ | ++ |
| XXXV-2 | $CH_3$ | H | 7-Cl | H | − | − | − |

[a] % of cell viability remaining after a dose of 10 μM

Compounds of General Formula (I'''):

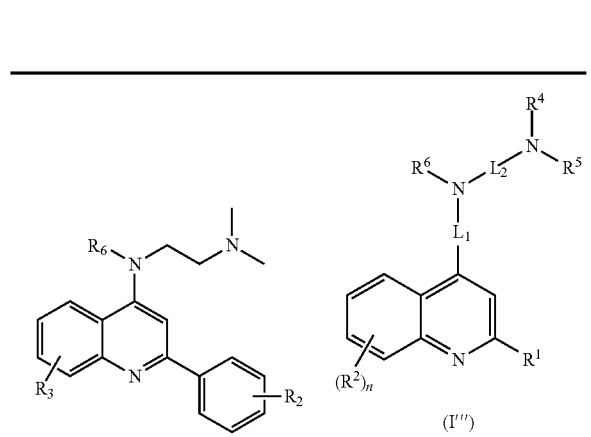

| ID | R₂ | R₃ | R₆ | A375 | HCT-116 | MOLM-14 |
|---|---|---|---|---|---|---|
| XXXVI-2 | 2-Naphtyl | H | H | ND | ND | ND |
| XXXVII-2 | 2-Naphtyl | H | CH₃ | ++ | − | ++ |

$^a$% of cell viability remaining after a dose of 10 μM

Compounds of General Formula (I'''):

| ID | R₁ | R₂ | R₃ | R₆ | A375 | HCT-116 | MOLM-14 |
|---|---|---|---|---|---|---|---|
| XXXVIII-2 | H | H | 7-Cl | CH₃ | ++++ | ++++ | ++ |

$^a$% of cell viability remaining after a dose of 10 μM

Compounds of General Formula (I'''):

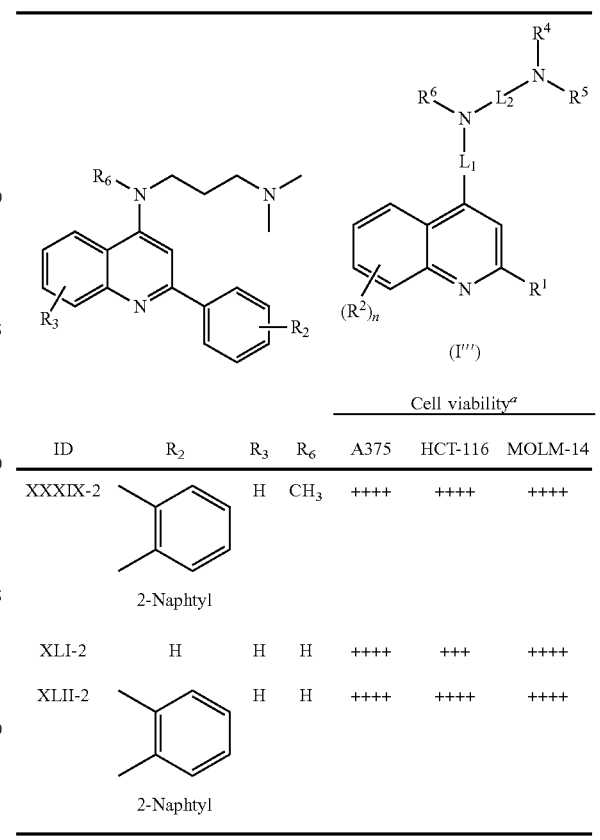

| ID | R₂ | R₃ | R₆ | A375 | HCT-116 | MOLM-14 |
|---|---|---|---|---|---|---|
| XXXIX-2 | 2-Naphtyl | H | CH₃ | ++++ | ++++ | ++++ |
| XLI-2 | H | H | H | ++++ | +++ | ++++ |
| XLII-2 | 2-Naphtyl | H | H | ++++ | ++++ | ++++ |

$^a$% of cell viability remaining after a dose of 10 μM

Compounds of General Formula (I'''):

| ID | R₁ | R₂ | R₃ | R₆ | A375 | HCT-116 | MOLM-14 |
|---|---|---|---|---|---|---|---|
| XLIII-2 | =O | H | 7-Cl | H | ++++ | − | + |
| XLIV-2 | H | H | 7-Cl | H | ++++ | ++++ | ++++ |

$^a$% of cell viability remaining after a dose of 10 μM

"−" indicates cell viability %>80
"+" indicates cell viability 60>%<80
"++" indicates cell viability 40>%<60
"+++" indicates cell viability 20>%<40
"++++" indicates cell viability %<20
ND: Not Determined

Example 53

EC$_{50}$ Determination of Compounds in Cancer Cell Lines A-375, HCT-116, MOLM-14, HepG2, MV4-11, KG-1, SK-MEL-28, SK-MEL-5, Colo205 and HT-29

The human melanoma cell line A375, colorectal carcinoma cell line HCT-116, hepatocellular carcinoma cell line HepG2 were cultured in Dulbecco's modified Eagle's medium supplemented with 10% fetal bovine serum and 1% Penicillin-Streptomycin. The human melanoma cell lines SK-MEL-28 and SK-MEL-5 were cultured in Minimum Essential Medium. The colorectal carcinoma cell lines HT-29 and Colo205 were respectively cultured in Mc Coy's and RPMI media. The human leukemia cell lines MV4-11 and KG-1 were cultured in Iscove's Modified Dulbecco's Media. The human leukemia cell line MOLM-14 was cultured in Minimum Essential Medium Alpha Medium supplemented with 10% Fetal Bovine Serum and 1% Penicillin-Streptomycin All culture media were supplemented with 10% fetal bovine serum and 1% Penicillin-Streptomycin except for MV4-11 cell line 20% fetal bovine serum and 1% Penicillin-Streptomycin. All the cell lines were maintained at 37° C. with 5% C02.

Briefly, adherent cells, A375, HCT-116, HepG2, SK-MEL-28, SK-MEL-5, HT-29 and Colo205 cells were respectively plated at 800, 5,000, 7,000, 2,500, 3,000-5,000, 5,000 or 5,000 cells per well onto 96-well plates in 90 µL of media per well and were allowed to grow overnight before the assay. For MV4-11 and KG-1 cells that grow in suspension, 40,000-60,000 cells were plated onto 96-well plates immediately before the assay. MOLM-14 cell line, that grow in suspension, 30,000 cells were plated onto 96-well plates immediately before the assay.

The cell growth measure was the same as described in example 51.

The experimental data are analyzed using a computer program, Graphpad Prism (GraphPad Software, Inc. La Jolla, Calif.) and EC$_{50}$ values were determined as the dose of compound required to reduce absorbance values to 50% of the signal obtained for vehicle treated cell cultures and were a mean of at least two independent experiments except for EC$_{50}$ values with (*) where n>2.

TABLE 2

EC$_{50}$ (µM) determination of phenylquinoline derivatives in cancer cell lines A-375, HCT-116, MOLM-14 and HepG2.

| ID | A-375 | HCT-116 | MOLM-14 | HepG2 |
|---|---|---|---|---|
| XIX-3 | 9 | 12 | 11 | 22 |
| XII-4 | 5 | ND | 3 | ND |
| XIV-8 | 6 | 5 | 5 | ND |
| XXIV-3 | 3 | 4 | 4 | 11 |
| XIII-8 | 6 | 8 | 3 | 17 |
| XXVIII-2 | 9 | 12 | 10 | 26 |
| XXXIII-2 | 9 | 13 | 9 | 16 |
| XL-2 | 3 | 5 | 3 | 17 |
| XLII-2 | 3 | 11 | 4 | 19 |
| XLI-1 | 2 | 4 | 3 | 10 |
| II-3 | 3 | 4 | 5 | 8 |
| XLIV-1 | 4 | 6 | 6 | 10 |
| XVI-4 | 4 | 6 | 6 | 13 |
| XVII-6 | 3 | 4 | 5 | 8 |
| VI-5 | 4 | 6 | 5 | 11 |
| IX-2 | 3 | 4 | 4 | 13 |
| XXIII-2 | 8 | 11 | 6 | 18 |
| XV-8 | 10 | 17 | 3 | 27 |

TABLE 3

EC$_{50}$ (µM) determination of phenylquinoline derivatives in cancer cell lines MV4-11, KG-1, SK-MEL-28, SK-MEL-5, Colo205 and HT-29.

| | EC$_{50}$ (µM) | | | | | |
|---|---|---|---|---|---|---|
| ID | MV4-11 | KG-1 | SK-MEL-28 | SK-MEL-5 | Colo205 | HT-29 |
| XIX-3 | 9 | 14 | 6 | 6 | ND | 18 |
| XII-4 | 2 | 4 | 3 | 5 | ND | ND |
| XIV-8 | 4 | 4 | 4 | 6 | ND | ND |
| XXIV-3 | 3 | 4 | 3 | 3 | 5 | 7 |
| XIII-8 | 2 | 9 | 5 | 7 | 8* | 16* |
| XXVIII-2 | 5 | 10 | 7 | 9 | 9* | 13* |
| XXXIII-2 | 5 | 8 | 6 | 6 | 9 | 14 |

Example 54

Cell Growth Inhibition Assay (EC$_{50}$) from Patient Derived Acute Myeloid Leukemia (AML) Cell Lines The patient derived acute myeloid leukemia (AML) cells were obtained after written informed consent under the Institut Paoli Calmette (IPC) institutional review board approval and under the strict compliance of the Helsinki declaration on medical research involving human subjects.

The patient derived acute myeloid leukemia (AML) cell lines were cultured in RPMI-1640 Medium supplemented with 10% v/v Fetal Bovine Serum (FBS), 1% Penicillin-Streptomycin and maintained at 37° C. with 5% CO$_2$. 10,000 cells were plated onto 96-well plates immediately before the assay.

Each compound was added at different concentrations (combinations of six concentrations) to each well, and cell cultures were incubated for 48 h. Vehicle (H$_2$O) was used as a control, and all compounds were tested in a constant percentage of vehicle. Cell outgrowth was measured using the CellTiter-Glo luminescent cell viability assay as described by the manufacturer (Promega, Ref G7571 Madison, Wis., USA) using a Centro (Berthold, France) plate reader.

In each experiment, each point represents the average of triplicates in cell culture.

The experimental data are analyzed using a computer program, Graphpad Prism (GraphPad Software, Inc. La Jolla, Calif.) and EC$_{50}$ values were determined as the dose of compound required to reduce absorbance values to 50% of the signal obtained for vehicle treated cell cultures.

TABLE 4

Cell growth inhibition assay (EC$_{50}$, μM) from patient derived acute myeloid leukemia (AML) cell lines

| Patients derived cells | Subtype[a] | Able to xenograft | Compounds, EC$_{50}$ (μM)[b] | | | | | |
|---|---|---|---|---|---|---|---|---|
| | | | AraC | XIX-3 | XII-4 | XIV-8 | XXIV-3 | XIII-8 |
| Patient 3 | Tri8 | + | 44 | 8 | 5 | 8 | 2 | 15 |
| Patient 8 | FLT3− | + | 51 | 21 | 21 | 25 | 10 | 27 |
| Patient 9 | FLT3+ | − | 21 | 18 | >40 | 40 | 17 | 22 |
| Patient 10 | Inv 3 | + | 36 | 28 | 25 | 20 | 13 | 35 |
| Patient 12 | 5 & 7 | − | >40 | 16 | >40 | >40 | 11 | 21 |
| Patient 13 | MLL | − | 3 | 16 | 27 | >40 | 8 | 25 |
| Patient 16 | Inv 3 | + | 11 | 22 | 19 | 17 | 6 | 24 |
| PBMC Healthy voluntary donor 1 | | | 13 | ND | 43 | 31 | 8 | 42 |
| PBMC Healthy voluntary donor 2 | | | ND | 21 | 15 | 14 | 7 | 16 |

[a]Vardiman, J. W. et al. Blood 2009 (114) 937-951
[b]each point represents the average of triplicates in cell culture
ND: Not Determined Example 55

NCI-60 Results as Cell Growth Percent Observed at 10 μM with Compound XIX-3

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO$_2$, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drug is solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO$_2$, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels.

Percentage growth inhibition is calculated as:

$$[(Ti-Tz)/(C-Tz)] \times 100 \text{ for concentrations for which } Ti >/= Tz \quad (1)$$

$$[(Ti-Tz)/Tz] \times 100 \text{ for concentrations for which } Ti < Tz \quad (2)$$

Three dose response parameters are calculated for each experimental agent.

Growth inhibition of 50% (GI$_{50}$) is calculated from $$[(Ti-Tz)/(C-Tz)] \times 100 = 50 \quad (3)$$

which is the drug concentration resulting in a 50% reduction in the net protein increase (as measured by SRB staining) in control cells during the drug incubation.

The drug concentration resulting in total growth inhibition (TGI) is calculated from $$Ti = Tz \quad (4)$$

The LC$_{50}$ (concentration of drug resulting in a 50% reduction in the measured protein at the end of the drug treatment as compared to that at the beginning) indicating a net loss of cells following treatment is calculated from $$[(Ti-Tz)/Tz] \times 100 = -50 \quad (5)$$

Values are calculated for each of these three parameters if the level of activity is reached; however, if the effect is not reached or is exceeded, the value for that parameter is expressed as greater or less than the maximum or minimum concentration tested.

Reference

Shoemaker, R. H. Nature Reviews. Cancer 2006 (6) 813-823.

TABLE 5

Results obtained as cell growth % observed at 10 μM on NCI-60 cancer cell lines for compound XIX-3.

| Cancers | Cell lines | Growth percent at 10 μM |
|---|---|---|
| Leukemia | CCRF-CEM | ++ |
| | HL-60 | ++ |
| | K-562 | x |
| | MOLT-4 | ++++ |
| | RPMI-8226 | ++++ |
| | SR | x |
| Non-Small Cell Lung | A549/ATCC | + |
| | HOP-62 | − |
| | HOP-92 | ++ |
| | NCI-H226 | − |
| | NCI-H23 | − |
| | NCI-H322M | + |
| | NCI-H460 | + |
| | NCI-H522 | +++ |
| Colon | COLO205 | xxx |
| | HCC-2998 | ++ |
| | HCT-116 | ++ |
| | HCT-15 | ++++ |
| | HT29 | ++++ |
| | KM12 | ++ |
| | SW-620 | ++ |
| CNS | SF-268 | + |
| | SF-295 | − |
| | SF-539 | ++ |
| | SNB-19 | − |
| | SNB-75 | +++ |
| | U251 | +++ |
| Melanoma | LOX IMVI | ++ |
| | MALME-3M | xx |
| | M14 | xxx |
| | MDA-MB-435 | ++++ |
| | SK-MEL-2 | ++ |
| | SK-MEL-28 | xxx |
| | SK-MEL-5 | xxxxx |
| | UACC-257 | xxx |
| | UACC-62 | xxxx |
| Ovarian | IGROVI | ++ |
| | OVCAR-3 | + |
| | OVCAR-4 | ++ |
| | OVCAR-5 | + |
| | OVCAR-8 | + |
| | NCI/ADR-RES | + |
| | SK-OV3 | − |
| Renal | 786-0 | ++ |
| | A498 | ++ |
| | ACHN | + |
| | CAKI-1 | + |
| | SN12C | + |
| | TK-10 | − |
| | UO-31 | ++ |
| Prostate | PC-3 | + |
| | DU-145 | − |

TABLE 5-continued

Results obtained as cell growth % observed at 10 μM on NCI-60 cancer cell lines for compound XIX-3.

| Cancers | Cell lines | Growth percent at 10 μM |
|---|---|---|
| Breast | MCF7 | ++ |
| | MDA-MB-231/ATCC | ++ |
| | HS 578T | + |
| | BT-549 | + |
| | T-47D | ++ |
| | MDA-MB-468 | +++ |

"−" indicates cell growth % > 80
"+" indicates cell growth 60 > % < 80
"++" indicates cell growth 40 > % < 60
"+++" indicates cell growth 20 > % < 40
"++++" indicates cell growth % < 20
ND: Not Determined
"x" indicates cell growth 0 > % > −20
"xx" indicates cell growth −20 > % < −40
"xxx" indicates cell growth −40 > % < −60
"xxxx" indicates cell growth −60 > % < −80
"xxxxx" indicates cell growth % < −80
ND: Not Determined Example 56

NCI-60 Results as $GI_{50}$, TGI and $LC_{50}$ Obtained with Compound XIX-3

The general assay procedure is the same as described in example 55 for compound XIX-3.

TABLE 6

$GI_{50}$, TGI and $LC_{50}$ obtained on NCI-60 cancer cell lines for compound XIX-3.

| Cancers | Cell lines | $GI_{50}$ (μM) | TGI (μM) | $LC_{50}$ (μM) |
|---|---|---|---|---|
| Leukemia | CCRF-CEM | 9 | 25 | 62 |
| | HL-60 | 17 | 33 | 66 |
| | K-562 | 2 | 5 | 15 |
| | MOLT-4 | 4 | 15 | 49 |
| | RPMI-8226 | 2 | 5 | 26 |
| | SR | 3 | 7 | 49 |
| Non-Small Cell Lung | A549/ATCC | 15 | 31 | 63 |
| | HOP-62 | 9 | 22 | 52 |
| | HOP-92 | 3 | 17 | 47 |
| | NCI-H226 | 19 | 38 | 74 |
| | NCI-H23 | >100 | >100 | >100 |
| | NCI-H322M | 11 | 24 | 52 |
| | NCI-H460 | 7 | 22 | 54 |
| | NCI-H522 | 15 | 32 | 66 |
| Colon | COLO205 | 2 | 4 | 7 |
| | HCC-2998 | 4 | 13 | 44 |
| | HCT-116 | 5 | 19 | 51 |
| | HCT-15 | 3 | 14 | 47 |
| | HT29 | 2 | 7 | 32 |
| | KM12 | 10 | 22 | 50 |
| | SW-620 | 4 | 17 | 45 |
| CNS | SF-268 | 10 | 24 | 55 |
| | SF-295 | 4 | 15 | 48 |
| | SF-539 | 11 | 23 | 50 |
| | SNB-19 | 13 | 28 | 59 |
| | SNB-75 | 12 | 26 | 55 |
| | U251 | 6 | 20 | 49 |
| Melanoma | LOX IMVI | 4 | 15 | 44 |
| | MALME-3M | 2 | 4 | 7 |
| | M14 | 2 | 4 | 8 |
| | MDA-MB-435 | 2 | 5 | 14 |
| | SK-MEL-2 | 3 | 7 | 27 |
| | SK-MEL-28 | 2 | 3 | 6 |
| | SK-MEL-5 | 2 | 3 | 6 |
| | UACC-257 | 2 | 4 | 8 |
| | UACC-62 | ND | ND | ND |

TABLE 6-continued

GI$_{50}$, TGI and LC$_{50}$ obtained on NCI-60 cancer cell lines for compound XIX-3.

| Cancers | Cell lines | GI$_{50}$ (μM) | TGI (μM) | LC$_{50}$ (μM) |
|---|---|---|---|---|
| Ovarian | IGROVI | 5 | 21 | 63 |
| | OVCAR-3 | 14 | 28 | 55 |
| | OVCAR-4 | 11 | 24 | 52 |
| | OVCAR-5 | 13 | 28 | 58 |
| | OVCAR-8 | 14 | 30 | 62 |
| | NCI/ADR-RES | 12 | 26 | 56 |
| | SK-OV3 | 17 | 31 | 59 |
| Renal | 786-0 | 8 | 23 | 54 |
| | A498 | 5 | 20 | 54 |
| | ACHN | 11 | 23 | 50 |
| | CAKI-1 | 13 | 28 | 58 |
| | SN12C | 12 | 26 | 26 |
| | TK-10 | 13 | 26 | 26 |
| | UO-31 | 8 | 22 | 22 |
| | RXF393 | 4 | 17 | 17 |
| Prostate | PC-3 | ND | ND | ND |
| | DU-145 | 14 | 28 | 54 |
| Breast | MCF7 | 8 | 22 | 56 |
| | MDA-MB-231/ATCC | 3 | 14 | 47 |
| | HS 578T | 11 | 35 | 100 |
| | BT-549 | 13 | 27 | 56 |
| | T-47D | 5 | 19 | 52 |
| | MDA-MB-468 | 3 | 10 | 38 |

ND: Not Determined

Examples 57

Activity Profile of Compound XIX-3 Against Human Cancer Cell Lines

Cell Lines BxPC-3, Capan-1, Capan-2, MIAPaCa-2, Panc-1 Cells

MiaPaCa-2, Panc-1 cells were grown in Dulbecco's modified eagle's medium (DMEM) (Gibco) supplemented with 10% fetal bovine serum (FBS), while BxPC-3, Capan-1, Capan-2 cells were grown in Roswell Park Memorial Institute 1640 (RPMI 1640) (Gibco) supplemented with 10% FBS. Gemcitabine (Gemzar) was purchased from Lilly France S.A.S (Suresnes, France). (3-(4,5-dimethylthiazol-2-yl)-2,5diphenyltetrazolium bromide, MTT) was purchased from Sigma-Aldrich.

BxPC-3, MiaPaCa-2, Panc-1 cells were seeded into a 96-well plate at 10,000 10,000 15,000 cells per well respectively, while Capan-1 and Capan-2 cells at 20,000 cells per well and allowed to adhere overnight. Then the culture medium was removed and replaced with fresh media alone as control or containing various concentrations of different compounds. In dose-dependent assay, the cells were treated with compound XIX-3 at the concentration varying from 0.1 μM to 100 μM while the cells being cultured by fresh media alone were used as control. After 48 h treatment, the number of remained viable cells was determined by (3-(4,5-dimethylthiazol-2-yl)-2,5diphenyltetrazolium bromide, MTT) colorimetric assay (see Sigma Aldrich protocol and Riss T. L. et al. Cell Viability Assays in Assay Guidance Manual 2013 ppl.). All experiments were done in duplicate and repeated two independent times.

Cell Lines LNCaP, SkBr3, HepG2, U937, NB4, KG-1, Kasumi, SKM-1, HL60 and MOLM-14

The human breast cancer cell line SkBr3 and the human metastatic prostate carcinoma cell line LnCAP were cultured in Dulbecco's modified Eagle's medium (DMEM) supplemented with 10% fetal bovine serum (FBS) and 0.1% sodium pyruvate. The human myelocytic cell line U937 and NB4 were maintained in RPMI medium 1640 1× (Gibco 21875-034) supplemented with 10 % Fetal Bovine Serum (FBS, Eurobio S39130-0808) Kasumi and SKM-1 were maintained in RPMI medium 1640 1× (Gibco 21875-034) supplemented with 20 % Fetal Bovine Serum (FBS, Eurobio S39130-0808), HL60 was maintained in Iscove's modified Dulbecco's medium 1× (IMDM, Gibco 21890) supplemented with 20% Fetal Bovine Serum (FBS, Eurobio S39130-0808), cell line was maintained in MEM alpha medium (Gibco 22561-021) supplemented with 10% FBS at 37° C. with 5% $CO_2$. Cell outgrowth was measured using the CellTiter-Glo luminescent cell viability assay as described by the manufacturer (Promega, Ref G7571 Madison, Wis., USA) using a FLUOstar optima luminometer (BMG Labtech, Ortenberg, Germany).

Briefly, for adherent cells, $10^4$ cells were plated onto 96-well plates (white with clear bottom (3610, Corning Costar) in 100 μL of media per well and were allowed to grow overnight before the assay. For cells growing in suspension, $10^4$ cells were plated onto 96-well plates immediately before the assay. Compounds were added at different concentrations (varying from 0.1 μM to 100 μM) to each well, and cell cultures were incubated for 48 h. Vehicle (DMSO) was used as a control, and all compounds were tested in a constant percentage of DMSO (1%). After addition of 50 μL of CellTiter GLO, luminescence was measured using a Centro luminometer (Berthold). $EC_{50}$ values were determined as the dose of compound required to reduce luminescent values to 50% of the signal obtained for untreated cell cultures. All experiments were done in duplicate and repeated two independent times.

U87-MG Cell Line

The human glioblastoma cell line U87-MG was cultured in Minimum Essential Medium (Life Invitrogen, 31095029) supplemented with 10% fetal bovine serum (GIBCO, 10500-056) and 1 % penicillin-streptomycin (GIBCO, 15140-122). Flasks and plated used for the cell culture were coated with 25 μg/mL poly-D-lysine (Sigma, P7280).

Cell outgrowth was measured using a tetrazolium compound (3-[4,5-dimethylthiazol-2-yl]-5-[3-carboxymethoxyphenyl]-2-[4-sulfophenyl]-2H tetrazolium, inner salt [MTS]) from the CellTiter 96® Aqu$_{eous}$ One Solution Cell Proliferation Assay (Promega, Ref G3580) and according to the manufacturer procedure.

5000 cells were plated onto 96-well plates in 100 μL of media per well and were allowed to grow overnight before the assay. Compounds were added at different concentrations to each well, and cell cultures were incubated for 72 h. Control compound was the diluent used for compound resuspension ($H_2O$). After addition of 20 μL of CellTiter 96® Aqu$_{eous}$ One Solution, absorbance at 492 nm was measured using a microplate reader Sunrise (Tecan). $EC_{50}$ values were determined as the dose of compound required to reduce luminescent values to 50% of the signal obtained for untreated cell cultures. In each experiment, each datum point represents the average of three replicates in cell culture. The experimental data are analyzed using a computer program, Graphpad Prism (GraphPad Software, Inc. La Jolla, Calif.).

TABLE 7

EC$_{50}$ (μM) determination of compound XIX-3 in cancer cell lines LNCaP, SkBr3, HepG2, HT29, B16F10, U87-MG

| | Cell Line | | | | | |
|---|---|---|---|---|---|---|
| | LNCaP (μM)$^{a,c}$ | SkBr3 (μM)$^{a,c}$ | HepG2 (μM)$^{a,c}$ | HT29 (μM)$^{a,c}$ | B16F10 (μM)$^{a,c}$ | U87-MG (μM)$^{b,c,e}$ |
| | Cancer type | | | | | |
| | Prostate | Breast | Liver | Colon | Melanoma | Glioma |
| XIX-3 | 25 | 20 | 22$^f$ | 18$^f$ | 10 | 26 |
| Gemcitabine | 0.04 | 0.2 | 0.02 | 0.2 | ND | ND |
| HCQ | 25 | 20 | 20 | 20 | 20 | 55 |
| Doxorubicine | ND | ND | ND | ND | 0.2 | ND |

$^a$EC$_{50}$ Cell viability was evaluated with Cell Titer-Glo luminescent Cell Viability assay (Promega, Ref G7571),
$^b$EC5$_{50}$ Cell viability was evaluated with Cell Titer 96 Aq$_{ueous}$ One Solution Cell Proliferation Assay (Promega, Ref G3581),
$^c$Cell viability was evaluated during 72 h,
$^d$Cell viability was evaluated during 48 h
$^e$mean of seven independend triplicate assays,
ND: Not Determined,
$^f$data from example 53.

TABLE 8

EC$_{50}$ (μM) determination of compound XIX-3 in cancer cell lines BxPC-3, Capan-1, Capan-2, MIA-PaCa-2, Panc-1

| | Cell Line | | | | |
|---|---|---|---|---|---|
| | BxPC-3 (μM)$^{a,d}$ | Capan-1 (μM)$^{a,d}$ | Capan-2 (μM)$^{a,d}$ | MIA PaCa-2 (μM)$^{a,d}$ | Panc-1 (μM)$^{a,d}$ |
| | Cancer type | | | | |
| | Pancreas | Pancreas | Pancreas | Pancreas | Pancreas |
| XIX-3 | 33 | 27 | 32 | 34 | 34 |
| Gemcitabine | 0.02 | ND | ND | ND | ND |
| HCQ | 53 | 41 | 47 | 47 | 57 |

$^a$EC$_{50}$ Cell viability was evaluated with Cell Titer-Glo luminescent Cell Viability assay (Promega, Ref G7571),
$^b$EC5$_{50}$ Cell viability was evaluated with Cell Titer 96 Aq$_{ueous}$ One Solution Cell Proliferation Assay (Promega, Ref G3581),
$^c$Cell viability was evaluated during 72 h,
$^d$Cell viability was evaluated during 48 h
ND: Not Determined.

TABLE 9

EC$_{50}$ (μM) determination of compound XIX-3 in cancer cell lines MOLM-14, U937, KG-1, Kasumi-1, HL60, NB4, SKM-1

| | Cell Line | | | | | | |
|---|---|---|---|---|---|---|---|
| | MOLM-14 (μM)$^{a,c}$ | U937 (μM)$^{a,c}$ | KG-1 (μM)$^{a,c}$ | Kasumi-1 (μM)$^{a,c}$ | HL60 (μM)$^{a,c}$ | NB4 (μM)$^{a,c}$ | SKM-1 (μM)$^{a,c}$ |
| | Cancer type | | | | | | |
| | Leukemia | Leukemia | Leukemia | Leukemia | Leukemia | Leukemia | Leukemia |
| XIX-3 | 11$^f$ | 35 | 14$^f$ | 30 | 40 | 37 | 30 |
| HCQ | 50 | 60 | 60 | 20 | 40 | 57 | 70 |
| Cytarabine | 3 | 0.03 | 0.15 | 0.15 | 2 | 0.02 | 2 |

$^a$EC$_{50}$ Cell viability was evaluated with Cell Titer-Glo luminescent Cell Viability assay (Promega, Ref G7571),
$^b$EC5$_{50}$ Cell viability was evaluated with Cell Titer 96 Aq$_{ueous}$ One Solution Cell Proliferation Assay (Promega, Ref G3581),
$^c$Cell viability was evaluated during 72 h,
$^d$Cell viability was evaluated during 48 h,
ND: Not Determined,
$^f$data from example 53

Examples 58

XIX-3 Preliminary Results Demonstrated a Synergy Effect with Standard Chemotherapy Agents in HT29 Cells (Human Colon Adenocarcinoma Cell Line)—See FIG. 1

Anticancer drugs were tested around their EC$_{50}$ in HT92 cell line, The general assay procedure is the same as described in example 53 for compound XIX-3.

Analysis of Combination Data for Synergistic Effect

Loewe additivity model: The experimental data are analyzed by using CalcuSyn (Biosoft, Stapleford, UK), a computer program based on the method of Chou and Talalay. Briefly, the dose-effect curves for each drug or drug combination were converted to median-effect plots with CalcuSyn. Then, a combination index (CI) value for each experimental combination was calculated on the basis of the following equation:

$$CI = \sum_{i=1}^{n} \frac{di}{Di} \qquad (6)$$

Where for n=2 (combination of 2 compounds):

D1 and D2 are the doses of drug 1 and drug 2 that have x effect when each drug is used alone d1 and d2 are the doses of drug 1 and drug 2 that have the same x effect when they are used in combination.

TABLE 10

Description of CI values in drug combination studies

| Range of CI | Description |
| --- | --- |
| 0.10-0.30 | strong synergism |
| 0.30-0.70 | synergism |
| 0.70-0.85 | moderated synergism |
| 0.85-0.90 | slight synergism |
| 0.90-1.10 | nearly additive |
| 1.10-1.20 | slight antagonism |
| 1.20-1.40 | moderated antagonism |

Chou, T. C. Cancer Research 2010 (70) 440-446.

TABLE 11

Drugs associated to compound XIX-3 for combination study in HT-29 cell line (example 58)

| Entry | Standard chemotherapy agents | Class of inhibitor |
| --- | --- | --- |
| 1 | HCQ | Lysosome disrupter |
| 2 | Tamoxifen | Estrogen receptors antagonist |
| 3 | Bortezomib | Proteasome |
| 4 | Metformin | Metabolism |
| 5 | S78454 | HDAC |
| 6 | SAHA | HDAC 1, 3 |
| 7 | MK-2206 | AKT 1, 2 and 3 |
| 8 | CI-1040 | MEK 1, 2 |
| 9 | BX-912 | PDK 1 |
| 10 | BKM-120 | p110 |
| 11 | Lapatinib | Tyrosine kinase inhibitor (HER2/neu EGFR pathway) |
| 12 | Saracatinib | Src tyosine kinase inhibitor (C-Yes, Fyn, Lyn, Blk, Fgr, Lck) |
| 13 | Sunitinib | Tyrosine kinase inhibitor (VEGFR, PDGFR, Kit, Flt3) |
| 14 | Doxorubicin | Genotoxic |
| 15 | Daunorubicin | Genotoxic |
| 16 | Gemcitabine | Antimetabolite |

Examples 59

Figure 2:
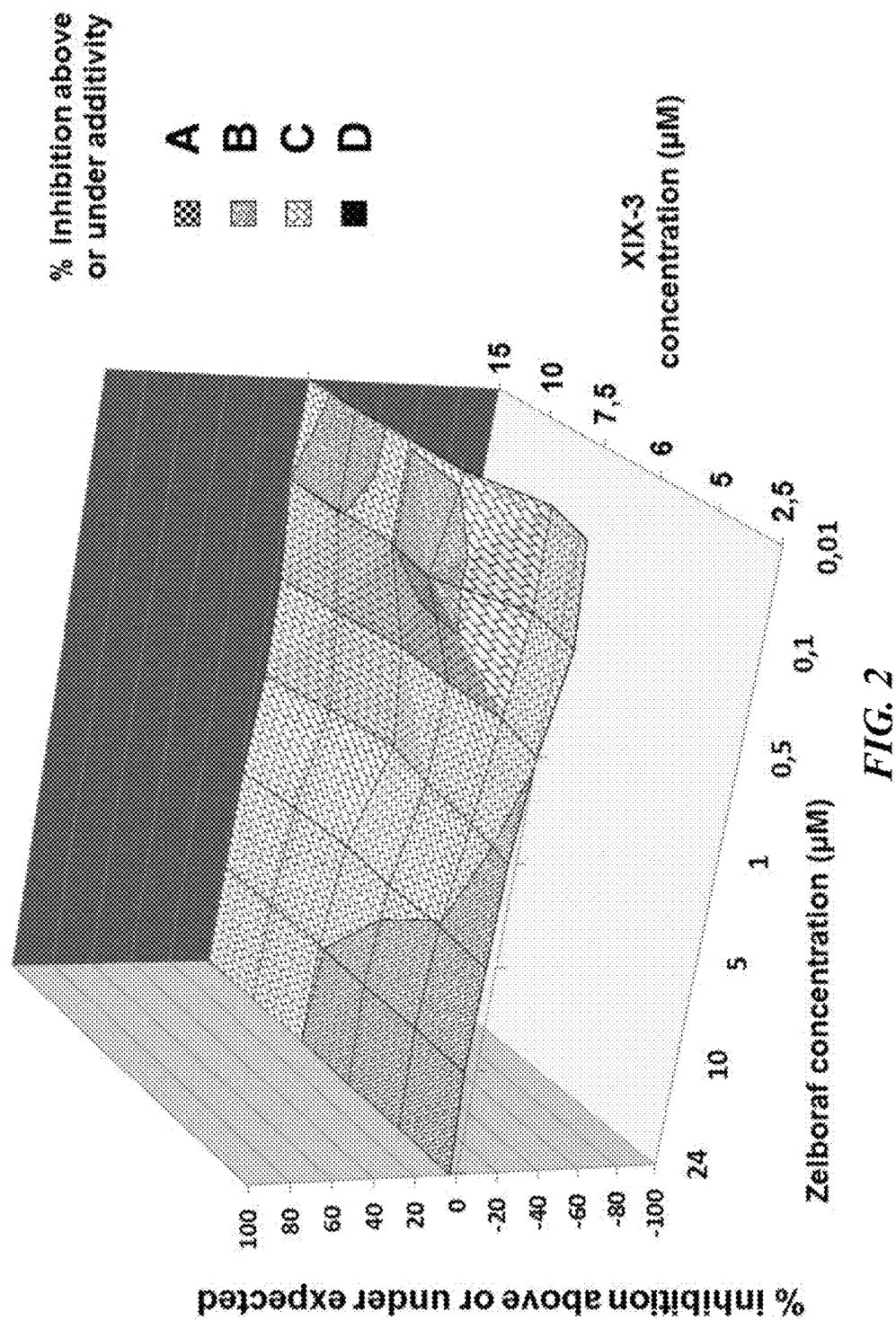
FIG. 2 shows a Bliss independence model analysis of the combination effect of compound XIX-3 associated with Zelboraf on the cell viability of SK-MEL-28 cell line (Human skin malignant melanoma cell line). The Bliss independence model analysis of the combination of compound XIX-3 with Zelboraf shows a global additive effect. SK-MEL-28 cell line expresses the mutated B-Raf mutation V600E and wild-type N-Ras.

Synergistic Growth Inhibition Study by the Combination of XIX-3 and Zelboraf in Melanoma SK-MEL-28 Cell Line—See FIG. 2

The human melanoma cell line SK-MEL-28 was cultured in Minimum Essential Medium (MEM) supplemented with 10% Fetal Bovine Serum and 1% Penicillin-Streptomycin and maintained at 37° C. with 5% $CO_2$.

SK-MEL-28 cells were plated at 2,500 cells per well onto 96-well plates in 90 µL of media per well and were allowed to grow overnight before the assay. XIX-3 and Zelboraf, a compound used for treatment for BRAF V600E mutation-positive metastatic melanoma, were added at different concentrations (combinations of five concentrations of XIX-3 and six concentrations of Zelboraf) to each well, and cell cultures were incubated for 72 h. Vehicle ($H_2O$) was used as a control, and all compounds were tested in a constant percentage of vehicle. Cell outgrowth was measured using a CellTiter 95® Aqu$_{eous}$ One Solution Cell Proliferation Assay (Promega) and a TECAN Sunrise plate reader.

In each experiment, each point represents the average of triplicates in cell culture. The effects of drug-drug combinations are evaluated in the Bliss independence model (Prichard M. N. and Shipman C. Jr. Antivir. Res. 1990 (14) 181-205; Prichard, M. L. et al. Antimicrob Agents Chemother 1993 (37) 540-545). The theoretical additive effect is calculated from the dose-response curves of individual compounds by the equation:

$$Z=X+Y(1-X) \qquad (7)$$

Where:

Z represents the total inhibition produced by the combination of drugs X and Y.

X and Y represent the inhibition produced by drugs X and Y alone, respectively.

The theoretical additive surface is subtracted from the actual experimental surface, resulting in a horizontal surface that equals the zero plane when the combination is additive. A surface that lies higher than +20% above the zero plane indicates a synergistic effect of the combination, a surface lower than −20% below the zero plane indicates antagonism effect and between −20% to +20% indicates additive effect.

Examples 60

Figure 3:
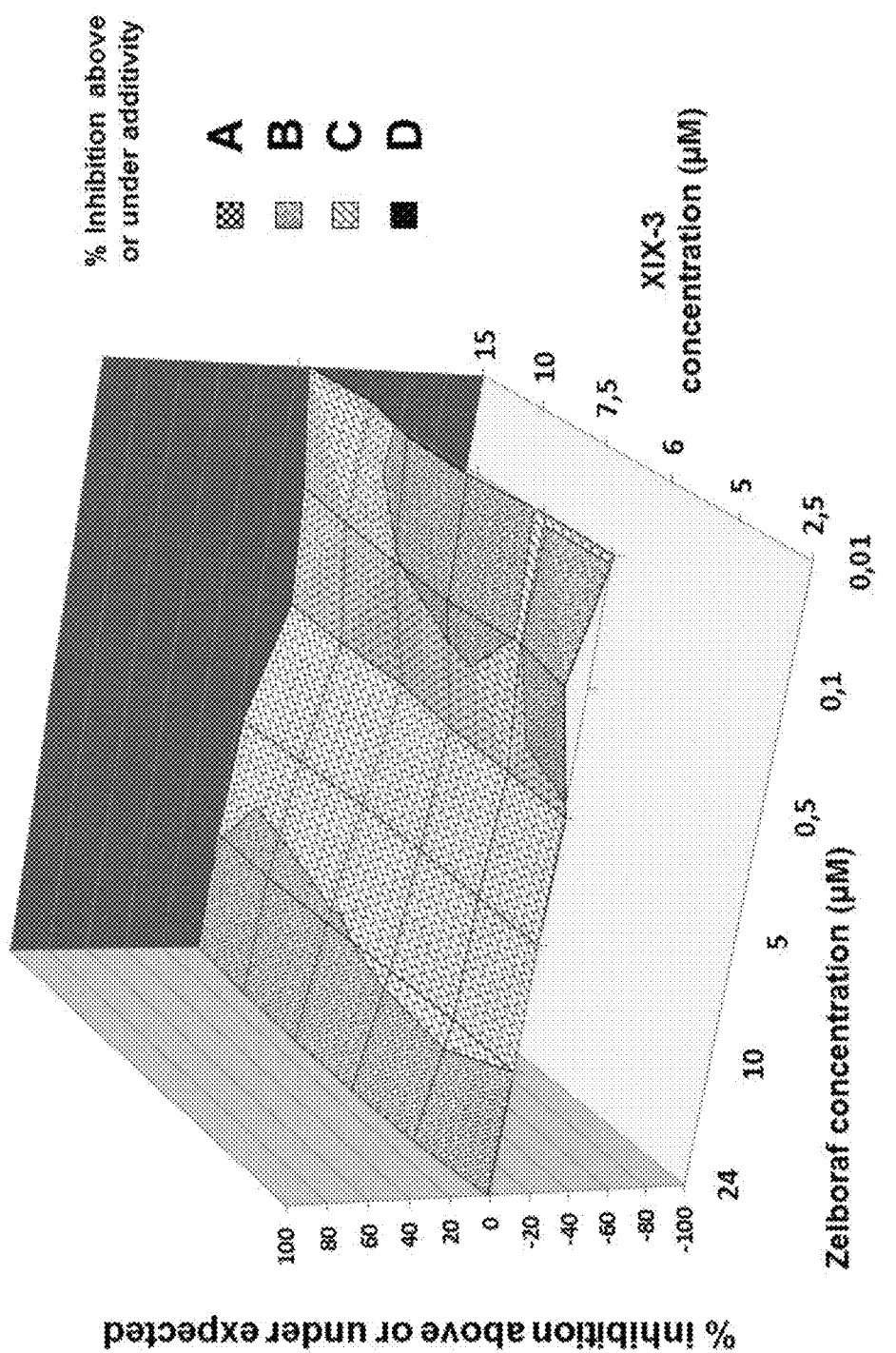
FIG. 3 shows a Bliss independence model analysis of the combination effect of compound XIX-3 associated with Zelboraf on the cell viability of A375 cell line (Human skin malignant melanoma cell line). The Bliss independence model analysis of the combination of compound XIX-3 with Zelboraf shows a global additive effect. A375 cell line expresses the mutated B-Raf mutation 600E.

Synergistic Growth Inhibition Study by the Combination of XIX-3 and Zelboraf in Melanoma A-375 Cell Line—See FIG. 3

The human melanoma cell lines A375 cultured in Dulbecco's modified Eagle's medium supplemented with 10% Fetal Bovine Serum and 1% Penicillin-Streptomycin and maintained at 37° C. with 5% $CO_2$.

A375 cells were plated at 800 cells per well onto 96-well plates in 90 µL of media per well and were allowed to grow overnight before the assay. XIX-3 and Zelboraf, a compound used for treatment for BRAF V600E mutation-positive metastatic melanoma, were added at different concentrations (combinations of five concentrations of XIX-3 and six concentrations of Zelboraf) to each well, and cell cultures were incubated for 72 h. Vehicle ($H_2O$) was used as a control, and all compounds were tested in a constant percentage of vehicle. Cell outgrowth was measured using a CellTiter 95® Aqu$_{eous}$ One Solution Cell Proliferation Assay (Promega) and a TECAN Sunrise plate reader. In each experiment, each point represents the average of triplicates in cell culture. The effects of drug-drug combinations are evaluated in the Bliss independence model (Prichard M. N. and Shipman C. Jr. Antivir. Res. 1990 (14) 181-205; Prichard, M. L. et al. Antimicrob Agents Chemother 1993 (37) 540-545). The theoretical additive effect is calculated from the dose-response curves of individual compounds by the equation:

$$Z=X+Y(1-X) \qquad (7)$$

Where:
Z represents the total inhibition produced by the combination of drugs X and Y.
X and Y represent the inhibition produced by drugs X and Y alone, respectively.

The theoretical additive surface is subtracted from the actual experimental surface, resulting in a horizontal surface that equals the zero plane when the combination is additive. A surface that lies higher than +20% above the zero plane indicates a synergistic effect of the combination, a surface lower than −20% below the zero plane indicates

Examples 61

NCI-60 Results as Growth Inhibition at 10 μm with Compound XII-4

The general assay procedure is the same as described in example 55 for compound XIX-3.

TABLE 12

Results obtained as growth % observed at 10 μM on various cancer cell lines for compound XII-4.

| Cancers | Cell lines | Growth percent at 10 μM |
| --- | --- | --- |
| Leukemia | CCRF-CEM | +++ |
|  | K-562 | × |
|  | MOLT-4 | ++ |
|  | SR | ++++ |
| Non-Small Cell Lung | A549/ATCC | ++ |
|  | HOP-62 | + |
|  | HOP-92 | ++ |
|  | NCI-H226 | − |
|  | NCI-H23 | − |
|  | NCI-H322M | ++ |
|  | NCI-H460 | ++ |
|  | NCI-H522 | + |
| Colon | COLO205 | xxxx |
|  | HCC-2998 | ++++ |
|  | HCT-116 | +++ |
|  | HCT-15 | ++++ |
|  | HT29 | × |
|  | KM12 | + |
|  | SW-620 | ++++ |
| CNS | SF-268 | + |
|  | SF-295 | − |
|  | SF-539 | ++ |
|  | SNB-19 | − |
|  | SNB-75 | ++ |
|  | U251 | ++ |
| Melanoma | LOX IMVI | ++++ |
|  | MALME-3M | xxx |
|  | M14 | xxxx |
|  | MDA-MB-435 | ++++ |
|  | SK-MEL-2 | − |
|  | SK-MEL-28 | xxxx |
|  | SK-MEL-5 | ++++ |
|  | UACC-257 | xxx |
|  | UACC-62 | xxxxx |
| Ovarian | IGROVI | ++ |
|  | OVCAR-3 | − |
|  | OVCAR-5 | ++ |
|  | OVCAR-8 | − |
|  | NCI/ADR-RES | + |
|  | SK-OV3 | − |
| Renal | 786-0 | ++ |
|  | A498 | +++ |
|  | ACHN | + |
|  | CAKI-1 | +++ |
|  | RXF393 | +++ |
|  | SN12C | ++ |
|  | TK-10 | − |
|  | UO-31 | +++ |

TABLE 12-continued

Results obtained as growth % observed at 10 μM on various cancer cell lines for compound XII-4.

| Cancers | Cell lines | Growth percent at 10 μM |
| --- | --- | --- |
| Prostate | PC-3 | +++ |
|  | DU-145 | − |
| Breast | MCF7 | ++ |
|  | MDA-MB-231/ATCC | xx |
|  | HS 578T | + |
|  | BT-549 | − |
|  | T-47D | ++ |
|  | MDA-MB-468 | xx |

"−" indicates cell growth % > 80
"+" indicates cell growth 60 > % < 80
"++" indicates cell growth 40 > % < 60
"+++" indicates cell growth 20 > % < 40
"++++" indicates cell growth 0 > % < 20
ND: Not Determined
"x" indicates cell growth 0 < % > −20
"xx" indicates cell growth −20 < % > −40
"xxx" indicates cell growth −40 < % > −60
"xxxx" indicates cell growth −60 < % > −80
"xxxxx" indicates cell growth % < −80

Examples 62

Figure 4:
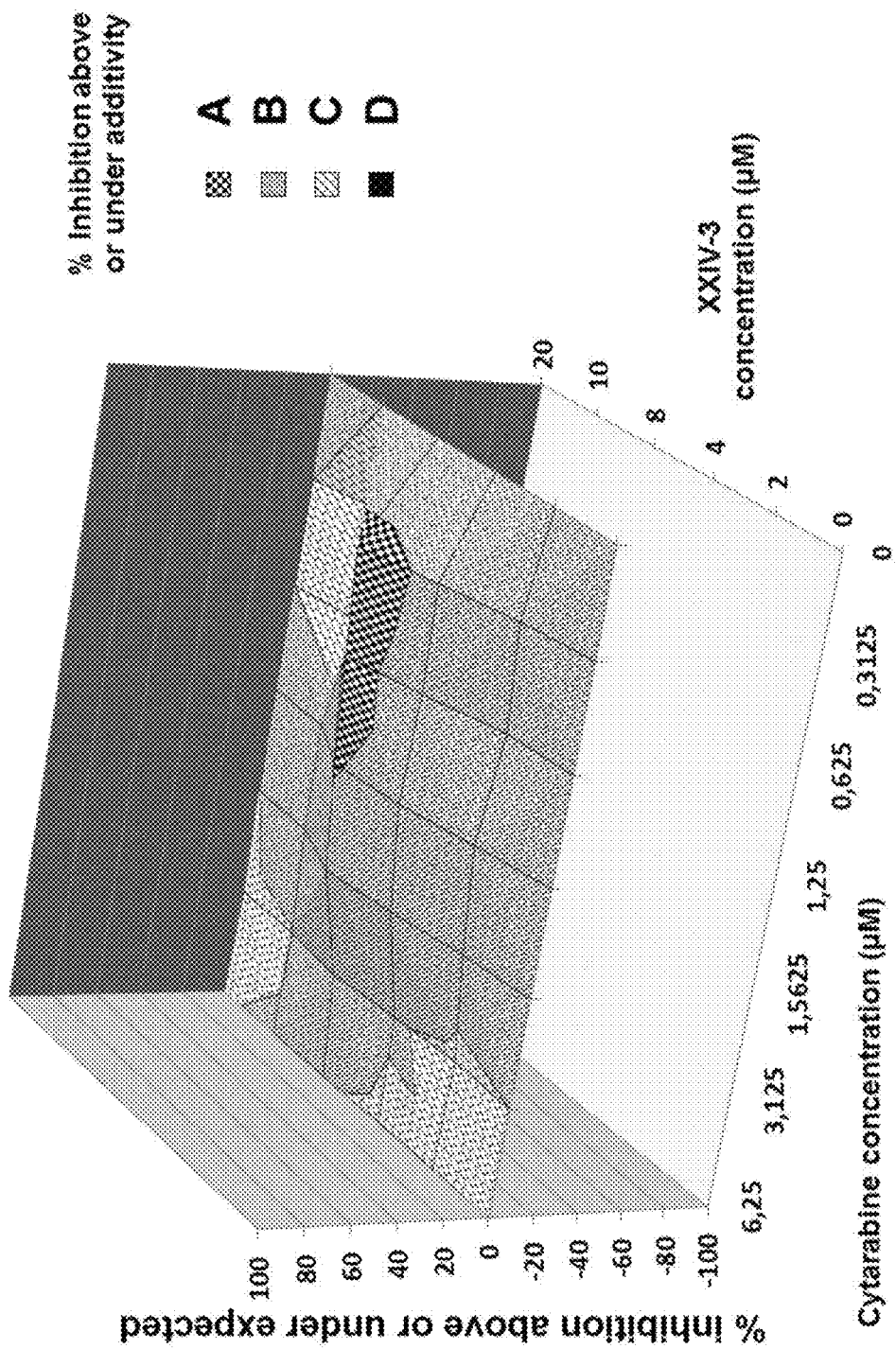
FIG. 4 shows a Bliss independence model analysis of the combination effect of compound XXIV-3 associated with Cytarabine on the cell viability of MOLM-14 cell line (Human acute myeloid leukemia cell line). The Bliss independence model analysis of the combination of compound XXIV-3 with Cytarabine shows a global additive effect. The MOLM-14 cell line expresses FLT3/ITD mutations.

Synergistic Growth Inhibition Study by the Combination of XXIV-3 and Cytarabine in Human Leukemia MOLM-14 Cell Line—See FIG. 4

The human leukemia cell line MOLM-14 was cultured in Minimum Essential Medium Alpha Medium (MEM) supplemented with 10% Fetal Bovine Serum (FBS) and 1% Penicillin-Streptomycin and maintained at 37° C. with 5% $CO_2$. 30,000 cells in 180 μL of MEM 5% FBS 1% P/S were plated onto 96-well plates immediately before the assay. Compounds were added at different concentrations (combinations of five concentrations of XXIV-3 and six concentrations of Cytarabine) to each well, and cell cultures were incubated for 72 h. Vehicle ($H_2O$) was used as a control, and all compounds were tested in a constant percentage of vehicle. Cell outgrowth was measured using the CellTiter-Glo luminescent cell viability assay as described by the manufacturer (Promega, Ref G7571 Madison, Wis., USA) using an Infinite F200 Pro TECAN plate reader.

In each experiment, each point represents the average of triplicates in cell culture.

The effects of drug-drug combinations are evaluated in the Bliss independence model (Prichard M. N. and Shipman C. Jr. Antivir. Res. 1990 (14) 181-205; Prichard, M. L. et al. Antimicrob Agents Chemother 1993(37) 540-545). The theoretical additive effect is calculated from the dose-response curves of individual compounds by the equation:

$$Z = X + Y(1-X) \qquad (7)$$

Where:
Z represents the total inhibition produced by the combination of drugs X and Y.
X and Y represent the inhibition produced by drugs X and Y alone, respectively.

The theoretical additive surface is subtracted from the actual experimental surface, resulting in a horizontal surface that equals the zero plane when the combination is additive. A surface that lies higher than +20% above the zero plane indicates a synergistic effect of the combination, a surface lower than −20% below the zero plane indicates antagonism effect and between −20% to +20% indicates additive effect.

Examples 63

ALDH+ Compartment Analysis in MOLM-14 Cell Line

MOLM-14 cell line was cultured in RPMI-1640 Medium supplemented with 10% v/v Fetal Bovine Serum (FBS), 1% Penicillin-Streptomycin and maintained at 37° C. with 5% $CO_2$. 10,000 cells were plated onto 96-well plates immediately before the assay.

Each compound was added at different concentrations (combinations of six concentrations) to each well, and cell cultures were incubated for 48 h. Vehicle ($H_2O$) was used as a control, and all compounds were tested in a constant percentage of vehicle. Cell outgrowth was measured using the CellTiter-Glo luminescent cell viability assay as described by the manufacturer (Promega, Ref G7571 Madison, Wis., USA) using a Centro (Berthold, France) plate reader.

In each experiment, each point represents the average of triplicates in cell culture.

The experimental data are analyzed using a computer program, Graphpad Prism (GraphPad Software, Inc. La Jolla, Calif.) and $EC_{50}$ values were determined as the dose of compound required to reduce absorbance values to 50% of the signal obtained for vehicle treated cell cultures.

Analysis of the of aldehyde dehydrogenase (ALDH) compartment and high activity level of aldehyde dehydrogenase activity (ALDH+) was used to detect tumor initiating cells (cancer stem cells, CSC) population. The Aldefluor™ kit assay (StemCell Technologies) allowed to assess the activity of drugs on CSC cells like in aa MOLM-14 acute myeloid leukemia cell line population. The Aldefluor™ kit assay was used according to the procedure described by the manufacturer. Briefly, MOLM-14 cell line was cultured in RPMI-1640 Medium supplemented with 10% v/v Fetal Bovine Serum (FBS), 1% Penicillin-Streptomycin and maintained at 37° C. with 5% $CO_2$. $5 \cdot 10^5$ cells were used in this assay. Each compound was added at different concentrations (see table 13 and 14), and cell cultures were incubated for 72 h. Vehicle ($H_2O$) was used as a control, and all compounds were tested in a constant percentage of vehicle. Cells obtained from cell culture were incubated for 45 minutes at 37° C. with Aldefluor™ buffer assay containing the Bodipy™-aminoacetaldehyde (BAAA), a fluorescent ALDH aldehyde substrate. ALDH converts the fluorescent substrate BAAA to the Bodipy™-aminoacetic acid (BAA) which is retained in the cell. An active efflux inhibitor is present in the Adelfluor™ assay buffer in order to avoid the active efflux from the cell of the substrate product ALDH dependent converted BAA. The fluorescent signal is directly proportional to the ALDH activity in the cells and is measured by flow cytometry. A negative control is used to measure the background fluorescence level. For such purpose, 4-(N,N-diethylamino)-benzaldehyde (DEAB) was used as selective ALDH inhibitor. A viability cell count was performed using LIVE/DEAD® Fixable Far Red Dead Cell Stain Kit (Invitrogen). The experimental data are analyzed using a computer program, Graphpad Prism (GraphPad Software, Inc. La Jolla, Calif.) and $EC_{50}$ values were determined as the dose of compound required to reduce absorbance values to 50% of the signal obtained for vehicle treated cell cultures.

TABLE 13

Growth inhibition assay ($EC_{50}$, µM) of MOLM-14
Cell line in presence of compound XIII-8 and XIX-3[a]

|  | Cytarabine | XIII-8 | XIX-3 |
|---|---|---|---|
| $EC_{50}$ (µM)[b] | 1 | 6 | 22 |

[a]$EC_{50}$ obtained from the method described in example 63
[b]each point represents the average of triplicates in cell culture

TABLE 14

ALDH population decreases in MOLM-14 cell line by compound XIX-3 using Aldefluor™ kit assay

|  | Vehicle | Cytarabine | XIX-3 | | | | |
|---|---|---|---|---|---|---|---|
|  | $H_2O$ | 1 µM | 3 µM | 5 µM | 10 µM | 20 µM | 40 µM |
| Aldefluor™ positive CSCs (% of control) | 100 | 130 | 116 | 86 | 66 | 42 | 25 |

Compound XIX-3 reduced the proportion of CSCs in Aldefluor™ assay, in dose dependent manner in MOLM-14 cell line, whereas Cytarabine is not active against CSCs even at 3-folds higher than its $EC_{50}$.

TABLE 15

ALDH population decreases in MOLM-14 cell line by compound XIII-8 using Aldefluor™ kit assay

|  | Vehicle | Cytarabine | XIII-8 | | | | |
|---|---|---|---|---|---|---|---|
|  | $H_2O$ | 1 µM | 3 µM | 5 µM | 10 µM | 20 µM | 40 µM |
| Aldefluor™ positive CSCs (% of control) | 100 | 130 | 116 | 84 | 83 | 58 | 23 |

Compound XIII-8 reduced the proportion of CSCs in Aldefluor™ assay, in dose dependent manner in MOLM-14 cell line, whereas Cytarabine is not active against CSCs even at 3-folds higher than its $EC_{50}$.

Examples 64

Figure 5:
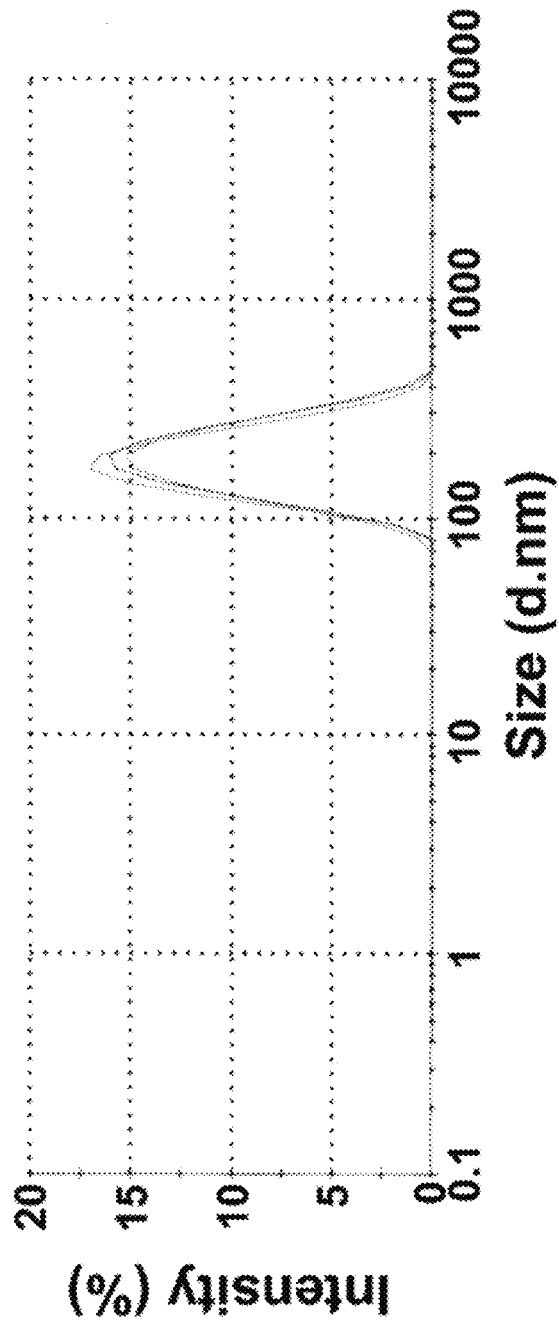
FIG. 5 shows the size distribution of the PLGA-PL-GAPEG:XIX-2 nanoparticles measured by dynamic light scattering technology, using a NanoSizer Zeta Series, Malverne Instruments. This Dynamic Light Scattering (DLS) analysis shows a hydrodynamic diameter average of the nanoparticle size of 173 nm with a polydispersity index (PDI) of 0.103.
Figure 6:
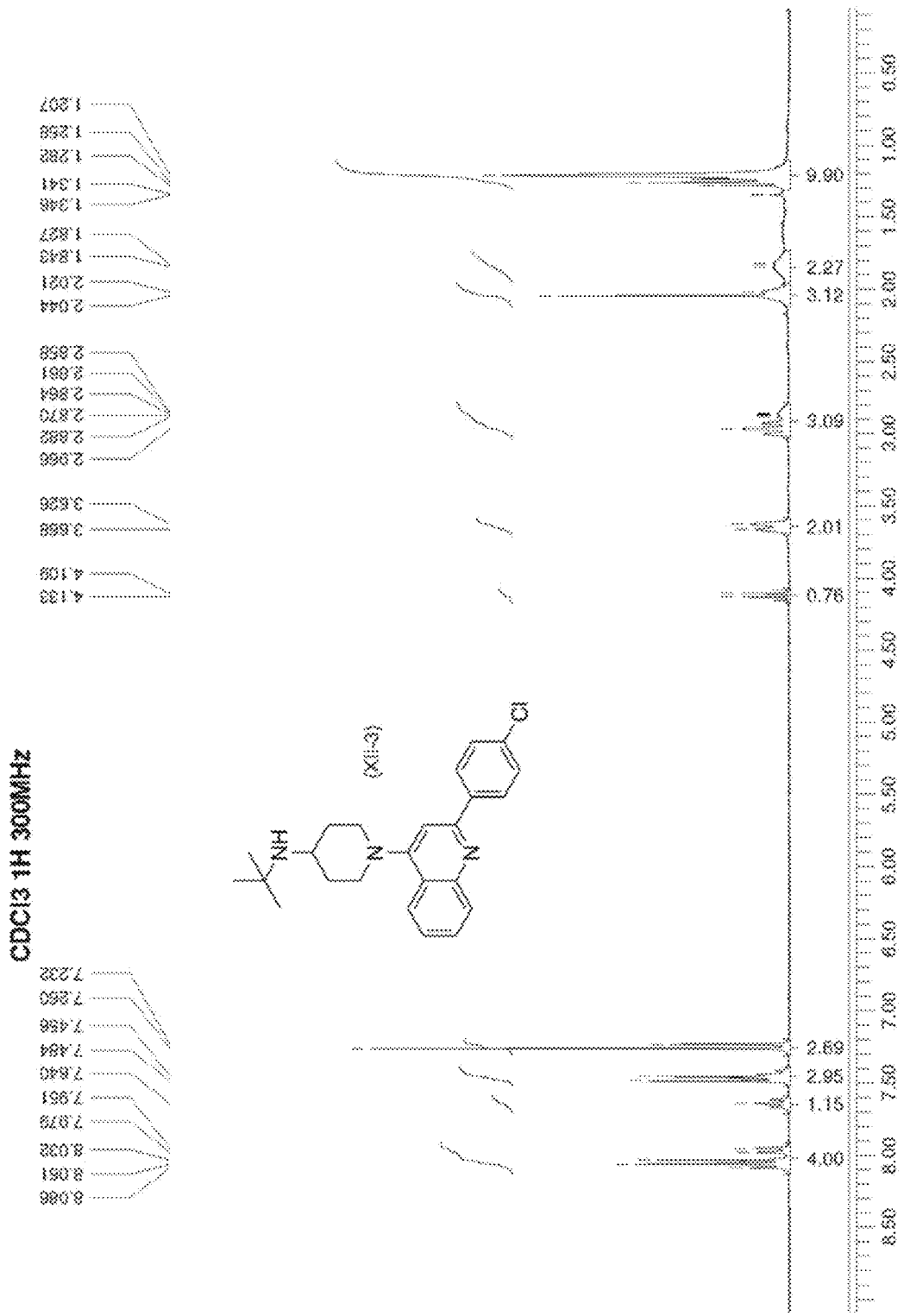
FIG. 6 shows the 1H NMR spectra of compound XII-3 in $CDCl_3$.
Figure 7:
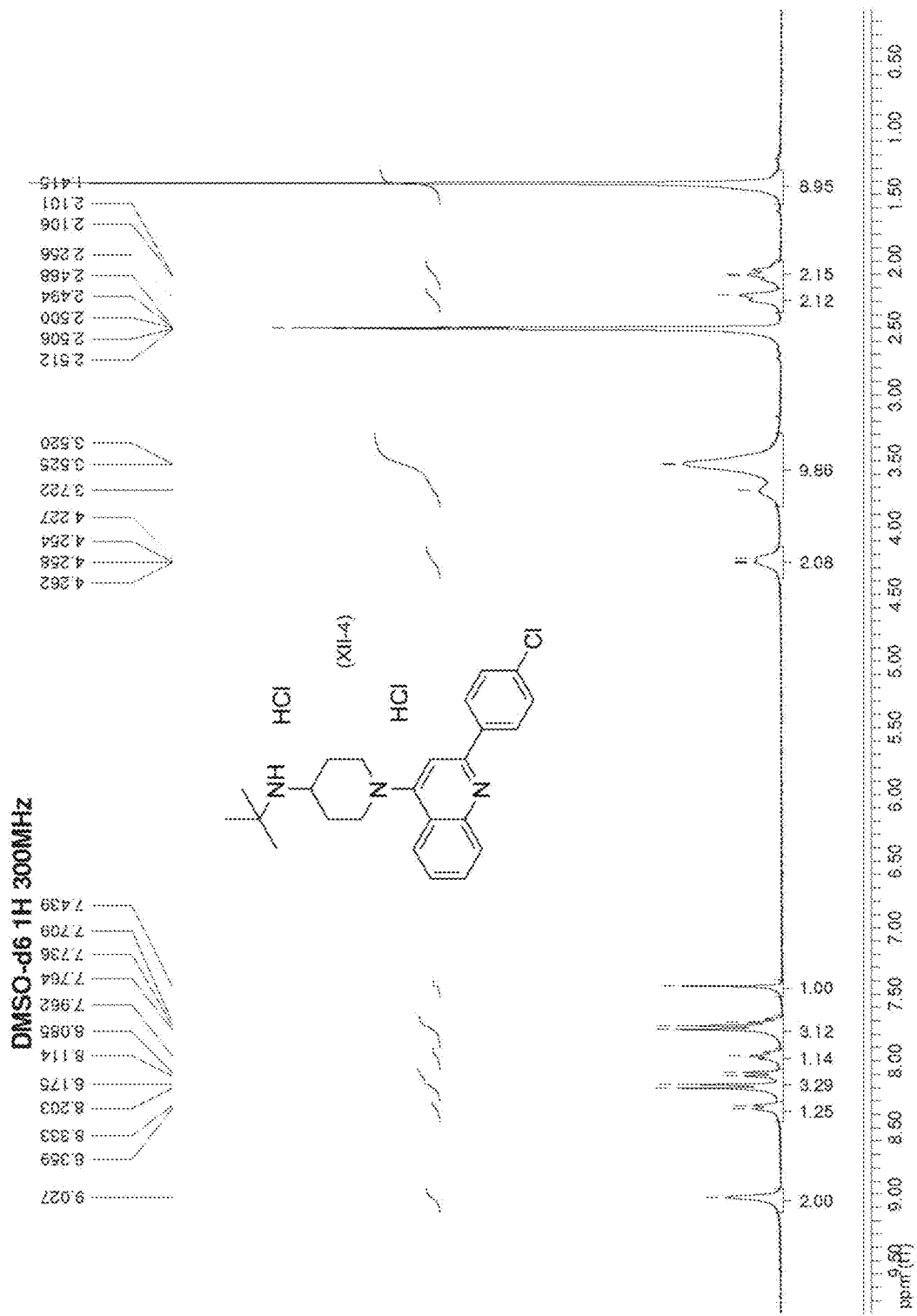
FIG. 7 shows the 1H NMR spectra of compound XII-4 in $DMSO-d_6$.
Figure 8:
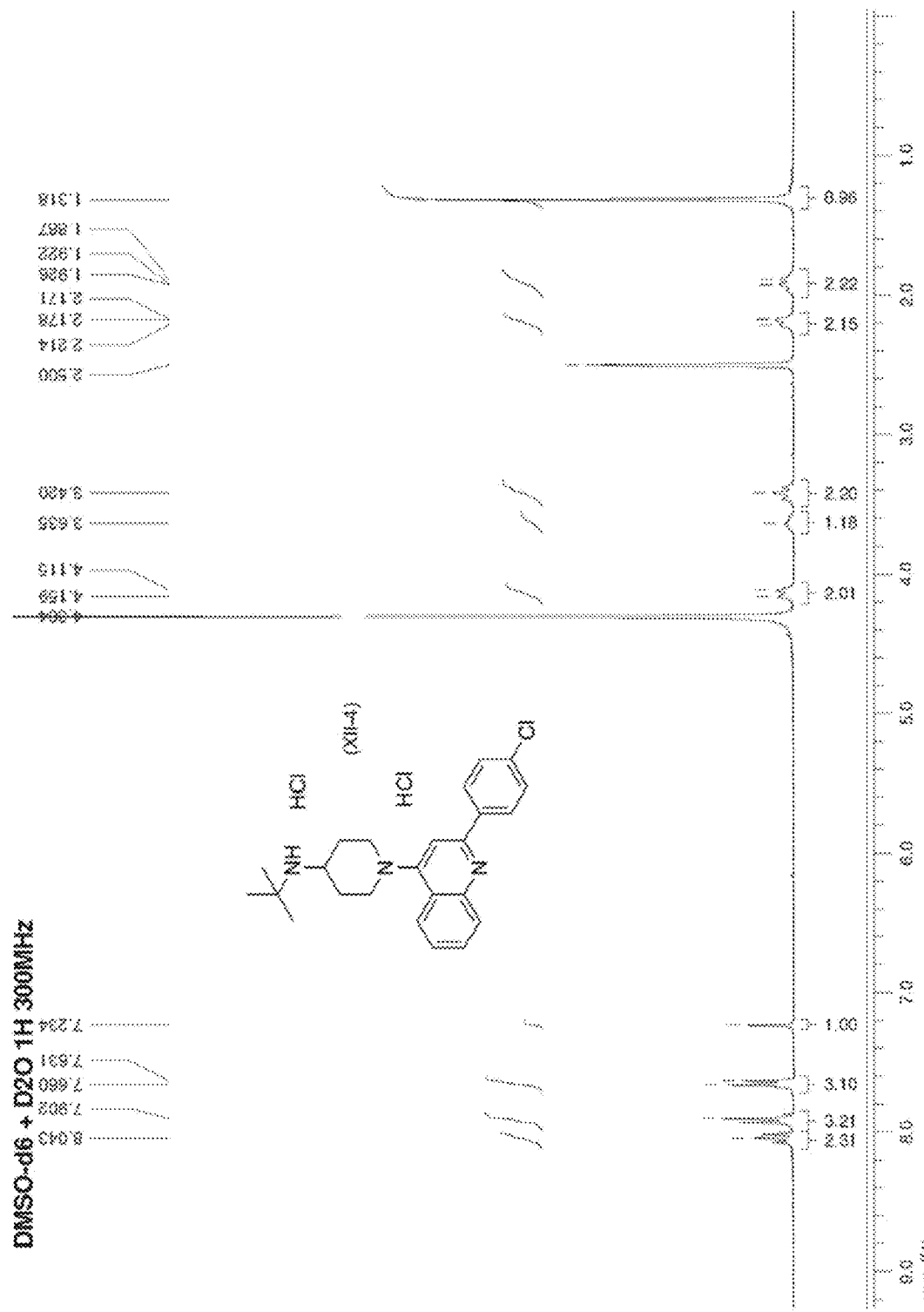
FIG. 8 shows the 1H NMR spectra of compound XII-4 in $DMSO-d_6+D_2O$.
Figure 9:
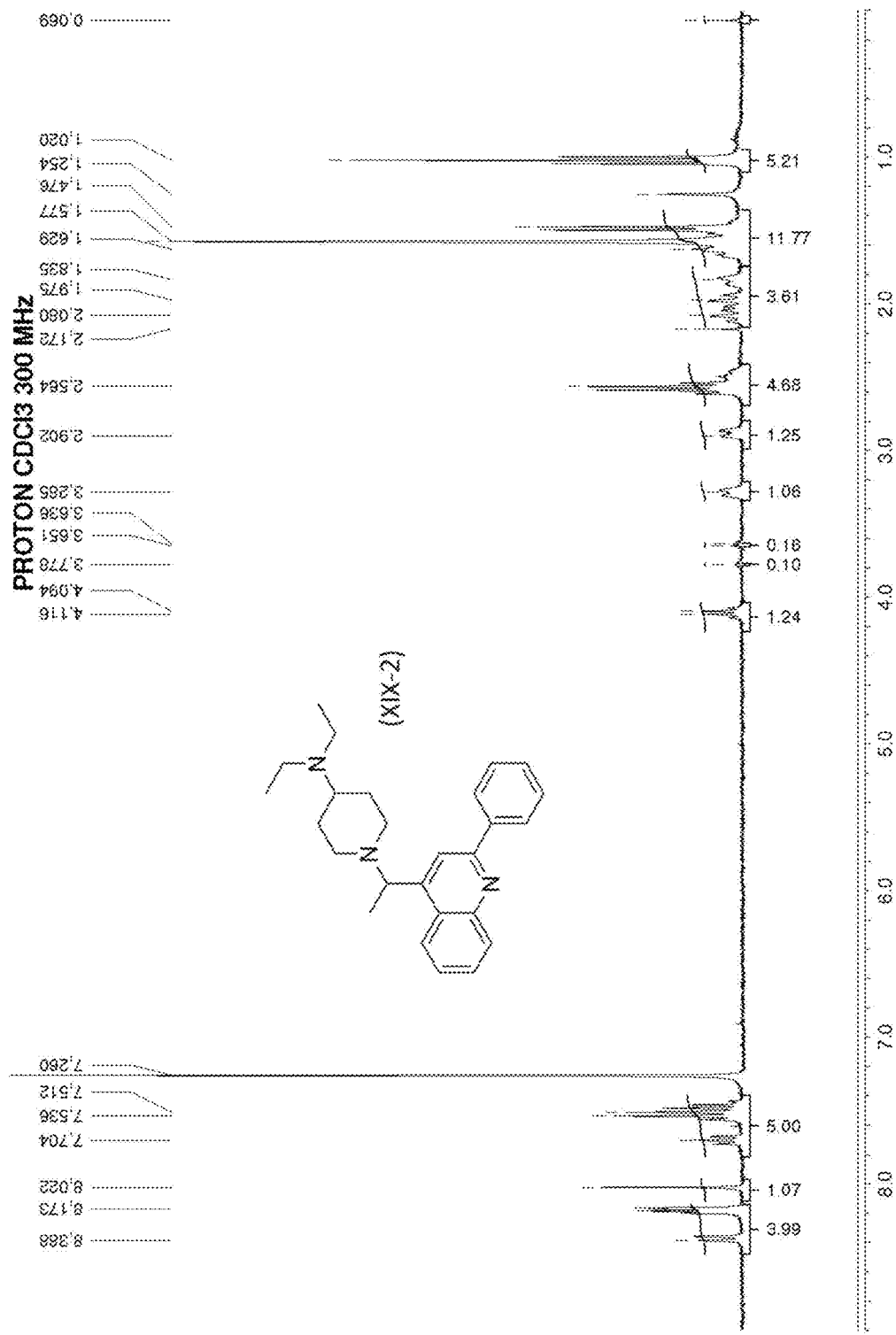
FIG. 9 shows the 1H NMR spectra of compound XIX-2 in $CDCl_3$.
Figure 10:
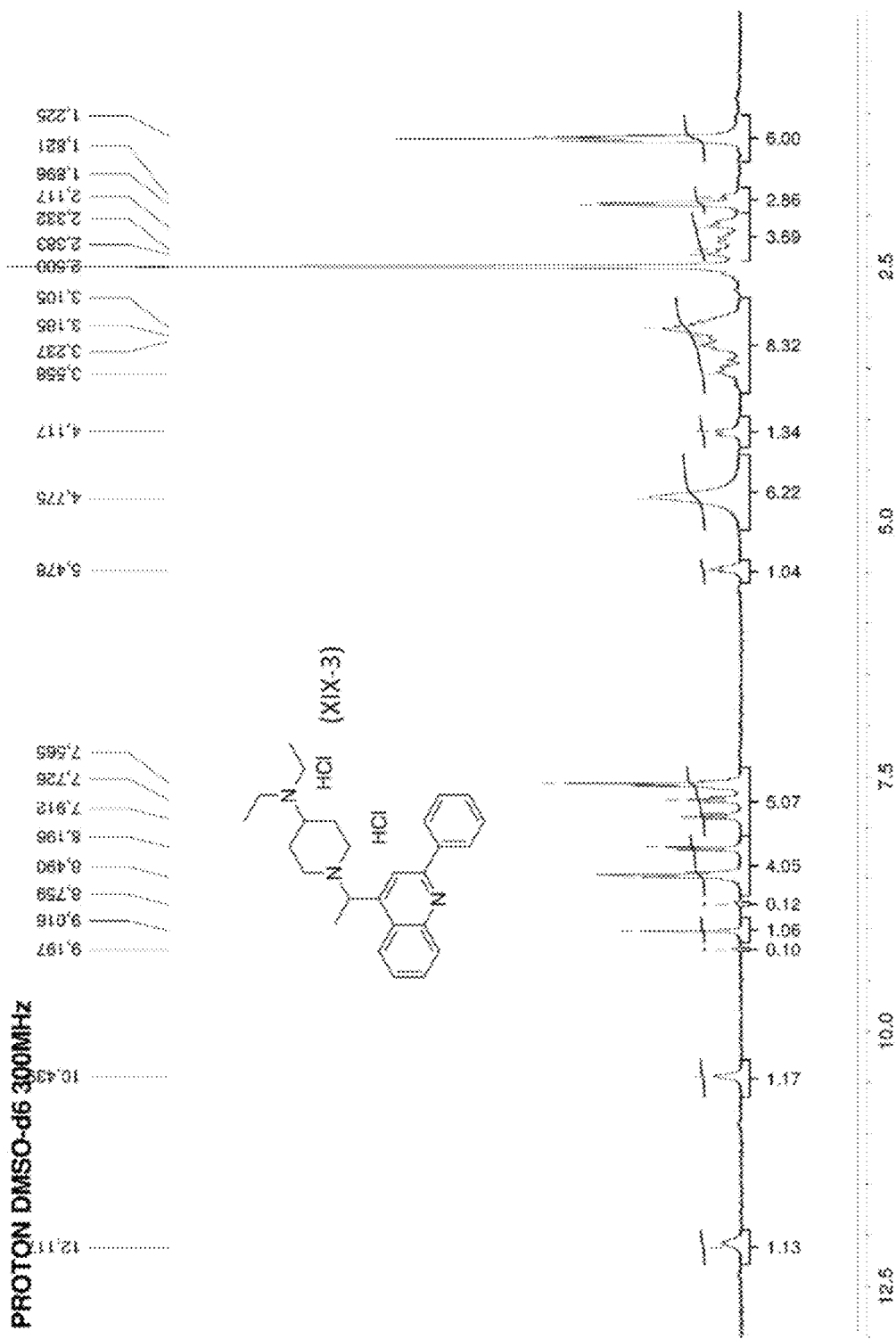
FIG. 10 shows the 1H NMR spectra of compound XIX-3 in $DMSO-d_6$.
Figure 11:
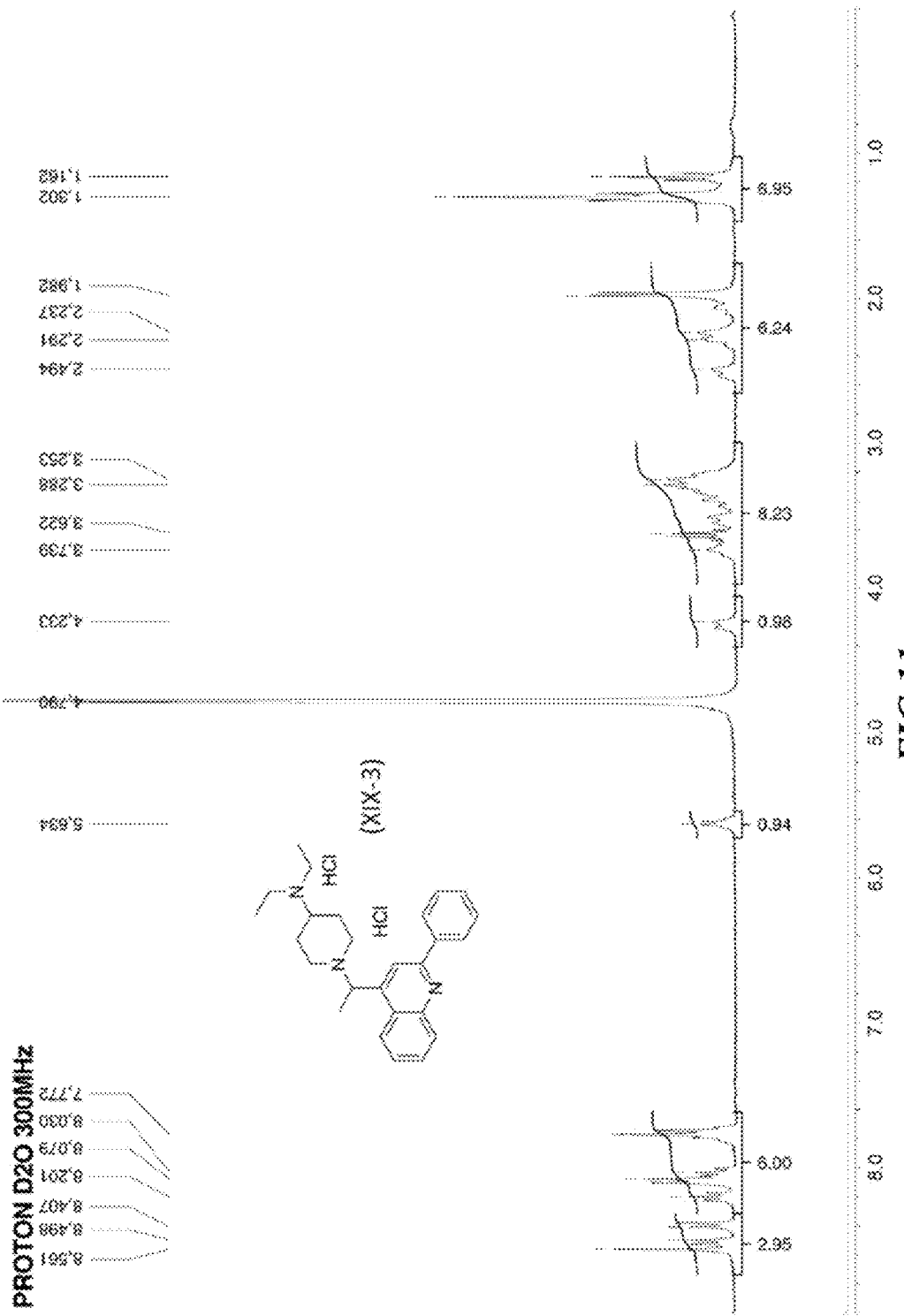
FIG. 11 shows the 1H NMR spectra of compound XIX-3 in $D_2O$.
Figure 12:
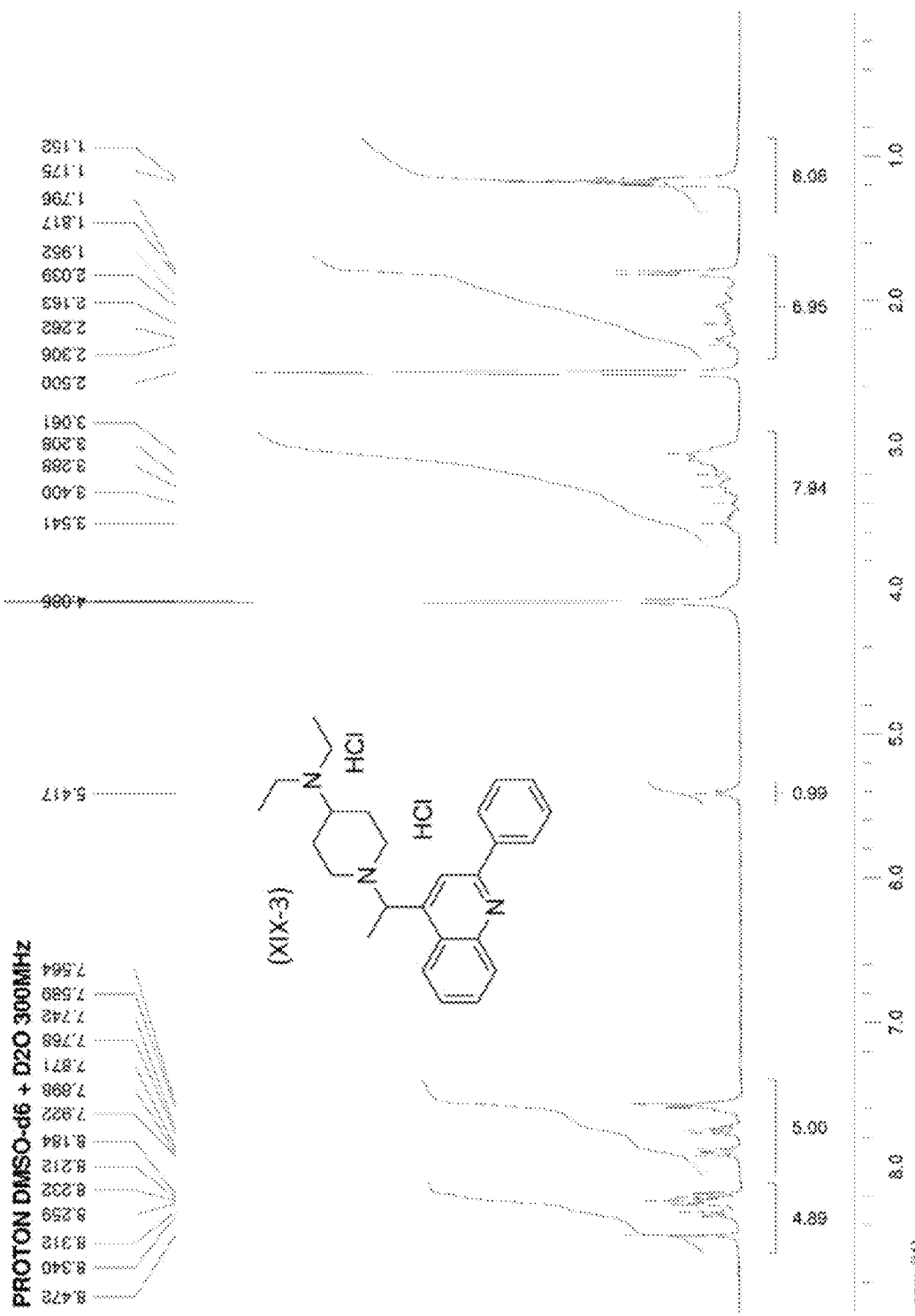
FIG. 12 shows the 1H NMR spectra of compound XIX-3 in $DMSO-d_6+D_2O$.
Figure 13:
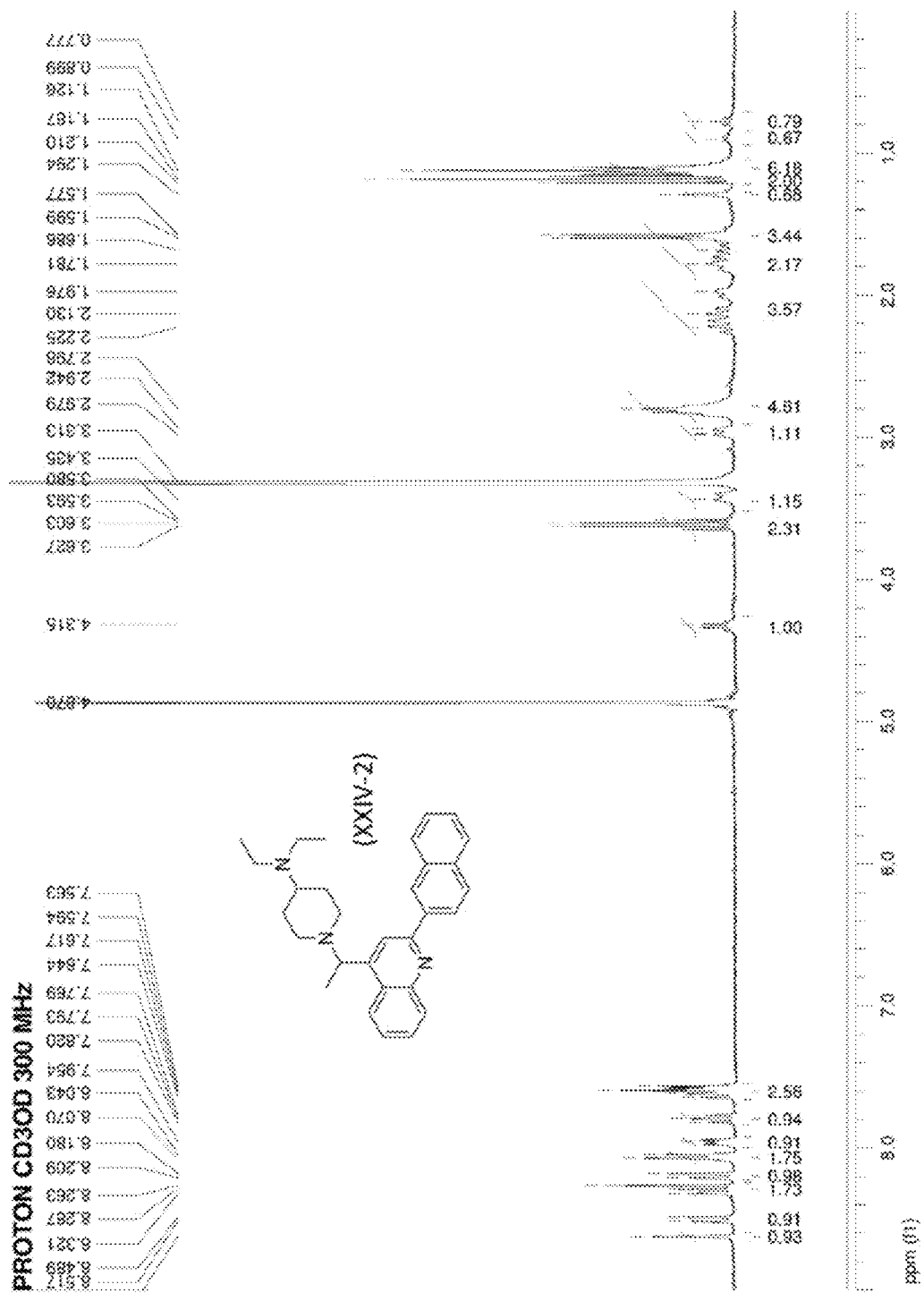
FIG. 13 shows the 1H NMR spectra of compound XXIV-2 in $CD_3OD$.
Figure 14:
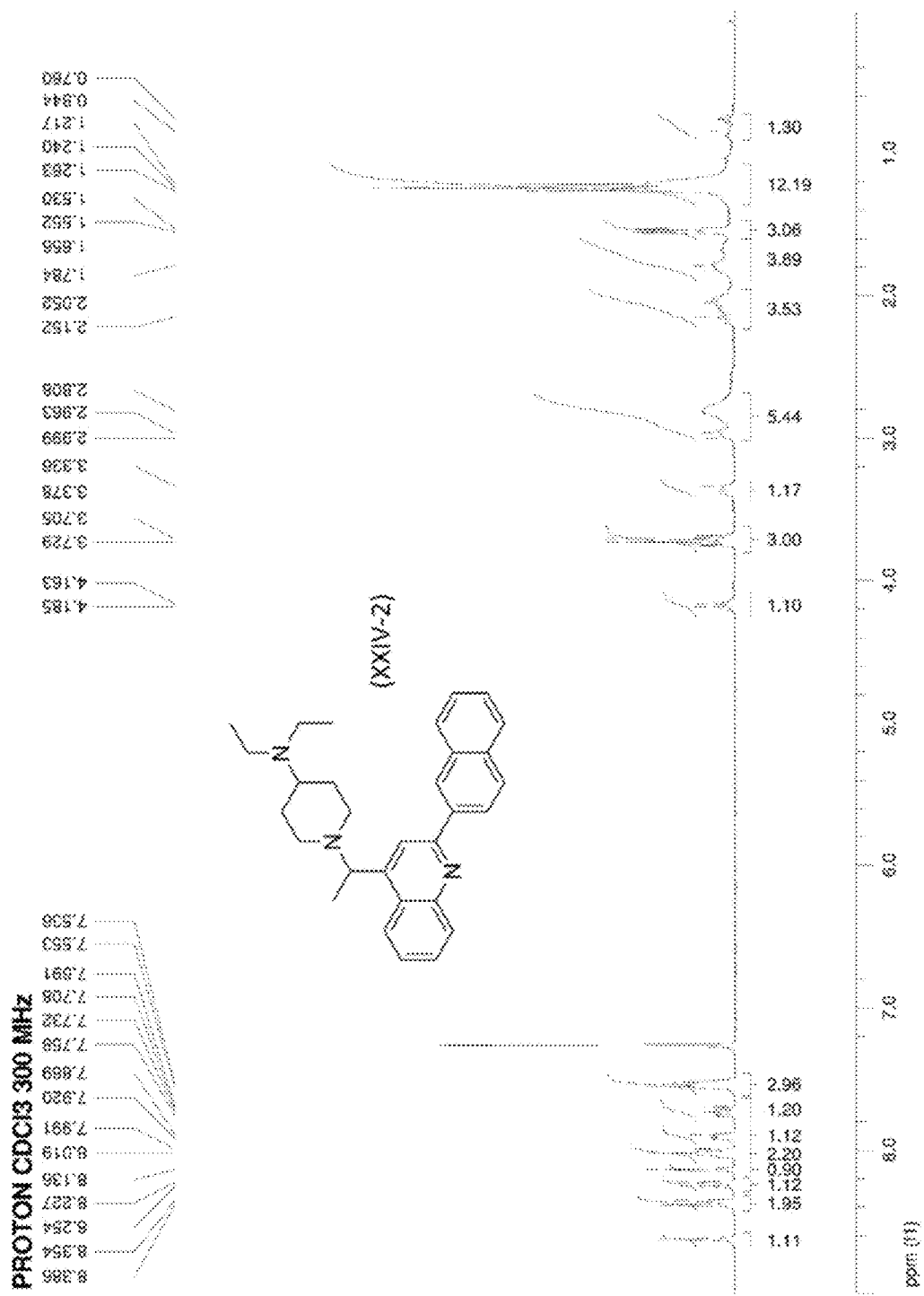
FIG. 14 shows the 1H NMR spectra of compound XXIV-2 in $CDCl_3$.
Figure 15:
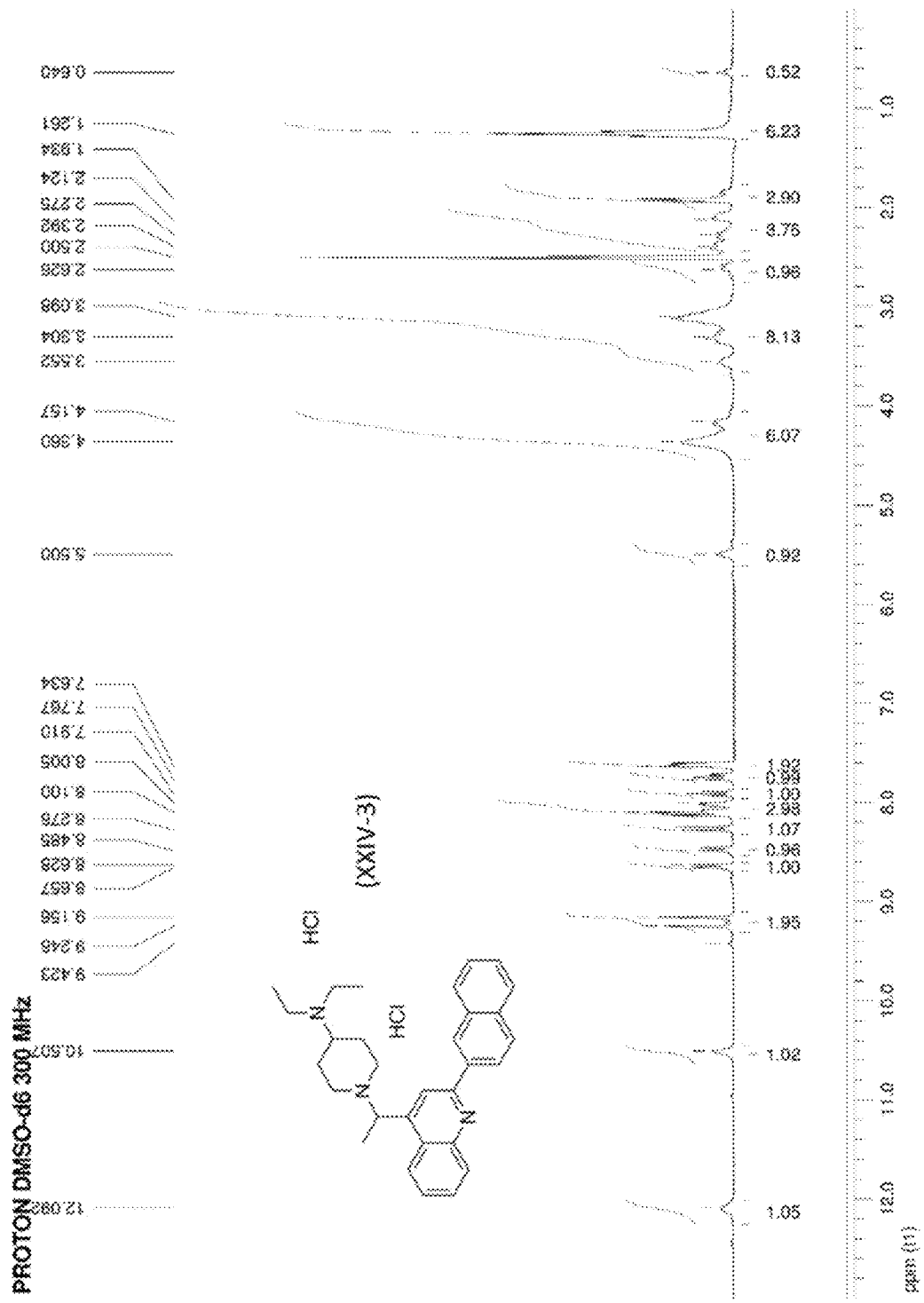
FIG. 15 shows the 1H NMR spectra of compound XXIV-3 in $DMSO-d_6$.
Figure 16:
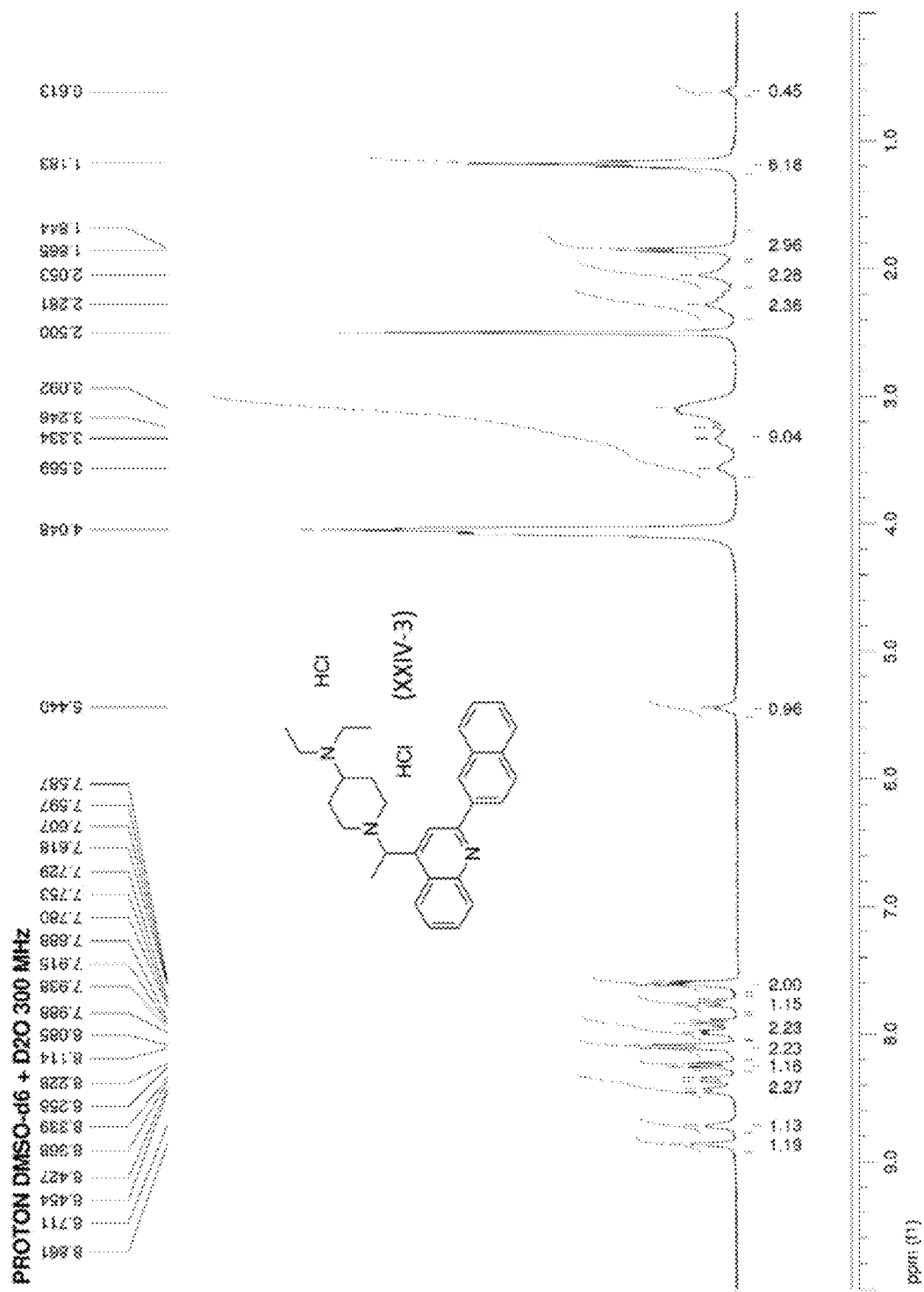
FIG. 16 shows the 1H NMR spectra of compound XXIV-3 in $DMSO-d_6+D_2O$.
Figure 17:
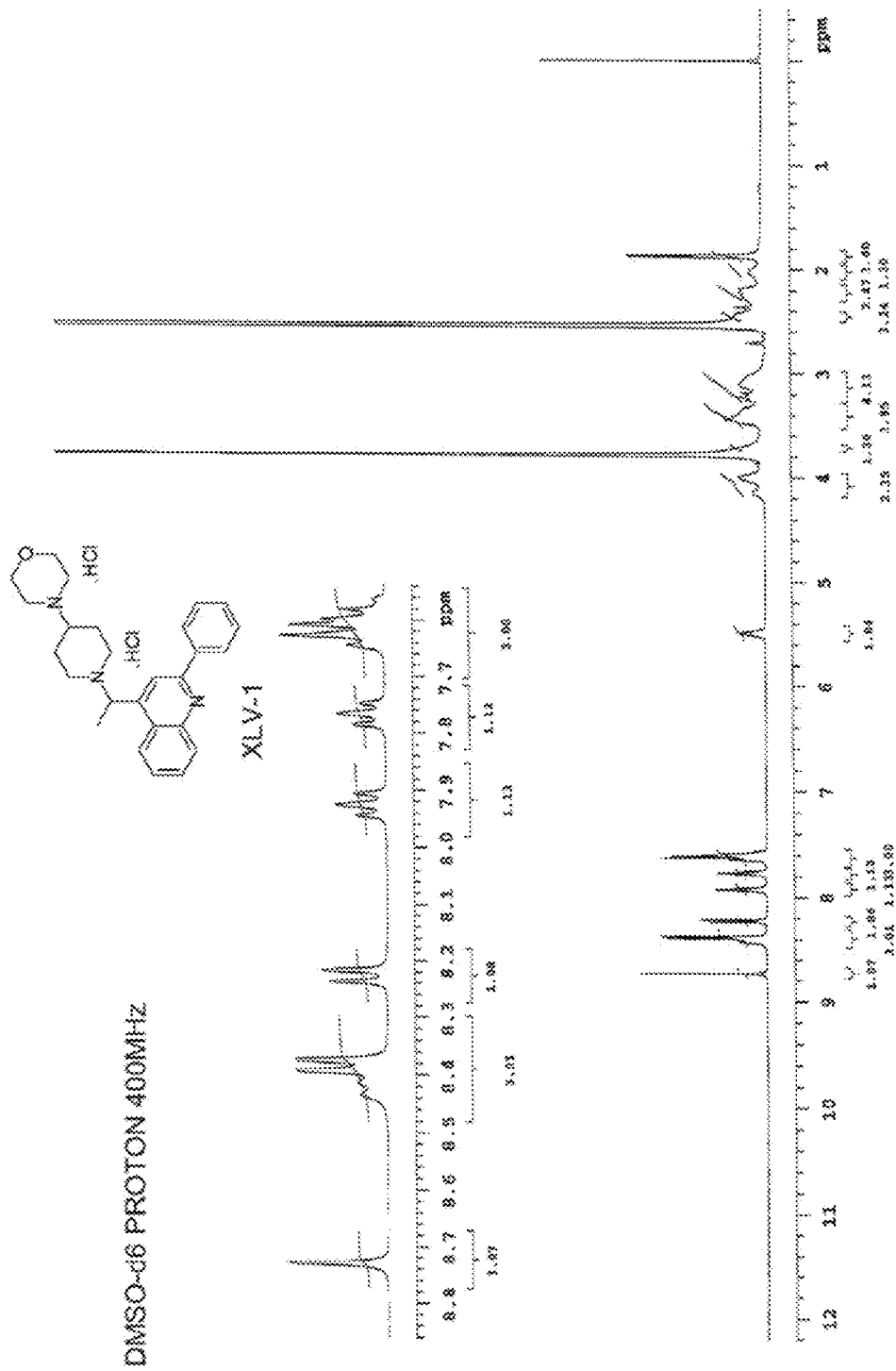
FIG. 17 shows the 1H NMR spectra of compound XLV-1 in $DMSO-d_6$.

Preparation of XIX-2 Loaded Nanoparticules—See FIG. 5

Nanoparticule can be prepared by simple emulsion technique. Briefly PLGA and/or PLGA-PEG or PLGA derived co-polymers for cell targeting was dissolved in organic solvent preferentially, but not limited to: dichloromethane, ethyl acetate (an immiscible organic solvent to water for emulsion preparation). Active compound alone or combined to another drug(s) and formulation additive(s) was added to this solution (as powder form or in organic solution). Aqueous solution was added (e.g. 1% sodium cholate, 2% polyvinyl alcohol) and then the resulting mixture was sonicated for 15-30 seconds (70 W, 2-5 ml). The resulting emulsion was added dropwise under agitation to an aqueous solution (e.g. sodium cholate 0.3%) and the resulting mixture was stirred at 37° C. for solvent evaporation.

Nanoparticules may be prepared equally according to the nanoprecipitation method (interfacial deposition technique). For that purpose, active compound alone or associated with another drug(s) was dissolved under agitation in organic solution of PLGA and/or PLGA-PEG or PLGA derived co-polymers for cell targeting (preferentially, but not limited to, acetone). The resulting organic solution was slowly added to a water solution (using for example syringe pomp), and then the organic solvent was removed by evaporation.

The non-encapsulated drug can be removed from the solution by size exclusion chromatography. The solution containing the nanoparticles and free drug(s) was filtered (e.g. pore size 1.2 μm) and then ultracentrifuged at 4° C. The nanoparticules obtained were then suspended in ultra-pure water, vacuum freeze-dried and can be sterilized by $Co^{60}$ irradiation.

According to the general procedure described elsewhere (see for example Kumar, K. et al. J. Controlled Release 2013 (171) pp 208-215 and Danhier, F. et al. Int. J. Pharm. 2010 (392) pp 20-28) a nanoparticule PLGA-PLGAPEG (70/30, w/w) formulation of compound XIX-2 was prepared. Briefly, XIX-2 loaded PLGA (L:G 50:50, Mw 7,000-17,000, acid terminated) and PLGA-PEG (L:G 50:50, 15% of PEG, PLGA Mw 28,000; PEG Mw 5,000) nanoparticles were prepared by O/W emulsion-solvent evaporation technique. 35 mg of PLGA polymer and 15 mg of PLGA-PEG polymer was dissolved in 1 ml of a solution of XIX-2 in dichloromethane (10 mg/ml) and vortexed to obtain a uniform PLGA-PLGAPEG solution. Then, 2 ml of a 1% sodium cholate aqueous solution was added and the resulting biphasic system was sonicated (Branson sonifier, USA) at 70 W for 15 s. This emulsion was added dropwise to 100 ml of a 1% sodium cholate aqueous solution at 37° C. and stirred at 600 rpm for 1 h. The nanoparticle suspension was then washed twice in distilled water by centrifugation (Avanti-JE centrifuge, Beckman coulter, USA) for 60 min at 10,000 t·min$^{-1}$ and 4° C. Supernatants were collected to evaluate encapsulation efficiency of XIX-2. Empty nanoparticles were prepared with the same procedure except the addition of XIX-2 during the preparation of the formulation. The particles can be stored in solution at +4° C. or then freeze dried (Labconco, USA) and stored at 4° C. until further use.

Particle size, poly dispersity and zeta potential assessment: The particle size and poly dispersity index (PDI) of PLGA-PLGAPEG:XIX-2 nanoparticles were measured by dynamic light scattering and the zeta potential was determined using a zeta potential analyzer (NanoSizer Zeta Series, Malvern Instruments, Malvern, UK).

Encapsulation efficiency estimated the amount of XIX-2 encapsulated in PLGA-PLGAPEG nanoparticules. Supernatants were used to measure the non-encapsulated XIX-2. Nanoparticules were dissolved in 1 ml of mobile phase to evaluate the encapsulated XIX-2. An HPLC system (Waters Breeze) with a diode array detector and multiple wavelength detector was used for the quantification of XIX-2 in supernatants and nanoparticles. The column used was an EC 125/4 Nucleodur 100-5 C18 ec (Macherey-Nagel, DE). The sample (25 μl) in a series of dilutions was eluted with the mobile phase composed of A: $H_2O$-0.1% $HCO_2H$, B: MeCN-0.1% $HCO_2H$. Eluting conditions comprised a linear gradient (minute/% B): 0/10% B, 0.5/10% B, 2.5/90% B, 4.0/90% B. Flow rate 1 ml/min. Detection was achieved at 257 nm and the retention time of XIX-2 was 3.1 min.

The coefficients of variation (CV) for intra- and inter-assay measurements were within 5%. The encapsulation efficiency of XIX-2 is given by [XIX-2 used–XIX-2 non-encapsulated)/XIX-2 used]×100 and XIX-2 recovery was calculated.

TABLE 16

Encapsulation efficiency of XIX-2 in PLGA-PLGAPEG nanoparticules described in FIG. 5

| Compound | Concentration of XIX-2 in nanoparticules dispersion | Encapsulation efficiency$^a$ | Loading$^b$ |
|---|---|---|---|
| XIX-2 | 3.21 mM | 9.4% | 2.5% |

$^a$[XIX-2 used – XIX-2 nonencapsulated)/XIX-2 used] × 100
$^b$[XIX-2 encapsulated/PLGA-PLGAPEG used] × 100

Examples 65

1H NMR Spectras of Compounds XII-3, XII-4, XIX-2, XIX-3, XXIV-2, XXIV-3, XLV-1 (see FIGS. 6-17)

The invention claimed is:

1. A compound of formula (I)

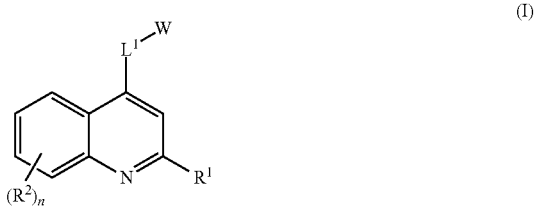

wherein:

$R^1$ is selected from optionally substituted aryl, optionally substituted heteroaryl, optionally substituted heteroaromatic 5 to 9 membered ring comprising 1, 2 or 3 heteroatoms independently selected from O, N, and S;

$R^2$ is selected from Cl, F, I, Br, $C_1$-$C_6$ alkyl, $C_1$-$C_6$ alkyl substituted with one or more halogens, $C_1$-$C_6$ alkoxy, hydroxy, nitro or $NR^7R^8$, $NR^7$—(CO)—$R^8$, $NR^7$—(CO)—O—$R^8$, $NR^7$—(CO)—$NR^7R^8$, O—(CO)$R^7$, O—(CO)—O—$R^7$, O—(CO)—$NR^7R^8$, (CO)$R^7$, (CO)—O—$R^7$, (CO)—$NR^7R^8$, $SO_2$—$R^7$, $SO_2NR^7R^8$, $NR^7$—$SO_2$—$R^8$, with $R^7$ and $R^8$ representing independently hydrogen, $C_1$-$C_6$ alkyl, phenyl (optionally substituted with one or more substituent groups selected from Cl, F, I, Br, C1-C6 alkyl, $C_1$-$C_6$ alkyl substituted with one or more halogens, $C_1$-$C_6$ alkoxy, hydroxy, cyano, nitro or $NR^7R^8$) or benzyl (optionally substituted with one or more substituent groups selected from Cl, F, I, Br, $C_1$-$C_6$ alkyl, $C_1$-$C_6$ alkyl substituted with one or more halogens, $C_1$-$C_6$ alkoxy, hydroxy, cyano, nitro or $NR^7R^8$), alkenyl, alkynyl, cycloalkyl, cycloalkenyl, cycloalkynyl, aryl and heteroaryl;

$L^1$ is selected from a bond or from optionally substituted $C_1$-$C_{14}$ alkyl(-$R^3$), N(—$R^3$), (CO)—O, (CO)—$NR^7$, and O;

n is 0, 1, 2, 3 or 4; and

W is

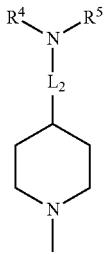

wherein:
L₂ is selected from a bond or from optionally substituted C₁-C₁₄ alkyl(-R³), N(—R³), (CO)—O, (CO)—NR⁷, and O; wherein R³ is selected from H, optionally substituted aryl, optionally substituted heteroaryl, optionally substituted heterocycloalkyl, optionally substituted C₁-C₈ alkyl, optionally substituted C₂-C₈ alkenyl, optionally substituted C₂-C₈ alkynyl, optionally substituted C₃-C₁₂ cycloalkyl, and optionally substituted C₃-C₁₂ cycloalkenyl; and wherein R⁷ is as defined above; and R⁴ and R⁵ are independently selected from hydrogen, C₁-C₆ alkyl or phenyl (optionally substituted with one or more substituent groups selected from Cl, F, I, Br, C₁-C₆ alkyl, C₁-C₆ alkyl substituted with one or more halogens, C₁-C₆ alkoxy, hydroxy, cyano, nitro or NR⁷R⁸) or benzyl (with the phenyl group optionally substituted with one or more substituent groups selected from Cl, F, I, Br, C₁-C₆ alkyl, C₁-C₆ alkyl substituted with one or more halogens, C₁-C₆ alkoxy, hydroxy, cyano, nitro or NR⁷R⁸) or CH₂—CH₂-Phenyl (with the phenyl group optionally substituted with one or more substituent groups selected from Cl, F, I, Br, C1-C6 alkyl, C₁-C₆ alkyl substituted with one or more halogens, C₁-C₆ alkoxy, hydroxy, cyano, nitro or NR⁷R⁸), (CO)—R⁷, (CO)—OR⁷, (CO)—NR⁷R⁸, alkenyl, alkynyl, cycloalkyl, cycloalkenyl, cycloalkynyl, aryl, monocyclic or bicyclic heteroaryl or R⁴ and R⁵ are linked to form a heterocyclic group, wherein the term "optionally substituted" means optionally substituted with one or more substituents independently selected from Cl, F, I, Br, C₁-C₆ alkyl, C₁-C₆ alkyl substituted with one or more halogens, C₁-C₆ alkoxy, hydroxy, cyano, nitro or NR⁷R⁸ with R⁷ and R⁸ representing independently hydrogen, C₁-C₆ alkyl, phenyl (optionally substituted with one or more substituent groups selected from Cl, F, I, Br, C₁-C₆ alkyl, C₁-C₆ alkyl substituted with one or more halogens, C₁-C₆ alkoxy, hydroxy, cyano, nitro or NR⁷R⁸) or benzyl (optionally substituted with one or more substituent groups selected from Cl, F, I, Br, C₁-C₆ alkyl, C₁-C₆ alkyl substituted with one or more halogens, C₁-C₆ alkoxy, hydroxy, cyano, nitro or NR⁷R⁸), alkenyl, alkynyl, cycloalkyl, cycloalkenyl, cycloalkynyl, aryl and heteroaryl;

and any pharmaceutically acceptable salt, solvate or prodrug thereof.

2. A compound according to claim 1 of formula (I')

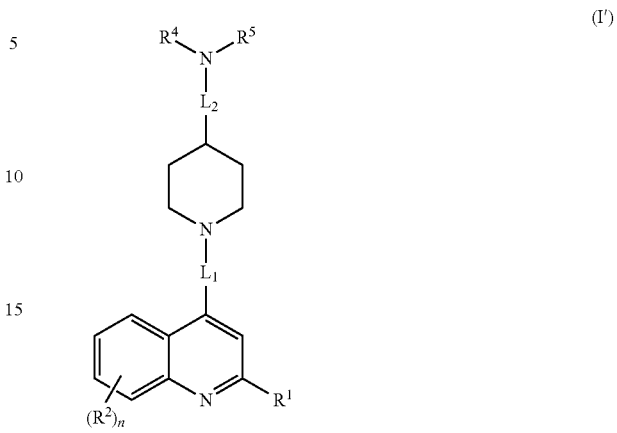

wherein L₁, L₂, R¹, R², R⁴, R⁵ and n are as defined in claim 1;

and any pharmaceutically acceptable salt, solvate or prodrug thereof.

3. A compound according to claim 1 selected from the group consisting of:
2-phenyl-4-(4-N,N-diethylamino-piperidin-1-yl)quinoline (I-3);
7-chloro-2-phenyl-4-(4-N,N-diethylamino-piperidin-1yl) quinoline (II-3);
2-phenyl-4-([1,4']-bipiperidin-1'-yl)quinoline (III-3);
2-phenyl-4-(4-N-tert-butylamino-piperidin-1-yl)quinoline (IV-1);
2-phenyl-4-[(4-morpholin-4-yl)piperidin-1-yl]quinoline (V-1);
2-(2-naphtyl)-4-(4-N,N-diethylamino-piperidin-1-yl)quinoline (VI-5);
2-(4-bromo-phenyl)-7-chloro-4-(4-N,N-diethylamino-piperidin-1-yl)quinoline (VII-4);
2-(4-bromo-phenyl)-4-(4-N,N-diethylamino-piperidin-1-yl)quinoline (VIII-5);
2-(1,1'-biphenyl)-4-yl-4-(4-N,N-diethylamino-piperidin-1-yl)quinoline (IX-1);
2-(4-chloro-phenyl)-4-(4-N,N-diethylamino-piperidin-1-yl)quinoline (X-5);
2-(1,1'-biphenyl)-4-yl-7-chloro-4-(4-N,N-diethylamino-piperidin-1-yl)quinoline (XI-1);
2-(4-chloro-phenyl)-4-(4-N-tert-butylamino-piperidin-1-yl)quinoline (XII-3);
2-(4-methyl-phenyl)-4-(4-N-tert-butylamino-piperidin-1-yl)quinoline (XIII-7);
2-(3,4-dichloro-phenyl)-4-(4-N-tert-butylamino-piperidin-1-yl)quinoline (XIV-7);
2-(4-methoxy-phenyl)-4-(4-N-tert-butylamino-piperidin-1-yl)quinoline (XV-7);
7-Chloro-2-phenyl-4-{1-[4-(N,N-diethylamino)-piperidin-1-yl]-eth-1-yl}1quinoline (XVI-3);
7-Chloro-2-phenyl-4-[4-(N,N-diethylamino)-piperidin-1-ylmethyl]quinoline (XVII-5);
2-phenyl-4-{1-[4-(N,N-diethylamino)-piperidin-1-yl]-eth-1-yl}quinoline (XIX-2);
2-phenyl-4-[4-(N,N-diethylamino)-piperidin-1-ylmethyl] quinoline (XX-4);
2-phenyl-4-{1-{4-[benzyl(phenethyl)amino]-piperidin-1-yl}-eth-1-yl}quinoline (XXI-3);

2-phenyl-4-{1-[(1.4'-bipiperidin)-1'-yl]-eth-1-yl}quinoline (XXII-3);
2-phenyl-4-{1-[4-(tert-butylamino)-piperidin-1-yl]-eth-1-yl}quinoline (XXIII-1);
2-(2-naphtyl)-4-{1-[4-(N,N-diethylamino)-piperidin-1-yl]-eth-1-yl}quinoline (XXIV-2);
2-phenyl-4-{2-[4-(N,N-diethylamino)-piperidin-1-yl]-propan-2-yl}quinoline trifluoroacetate salt (XXV-6);
7-chloro-2-phenyl-4-[4-(N,N-diethylaminomethyl)-piperidin-1-yl]quinoline (XXVI-3);
2-phenyl-4-[4-(N,N-diethylaminomethyl)-piperidin-1-yl)quinoline (XXVII-1); and
2-phenyl-4-{1-[4-(morpholino)-piperidinyl]-eth-1-yl}quinoline (XLV-1).

4. A compound according to claim 1 selected from the group consisting of:
2-phenyl-4-(4-N,N-diethylamino-piperidin-1-yl)quinoline hydrochloride salt (I-4);
7-chloro-2-phenyl-4-(4-N,N-diethylamino-piperidin-1-yl)quinoline hydrochloride salt (II-4);
2-phenyl-4-([1,4']-bipiperidin-1'-yl)quinoline hydrochloride salt (III-4);
2-phenyl-4-(4-N-tert-butylamino-piperidin-1-yl)quinoline hydrochloride salt (IV-2);
2-phenyl-4-[(4-morpholin-4-yl)piperidin-1yl]quinoline hydrochloride salt (V-2);
2-(2-naphtyl)-4-(4-N,N-diethylamino-piperidin-1-yl)quinoline hydrochloride salt (VI-6);
2-(4-bromo-phenyl)-7-chloro-4-(4-N,N-diethylamino-piperidin-1-yl)quinoline hydrochloride salt (VII-5);
2-(4-bromo-phenyl)-4-(4-N,N-diethylamino-piperidin-1-yl)quinoline hydrochloride salt (VIII-6);
2-(1,1'-biphenyl)-4-yl-4-(4-N,N-diethylamino-piperidin-1-yl)quinoline hydrochloride salt (IX-2);
2-(4-chloro-phenyl)-4-(4-N,N-diethylamino-piperidin-1-yl)quinoline hydrochloride salt (X-6);
2-(1,1'-biphenyl)-4-yl-7-chloro-4-(4-N,N-diethylamino-piperidin-1-yl)quinoline hydrochloride salt (XI-2);
2-(4-chloro-phenyl)-4-(4-N-tert-butylamino-piperidin-1-yl)quinoline hydrochloride salt (XII-4);
2-(4-methyl-phenyl)-4-(4-N-tert-butylamino-piperidin-1-yl)quinoline hydrochloride salt (XIII-8);
2-(3,4-dichloro-phenyl)-4-(4-N-tert-butylamino-piperidin-1-yl)quinoline hydrochloride salt (XIV-8);
2-(4-methoxy-phenyl)-4-(4-N-tert-butylamino-piperidin-1-yl)quinoline hydrochloride salt (XV-8);
7-Chloro-2-phenyl-4-{1-[4-(N,N-diethylamino)-piperidin-1-yl]-eth-1-yl}quinoline hydrochloride salt (XVI-4);
7-Chloro-2-phenyl-4-[4-(N,N-diethylamino)-piperidin-1-ylmethyl]quinoline hydrochloride salt (XVII-6);
2-phenyl-4-{1-[4-(N,N-diethylamino)-piperidin-1-yl]-eth-1-yl }quinoline hydrochloride salt (XIX-3);
2-phenyl-4-[4-(N,N-diethylamino)-piperidin-1-ylmethyl]quinoline hydrochloride salt (XX-5);
2-phenyl-4-{1-{4-[benzyl(phenethyl)amino]-piperidin-1-yl}-eth-1-yl}quinoline hydrochloride salt (XXI-4);
2-phenyl-4-{1-[(1.4'-bipiperidin)-1'-yl]-eth-1-yl}quinoline hydrochloride salt (XXII-4);
2-phenyl-4-{1-[4-(tert-butylamino)-piperidin-1-yl]-eth-1-yl}quinoline hydrochloride salt (XXIII-2);
2-(2-naphtyl)-4-{1-[4-(N,N-diethylamino)-piperidin-1-]-eth-1-yl}quinoline hydrochloride salt (XXIV-3);
2-phenyl-4-{2-[4-(N,N-diethylamino)-piperidin-1-yl]-propan-2-yl}quinoline trifluoroacetate salt (XXV-6);
7-chloro-2-phenyl-4-[4-(N,N-diethylaminomethyl)-piperidin-1-yl]quinoline hydrochloride salt (XXVI-4);
2-phenyl-4-[4-(N,N-diethylaminomethyl)-piperidin-1-yl)quinoline hydrochloride salt (XXVII-2); and
2-phenyl-4-{1-[4-(morpholino)-piperidinyl]-eth-1-yl}quinoline hydrochloride salt (XLV-1).

5. A compound according to claim 1 of formula (Ia) (XIX-2):

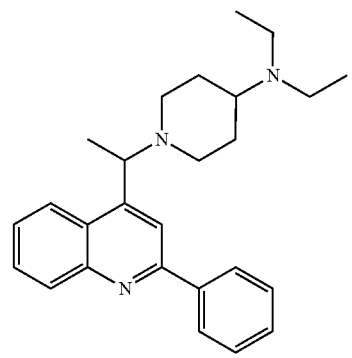

(Ia)

or a pharmaceutically acceptable salt, solvate or prodrug thereof.

6. A compound according to claim 1 of formula (Ib) (XLV-1):

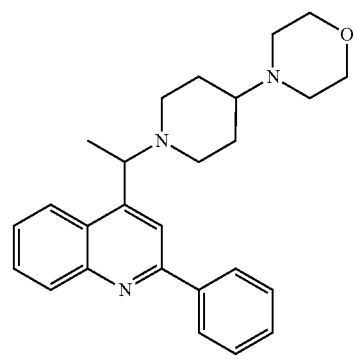

(Ib)

or a pharmaceutically acceptable salt, solvate or prodrug thereof.

7. A compound according to claim 1 of formula (Ic) (XII-3):

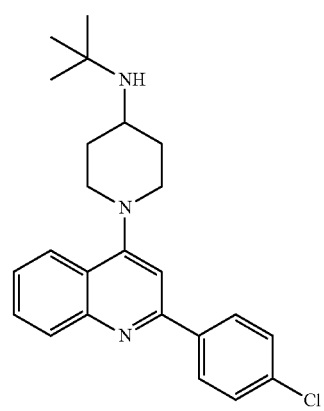

(Ic)

or a pharmaceutically acceptable salt, solvate or prodrug thereof.

8. A compound according to claim 1 of formula (Id) (XXIV-2):

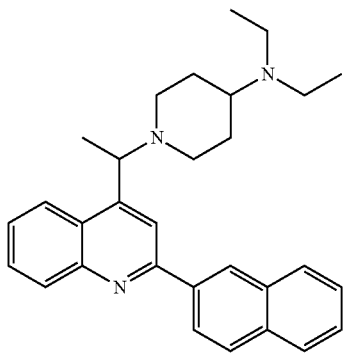

(Id)

or a pharmaceutically acceptable salt, solvate or prodrug thereof.

9. A pharmaceutical composition comprising a therapeutically effective amount of a compound according to claim 1, or a pharmaceutically acceptable salt, solvate or prodrug thereof, and a pharmaceutically acceptable adjuvant, diluent or carrier.

10. A pharmaceutical composition according to claim 9 further comprising in combination one or more anti-neoplastic agents.

11. A pharmaceutical composition according to claim 9, wherein the therapeutically effective amount of the compound is formulated or co-formulated in nanoparticles.

12. The pharmaceutical composition according to claim 11, wherein the nanoparticles comprise a polymeric biodegradable composition.

13. The pharmaceutical composition according to claim 12, wherein the polymer is based on Poly (DL-Lactic-co-glycolic acid) having molecular weight from 7 to 240 kDa; or a copolymer of polylactic acid (PLA and polyglycolic acid (PGA) where the molecular ratio is between 95:5 and 50:50.

14. The pharmaceutical composition according to claim 11, wherein the nanoparticles comprise a lisosomal biodegradable composition.

15. The pharmaceutical composition according to claim 11, wherein the nanoparticles comprise a biocompatible polymer or copolymer.

16. The pharmaceutical composition according to claim 11, wherein the nanoparticles are associated covalently or non-covalently with a polyethylene glycol (PEG).

17. The pharmaceutical composition according to claim 11, wherein the nanoparticles have an average size of from about 80 to about 600 nm.

18. The pharmaceutical composition according to claim 11, wherein the compound is associated with at least one therapeutically active anti-cancer agent.

19. The pharmaceutical composition according to claim 11, which is suitable for oral-, parenteral-, ocular-, transdermal-, nasal-administration, or for inhalation.

20. A pharmaceutical composition according to claim 11, wherein the nanoparticles comprise an item selected from PLGA nanoparticles, PLGA-PEG nanoparticles (block type AB, BA, ABA or BAB, where A =PLGA and B =PEG) and targeted nanoparticules.

21. A pharmaceutical composition according to claim 20, wherein the nanoparticle is a targeted nanoparticle containing a signaling motif.

22. A pharmaceutical composition comprising a combination of a therapeutically effective amount of a compound according to claim 1, and a therapeutically effective amount of one or more anti-neoplastic agents, wherein the components constituting said combination are for simultaneous, separate or sequential use in cancer therapy.

23. The pharmaceutical composition of claim 10, wherein the anti-neoplastic agent is selected from the group consisting of everolimus, chloroquine, hydroxychloroquine, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, TNO 1001, IPdR1 KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709,seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinem-ethyl)-indolyl]-quinolone, vatalanib, AG-013736, AVE-0005, the acetate salt of [D-Ser(But)$_6$, Azgly$_{10}$](pyro-Glu-His-Trp-Ser-Tyr-D-Ser(But)-Leu-Arg-Pro-Azgly-NH$_2$ acetate [C$_{59}$H$_{84}$N$_{18}$O$_{14}$—(C$_2$H$_4$O$_2$)x where x =1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PM-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, 1M862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, nitrogen mustard, methylprednisolone, ibritumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, sspegfilgrastim, epoetin alfa and darbepoetin alfa, ipilumumab, vemurafenib, FLT-3 inhibitor, a VEGFR inhibitor, an EGFR TK inhibitor, an aurora kinase inhibitor, a PIK-1 modulator, a mTOR inhibitor, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trap antibody, and mixtures thereof.

24. The pharmaceutical composition according to claim 9, which is suitable for slow- or sustained-release.

25. A method for the treatment and/or prevention of a proliferative and/or neoplastic disease, comprising the step of administering a therapeutically active amount of a compound according to claim 1, or a pharmaceutical composition comprising a therapeutically effective amount of the compound or a pharmaceutically acceptable salt, solvate or prodrug thereof, and a pharmaceutically acceptable adjuvant, diluent or carrier, to a human being or animal in need thereof.

26. A method according to claim 25, wherein the proliferative and/or neoplastic disease is selected from the group consisting of: carcinoma; a leukemia; a malignant lymphoma; a malignant melanoma; myeloproliferative diseases; a sarcoma; a tumor of the central nervous system; a germline tumor; testicular cancer; thyroid cancer; astrocytoma; colon cancer, melanoma, and a mixed type of neoplasia.

27. A method according to claim 26, wherein the carcinoma is a cancer of the esophagus, head, kidney, liver, lung, nasopharyngeal, neck, ovary, pancreas, prostate, stomach, breast or colon.

28. A method according to claim 26, wherein the leukemia is acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia.

29. A method for inhibiting the growth or differentiation of a Cancer Stem Cell (CSC), a tumor initiating cell, a mesenchymal-like cell associated with cancer, a mesenchymal cancerous cell, or a mesenchymal cell comprising the step of administering a therapeutically active amount of a compound according to claim 1, or a pharmaceutical composition comprising a therapeutically effective amount of the compound or a pharmaceutically acceptable salt, solvate or prodrug thereof, and a pharmaceutically acceptable adjuvant, diluent or carrier, to a human being or an animal in need thereof.

* * * * *